(12) United States Patent
Zhou et al.

(10) Patent No.: US 8,633,190 B2
(45) Date of Patent: Jan. 21, 2014

(54) SPIROLACTAM DERIVATIVES AND USES OF SAME

(75) Inventors: Hao Zhou, Paramus, NJ (US); Guiying Li, River Edge, NJ (US); Dario Doller, Sparta, NJ (US); Gil Ma, Englewood, NJ (US)

(73) Assignee: H. Lundbeck A/S (DK)

( * ) Notice: Subject to any disclaimer, the term of this patent is extended or adjusted under 35 U.S.C. 154(b) by 262 days.

(21) Appl. No.: 12/912,124

(22) Filed: Oct. 26, 2010

(65) Prior Publication Data

US 2011/0098299 A1    Apr. 28, 2011

Related U.S. Application Data

(60) Provisional application No. 61/255,837, filed on Oct. 28, 2009.

(51) Int. Cl.
| | |
|---|---|
| *A61K 31/535* | (2006.01) |
| *A61K 31/4965* | (2006.01) |
| *A61K 31/44* | (2006.01) |
| *A61K 31/40* | (2006.01) |
| *C07D 401/02* | (2006.01) |
| *C07D 295/02* | (2006.01) |
| *C07D 237/02* | (2006.01) |
| *C07D 211/92* | (2006.01) |
| *C07D 277/60* | (2006.01) |
| *C07D 209/54* | (2006.01) |

(52) U.S. Cl.
USPC ............ 514/235.5; 514/255.05; 514/256; 514/278; 514/365; 514/409; 544/70; 544/230; 546/15; 548/147; 548/408

(58) Field of Classification Search
USPC ......... 514/235.5, 255.05, 256, 278, 365, 409; 544/70, 230; 546/15; 548/147, 408
See application file for complete search history.

(56) References Cited

U.S. PATENT DOCUMENTS

| | | | |
|---|---|---|---|
| 4,463,013 | A | 7/1984 | Collins et al. |
| 6,071,928 | A | 6/2000 | Curtis et al. |
| 2008/0004304 | A1 | 1/2008 | Bell et al. |
| 2009/0099180 | A1 | 4/2009 | Mabry et al. |

FOREIGN PATENT DOCUMENTS

| | | |
|---|---|---|
| WO | 2006/071730 | 7/2006 |
| WO | 2008/032191 | 3/2008 |

OTHER PUBLICATIONS

Aggleton J.P., et al., 1986. "The Effects of Hippocampal Lesions Upon Spatial and Non-Spatial Tests of Working Memory," Behavioral Brain Research, 19(2):133-146.

Annett, L.E., 1994. "Behavioral Assessment of the Effects of Embryonic Nigral Grafts in Marmosets with Unilateral 6-OHDA Lesions of the Nigrostriatal Pathway," Experimental Neurology, 125:228-246.
Bach, P., et al., 2007. "Metabotropic Glutamete Receptor 5 Modulators and Their Potential Therapeutic Applications," Expert Opinion on Therapeutic Patents, 17(4): 371-384.
Berge, S.M., et al., 1977. "Pharmaceutical Salts," Journal of Pharmaceutical Science, 66(1):2.
Bontempi, B., et al., 1996. "Differential Temporal Evolution of Post-Training Changes in Regional Brain Glucose Metabolism Induced by Repeated Spatial Discrimination Training in Mice: Visualization of the Memory Consolidation Process?," European Journal of Neuroscience, 8:2348-2360.
Breysse, N., et al., 2002. "Chronic But Not Acute Treatment with a Metabotropic Glutamate 5 Receptor Antagonist Reverses the Akinetic Deficits in a Rat Model of Parkinsonism," Journal of Neuroscience, 22(13):5669-5678.
Chen, L., et al., 2009. "Chronic, Systemic Treatment with a Metabotropic Glutamate Receptor 5 Antagonist in 6-Hydroxydopamine Partially Lesioned Rats Reverses Abnormal Firing of Dopaminergic Neurons," Brain Research, 1286:192-200.
Cheng, Y., et al.,1973. "Relationship Between the Inhibition Constant (KI) and the Concentration of Inhibitor which Causes 50 Per Cent Inhibition (I50) of an Enzymatic Reaction," Biochemical Pharmacology, 22:3099-3108.
Cryan, J.F., et al., 2000. "Antidepressant-Like Behavioral Effects Mediated by 5-Hydroxytryptamine 2C Receptors1," Pharmcol. & Exp. Therap., 295(3):1120-1126.
Cryan, J.F., et al., 2005. "Assessing Substrates Underlying the Behavioral Effects of Antidepressants Using the Modified Rat Forced Swimming Test," Neuroscience and Biobehavioral Reviews, 29:547-569.
David, D.J., et al., 2007. "An Animal Model of Altered HPA Axis Responsive to Chronic Antidepressants," SFN meeting in San Diego.
Day, M., 2005. "Ovariectomy-Induced Disruption of Long-Term Synaptic Depression in the Hippocampal CA1 Region in Vivo is Attenuated with Chronic Estrogen Replacement," Neurobiology of Learning and Memory, 83:13-21.

(Continued)

*Primary Examiner* — James O Wilson
*Assistant Examiner* — Ebenezer O Sackey
(74) *Attorney, Agent, or Firm* — Kitae Lim

(57) ABSTRACT

The present invention provides spirolactam derivatives of formula (I):

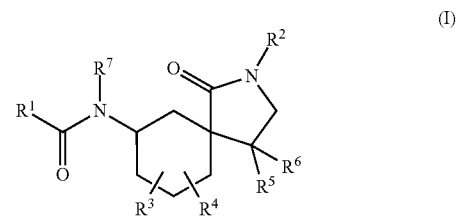

Figure 1:
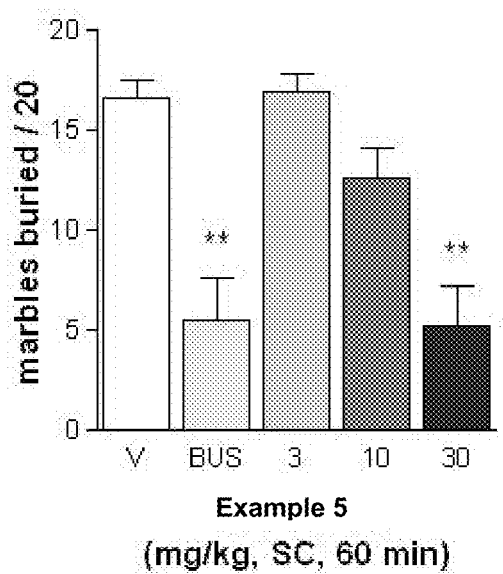

wherein $R^1$-$R^7$ are as defined herein; or a pharmaceutically acceptable salt thereof; and pharmaceutical compositions and uses of the same.

14 Claims, 4 Drawing Sheets

(56) References Cited

OTHER PUBLICATIONS

Depoortere, R., et al., 2003. "SSR181507, A Dopamine D2 Receptor Antagonist and 5-HT1A Receptor Agonist II: Behavioral Profile Predictive of an Atypical Antipsychotic Activity," Neuropsychopharmacology, 28:1889-1902.
Dolen G., et al., 2007. "Correction of Fragile X Syndrome in Mice," Neuron, 56:955-962.
Dulawa, S.C., et al., 2004. "Effects of Chronic Fluoxetine in Animal Models of Anxiety and Depression," Neuropsychopharmcology, 29:1321-1330.
File, S.E., et al., 2003. "A Review of 25 Years of the Social Interaction Test," European Journal of Pharmacology, 463:35-53.
Freed, W.J., et al., 1984. "Effects of Neuroleptics on Phencyclidine (PCP)-Induced Locomotor Stimulation in Mice," Neuropharmacology, 23(2A):175-181.
Fung, Y.K., et al., 1986. "Modulation of Apomorphine-Induced Climbing Behavior by Estradiol," Pharmacology Biochemistry and Behavior, 24(1):139-141.
Fung, Y.K., et al., 1987. "Inhibition by Bromoestrogens of the Effects of Estradiol on Apomorphine-Induced Climbing Behavior," Steroids, 49(4-5):287-294.
Gensler, W., et al., 1973. "Synthesis of chaminic acid," J. Org. Chem., 38(9):1726-1731.
Gould, T.J., et al., 2002. "MK-801 Disrupts Acquisition of Contextual Fear Conditioning but Enhances Memory Consolidation of Cued Fear Conditioning," Behavioral Pharmacology 13:287-294.
Hamm, A.O., et al., 2003. "Affective Blindsight: Intact Fear conditioning to a Visual Cue in a Cortically Blind Patient," Brain, 126:267-275.
Holick, K.A., et al., 2008. "Behavioral Effects of Chronic Fluoxetine in BALB/cJ Mice Do Not Require Adult Hippocampal Neurogenesis or the Serotonin 1A Receptor," Neuropsychopharmcology, 33:406-417.
Jaeschke, G., et al., 2008. "mGlu5 Receptor Antagonists and Their Therapeutic Potential," Expert Opinion on Therapeutic Patents, 18(2):123-142.
Kim, S.H., et al., 1992. "An Experimental Model for Peripheral Neuropathy Produced by Segmental Spinal Nerve Ligation in the Rat," Pain, 50:355-363.
Korte, S.M., et al., 2003. "A Robust Animal Model of State Anxiety: Fear—Potentiated Behaviour in the Elevated Plus-Maze," European Journal of Pharmacology, 463:163-175.
Lee, E. H., et al., 1992. "Comparative Studies of the Neurotoxicity of MPTP in Rats of Different Ages," Chinese Journal of Physiology, 35(4):317-336.
Liu, H.Y., et al., 2002. "Estrogen Inhibition of EAE Involves Effects on Dendritic Cell Function," Journal of Neuroscience Research, 70:238-248.

May, L.T., 2007. "Allosteric Modulation of G Protein-Coupled Receptors," Annual Review of Pharmacology Toxicology, 47:1-51.
Moore, N.A., et al., 1994. "Effects of Olanzapine and Other Antipyschotic Agents on Responding Maintained by a Conflict Schedule," Behavioural Pharmacology, 5:196-202.
Morris, R. G. M., 1981. "Spatial Localization Does Not Require the Presence of Local Cues," Learning and Motivation 12:239-260.
Muir, J.L., et al., 1995. "Reversal of Visual Attentional Dysfunction and Following Lesions of the Cholinergic Basal Forebrain by Physostigmine and Nicotine but not by the 5-HT3 Receptor Antagonist Ondansetron," Pyschopharmacology (Berl), 118:82-92.
Njung'e K., et al., 1991. "Evaluation of Marble-Burying Behavior as a Model of Anxiety," Pharmacology Biochemistry and Behavior, 38:63-67.
O'Brien, J.A., et al., 2003. "A Family of Highly Selective Allosteric Modulators of the Metabotropic Glutamate Receptor Subtype 5," Mol. Pharmacol., 64:731-740.
Overstreet, D.H., et al., 2005. "Antidepressant-Like Effects of the Vasopressin V1B Receptor Antagonist SSR149415 in the Flinders Sensitive Line Rat," Pharmacology, Biochemistry, and Behavior, 82:223-227.
Paulekuhn, G.S., et al., 2007. "Trends in Active Pharmaceutical Ingredient Salt Selection Based on Analysis of the Orange Book Database," Journal of Medicinal Chemistry, 50:6665-6672.
Robbins, T.W., et al., 1998. "Neural Systems Underlying Arousal and Attention," Annals NY Academy of Science, 846:222-237.
Rylander, D., et al., 2009. "Pharmacological Modulation of Glutamate Transmission in a Rat Model of L-DOPA-Induced Dyskinesia: Effects on Motor Behavior and Striatel Nuclear Signaling," Journal of Pharmacology and Experimental Therapeutics, 330(1):227-235.
Sams-Dodd, F., 1998. "Effects of Continuous D-Amphetamine and Phencyclidine Administration on Social Behaviour, Stereotyped Behaviour, and Locomotor Activity in Rats," Neuropharmacology, 19(1):18-25.
Santarelli L., et al., 2003. "Requirement of Hippocampal Neurogenesis for Behavioral Effects of Antidepressants," Science, 301:805-809.
Schultz, W., 1982. "Depletion of Dopamine in the Striatum as an Experimental Model of Parkinsonism: Direct Effects and Adaptive Mechanisms," Progress in Neurobiology, 18:121-166.
Vogel, J., et al., 1971. "A Simple and Reliable Conflict Procedure for Testing Anti-Anxiety Agents," Psychopharmacologia, 21:1-7.
Walker, D., et al., 1997. "Anxiogenic Effects of High Illumination Levels Assessed with the Acoustic Startle Response in Rats," Biological Psychiatry, 42:463-471.
Wheeler-Aceto, H., et al., 1991. "Standardization of the Rat Paw Formalin Test for the Evaluation of Analgesics," Psychopharmacology, 104:35-44.
International Search Report for International Application No. PCT/US2010/054054, dated Dec. 9, 2010 (mailed Dec. 27, 2010).

CDP: chlordiazepoxide (30 mg/kg, PO, 1 hr)
+ p < 0.01 vs. O using Student's t-test
** p <0.01 using one-way ANOVA and post-hoc Dunnett's test
n = 10

SPIROLACTAM DERIVATIVES AND USES OF SAME

FIELD OF THE INVENTION

The present invention provides spirolactam derivatives, as well as pharmaceutical compositions and methods of treatment using same.

BACKGROUND OF THE INVENTION

This invention concerns spirolactam derivatives, which act as allosteric modulators of the metabotropic glutamate receptor 5 (mGlu5 receptors or mGluR5), as well as pharmaceutical compositions and methods of treatment utilizing these compounds.

Glutamate is the major excitatory neurotransmitter in the mammalian central nervous system. One means of modulating glutamate neurotransmission is through metabotropic glutamate receptors (mGluRs); another means being ionotropic receptors. Presently, eight mGluRs have been cloned and classified into three groups based on sequence homology, preferred signal transduction pathway and pharmacology. Group I of mGluRs includes mGluR1 and mGluR5, while Group II comprises mGluR2 and mGluR3 and Group III comprises mGlu4, 6, 7 and 8 receptors.

mGlu receptors have an essential role in normal brain functions, as well as in neurological, psychiatric, and neuromuscular disorders. mGlu5 receptors are located primarily postsynaptically and highly expressed in the limbic brain regions. mGlu5 receptors also are expressed in the thalamus, spinal cord, and vagal nerve systems, as well as peripherally in the skin on nerve endings and C fibers.

Ligands to the mGlu5 receptors have been shown to have promise for peripheral and central nervous system disorders. See e.g., G. Jaeschke et al., "mGlu5 receptor antagonists and their therapeutic potential," *Expert Opin. Ther. Patents*, 2008, 18, 2: 123-142. Yet some proffer that glutamate analogs targeting the orthosteric binding site may be limited by low brain penetration and insufficient selectivity with respect to the different mGluRs subtypes. Synthetic agonists may lead to continuous stimulation of the receptor since they are often designed to be metabolically stable. This continuous stimulation is not necessarily desirable, due to potential receptor desensitization issues. Also, with respect to receptor occupancy, synthetic antagonists may lead to prolonged blockade of receptor function, which may not be compatible with the kinetics of the pathology of a central nervous system disorder.

However, a more selective and controlled "fine-tuning" action on the mGlu5 receptor is feasible through allosteric modulation. See e.g., P. Bach et al., "Metabotropic glutamate receptor 5 modulators and their potential therapeutic applications," *Expert Opin. Ther. Patents*, 2007, 17, 4: 371-381. Allosteric modulation refers to binding by a modulator ligand to a site on a receptor that is different from the orthosteric primary substrate or ligand binding site. This ligand binding process results in conformational changes, which may profoundly influence the function of the protein (e.g., G protein-coupled receptors such as mGluRs, including mGluR5). Novel mGluR5 ligands that allosterically modulate the mGlu5 receptor may improve the therapeutic window of traditional central nervous system agents and/or the treatment of central nervous system disorders. The present invention is directed these, and other important, ends.

SUMMARY OF THE INVENTION

The present invention provides a compound of formula (I):

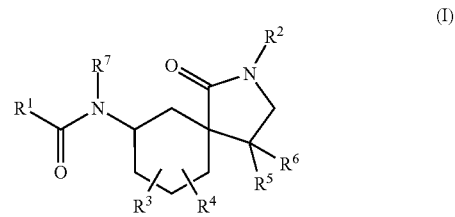

wherein:
$R^1$ and $R^2$ are each independently aryl, heteroaryl, alkyl, cycloalkyl, ketocycloalkyl, or heterocyclyl, which is optionally mono-, di-, or tri-substituted independently with alkyl, cycloalkyl, alkoxy, hydroxy, halogen, cyano, trifluoroalkyl, amino, acyl, aryl, heteroaryl, heterocyclyl, —C(O)NHR$^{30}$, —C(O)N(R$^{30}$)R$^{31}$, —NHC(O)$^{30}$, —N(R$^{30}$)C(O)R$^{31}$, —NHR$^{30}$, —N(R$^{30}$)R$^{31}$, or —OR$^{30}$; wherein:
$R^{30}$ and $R^{31}$ are each independently $C_1$-$C_6$alkyl or $C_1$-$C_6$cycloalkyl that is optionally substituted with acyl, halogen, —CN, —NH$_2$, —NH($C_1$-$C_3$alkyl), —N($C_1$-$C_3$alkyl)$_2$, $C_1$-$C_3$alkylheterocyclyl, $C_1$-$C_3$alkylcarbamate, —C(O)NH($C_1$-$C_3$alkyl), —C(O)N($C_1$-$C_3$alkyl)$_2$, —NHC(O)—$C_1$-$C_3$alkyl, —N($C_1$-$C_3$alkyl)-C(O)—$C_1$-$C_3$alkyl, OH, or —O—$C_1$-$C_6$alkyl; and
each aryl, heteroaryl, heterocyclyl substituent is optionally substituted with $C_{1-3}$alkyl, $C_{3-5}$cycloalkyl, $C_{1-3}$alkoxy, hydroxy, halogen, cyano, trifluoroalkyl, or amino;
$R^3$, $R^4$, $R^5$ and $R^6$ are each independently H, $C_{1-3}$alkyl, $C_{3-5}$cycloalkyl, halogen, or hydroxy;
$R^7$ is H; or
$R^1$ and $R^7$ taken together with the —C(O)N— to which they are attached form a mono- or bicyclic 4- to 12-membered heterocycloalkyl or heteroaryl, which optionally contains 1-3 additional heteroatoms; or
a pharmaceutically acceptable salt thereof.

The present invention also provides a pharmaceutical composition comprising at least one compound of formula (I) or a pharmaceutically acceptable salt thereof, and at least one pharmaceutically acceptable carrier.

The present invention also provides a method of treating a disease or disorder, the method comprises administering a therapeutically effective amount of at least one compound of the present invention or a pharmaceutically acceptable salt thereof to a mammal in need thereof, wherein the disease or disorder is a central nervous system disease or disorder. In some embodiments of the method, a symptom of the disease or disorder is treated.

FIGURES

FIG. 1: Effect of a compound of formula (I) in a mouse model for affective diseases and disorders in accordance with an embodiment of the invention.

Figure 2:
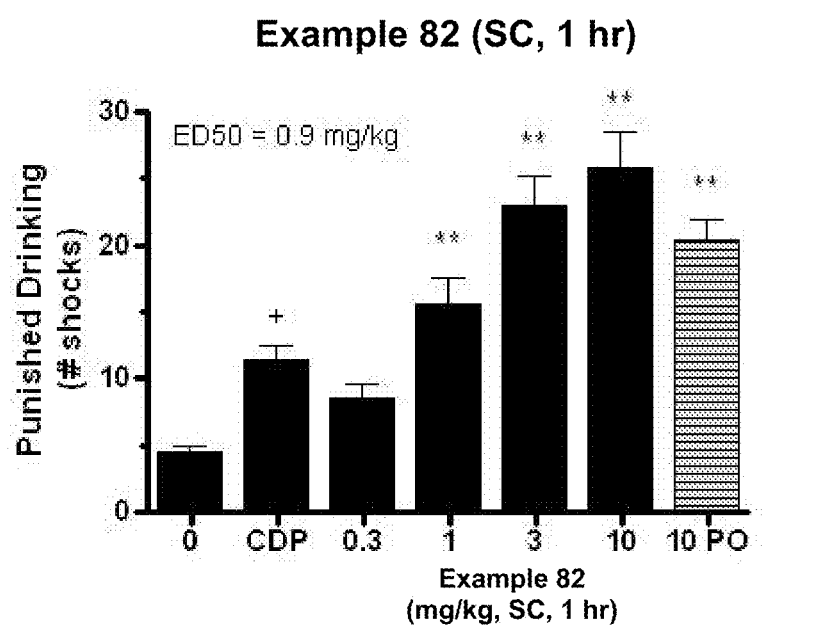

FIG. 2: Effect of a compound of formula (I) in a rat model for affective diseases and disorders in accordance with an embodiment of the invention.

Figure 3:
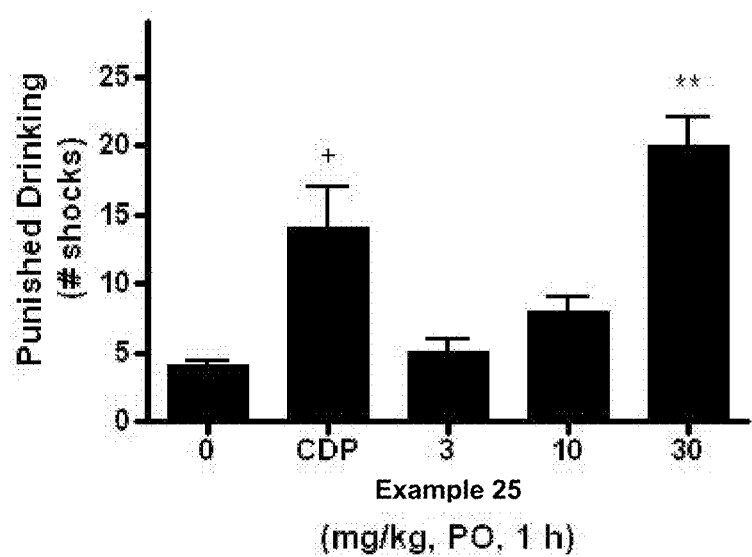

FIG. 3: Effect of a compound of formula (I) in a rat model for affective diseases and disorders in accordance with an embodiment of the invention.

Figure 4:
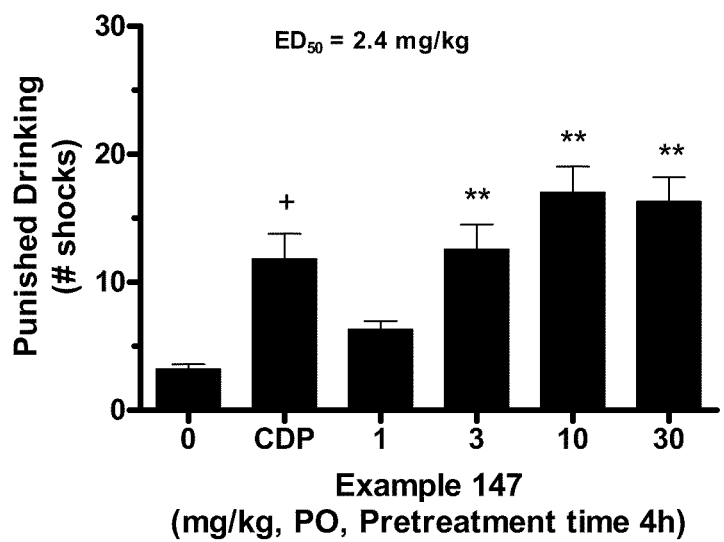

FIG. 4: Effect of a compound of formula (I) in a rat model for affective diseases and disorders in accordance with an embodiment of the invention.

DETAILED DESCRIPTION OF THE INVENTION

In one aspect, the present invention provides spirolactam derivatives. The spirolactam derivatives are compounds of formula (I):

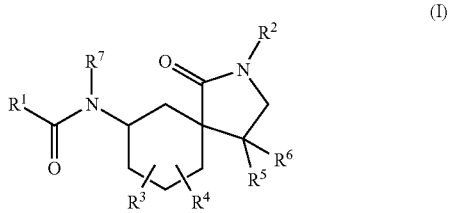

wherein:
  $R^1$ and $R^2$ are each independently aryl, heteroaryl, alkyl, cycloalkyl, ketocycloalkyl, or heterocyclyl, which is optionally mono-, di-, or tri-substituted independently with alkyl, cycloalkyl, alkoxy, hydroxy, halogen, cyano, trifluoroalkyl, amino, acyl, aryl, heteroaryl, heterocyclyl, —C(O)NHR$^{30}$, —C(O)N(R$^{30}$)R$^{31}$, —NHC(O)$^{30}$, —N(R$^{30}$)C(O)R$^{31}$, —NHR$^{30}$, —N(R$^{30}$)R$^{31}$, or —OR$^{30}$; wherein:
    $R^{30}$ and $R^{31}$ are each independently $C_1$-$C_6$alkyl or $C_1$-$C_6$cycloalkyl that is optionally substituted with acyl, halogen, —CN, —NH$_2$, —NH($C_1$-$C_3$alkyl), —N($C_1$-$C_3$alkyl)$_2$, $C_1$-$C_3$alkylheterocyclyl, $C_1$-$C_3$alkylcarbamate, —C(O)NH($C_1$-$C_3$alkyl), —C(O)N($C_1$-$C_3$alkyl)$_2$, —NHC(O)—$C_1$-$C_3$alkyl, —N($C_1$-$C_3$alkyl)-C(O)—$C_1$-$C_3$alkyl, OH, or —O—$C_1$-$C_6$alkyl; and
    each aryl, heteroaryl, heterocyclyl substituent is optionally substituted with $C_{1-3}$alkyl, $C_{3-5}$cycloalkyl, $C_{1-3}$alkoxy, hydroxy, halogen, cyano, trifluoroalkyl, or amino;
  $R^3$, $R^4$, $R^5$ and $R^6$ are each independently H, $C_{1-3}$alkyl, $C_{3-5}$cycloalkyl, halogen, or hydroxy;
  $R^7$ is H; or
  $R^1$ and $R^7$ taken together with the —C(O)N— to which they are attached form a mono- or bicyclic 4- to 12-membered heterocycloalkyl or heteroaryl, which optionally contains 1-3 additional heteroatoms; or
a pharmaceutically acceptable salt thereof.

The term "alkyl", employed alone or as part of a group, is defined herein, unless otherwise stated, as either a straight-chain or branched saturated hydrocarbon of 1 to 8 carbon atoms. In some embodiments, the alkyl moiety contains 8, 7, 6, 5, 4, 3, 2 or 1 carbon atoms. Where the term "alkyl" appears herein without a carbon atom range it means a range of $C_1$-$C_8$. Where the term "alkyl" appears herein with a carbon range, it means an alkyl of any number within in the carbon range identified, such as a $C_1$-$C_3$alkyl means either methyl, ethyl or propyl. Examples of saturated hydrocarbon alkyl moieties include, but are not limited to, chemical groups such as methyl, ethyl, n-propyl, isopropyl, n-butyl, tert-butyl, isobutyl, sec-butyl, n-pentyl, n-hexyl, and the like. Alkyl also refers to alkyl moieties where the alkyl group is substituted by hydroxy, cyano, alkoxy, alkylamino, dialkylamino, alkylamide, dialkylamide, and the like, including without limitation, —OC$_1$-C$_4$alkyl-OH, —OC$_1$-C$_4$alkyl-OCH$_3$, —OC$_1$-C$_4$alkyl-NHCH$_3$, —OC$_1$-C$_4$alkyl-N(CH$_3$)$_2$, —OC$_1$-C$_4$alkyl-CONHCH$_3$, —OC$_1$-C$_4$alkyl-CON(CH$_3$)$_2$, —OC$_1$-C$_4$alkyl-NHCOCH$_3$, and —OC$_1$-C$_4$alkyl-N(CH$_3$)COCH$_3$.

The term "alkoxy", employed alone or in combination with other terms, is defined herein, unless otherwise stated, as —O-alkyl, where "alkyl" is as previously defined herein. Examples of alkoxy moieties include, but are not limited to, chemical groups such as methoxy, ethoxy, iso-propoxy, sec-butoxy, tert-butoxy, and homologs, isomers, and the like. Alkoxy also refers to —O-alkyl moieties where the alkyl group is substituted by hydroxy, cyano, alkoxy, alkylamino, dialkylamino, alkylamide, dialkylamide, and the like, including without limitation, —OC$_1$-C$_4$alkyl-OH, —OC$_1$-C$_4$alkyl-OCH$_3$, —OC$_1$-C$_4$alkyl-NHCH$_3$, —OC$_1$-C$_4$alkyl-N(CH$_3$)$_2$, —OC$_1$-C$_4$alkyl-CONHCH$_3$, —OC$_1$-C$_4$alkyl-CON(CH$_3$)$_2$, —OC$_1$-C$_4$alkyl-NHCOCH$_3$, and —OC$_1$-C$_4$alkyl-N(CH$_3$)COCH$_3$.

The term "hydroxyalkyl", employed alone or in combination with other terms, is defined herein, unless otherwise stated, as -alkyl-OH, where "alkyl" is as previously defined herein. Nonlimiting examples include methyl-OH, ethyl-OH, n-propyl-OH, and the like.

As used herein, the term "cycloalkyl", employed alone or in combination with other terms, is defined herein, unless otherwise stated, as a cyclized alkyl group having from 3 to 8 ring carbon atoms, where "alkyl" is as defined herein. Examples of cycloalkyl moieties include, but are not limited to, chemical groups such as cyclopropyl, cyclobutyl, cyclopentyl, and cyclohexyl.

As used herein, the term "ketocycloalkyl", employed alone or in combination with other terms, is defined herein, unless otherwise stated, as a cycloalkyl having a keto radical attached thereto, where "cycloalkyl" is as defined herein. Examples include cyclopentanone or cyclohexanone.

The terms "halo" or "halogen", employed alone or in combination with other terms, is defined herein, unless otherwise stated, as fluoro, chloro, bromo, or iodo.

The term "aryl", employed alone or in combination with other terms, is defined herein, unless otherwise stated, as an aromatic hydrocarbon of up to 14 carbon atoms, which can be a single ring (monocyclic) or multiple rings (e.g., bicyclic, tricyclic, polycyclic) fused together or linked covalently. Any suitable ring position of the aryl moiety can be covalently linked to the defined chemical structure. Examples of aryl moieties include, but are not limited to, chemical groups such as phenyl, benzyl, 1-naphthyl, 2-naphthyl, and the like. An aryl group can be unsubstituted or substituted as described herein.

The term "heteroaryl" employed alone or in combination with other terms, is defined herein, unless otherwise stated, as a monocyclic or polycyclic (fused together or linked covalently) aromatic hydrocarbon ring comprising one or more heteroatoms independently selected from nitrogen, oxygen, and sulfur. A heteroaryl group comprises up to 14 carbon atoms and 1 to 6 heteroatoms. Examples of heteroaryl groups include, but are not limited to, pyridinyl, pyridazinyl, triazinyl, pyrrolyl, pyrazolyl, imidazolyl, (1,2,3,)- and (1,2,4)-triazolyl, pyrazinyl, pyrimidinyl, tetrazolyl, furyl, thienyl, isoxazolyl, thiazolyl, oxazolyl, 2-quinolinyl, 2-quinazolinyl, 3-phenyl-2-quinolinyl and the like. A heteroaryl group can be unsubstituted or substituted as described herein.

The term "heterocyclyl" employed alone or in combination with other terms, is defined herein, unless otherwise stated, as a univalent group formed by removing a hydrogen atom from any ring atom of a heterocycle.

The term "acyl" employed alone or in combination with other terms, is defined herein, unless otherwise stated, as groups of formula —C(O)-alkyl, where alkyl is a previously described herein; i.e., an alkylcarbonyl, such as formyl, acetyl and the like.

The term "aminoalkyl" employed alone or in combination with other terms, is defined herein, unless otherwise stated, as alkyl-amino, where the term "alkyl" is as previously defined herein and the term "amino" is —NH$_2$, —NH—, or —N<. Non-limiting examples include —CH$_3$NH—, CH$_3$CH$_2$NH—, (C$_1$-C$_3$alkyl)NH—, (C$_1$-C$_3$alkyl)$_2$N—, and the like.

The term "alkylamino" employed alone or in combination with other terms, is defined herein, unless otherwise stated, as amino-alkyl, where the term "alkyl" is as previously defined herein and the term "amino" is —NH$_2$, —NH—, or —N<. Non-limiting examples include —NHCH$_3$, —NHCH$_2$CH$_3$, —NH(C$_1$-C$_3$alkyl), —N(C$_1$-C$_3$alkyl)$_2$, and the like.

In some embodiments, $R^1$ and $R^2$ are both aryl. In some embodiments, $R^1$ and $R^2$ are both heteroaryl. In some embodiments, $R^1$ is aryl and $R^2$ is heteroaryl. In some embodiments, $R^1$ is heteroaryl and $R^2$ is aryl. In some embodiments, either $R^1$ or $R^2$ is heteroaryl. In some embodiments, either $R^1$ or $R^2$ is aryl.

In some embodiments, either $R^1$ or $R^2$ is alkyl. In some embodiments, either $R^1$ or $R^2$ is cycloalkyl. In some embodiments, either $R^1$ or $R^2$ is ketocycloalkyl. In some embodiments, either $R^1$ or $R^2$ is heterocyclyl.

In some embodiments, at least one aryl is phenyl. In some embodiments, at least one heteroaryl is pyridinyl, pyrimidinyl, pyridazinyl, pyrazinyl, thiazolyl, pyrazolyl, indazolyl, thiophenyl, furanyl, or benzofuranyl. In some embodiments, both aryls are phenyl. In some embodiments, both heteroaryls are selected from a group consisting of pyridinyl, pyrimidinyl, pyridazinyl, pyrazinyl, thiazolyl, pyrazolyl, indazolyl, indazolylimidazolyl, thiophenyl, furanyl, and benzofuranyl. In some embodiments, at least one heteroaryl is pyridinyl, pyrimidinyl, pyridazinyl, pyrazinyl, thiazolyl, pyrazolyl, indazolyl, thiophenyl, furanyl, benzofuranyl, benzo[c]isoxazolyl, benzoxazolyl, benzothiazolyl, dihydrothieno[3,4-b][1,4]dioxinyl, furanyl, imidazo[1,2-a]pyridinyl, indazolyl, indolinyl, indolyl, isoquinolinyl, isoxazolyl, naphthyridinyl, oxazolyl, pyrazinyl, pyrazolyl, pyridazinyl, pyridinyl, pyrimidinyl, pyrrolo[3,2-c]pyridinyl, quinolinyl, quinoxalinyl, thiazolyl, or thiophenyl.

In some embodiments, $R^1$ is aryl or heteroaryl and $R^2$ is cycloalkyl, ketocycloalkyl or heterocyclyl. In some embodiments, $R^2$ is aryl or heteroaryl and $R^1$ is cycloalkyl, ketocycloalkyl or heterocyclyl.

In some embodiments, either $R^1$ or $R^2$ is cycloalkyl. In some embodiments, at least one cycloalkyl is cyclobutyl, cyclohexyl, cycloheptyl, cyclopentyl, or cyclopropyl. In some embodiments, the cycloalkyl is further substituted beyond the tri-substitution previously defined, i.e., the cycloalkyl is substituted more than three times as previously described; for example, the cycloalkyl is tetra-substituted with fluorine.

In some embodiments, the heteroaryl is pyridinyl, and the pyridinyl is mono-, di-, or tri-substituted as previously defined. In some such embodiments, the mono-, di-, or tri-substitutions are independently aryl, heteroaryl, and heterocyclyl. In some such embodiments, the aryl, heteroaryl and heterocyclyl substitutent is further substituted, such as, e.g., with halogen or C$_{1-3}$alkyl.

In some embodiments, at least one aryl or heteroaryl is substituted as previously described.

In some some embodiments, wherein the mono-, di-, or tri-substituents are independently selected from the group consisting of methyl, methoxy, dimethylamino-ethoxy, amino, methylamino, dimethylamino, cyano, chloro, cyano, dimethylamino, dimethylamino-ethoxy, methyl, methylamino, methoxy, fluoro, —C(O)NHCH$_3$, phenyl, furanyl, pyrrolidinyl, thiophenyl and trifluoromethyl. In some embodiments, the 1, 2, or 3 substituents are independently selected from the group consisting of methyl, methoxy, dimethylamino-ethoxy, amino, methylamino, dimethylamino, cyano, chloro, fluoro, phenyl, furanyl and thiophenyl.

In some embodiments, the phenyl, furanyl or thiophenyl substituent of at least one aryl or heteroaryl is substituted with at least one alkyl, alkoxy, hydroxyalkyl, halogen, cyano, or trifluoroalkyl. In some such embodiments, the phenyl is substituted with fluorine.

In some embodiments, $R^1$ and $R^2$ each are independently selected from a group consisting of the aryl, heteroaryl, alkyl, cycloalkyl, ketocycloalkyl and heterocyclyl groups of the compounds of Table 1 and 2, below.

In some embodiments, $R^3$, $R^4$, $R^5$ and $R^6$ are each independently H, C$_{1-3}$alkyl, C$_{3-5}$cycloalkyl, halogen, or hydroxy. In some embodiments, $R^3$, $R^4$, $R^5$ and $R^6$ are each independently methyl or fluorine.

In some embodiments, $R^7$ is hydrogen. In some embodiments, $R^7$ along with $R^1$ are taken together with the —C(O)N< to which they are attached form a mono- or bicyclic 4- to 12-membered heterocycloalkyl or heteroaryl, which optionally contains 1-3 additional heteroatoms.

In some embodiments, the compound of formula (I) is a compound disclosed in the Experimental Section below. In some embodiments, the compound is one from Table 1 or 2, below.

Another aspect of the present invention is a composition that comprises a pharmaceutically effective amount of a compound according to the present invention, and a pharmaceutically acceptable carrier or excipient.

A composition of the present invention may be adapted to any mode of administration, such as orally (including sublingually), via implants, parentally (including intravenous, intraperitoneal, intraarticularly and subcutaneous injections), rectally, intranasally, topically, ocularly (via eye drops), vaginally, and transdermally.

A compound of the present invention can be used either as a free base or in the form of a salt derived from pharmaceutically acceptable acids or bases. The salt includes without limitation the following: salts with inorganic acids, e.g., hydrochloric acid, hydrobromic acid, sulfuric acid, nitric acid, and phosphoric acid, and organic acids e.g., acetic acid, oxalic acid, citric acid, tartaric acid, succinic acid, maleic acid, benzoic acid, benzene sulfonic acid, fumaric acid, malic acid, methane sulfonic acid, pamoic acid, and para-toluene sulfonic acid. Other salts include salts with alkali metals or alkaline earth metals, e.g., sodium, potassium, calcium and magnesium, or with organic bases, including quaternary ammonium salts. Further non-limiting examples of pharmaceutically acceptable inorganic and organic acid addition salts include those listed in [S. M. Berge et al., *J. Pharm. Sci.* 1977, 66, 1: 2, and G. S. Paulekuhn, et al., *J. Med. Chem.* 2007, 50, 26: 6665-6672].

A compound of the present invention can also be used in the form of an ester, carbamate and other conventional prodrug form, which generally will be a functional derivative of the compound that is readily converted to the active moiety in vivo. Also included are metabolites of a compound of the present invention defined as active species produced upon introduction of the compound into a biological system.

When a compound of the present invention is employed as described above, it may be combined with one or more pharmaceutically acceptable excipients or carriers, e.g., solvents, diluents and the like. Such pharmaceutical preparations may be administered orally in such forms as tablets, capsules (including, e.g., time release and sustained release formulations), pills, lozenges, aerosols, dispersible powders, granules, solutions, suspensions (containing, e.g., a suspending agent, at, e.g., from about 0.05 to about 5% of suspending agent), syrups (containing, e.g., sugar or a sugar substitute such as aspartame, at, e.g., about 10 to about 50% sugar or sugar substitute), elixirs and the like, or parenterally in the form of sterile injectable solutions, suspensions or emulsions containing, e.g., from about 0.05 to about 5% suspending agent in an isotonic medium. Such preparations may contain, e.g., from about 25 to about 90% of the active ingredient in combination with the carrier, more customarily from about 5% and about 60% by weight. The effective dosage of an active ingredient (e.g., a compound or salt of the present invention and a prodrug or metabolite thereof) employed may vary depending on the particular compound, salt, prodrug or metabolite used, the mode of administration, age, weight, sex and medical condition of the patient, and the severity of the disease, disorder, condition, and/or system being treated. The selection of the appropriate administration and dosage form for an individual mammal will be apparent to those skilled in the art. Such determinations are routine to a physician, veterinarian or clinician of ordinary skill in the art (see e.g., *Harrison's Principles of Internal Medicine*, Anthony Fauci et al. (eds.) $14^{th}$ ed. New York: McGraw Hill (1998)). Further, the dosage regimen may be adjusted to provide the optimal therapeutic response. For example, several divided doses may be administered daily or the dose may be proportionally reduced as indicated by the needs of the therapeutic situation.

Solid carriers, e.g., starch, lactose, dicalcium phosphate, microcrystalline cellulose, sucrose and kaolin, liquid carriers, e.g., sterile water, polyethylene glycols, glycerol, non-ionic surfactants and edible oils such as corn, peanut and sesame oils, may be employed as are appropriate to the nature of the active ingredient and the particular form of administration desired. Adjuvants customarily employed in the preparation of pharmaceutical compositions may be advantageously included. Non-limiting examples of adjuvants include flavoring agents, coloring agents, preserving agents, and antioxidants, such as vitamin E, ascorbic acid, BHT and BHA.

An active compound also may be administered parenterally or intraperitoneally. Solutions or suspensions of the active compound as a free base, neutral compound or pharmacologically acceptable salt can be prepared in water suitably mixed with a surfactant such as hydroxypropylcellulose. Dispersions also can be prepared in glycerol, liquid polyethylene glycols and mixtures thereof in oils. These preparations may contain a preservative to prevent the growth of microorganisms under ordinary conditions of storage and use.

The pharmaceutical forms suitable for injectable or infusing use include sterile aqueous solutions, suspensions or dispersions, and sterile powders for the extemporaneous preparation of sterile injectable or infusing solutions, suspension or dispersions. In all cases, the form must be sterile and must be fluid to the extent that easy injectability and infusing exists. It must be stable under conditions of manufacture and storage and must be preserved against the contaminating action of microorganisms. The carrier can be a solvent or dispersion medium containing, for example, water, ethanol, and polyol (e.g., glycerol, propylene glycol, and liquid polyethylene glycol), suitable mixtures thereof, and vegetable oil.

Furthermore, active compounds of the present invention can be administered intranasally or transdermally using vehicles suitable for intranasal or transdermal delivery known to those ordinarily skilled in the art. Transdermal administration includes all administrations across the surface of the body and the inner linings of bodily passages including epithelial and mucosal tissues, using carrier systems such as lotions, creams, foams, pastes, patches, suspensions, solutions, and suppositories (rectal and vaginal). Creams and ointments may be viscous liquid or semisolid emulsions of either the oil-in-water or water-in-oil type. Pastes comprised of absorptive powders dispersed in petroleum or hydrophilic petroleum containing the active ingredient also may be suitable. A variety of occlusive devices may be used to release the active ingredient into the blood stream such as a semi-permeable membrane covering a reservoir containing the active ingredient with or without a carrier, or a matrix containing the active ingredient. Other occlusive devices are known in the literature. When using a transdermal delivery system, the dosage administration will be continuous rather than a single or divided daily dose.

A compound of the present invention can also be administered in the form of a liposome delivery system where the liposomal lipid bilayer is formed from a variety of phospholipids. A compound of the present invention also may be delivered by the use of a carrier such as monoclonal antibodies to which the compound is coupled. Other carriers to which a compound of the present invention also may be coupled are a soluble polymer or a biodegradable polymer useful in achieving controlled release of an active ingredient.

It is understood by those practicing the art that some of the compounds of the present invention may contain one or more asymmetric centers, and thus may give rise to enantiomers and diastereomers. The present invention includes all stereoisomers including individual diastereomers and resolved, enantiomerically pure stereoisomers, as well as racemates, and all other variations of stereoisomers, and mixtures and pharmaceutically acceptable salts thereof, which possess the indicated activity. Optical isomers may be obtained in pure form by procedures known to those skilled in the art, and include, but are not limited to, chiral chromatographic separations, diastereomeric salt formation, kinetic resolution, and asymmetric synthesis. It is also understood that this invention encompasses all possible regioisomers, endo-exo isomers, and mixtures thereof that possess the indicated activity. Such isomers can be obtained in pure form by procedures known to those skilled in the art, and include, but are not limited to, column chromatography, thin-layer chromatography, and high-performance liquid chromatography. It is understood by those practicing the art that some of the compounds of the present invention may be chiral due to hindered rotation, and give rise to atropisomers, which can be resolved and obtained in pure form by procedures known to those skilled in the art. It is further understood by those practicing the art that some of the compounds of the present invention include structural isomers, including tautomers.

Included also in this invention are polymorphs and hydrates of the compounds of the present invention, as well as isotopically labeled analogs thereof (e.g., $^2$H, $^3$H, $^{13}$C, $^{15}$N and the like).

Another aspect of the present invention is a method for using the compounds of the invention. The invention is to be understood as embracing all simultaneous, sequential or separate use of any combination of the compounds of the invention with any pharmaceutical composition useful in the methods and uses described herein.

In some embodiments, the method includes administering an effective amount of a compound of formula (I), or salt thereof. In some embodiments, the method in includes administering a therapeutically effective amount of a compound described herein, or salt thereof.

As used herein, the phrase "effective amount" when applied to a compound of the invention, is intended to denote an amount sufficient to cause an intended biological effect. The phrase "therapeutically effective amount" when applied to a compound of the invention is intended to denote an amount of the compound that is sufficient to ameliorate, palliate, stabilize, reverse, slow or delay the progression of a disorder or disease state, or of a symptom of the disorder or disease. In some embodiments, the method or use of the present invention provides for administration of combinations of compounds. In such instances, the "effective amount" is the amount of the combination sufficient to cause the intended biological effect.

In some embodiments, the method includes administering an effective amount of a combination of two or more of the compounds described herein, or salts thereof. It is specifically intended that the phrases "combination of two or more of the compounds described herein, or salts thereof," or "at least one compound as described herein, or a pharmaceutically acceptable salt thereof," or similar language describing specific compounds, includes the administration of such compounds in any proportion and combination of salt, neutral or free base forms; i.e., includes the administration of such compounds each in the base form, each in the neutral form or each in the salt form, or one or more in the base form and one or more in the neutral form, or one or more in the base form and one or more in the salt form, or one or more in the neutral form and one or more in the salt form, in any proportion of the neutral and/or basic compounds and/or salts.

The term "treatment" or "treating" as used herein means ameliorating or reversing the progress of a disease or disorder, or ameliorating or reversing one or more symptoms or side effects of such disease or disorder. For example, "treatment" or "treating" can refer to slowing, interrupting, controlling, lessening, stopping, or regulating the progression or continuation of a disease or disorder. "Treatment" or "treating", as used herein, also means to, inhibit or block, as in retard, arrest, restrain, impede or obstruct, the progress of a system, condition or state of a disease or disorder. For purposes of this invention, "treatment" or "treating" further means an approach for obtaining beneficial or desired clinical results, where "beneficial or desired clinical results" include, without limitation, alleviation of a symptom, diminishment of (or reducing) the extent of a disorder or disease, stabilized (i.e., not worsening) disease or disorder state, delay or slowing of a disease or disorder state, amelioration or palliation of a disease or disorder state, and remission of a disease or disorder, whether partial or total, detectable or undetectable.

The term "prevent" or "preventing" as used herein means to keep from happening or existing. The term "administering" as used herein refers to either directly administering a compound of the present invention, or administering a prodrug, derivative, or analog of same, that will form an effective amount of the compound within a mammal.

The present invention also provides a method of treating a disease or disorder, the method comprises administering a therapeutically effective amount of at least one compound of the present invention or a pharmaceutically acceptable salt thereof to a mammal in need thereof, wherein the disease or disorder is a central nervous system disease or disorder.

The present invention also provides a use of compound of the present invention, including a pharmaceutically acceptable salt thereof, in the preparation of a medicament for the treatment of a central nervous system disease or disorder. The present invention further provides a compound of the present invention for use in treating a disease or disorder.

A compound of the present invention can allosterically modulate the mGlu5 receptor. An allosteric modulator that enhances or potentiates the affinity of an orthosteric ligand for the mGluR5 receptor and/or enhances or potentiates an orthosteric agonist's efficacy is an allosteric enhancer (or potentiator) or positive allosteric modulator (PAM). See e.g., May, L. T. *Annu. Rev. Pharmacol. Toxicol.* 2007, 47, 1-51. An allosteric modulator that reduces or diminishes the affinity of an orthosteric ligand for the mGluR5 receptor and/or reduces or diminishes an orthosteric agonist's efficacy is an allosteric antagonist (or inhibitor) or negative allosteric modulator (NAM). Id. A silent allosteric modulator (SAM) binds to an allosteric site of the receptor but has no measurable intrinsic efficacy. A SAM may indirectly demonstrate efficacy by preventing an allosterically binding compound from displaying its own positive (PAM) or negative (NAM) efficacy.

In some embodiments, the mammal of the method of the invention is a human.

In some embodiments of the method or use of the invention, the central nervous system disease or disorder is a cognitive, neurodegenerative, psychiatric or neurological disease or disorder. In some such embodiments, the cognitive, neurodegenerative, psychiatric or neurological disease or disorder is selected from a group consisting of a mood disorder, an anxiety, a schizophrenia (including schizoaffective disorders), Alzheimer's disease, Parkinson's disease, multiple sclerosis, Huntington's chorea, amyotrophic lateral sclerosis, Creutzfeld-Jakob disease, a trauma-induced neurodegeneration, AIDS-induced encephalopathy, another infection-related encephalopathy (i.e., a non-AIDS-induced encephalopathy), Fragile X syndrome, an autism spectrum disorder, and a combination thereof.

As used herein, the phrase "mood disorder" refers to any of several psychological disorders characterized by abnormalities of emotional state, such as, without limitation, bipolar disorders, depressive disorders, cyclothymic disorders, dysthymic disorders, mood disorders due to a general medical condition, mood disorders not otherwise specified and substance-induced mood disorders; and as characterized by the *Diagnostic and Statistical Manual of Mental Disorders*, Fourth Edition (DSM-IV) (American Psychiatric Association: Arlington, Va., 1994).

As used herein, the phrase "autism spectrum disorder" (ASD) refers to a disorder that causes severe and pervasive impairment in thinking, feeling, language, and the ability to relate to others, which is often first diagnosed in early childhood and range from a severe form, called autistic disorder ("classic" autism), through pervasive development disorder not otherwise specified (PDD-NOS), to a much milder form, Asperger syndrome. The phrase, as used herein, also includes Rett syndrome and childhood disintegrative disorder, and as used herein, is synonymous with the phrase, "pervasive developmental disorders" (PDDs).

In some such embodiments, the mood disorder is a depression (i.e., a depressive disorder). In some such embodiments, the depression is selected from the group consisting of atypical depression, bipolar depression, unipolar depression, major depression, endogenous depression (i.e., acute depression with no obvious cause), involutional depression (i.e., depression that occurs in mid-life or the elderly), reactive depression (i.e., depression caused by an obvious traumatic life episode), postpartum depression, primary depression (i.e., depression that has no obvious physical or psychological cause such as a medical illness or disorder), psychotic depression, and secondary depression (i.e., depression that seems to be caused by some other underlying condition such another medical illness or disorder).

In some such embodiments, the anxiety disease or disorder is selected from a group comprising generalized anxiety disorder, panic anxiety, obsessive compulsive disorder, social phobia, performance anxiety, post-traumatic stress disorder, acute stress reaction, an adjustment disorder, a hypochondriacal disorder, separation anxiety disorder, agoraphobia, a specific phobia, anxiety disorder due to general medical condition, substance-induced anxiety disorder, alcohol withdrawal-induced anxiety, and a combination thereof.

In some embodiments, the central nervous system disease or disorder of the method or use comprising a compound of the invention is a seizure disease or disorder. In some embodiments, the seizure disease or disorder is selected from the group consisting of a convulsion, epilepsy, status epilepticus, and a combination thereof.

In some embodiments, the central nervous system disease or disorder of the method or use comprising a compound of the invention is a pain disease or disorder selected from the group consisting of inflammatory pain, neuropathic pain and migraine pain. In some embodiments, the neuropathic pain or migraine pain disease or disorder is selected from the group consisting of allodynia, hyperalgesic pain, phantom pain, neuropathic pain related to diabetic neuropathy, neuropathic pain related to migraine, and a combination thereof.

In some embodiments, the central nervous system disease or disorder of the method or use comprising a compound of the invention is a neuronal hyperexcitation state disease or disorder. In some embodiments, the neuronal hyperexcitation state disease or disorder is a neuronal hyperexcitation state in medicament withdrawal, a neuronal hyperexcitation state in intoxication, or a combination thereof.

In some embodiments of the method or use comprising a compound of the invention, at least one symptom of the cognitive neurodegenerative, psychiatric or neurological disease or disorder is treated.

In some embodiments, the cognitive, neurodegenerative, psychiatric or neurological disease or disorder is a depression. In some such embodiments, the at least one symptom of the depression is depressed feeling, depressed mood, loss of interest or pleasure in some or all activities, changes in appetite, changes in weight, changes in sleep patterns, lack of energy, fatigue, low self esteem, diminished capacity for thinking, concentration, or decisiveness, feelings of hopelessness or worthlessness, psychomotor agitation or retardation, self-reproach, inappropriate guilt, frequent thoughts of death or suicide, plans or attempts to commit suicide, or a combination thereof.

In some embodiments, the cognitive, neurodegenerative, psychiatric or neurological disease or disorder is an anxiety. In some such embodiments, the at least one symptom of anxiety is apprehension, fear, trembling, muscle aches, insomnia, abdominal upsets, dizziness, irritability, persistent, recurring thoughts, compulsions, heart palpitations, chest pain, chest discomfort, sweating, tingling sensations, feeling of choking, fear of losing control, flashbacks, nightmares, intrusive thoughts, intrusive recollections, avoidance behaviors, emotional numbing, an inability to sleep, anxious feelings, overactive startle response, hypervigilance, outbursts of anger, faintness, blushing, profuse sweating, or a combination thereof.

In some embodiments, the cognitive, neurodegenerative, psychiatric or neurological disease or disorder is schizophrenia. In some such embodiments, the at least one symptom of schizophrenia is a positive symptom selected from the group consisting of hallucination, delusion, paranoia, and a combination thereof. In some such embodiments, the symptom of schizophrenia is a negative symptom selected from the group consisting of social withdrawal, flat affect, anhedonia, decreased motivation, and a combination thereof. In some such embodiments, the symptom of schizophrenia is a cognitive symptom selected from the group consisting of severe deficit in attention, severe deficit in object naming, severe deficit in working memory, severe deficit in long-term memory storage, severe deficit in executive functioning, a slowing of information processing, a slowing of neural activity, long term depression, and a combination thereof.

In some embodiments of the method or use comprising a compound of the invention, the cognitive, neurodegenerative, psychiatric or neurological disease or disorder is Parkinson's disease. In some such embodiments, the at least one symptom of Parkinson's disease is levodopa-induced dyskinesia, poor balance, Parkinsonian gait, bradykinesia, rigidity, tremor, change in speech, loss of facial expression, micrographia, difficulty swallowing, drooling, pain, dementia, confusion, a sleep disturbance, constipation, a skin problem, depression, fear, anxiety, difficulty with memory, slowed thinking, sexual dysfunction, an urinary problem, fatigue, aching, loss of energy, or a combination thereof.

In some embodiments, the cognitive, neurodegenerative, psychiatric or neurological disease or disorder is Alzheimer's disease. In some such embodiments, the at least one symptom of Alzheimer's disease is impairment in memory, impairment in attention, impairment in judgment, impairment in decision-making, impairment in orientation to physical surroundings, language impairment, impairment in speed-dependent activities, impairment in abstract reasoning, impairment in visuospatial abilities, impairment in executive functioning, impairment in behavioral disturbances, disinterest and passivity, apathy, inappropriate dressing, poor self care, agitation, violent outburst, aggression, depression, anxiety, hallucination, delusion, change in personality, change in mood, dementia, or a combination thereof.

In some embodiments, the cognitive, neurodegenerative, psychiatric or neurological disease or disorder is multiple sclerosis. In some such embodiments, the at least one symptom of multiple sclerosis is optic neuritis blurred vision, eye pain, loss of color vision, blindness, diplopia double vision, nystagmus jerky eye movements, ocular dysmetria, constant under- or overshooting eye movements, internuclear ophthalmoplegia, nystagmus, diplopia, movement and sound phosphenes, diplopia, afferent pupillary defect, motor paresis, monoparesis, paraparesis, hemiparesis, quadraparesis plegia, paraplegia, hemiplegia, tetraplegia, quadriplegia, spasticity, dysarthria, muscle atrophy, spasms, cramps, hypotonia, clonus, myoclonus, myokymia, restless leg syndrome, footdrop dysfunctional reflexes (MRSs, Babinski's, Hoffman's, Chaddock's), paresthesia, anaesthesia, neuralgia, neuropathic pain, neurogenic pain, l' hermitte's, proprioceptive dysfunction, trigeminal neuralgia, ataxia, intention tremor, dysmetria, vestibular ataxia, vertigo, speech ataxia, dystonia, dysdiadochokinesia, frequent micturation, bladder spasticity, flaccid bladder, detrusor-sphincter dyssynergia, erectile dysfunction, anorgasmy, retrograde ejaculation, frigidity, constipation, fecal urgency, depression, cognitive dysfunction, dementia, mood swings, emotional lability, euphoria, bipolar syndrome, anxiety, aphasia, dysphasia, fatigue, uhthoffs symptom, gastroesophageal reflux, a sleeping disorder, or a combination thereof.

The present invention further provides a method of treating gastroesophageal reflux, the method comprises administering a therapeutically effective amount of at least one compound of claim 1 or a pharmaceutically acceptable salt thereof to a mammal in need thereof. The present invention further provides a use of a compound of the invention in the preparation of a medicament for the treatment of gastroesophageal reflux. The present invention further provides a compound of the invention for use in treating gastroesophageal reflux.

The present invention further provides a method of treating alcohol dependence, the method comprises administering a therapeutically effective amount of at least one compound of claim 1 or a pharmaceutically acceptable salt thereof to a mammal in need thereof. The present invention further provides a use of a compound of the invention in the preparation of a medicament for the treatment of alcohol dependence. The present invention further provides a compound of the invention for use in treating alcohol dependence.

In some embodiments, the compound of the present invention is used in the preparation of a medicament for treatment of a central nervous system disease or disorder. In some embodiments, the central nervous disease or disorder is as previously disclosed herein.

Another aspect of the present invention is a process for producing the compounds of the present invention.

Preparation of the Compounds of the Present Invention

The compounds of the present invention may be prepared, without limitation, according to one of the general methods outlined below. For example, Schemes 1-22 that follow are intended as an illustration of some embodiments of the invention and no limitation of the present invention is implied because of them.

The following defines acronyms as used herein unless specified otherwise in a particular instance.

BINAP=2,2'-Bis(diphenylphosphino)-1,1'-binaphthalene, CAS No. 98327-87-8
Boc=tert-butyloxycarbonyl
BOP=Benzotriazole-1-yl-oxy-tris-(dimethylamino)-phosphonium hexafluorophosphate, CAS No. 56602-33-6
CAN=Ceric ammonium nitrate, CAS No. 16774-21-3
DAST=(Diethylamino)sulfur trifluoride, CAS No. 38078-09-0
DCM=Dichloromethane or Methylene chloride, CAS No. 75-09-2
DIBAL or DIBAL-H=Diisobutylaluminium hydride, CAS No. 1191-15-7
DIEA=N,N-diisopropylethylamine, CAS No. 7087-68-5
DMA=N,N-dimethylacetamide, CAS No. 127-19-5
DMAP=4-dimethylaminopyridine, CAS No. 1122-58-3
DMC=2-Chloro-1,3-dimethylimidazolinium chloride, CAS No. 37091-73-9
DMF=N,N-dimethylformamide, CAS No. 68-12-2
DMPU=1,3-Dimethyl-3,4,5,6-tetrahydro-2(1H)-pyrimidinone, CAS No. 7226-23-5
DMSO=Dimethyl sulfoxide, CAS No. 67-68-5
DPPA=Diphenylphosphoryl azide, CAS No. 26386-88-9
EDCI=N-Ethyl-N'-(3-dimethylaminopropyl)carbodiimide hydrochloride, CAS No. 93128-40-6
HATU=2-(1H-7-Azabenzotriazol-1-yl)-1,1,3,3-tetramethyl uronium hexafluorophosphate Methanaminium, CAS No. 148893-10-1
HBTU=2-(1H-Benzotriazole-1-yl)-1,1,3,3-Tetramethyluronium hexafluorophosphate, CAS No. 94790-37-1
HOBt=1-Hydroxybenzotriazole, CAS No. 2592-95-2
LDA=Lithium diisopropylamide solution, CAS No. 4111-54-0
L-Selectride=Lithium tri-sec-butyl(hydrido)borate, CAS No. 38721-51-7
NMP=N-Methyl-Pyrrolidone, CAS No. 872-50-4
PDC=Pyridinium dichromate, CAS No. 20039-37-6
PMB=4-Methoxybenzyl
PTSA=p-Toluenesulfonic acid, CAS No. 6192-52-5
PyBOP=Benzotriazol-1-yl-oxytripyrrolidinophosphonium hexafluorophosphate, CAS No. 128625-52-5
rt=room temperature
RT=LC-MS retention time
TBAF=Tetrabutylammonium fluoride solution, CAS No. 429-41-4
TBSCl=tert-Butyldimethylsilyl chloride, CAS No. 18162-48-6
TBSOTf=tert-Butyldimethylsilyl trifluoromethanesulfonate, CAS No. 69739-34-0
TBS=tert-Butyldimethylsilyl
TEA=Triethyl amine, CAS No. 121-44-8
TFA=Trifluoroacetic acid, CAS No. 76-05-1
THF=Tetrahydrofuran, CAS No. 109-99-9

A compound of formula (I-a) can be prepared via the processes outlined in Scheme 1 by using customary amidation procedures from intermediate A and $R^1COCl$ or $R^1CO_2H$ (see e.g., steps a and b of Scheme 1), where $R^1$, $R^2$, $R^3$, $R^4$, $R^5$ and $R^6$ are as previously defined.

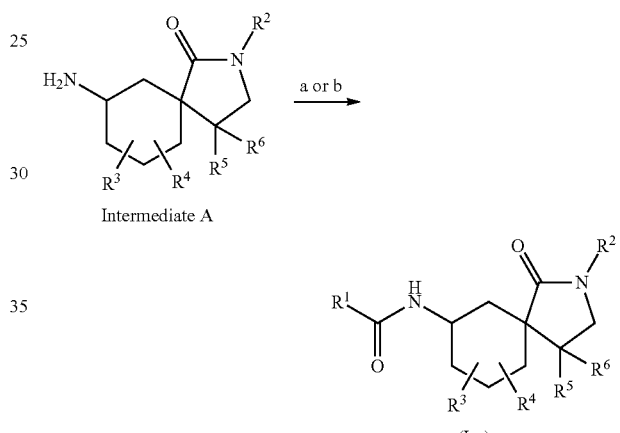

a) $R^1COCl$, DIEA or TEA, DCM; b) $R^1CO_2H$, PyBOP (or BOP or DMC or EDCI or HBTU, etc.), DIEA or TEA, DCM (or THF or DMF or $CH_3CN$, etc.); or $R^1CO_2H$, HATU, DMAP, THF.

A compound of formula (I-a) can also be made via the process outlined in Scheme 2. N-arylation of intermediate B with $R^2X$ ($R^2$ is aryl or heteroaryl, X is halogen such as iodo, bromo, chloro and fluoro) by using copper-assisting cross coupling (see e.g., step a in Scheme 2), or by palladium-catalyzed cross coupling (see e.g., step b of Scheme 2), or N-alkylation of intermediate B with $R^2X$ ($R^2$ is alkyl) in the presence of base (see e.g., step c of Scheme 2) affords a compound of formula of (I-a), where $R^1$, $R^2$, $R^3$, $R^4$, $R^5$ and $R^6$ are as defined herein.

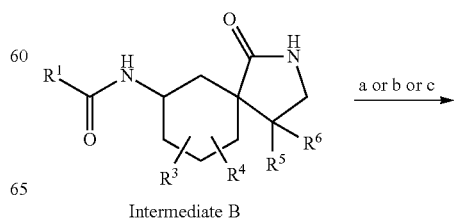

-continued

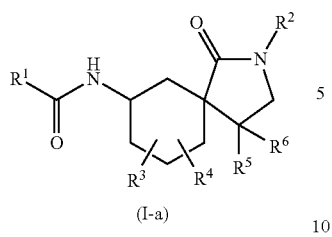

(I-a)

a) CuI, R²X, NHMeCH₂CH₂NHMe, K₂CO₃, dioxane, microwave, 160° C.; b) R²X, tris(dibenzylideneacetone)dipalladium(0) chloroform adduct, BINAP, Cs2CO3, toluene, 80° C.; c) R2X, NaH, THF, 0° C. to rt.

Intermediates A-1 and A-2 can be prepared via the processes outlined in Scheme 3.

Esterification of commercially available 3-oxo-cyclohexanecarboxylic acid (compound 1) by using customary procedures (see e.g., step a of Scheme 3), gives compound 2. Protection of the carbonyl group of compound 2 by using customary procedures (see e.g., step b of Scheme 3), followed by alkylation with allyl bromide in the presence of base (see e.g., step c of Scheme 3) yields compound 3. Oxidation of compound 3, such as ozonolysis in DCM affords aldehyde 4. Reductive amination of aldehyde 4 with amine R²NH₂ by using customary procedures (see e.g., step e of Scheme 3), followed by cyclization in the presence of base (see e.g., step f of Scheme 3), gives compound 5. In some cases (especially when R² is alkyl), lactam 5 can be formed directly from aldehyde 4 under reductive amination conditions without further treatment by base (step f). Hydrolysis of compound 5 by customary procedures (see e.g., step g of Scheme 3) affords ketone 6, which can be readily converted to intermediates A-1 and A-2 by reductive amination with ammonium acetate (see e.g., step h in Scheme 3). The trans isomer A-1 and cis isomer A-2, where R² is as defined herein, can be separated by silica gel chromatography or reverse-phase HPLC.

Scheme 3

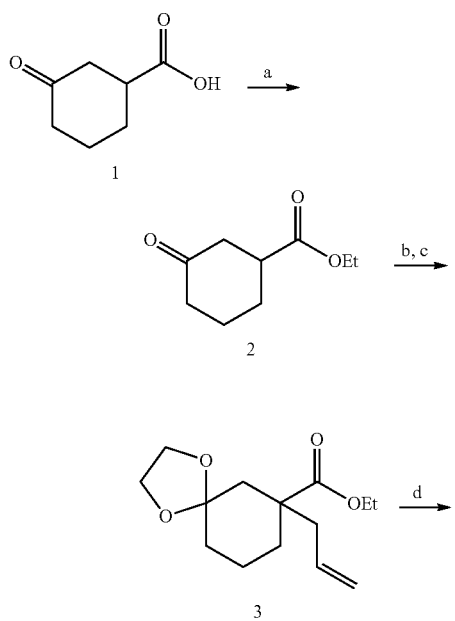

-continued

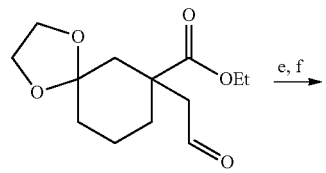

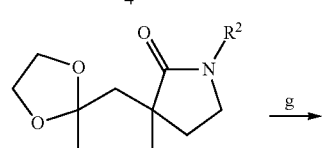

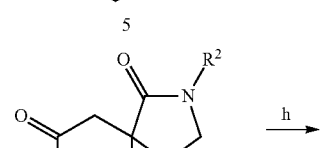

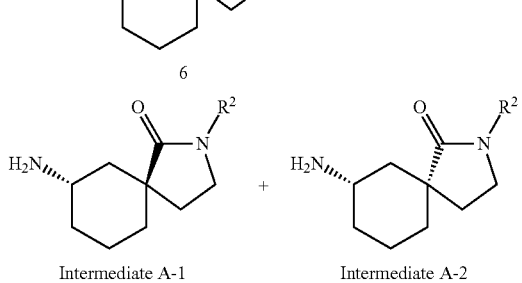

Intermediate A-1     Intermediate A-2 a) EtOH, PTSA, toluene, heat; b) (CH₂OH)₂, PTSA, toluene, heat; c) LDA, THF, -78° C., allyl bromide; d) O₃, CH₂Cl₂, Me₂S; e) R²NH₂, NaBH(OAc)₃, HOAc, THF; f) i-PrMgCl, THF, 0° C.; g) 2N HCl/THF, h) NH₄OAc, NaBH₃CN, MeOH.

Intermediates A-1 and A-2 can also be prepared via the processes outlined in Scheme 4. Esterification of commercially available cyclohexane-1,3-dicarboxylic acid (compound 7) by customary procedures (see e.g., step a in Scheme 4) gives bis-ethyl ester 8. Alkylation of compound 8 with allyl bromide (see e.g., step b in Scheme 4) affords compound 9. Oxidation of compound 9, such as ozonolysis (see e.g., step c of Scheme 4) or a two-step oxidation (see e.g., step d of Scheme 4: compound 9 is oxidized to diol first, then further oxidized to aldehyde), gives trans aldehyde 10 as a major product. Reductive amination of aldehyde 10 with amine R²NH₂ by using customary procedures (see e.g., steps e and f of Scheme 4), yields compound 11, which upon cyclization by treatment with base, such as i-PrMgCl in THF at 0° C., gives lactam 12. In some cases, especially when R² is alkyl, compound 10 can be directly converted to lactam 12 under reductive amination conditions. The trans lactam 12 can be epimerized to cis lactam 13 under basic conditions (see e.g., step h of Scheme 4). Saponification of compounds 12 and 13 using customary procedures see e.g., step i of Scheme 4) gives carboxylic acids 14 and 15, respectively. In some cases, depending on R² and reaction time, compound 11 can be converted to compound 15 under basic conditions, such as NaH, EtOH, 0° C. to reflux. Curtius rearrangement of compound 14 and 15 followed by acid hydrolysis by using customary procedures (see e.g., step j of Scheme 4) affords intermediate A-1 and intermediate A-2, where R² is as defined herein, respectively.

Scheme 4

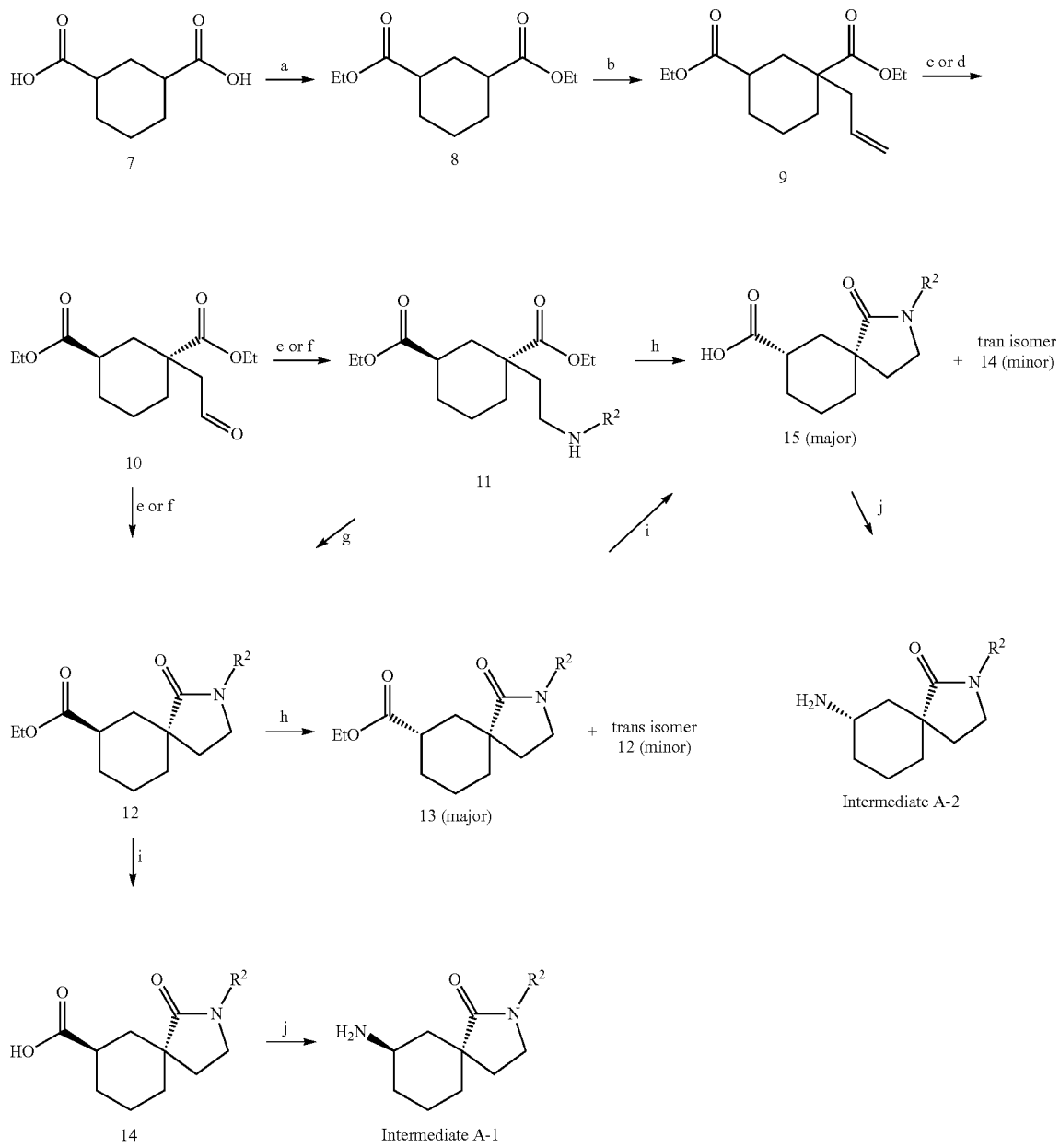

a) EtOH, H$_2$SO$_4$, reflux; b) i-Pr$_2$NH, BuLi, DMPU, THF, allyl bromide, -78° C. to rt; c) O$_3$, DCM, Me$_2$S; d) 1) K$_3$Fe(CN)$_6$, K$_2$OsO$_4$•2H$_2$O, K$_2$CO$_3$, quinuclidine, t-BuOH, H$_2$O; 2) NaIO$_4$, NaHCO$_3$, THF, t-BuOH; e) R$^2$NH$_2$, NaBH(OAc)$_3$, HOAc, THF; f) 1) R$^2$NH$_2$, AcOH, ClCH$_2$CH$_2$Cl; 2) NaBH(OAc)$_3$; g) i-PrMgCl, THF, 0° C.; h) NaH, EtOH, 0° C. to reflux; i) LiOH, THF; j) 1) DPPA, TEA, toluene, rt to 90° C.; 2) 6M HCl/H$_2$O, then basicified with Na$_2$CO$_3$.

Intermediate A-2 can also be prepared via the processes outlined in Scheme 5.

Compound 16 can be made in the same manner as compound 15 in Scheme 4. Curtius reaction of compound 16 by using customary procedures (see e.g., step a of Scheme 5) gives compound 17. Removal of protecting group 4-methoxybenzyl or 2,4-dimethoxybenzyl in compound 17 by using customary procedures (see e.g., step b of Scheme 5) yields compound 18. Compound 18 can also be made from compound 19 (intermediate A-2, R$^2$=4-methoxybenzyl or 2,4-dimethoxybenzyl), which can be prepared via the processes outlined in Scheme 4). Removal of the protecting group 4-methoxybenzyl or 2,4-dimethoxybenzyl in compound 19 by using customary procedures (see e.g., step b of Scheme 5) gives compound 20. Boc protection of compound 20 by using customary procedures (see e.g., step c of Scheme 5) affords compound 18. N-arylation of compound 18 with R$^2$X (R$^2$ is aryl or heteroaryl and X is as previously defined) by using copper-assisting cross coupling (see e.g., step d of Scheme 5), or by palladium-catalyzed cross coupling (see e.g., step e of Scheme 5), or N-alkylation of compound 18 with R$^2$X (R$^2$ is alkyl and X is as previously defined) in the presence of base (see e.g., step f of Scheme 5), yields compound 21. Removal of Boc group by using customary conditions (see e.g., step g of Scheme 5) affords intermediate A-2, where R$^2$ is as defined herein.

Scheme 5

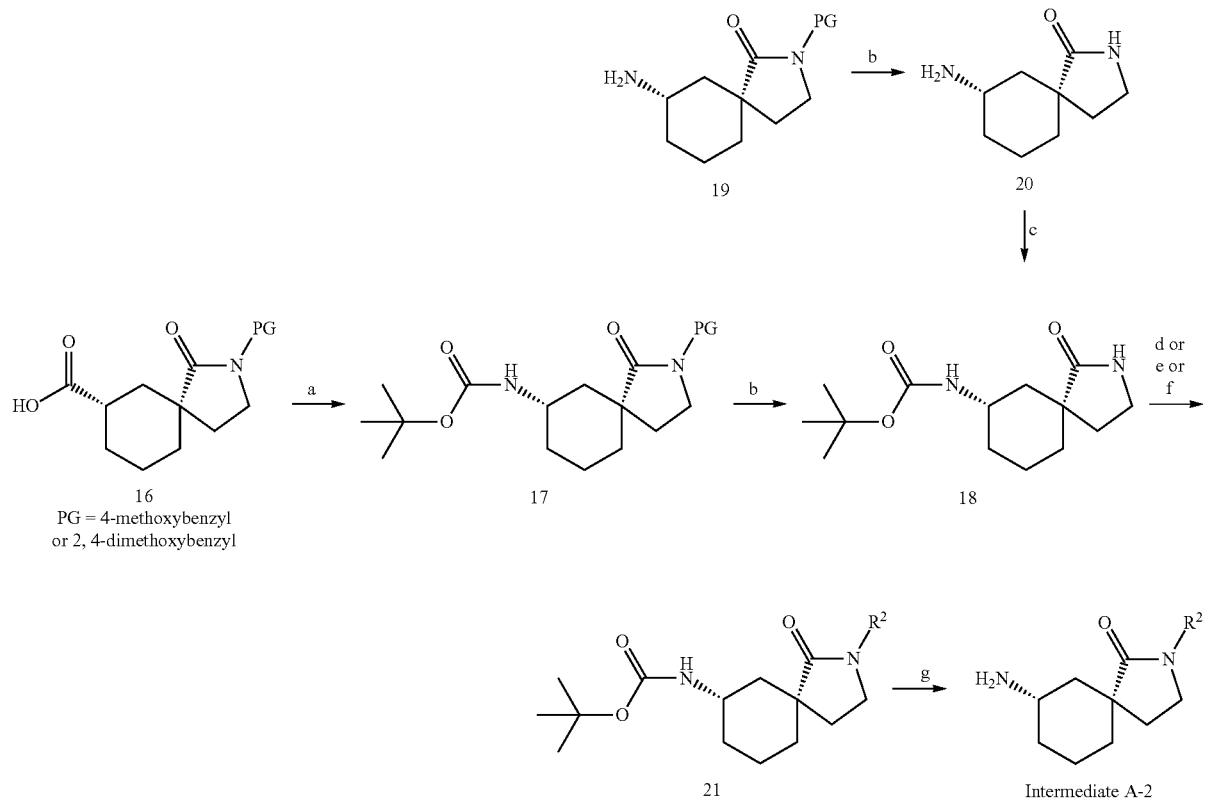

a) 1) DPPA, TEA, toluene, rt to 90° C.; 2) tBuOH; b) CAN, CH₃CN, H₂O; c) (Boc)₂O, TEA, THF; d) CuI, R²X, NHMeCH₂CH₂NHMe, K₂CO₃, dioxane, microwave, 160° C.; e) R²X, tris(dibenzylideneacetone)dipalladium(0) chloroform adduct, BINAP, Cs₂CO₃, toluene, 80° C.; f) R²X, NaH, THF, 0° C. to rt; g) 4M HCl in dioxane, DCM.

Intermediates A-3 and A-4 can be made via the processes outlined in Scheme 6. Reduction of commercially available 5-hydroxy-isophthalic acid dimethyl ester (compound 22) by using the procedures described by Gensler, W. J. et al. (*J. Org. Chem.*, 1973, 38, 1726; see step a of Scheme 6) gives compound 23. Fluorination of 23 by using customary procedures affords mono-fluorinated compound 24 ($R^3$=F, $R^4$=H, see e.g., step b of Scheme 6). Oxidation of alcohol 23 to its corresponding ketone, followed by fluorination by using customary conditions affords di-fluorinated compound 24 ($R^3$, $R^4$=F, see e.g., step c of Scheme 6). Alkylation of compound 24 with allyl bromide (see e.g., step d of Scheme 6) gives compound 25. Oxidation of compound 25, such as ozonolysis (see e.g., step e of Scheme 6), gives trans aldehyde 26 as a major product. Reductive amination of aldehyde 26 with $R^2NH_2$ by using customary procedures (see e.g., step f of Scheme 6) yields compound 27, which upon cyclization by treatment with base, such as i-PrMgCl in THF at 0° C., gives lactam 28. In some cases (especially when $R^2$ is alkyl), compound 26 can be directly converted to lactam 28 under reductive amination conditions. The trans lactam 28 can be epimerized to cis lactam 29 under basic conditions (see e.g., step h of Scheme 6). Saponification of compounds 28 and 29 by using customary procedures (see e.g., step i of Scheme 6) gives corresponding carboxylic acids 30 and 31, respectively. In some cases, depending on $R^2$ and reaction time, compound 28 can be converted to compound 31 under basic conditions, such as NaH, EtOH, 0° C. to reflux. Curtius rearrangement of compounds 30 and 31, followed by acid hydrolysis (see e.g., step j in Scheme 6), affords intermediates A-3 and A-4, where $R^2$-$R^4$ are as defined herein, respectively.

Scheme 6

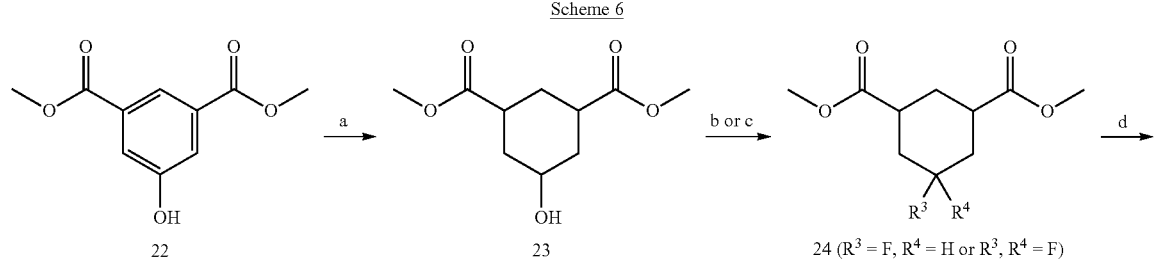

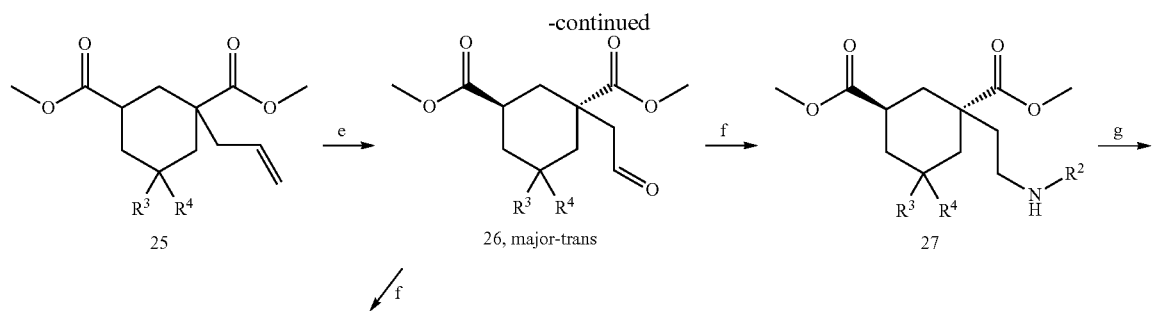

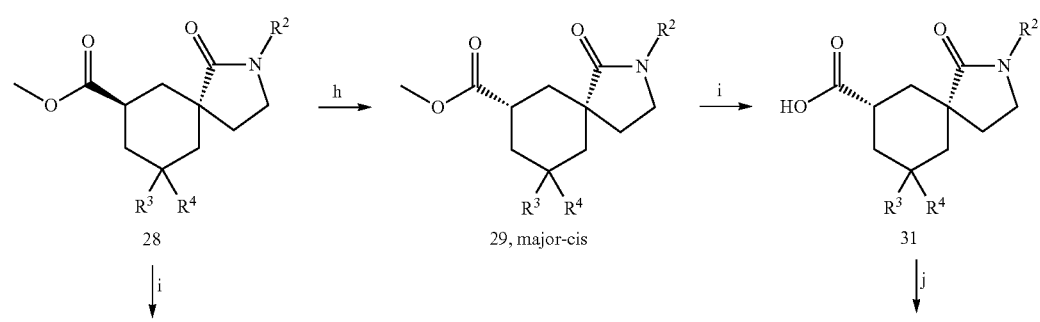

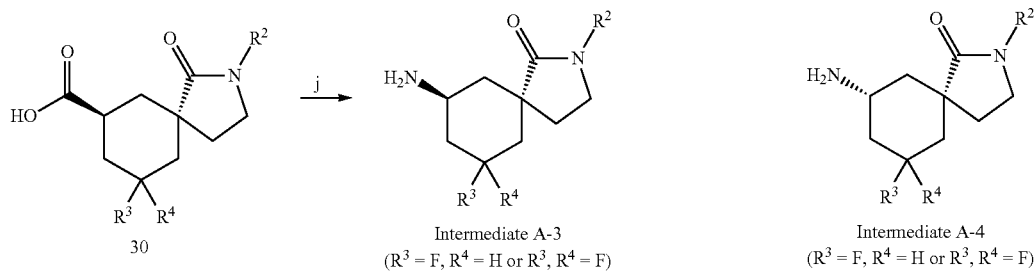

a) H₂, MeOH, Rh on alumina; b) DAST, DCM; c) 1) Py·SO₃, DMSO; 2) DAST, DCM; d) i-Pr₂NH, BuLi, DMPU, THF, allyl bromide, -78° C. to rt; e) O₃, DCM, Me₂S; f) R²NH₂, NaBH(OAc)₃, THF; g) i-PrMgCl, THF, 0° C.; h) NaH, EtOH, 0° C. to reflux; i) LiOH, THF; j) 1) DPPA, TEA, toluene, rt to 90° C.; 2) 6M HCl/H₂O, then basicified with Na₂CO₃.

Intermediate A-5 may be prepared via the processes outlined in Scheme 7. Alkylation of commercially available 4-oxo-cyclohexane-1,3-dicarboxylic acid dimethyl ester (compound 32) with ally bromide in the presence of base (such as under the conditions shown in step a of Scheme 7) could give compound 33. Reduction of 33, followed by fluorination by using customary procedures, such as those in step b of Scheme 7, could yield mono-fluorinated compound 34 ($R^3$=F, $R^4$=H). Fluorination of compound 33 by using customary procedures, such as those in step c of Scheme 7 could yield di-fluorinated compound 34 ($R^3$, $R^4$=F). Oxidation of compound 34, such as ozonolysis (see e.g., step d of Scheme 7), could give aldehyde 35. Reductive amination with $R^2NH_2$, followed by cyclization under conditions such as those shown in steps e and f of Scheme 7 could afford compound 36. In some cases (especially when $R^2$ is alkyl), compound 35 could be directly converted to lactam 36 under reductive amination conditions without step f. Saponification of 36, followed by Curtius rearrangement and acid hydrolysis using customary procedures, such as in steps g and h of Scheme 7, could give intermediate A-5, where $R^2$-$R^4$ are as defined herein.

Scheme 7

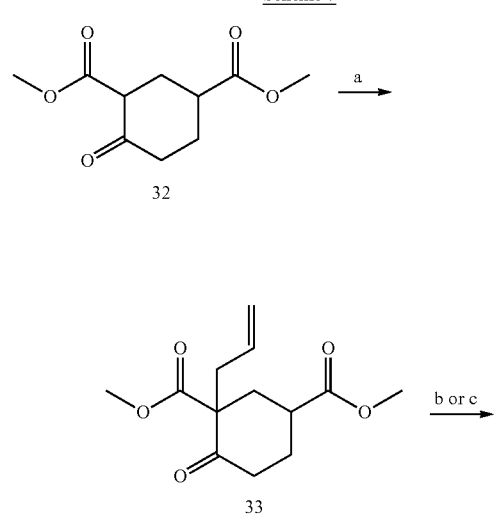

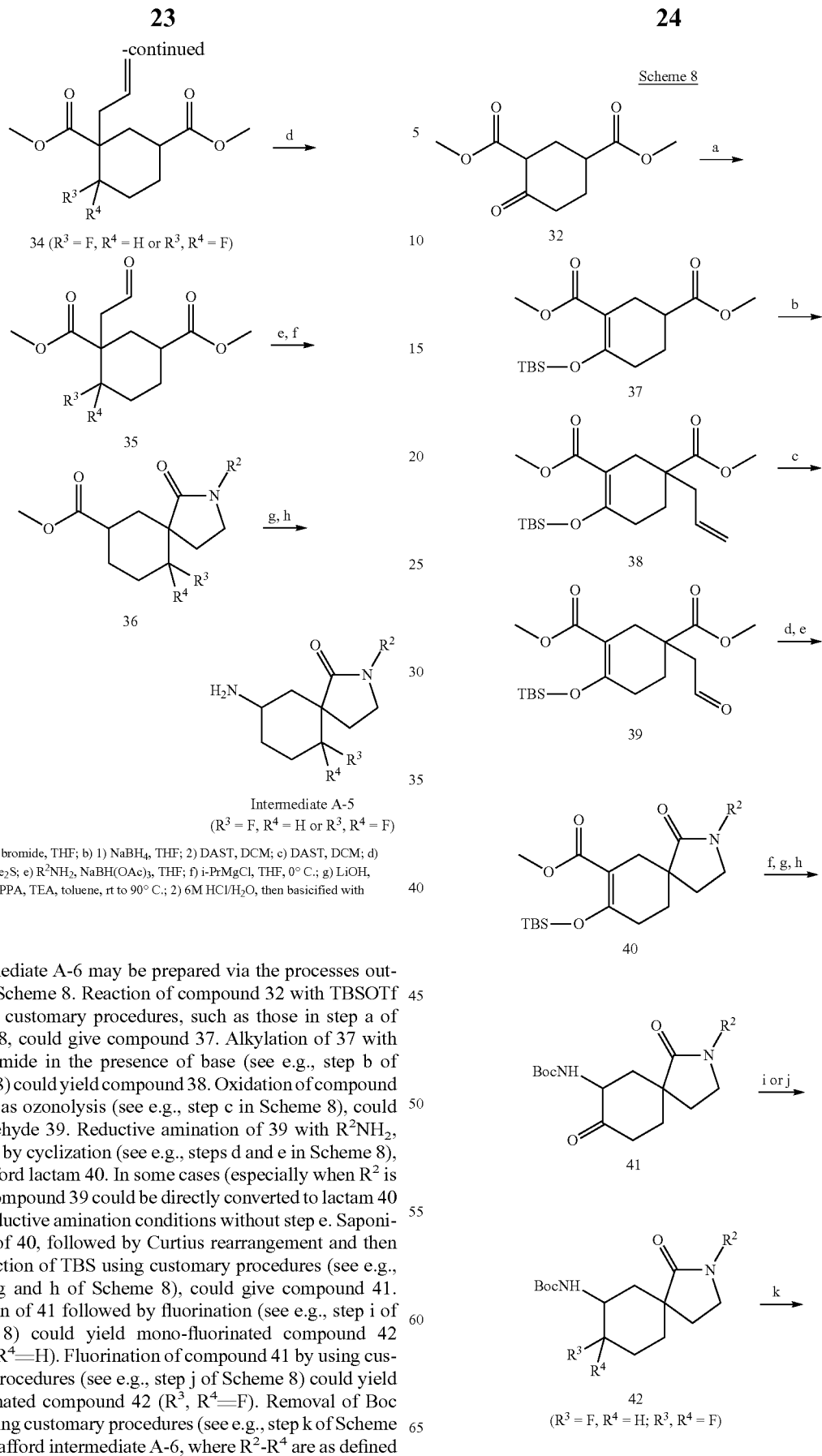

a) NaH, allyl bromide, THF; b) 1) NaBH₄, THF; 2) DAST, DCM; c) DAST, DCM; d) O₃, DCM, Me₂S; e) R²NH₂, NaBH(OAc)₃, THF; f) i-PrMgCl, THF, 0° C.; g) LiOH, THF; h) 1) DPPA, TEA, toluene, rt to 90° C.; 2) 6M HCl/H₂O, then basicified with Na₂CO₃.

Intermediate A-6 may be prepared via the processes outlined in Scheme 8. Reaction of compound 32 with TBSOTf by using customary procedures, such as those in step a of Scheme 8, could give compound 37. Alkylation of 37 with allyl bromide in the presence of base (see e.g., step b of Scheme 8) could yield compound 38. Oxidation of compound 38, such as ozonolysis (see e.g., step c in Scheme 8), could give aldehyde 39. Reductive amination of 39 with $R^2NH_2$, followed by cyclization (see e.g., steps d and e in Scheme 8), could afford lactam 40. In some cases (especially when $R^2$ is alkyl), compound 39 could be directly converted to lactam 40 under reductive amination conditions without step e. Saponification of 40, followed by Curtius rearrangement and then de-protection of TBS using customary procedures (see e.g., steps f, g and h of Scheme 8), could give compound 41. Reduction of 41 followed by fluorination (see e.g., step i of Scheme 8) could yield mono-fluorinated compound 42 ($R^3$=F, $R^4$=H). Fluorination of compound 41 by using customary procedures (see e.g., step j of Scheme 8) could yield di-fluorinated compound 42 ($R^3$, $R^4$=F). Removal of Boc group using customary procedures (see e.g., step k of Scheme 8) could afford intermediate A-6, where $R^2$-$R^4$ are as defined herein.

-continued

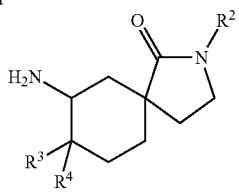

Intermediate A-6
($R^3$ = F, $R^4$ = H; $R^3$, $R^4$ = F)

a) TEA, TBSOTf, DCM; b) NaH, allyl bromide, THF; c) O$_3$, DCM, Me$_2$S; d) $R^2$NH$_2$, NaBH(OAc)$_3$, THF; e) NaH, MeOH; f) LiOH, THF; g) 1) DPPA, TEA, toluene, rt to 90° C.; 2) t-BuOH; h) TBAF, THF; i) 1) NaBH$_4$, THF; 2) DAST, DCM; j) DAST, DCM; k) 4M HCl/dioxane, DCM.

Intermediate A-7 may be prepared via the processes outlined in Scheme 9. Reaction of compound 8 with commercially available dibenzylamino-acetaldehyde (compound 43) in the presence of base, such as LDA at –78° C. in THF, could give compound 44. Protecting the hydroxyl group of compound 44 with TBS using customary procedures (see e.g., step b of Scheme 9) could yield compound 45. Removal of dibenzyl groups followed by cyclization (see e.g., steps c and d of Scheme 9) could afford lactam 46. N-arylation of compound 46 with $R^2X$ ($R^2$ is aryl or heteroaryl and X is as previously defined) using copper-assisting cross coupling (see e.g., step e of Scheme 9), or palladium-catalyzed cross coupling (see e.g., step f of Scheme 9), or N-alkylation of compound 47 with $R^2X$ ($R^2$ is alkyl and X is as previously defined) in the presence of base (see e.g., step g of Scheme 9) could give compound 47. Removal of the TBS group of compound 47 using customary procedures (see e.g., step h in Scheme 9) could afford alcohol 48, which could be readily oxidized to ketone 49 using customary procedures, such as step j of Scheme 9. Fluorination of compound 48 using customary procedures (see e.g., step i of Scheme 9) could yield mono-fluorinated compound 50 ($R^5$=F, $R^6$=H). Fluorination of ketone 49 using customary procedures, such as DAST in DCM, could yield di-fluorinated compound 50 ($R^5$, $R^6$=F). Saponification of compound 50 (see e.g., step k of Scheme 9) gives carboxylic acid 51, which upon Curtius rearrangement followed by acid hydrolysis using customary procedures (see e.g., step k of Scheme 9), could be converted to intermediate A-7, where $R^2$, $R^5$ and $R^6$ are as defined herein.

Scheme 9

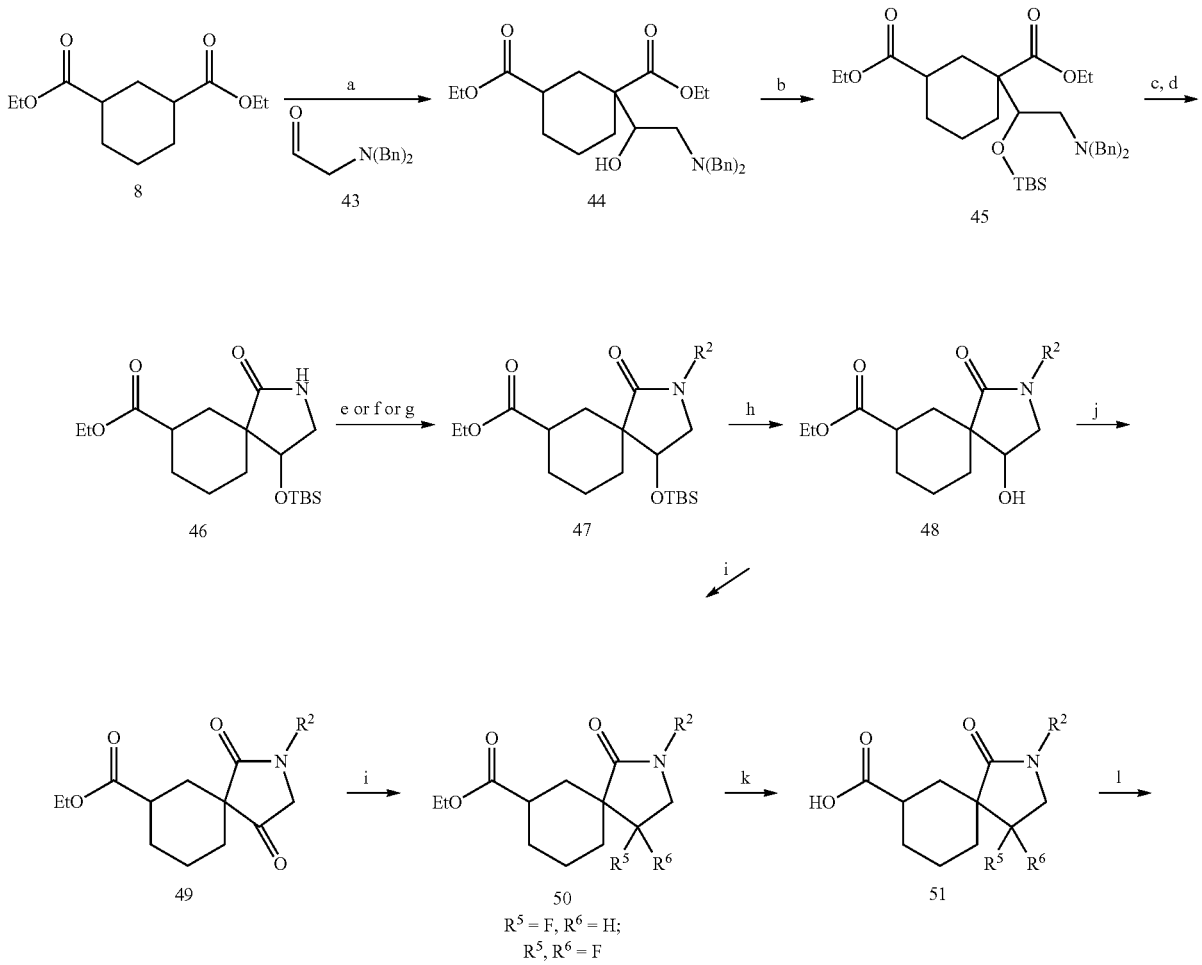

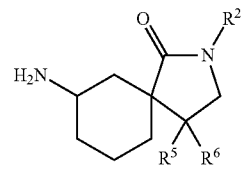

Intermediate A-7
$R^5 = F, R^6 = H$;
$R^5, R^6 = F$ a) LDA, THF, -78° C.; b) 1H-imidazole, TBSCl, DMF; c) $H_2$, Pd—C, EtOAc/EtOH, 50 psi; d) $K_2CO_3$, $CH_3CN$; e) CuI, $R^2X$, NHMeCH$_2$CH$_2$NHMe, $K_2CO_3$, dioxane, microwave, 160° C.; f) $R^2X$, tris(dibenzylidene-acetone)dipalladium(0) chloroform adduct, BINAP, $Cs_2CO_3$, toluene, 80° C.; g) $R^2X$, NaH, THF, 0° C. to rt; h) TBAF, THF; i) DAST, DCM; j) PySO$_3$, DMSO; k) LiOH, THF; l) 1) DPPA, TEA, toluene, rt to 90° C.; 2) 6M HCl/H$_2$O, then basicified with Na$_2$CO$_3$.

Intermediate B-1 can be made via the processes outlined in Scheme 10. Amidation of compound 20 with $R^1CO_2H$ or $R^1COCl$ using customary amidation procedures (see e.g., step a or b of Scheme 10) affords intermediate B-1, where $R^1$ is as defined herein.

Scheme 10

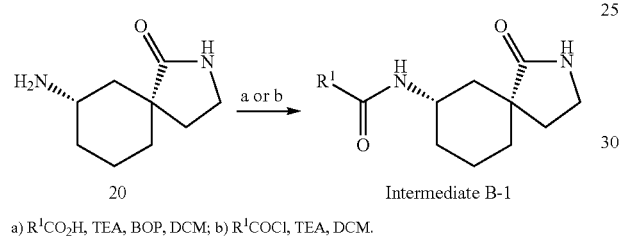

20          Intermediate B-1 a) $R^1CO_2H$, TEA, BOP, DCM; b) $R^1COCl$, TEA, DCM.

Intermediate B-1 can also be made via the processes outlined in Scheme 11. Amidation of compound 19 with $R^1CO_2H$ or $R^1COCl$ using customary procedures (see e.g., step a of Scheme 11) yields compound 52. Removal of the protecting group 4-methoxybenzyl or 2,4-dimethoxybenzyl of compound 52 using customary procedures (see e.g., step b of Scheme 11) affords intermediate B-1, where $R^1$ is as defined herein.

Scheme 11

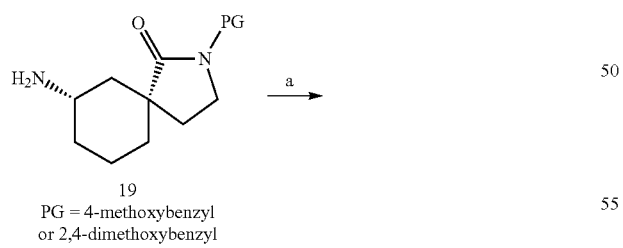

19
PG = 4-methoxybenzyl
or 2,4-dimethoxybenzyl

52

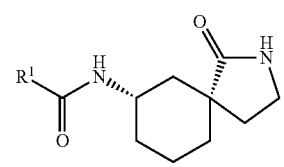

Intermediate B-1 a) $R^1CO_2H$, BOP, TEA, DCM; or $R^1COCl$, TEA, DCM; b) CAN, $CH_3CN$, $H_2O$; or TFA when PG is 2,4-dimethoxybenzyl.

In a similar manner to intermediate B-1, intermediate B-2 can be prepared from compound 53 (intermediate A-3 where $R^2$ is 4-methoxybenzyl or 2,4-dimethoxybenzyl) via the processes outlined in Scheme 12, where $R^1$, $R^3$ and $R^4$ are as defined herein.

Scheme 12

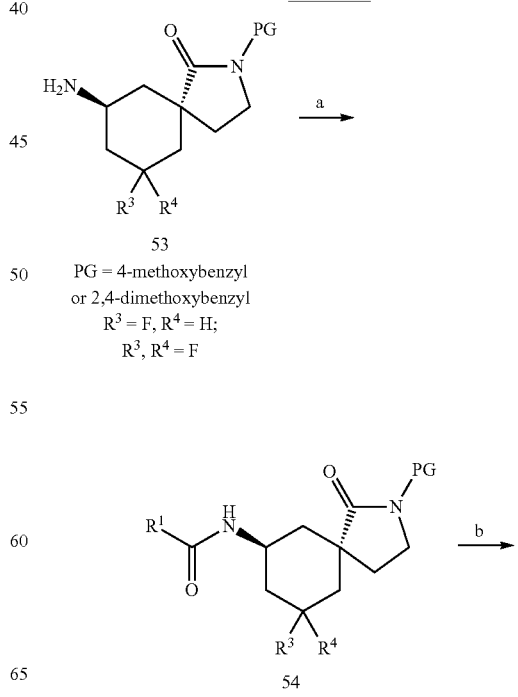

53
PG = 4-methoxybenzyl
or 2,4-dimethoxybenzyl
$R^3 = F, R^4 = H$;
$R^3, R^4 = F$

54

29
-continued

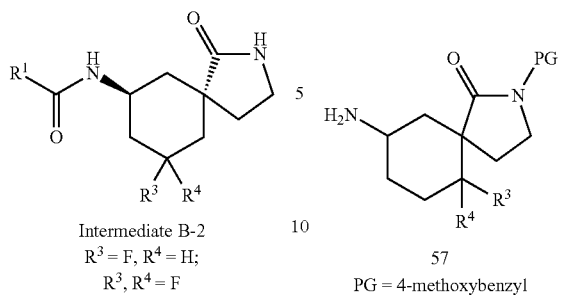

Intermediate B-2
$R^3 = F, R^4 = H;$
$R^3, R^4 = F$ a) $R^1CO_2H$, BOP, TEA, DCM; or $R^1COCl$, TEA, DCM; b) CAN, $CH_3CN$, $H_2O$; or TFA when PG is 2,4-dimethoxybenzyl.

In a similar manner to intermediate B-1, intermediate B-3 can be prepared from compound 55 (intermediate A-4 where $R^2$ is 4-methoxybenzyl or 2,4-dimethoxybenzyl) via the processes outlined in Scheme 13, where $R^1$, $R^3$ and $R^4$ are as defined herein.

Scheme 13

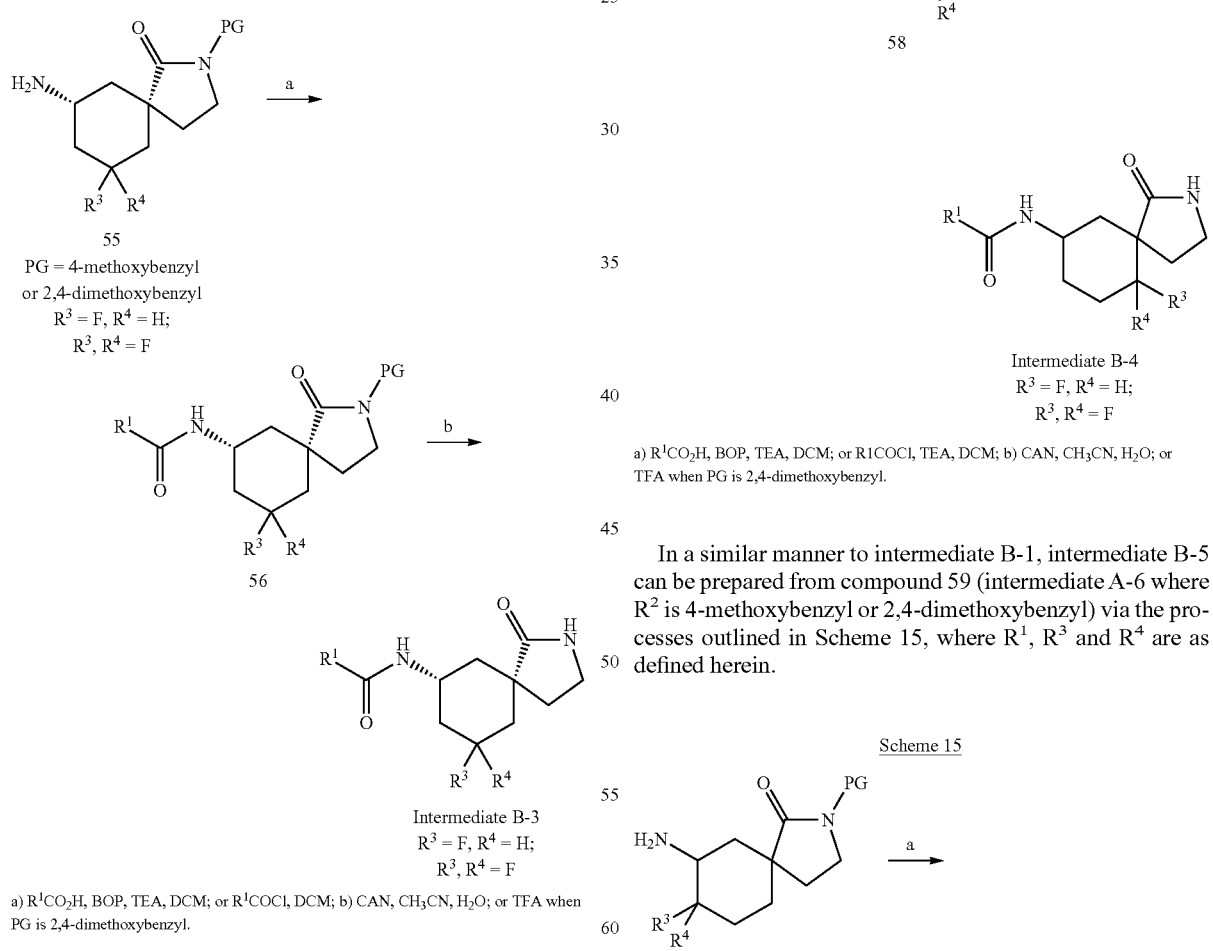

55
PG = 4-methoxybenzyl
or 2,4-dimethoxybenzyl
$R^3 = F, R^4 = H;$
$R^3, R^4 = F$

56

Intermediate B-3
$R^3 = F, R^4 = H;$
$R^3, R^4 = F$ a) $R^1CO_2H$, BOP, TEA, DCM; or $R^1COCl$, DCM; b) CAN, $CH_3CN$, $H_2O$; or TFA when PG is 2,4-dimethoxybenzyl.

In a similar manner to intermediate B-1, intermediate B-4 can be prepared from compound 57 (intermediate A-5 where $R^2$ is 4-methoxybenzyl or 2,4-dimethoxybenzyl) via the processes outlined in Scheme 14, where $R^1$, $R^3$ and $R^4$ are as defined herein.

30

Scheme 14

57
PG = 4-methoxybenzyl
or 2,4-dimethoxybenzyl
$R^3 = F, R^4 = H;$
$R^3, R^4 = F$

58

Intermediate B-4
$R^3 = F, R^4 = H;$
$R^3, R^4 = F$ a) $R^1CO_2H$, BOP, TEA, DCM; or R1COCl, TEA, DCM; b) CAN, $CH_3CN$, $H_2O$; or TFA when PG is 2,4-dimethoxybenzyl.

In a similar manner to intermediate B-1, intermediate B-5 can be prepared from compound 59 (intermediate A-6 where $R^2$ is 4-methoxybenzyl or 2,4-dimethoxybenzyl) via the processes outlined in Scheme 15, where $R^1$, $R^3$ and $R^4$ are as defined herein.

Scheme 15

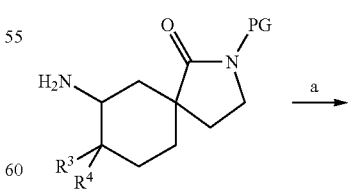

59
PG = 4-methoxybenzyl
or 2,4-dimethoxybenzyl
$R^3 = F, R^4 = H;$
$R^3, R^4 = F$

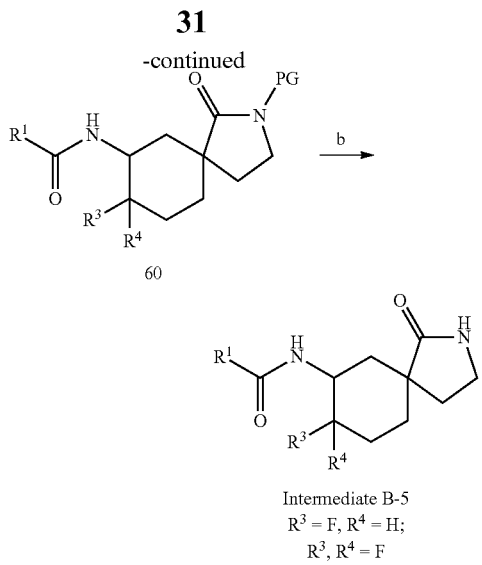

Intermediate B-5
R³ = F, R⁴ = H;
R³, R⁴ = F a) R¹CO₂H, BOP, TEA, DCM; or R¹COCl, TEA, DCM; b) CAN, CH₃CN, H₂O; or TFA when PG is 2,4-dimethoxybenzyl.

In a similar manner to intermediate B-1, intermediate B-6 can be prepared from compound 61 (intermediate A-7 where R² is 4-methoxybenzyl or 2,4-dimethoxybenzyl) via the processes outlined in Scheme 16, where R¹, R⁵ and R⁶ are as defined herein.

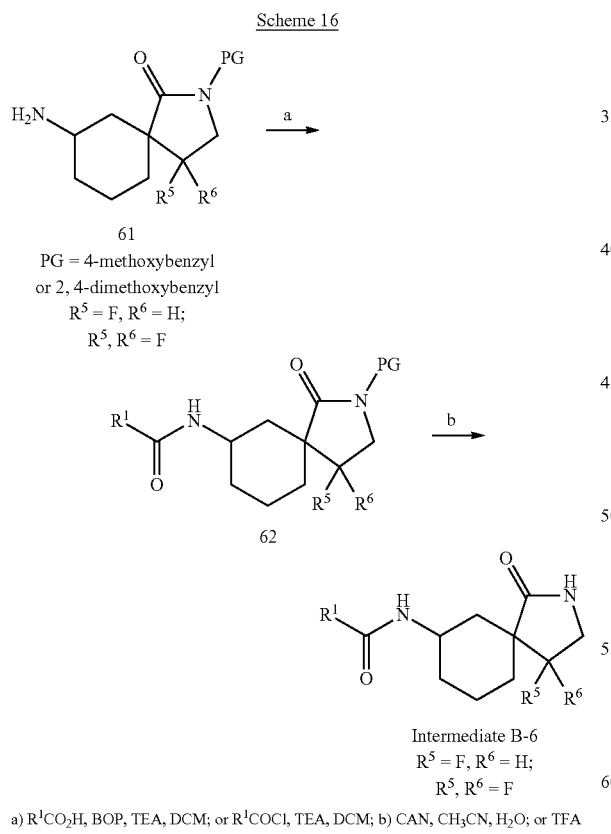

a) R¹CO₂H, BOP, TEA, DCM; or R¹COCl, TEA, DCM; b) CAN, CH₃CN, H₂O; or TFA when PG is 2,4-dimethoxybenzyl.

A compound of formula (I-b) may be prepared via the processes outlines in Scheme 17. Protecting the hydroxyl group of compound 23 with PMB using customary procedures (see e.g., step a of Scheme 17) could give compound 63. Alkylation of compound 63 with allyl bromide in the presence of base (see e.g., step b of Scheme 17) could yield compound 64. Oxidation of compound 64, such as oxonolysis (see step c in Scheme 17), could afford aldehyde 65. Reductive amination of aldehyde 65 with R²NH₂ using customary procedures (see e.g., step d of Scheme 17), followed by cyclization under basic conditions (see e.g., step e of Scheme 17), could give lactam 66. In some cases (e.g., when R² is alkyl), lactam 66 could be formed under reductive amination conditions. Saponification, followed by Curtius rearrangement and acid hydrolysis using customary conditions (see e.g., steps f and g of Scheme 17) could afford amine 67, which could be converted to amide 68 by reacting with R¹CO₂H or R¹COCl under customary conditions, such as step h of Scheme 17. Removal of the PMB group of compound 68 using customary procedures (see e.g., step i of Scheme 17) could give an alcohol, such as a compound of formula (I-b) where R³ is OH and R⁴ is H. Fluorination of this alcohol using customary procedures, such as DAST in DCM, could yield a compound of formula (I-b) where R³ is F and R⁴ is H. Oxidation of this alcohol using customary procedures (see e.g., step k of Scheme 17) could give ketone 69. Fluorination of 69 under customary conditions, such as DAST in DCM, could afford a compound of formula (I-b) where R³ and R⁴ are F. Grignard Reaction of 69 with MeMgBr using customary procedures (see e.g., step m of Scheme 17) could afford a tertiary alcohol, such as a compound of formula (I-b) where R³ is Me and R⁴ is OH. Fluorination of this alcohol using customary conditions, such as DAST in DCM, could afford a compound of formula (I-b) where R³ is Me and R⁴ is F. In each instance of the compound of formula (I-b), R¹ and R² are as defined herein.

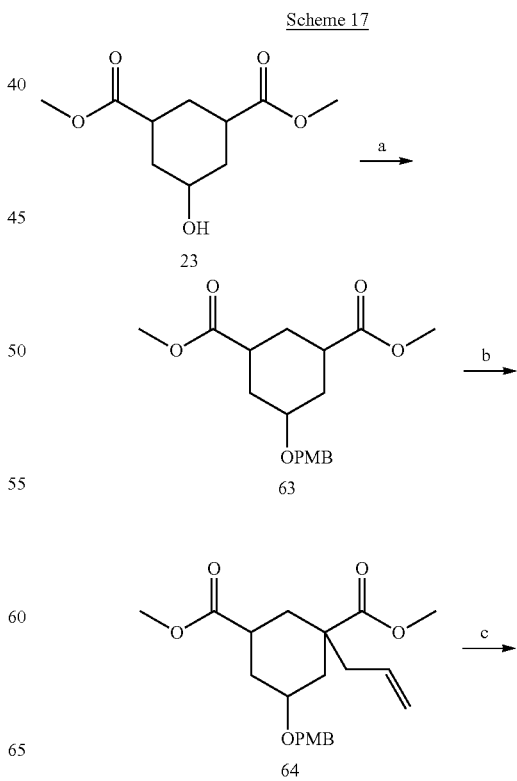

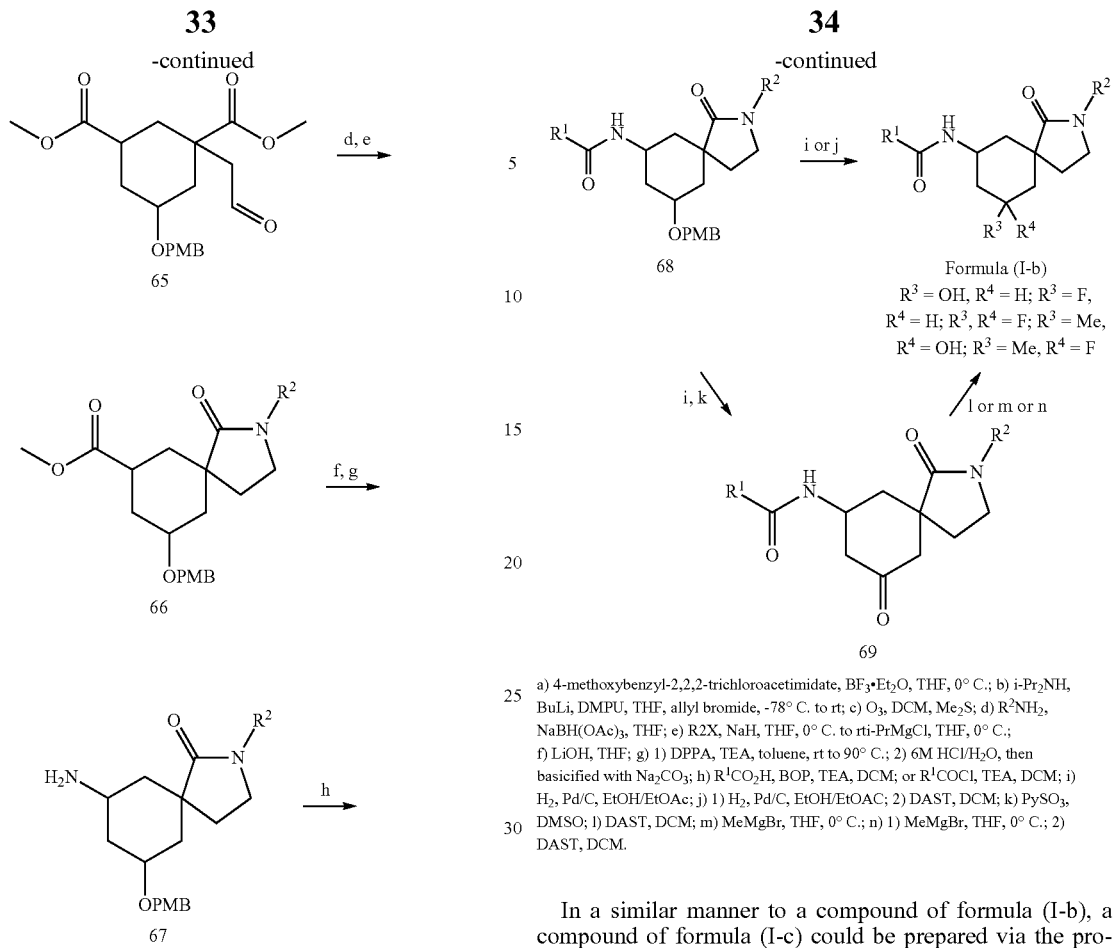

a) 4-methoxybenzyl-2,2,2-trichloroacetimidate, BF$_3$·Et$_2$O, THF, 0° C.; b) i-Pr$_2$NH, BuLi, DMPU, THF, allyl bromide, -78° C. to rt; c) O$_3$, DCM, Me$_2$S; d) R$^2$NH$_2$, NaBH(OAc)$_3$, THF; e) R2X, NaH, THF, 0° C. to rti-PrMgCl, THF, 0° C.; f) LiOH, THF; g) 1) DPPA, TEA, toluene, rt to 90° C.; 2) 6M HCl/H$_2$O, then basicified with Na$_2$CO$_3$; h) R$^1$CO$_2$H, BOP, TEA, DCM; or R$^1$COCl, TEA, DCM; i) H$_2$, Pd/C, EtOH/EtOAc; j) 1) H$_2$, Pd/C, EtOH/EtOAC; 2) DAST, DCM; k) PySO$_3$, DMSO; l) DAST, DCM; m) MeMgBr, THF, 0° C.; n) 1) MeMgBr, THF, 0° C.; 2) DAST, DCM.

In a similar manner to a compound of formula (I-b), a compound of formula (I-c) could be prepared via the processes outlined in Scheme 18 from compound 33. In the compound of formula (I-c), R$^1$-R$^4$ are as defined herein.

Scheme 18

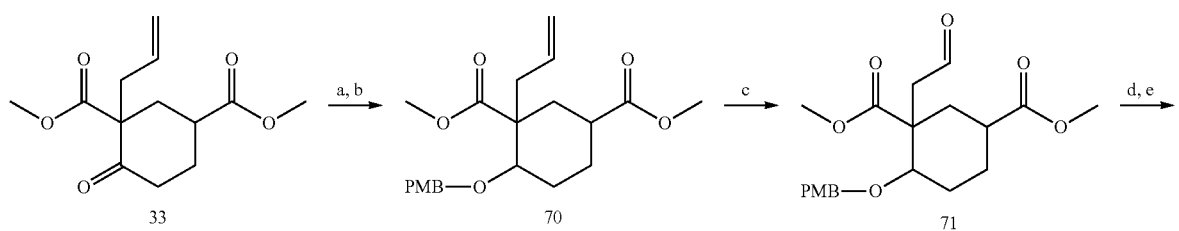

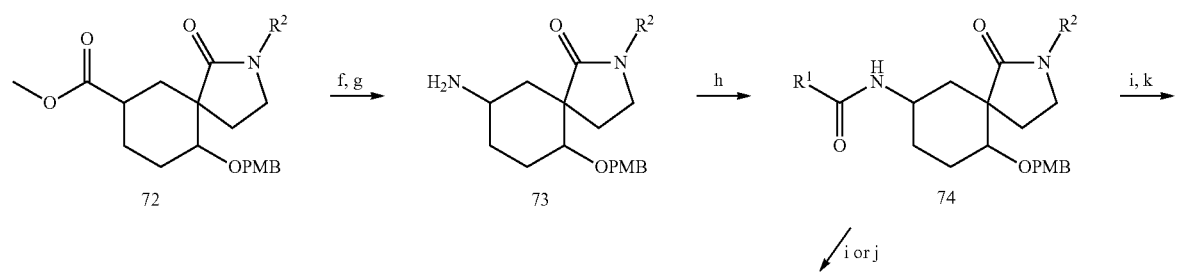

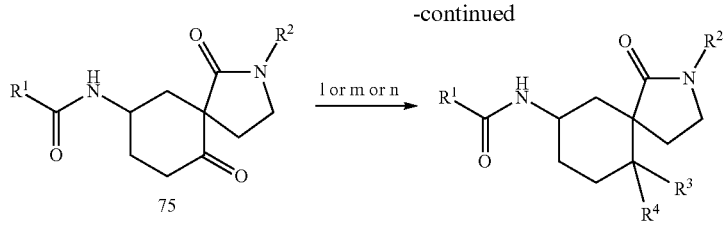

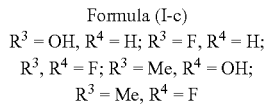

Formula (I-c)
$R^3 = OH, R^4 = H; R^3 = F, R^4 = H;$
$R^3, R^4 = F; R^3 = Me, R^4 = OH;$
$R^3 = Me, R^4 = F$ a) NaBH$_4$, THF; b) 4-methoxybenzyl-2,2,2-trichloroacetimidate, BF$_3$•Et$_2$O; THF, 0° C.; c) O$_3$, DCM, Me$_2$S; d) R$^2$NH$_2$, NaBH(OAc)$_3$, THF; e) i-PrMgCl, THF, 0° C.; f) LiOH, THF; g) 1) DPPA, TEA, toluene, rt to 90° C.; 2) 6M HCl/H$_2$O, then basicified with Na$_2$CO$_3$; h) R$^1$CO$_2$H, BOP, TEA, DCM; or R$^1$COCl, TEA, DCM; i) H$_2$, Pd/C, EtOH/EtOAc; j) 1) H$_2$, Pd/C, EtOH/EtOAc; 2) DAST, DCM; k) PySO$_3$, DMSO; l) DAST, DCM; m) MeMgBr, THF, 0° C.; n) 1) MeMgBr, THF, 0° C.; 2) DAST, DCM.

A compound of formula (I-d) may be prepared via the processes outlined in Scheme 19. Reduction of the carbonyl group of compound 41, followed by adding the protecting group PMB using customary procedures (see e.g., steps a and b of Scheme 19), could give compound 76. Removal of the Boc group followed by amidation under customary conditions (see e.g., steps c and d of Scheme 19) could afford compound 77. Removal of PMB using customary procedures (see e.g., step e of Scheme 19) could give an alcohol, such as a compound of formula (I-d) where $R^3$ is OH and $R^4$ is H. Fluorination of this alcohol using customary conditions, such as DAST in DCM, could afford a compound of formula (I-d) where $R^3$ is F and $R^4$ is H. Oxidation of this compound using customary conditions (see e.g., step f of Scheme 19) could yield ketone 78. Fluorination of this ketone under customary conditions (see e.g., step h of Scheme 19) could afford a compound of formula (I-d) where both $R^3$ and $R^4$ are F. Gringard reaction of compound 78 with MeMgBr under customary conditions (see e.g., step i of Scheme 19) could afford a tertiary alcohol, such as a compound of formula (I-d) where $R^3$ is Me and $R^4$ is OH. Fluorination of this tertiary alcohol using customary procedures, such as DAST in DCM, could give a compound of formula (I-d) where $R^3$ is Me and $R^4$ is F. In each instance of the compound of formula (I-d), $R^1$ and $R^2$ are as defined herein.

Scheme 19

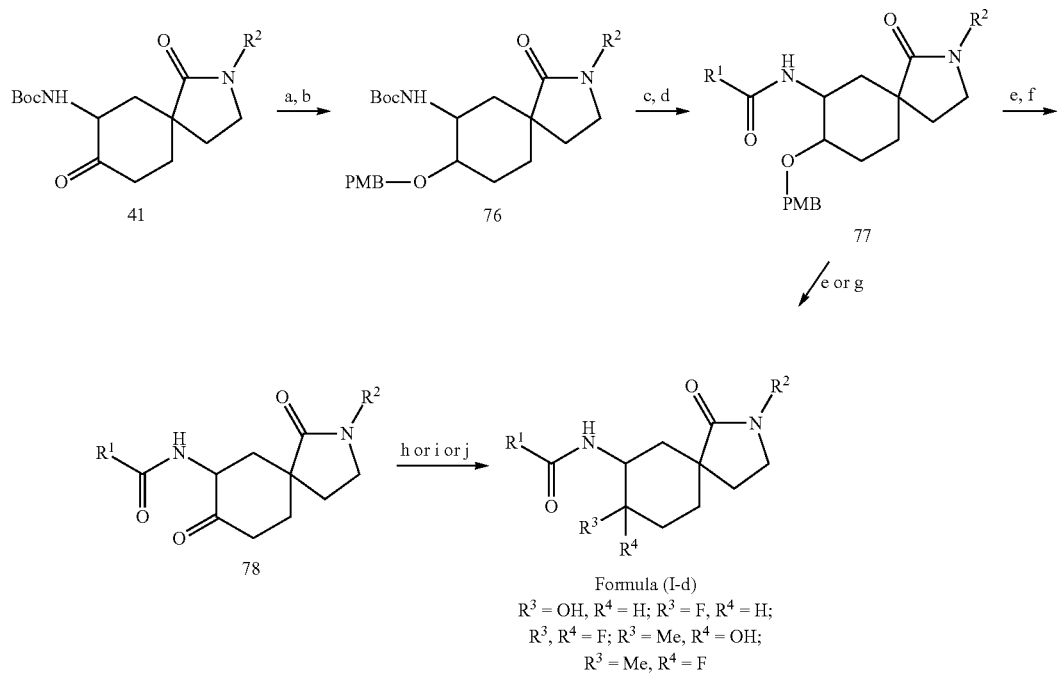

Formula (I-d)
$R^3 = OH, R^4 = H; R^3 = F, R^4 = H;$
$R^3, R^4 = F; R^3 = Me, R^4 = OH;$
$R^3 = Me, R^4 = F$ a) NaBH$_4$, THF; b) 4-methoxybenzyl-2,2,2-trichloroacetimidate, BF$_3$•Et$_2$O; THF, 0° C.; c) 4M HCl/dioxane, DCM; d) R$^1$CO$_2$H, BOP, TEA, DCM; or R$^1$COCl, TEA, DCM; e) H$_2$, Pd/C, EtOH/EtOAc; f) PySO$_3$, DMSO; g) 1) H$_2$, Pd/C, EtOH/EtOAc; 2) DAST, DCM; h) DAST, DCM; i) MeMgBr, THF, 0° C.; j) 1) MeMgBr, THF, 0° C.; 2) DAST, DCM.

A compound of formula (I-e) may be prepared via the processes outlined in Scheme 20. Reduction of the carbonyl group in compound 49, followed by adding the protecting group PMB using customary procedures (see e.g., steps a and b of Scheme 20), could give compound 79. Saponification of compound 79, followed by Curtius rearrangement and then amidation under customary conditions (see e.g., steps c, d and e of Scheme 20), could afford compound 80. Removal of PMB using customary procedures (see e.g., step f of Scheme 20) could give an alcohol, such as a compound of formula (I-e) where $R^5$ is OH and $R^6$ is H. Fluorination of this alcohol using customary conditions, such as DAST in DCM, could afford a compound of formula (I-e) where $R^5$ is F and $R^6$ is H. Oxidation of this compound using customary conditions (see e.g., step h of Scheme 20) could yield ketone 81. Fluorination of this ketone under customary conditions (see e.g., step i of Scheme 20) could afford a compound of formula (I-e) where both $R^5$ and $R^6$ are F. Gringard reaction of compound 81 with MeMgBr under customary conditions (see e.g., step j of Scheme 20) could afford a tertiary alcohol, such as a compound of formula (I-e) where $R^5$ is Me and $R^6$ is OH. Fluorination of this tertiary alcohol using customary procedures, such as DAST in DCM, could give a compound of formula (I-e) where $R^5$ is Me and $R^6$ is F. In each instance of the compound of formula (I-e), $R^1$ and $R^2$ are as defined herein.

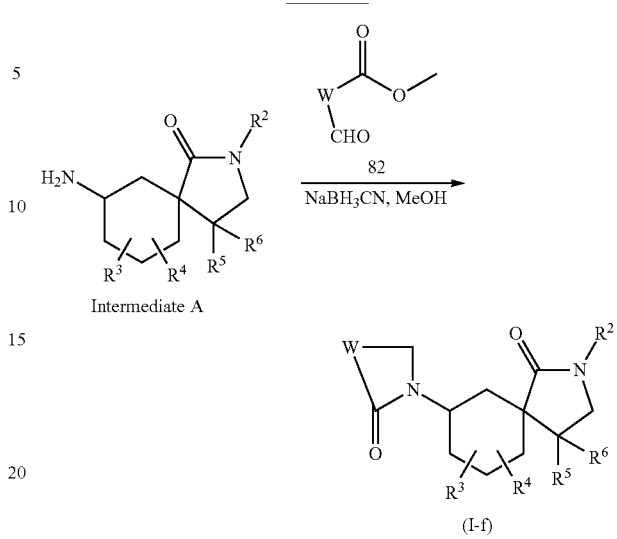

A compound of formula (I-g) may be made via the processes outlined in Scheme 22.

N-arylation of intermediate B-1 with X-Q-OMe (Q is an aryl or heteroaryl, X is as previously defined) using copper-

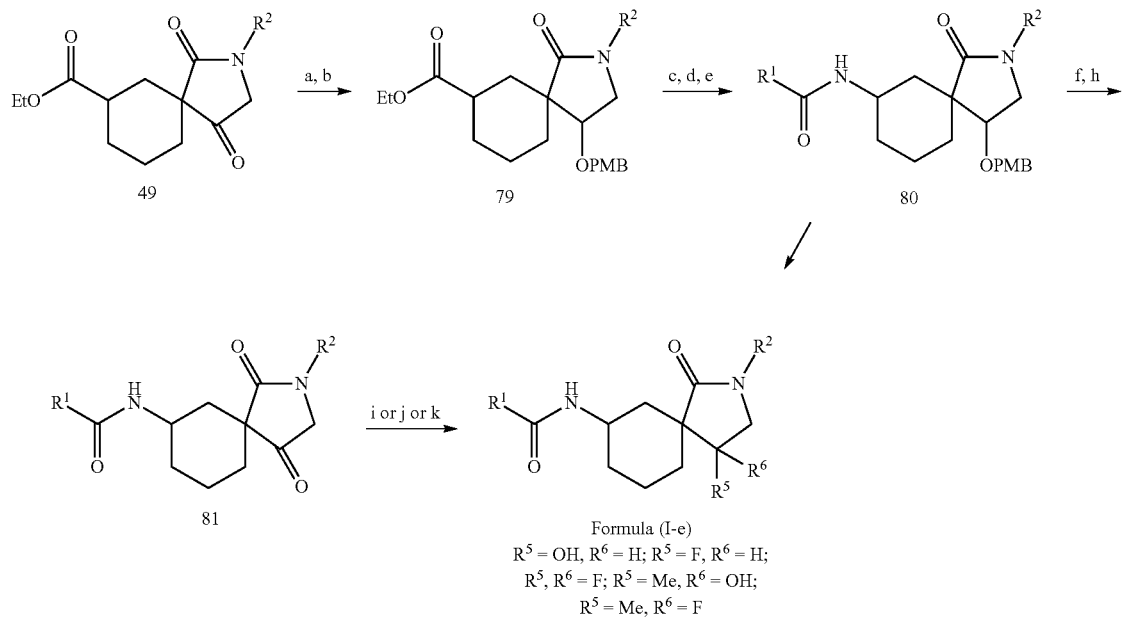

A compound of formula (I-f) can be made via the processes outlined in Scheme 21. Reaction of intermediate A with compound 82 (W is an aryl or heteroaryl, and —CO$_2$Me and —CHO are on the two adjacent carbons of W) under reductive amination conditions, such as NaBH$_3$CN in MeOH, could give a compound of formula (I-f), where $R^2$-$R^6$ are as defined herein.

assisting cross coupling see step a in Scheme 22) or palladium-catalyzed cross coupling (see step b in Scheme 22) could give compound 82. De-methylation using customary conditions, such as BBr$_3$ in DCM, could yield compound 83. O-Alkylation of compound 83 with $R^{30}$X in the presence of base, such as Cs$_2$CO$_3$ in DMF, at elevated temperature could afford a compound of formula (I-g), where $R^1$, $R^{30}$ and Q are as defined herein.

Scheme 22

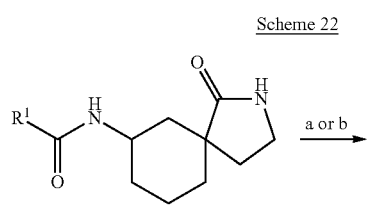

Intermediate B-1

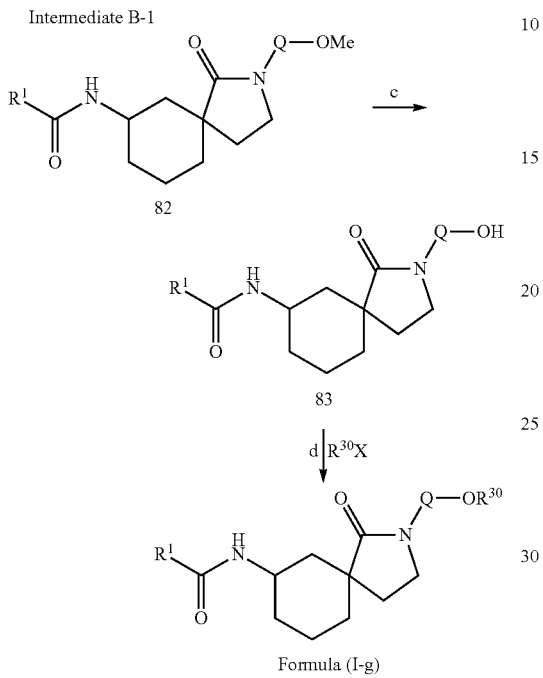

Formula (I-g)

a) CuI, X—Q—OMe, NHMeCH$_2$CH$_2$NHMe, K$_2$CO$_3$, dioxane, microwave, 160° C.;
b) X—Q—OMe, tris-(dibenzylideneacetone)dipalladium(0) chloroform adduct, BINAP, Cs$_2$CO$_3$, toluene, 80° C.; c) BBr$_3$, DCM; d) R$^{30}$X, Cs$_2$CO$^3$, DMF, heat.

A compound of formula (I-i) may be prepared via the processes outlines in Scheme 23. Oxidation of alcohol 23 to its corresponding ketone, followed by protecting the ketone by using customary conditions affords compound 84 (see e.g., step a of Scheme 23). Alkylation of compound 84 with allyl bromide in the presence of base (see e.g., step b of Scheme 23) could yield compound 85. Oxidation of compound 85, such as oxonolysis (see step c in Scheme 23), could afford aldehyde 86. Reductive amination of aldehyde 86 with R$^2$NH$_2$ using customary procedures (see e.g., step d of Scheme 23), followed by cyclization under basic conditions (see e.g., step e of Scheme 23), could give lactam 88. In some cases (especially when R$^2$ is alkyl), lactam 88 could be formed under reductive amination conditions. The trans lactam 88 can be epimerized to cis lactam 89 under basic conditions (see e.g., step f of Scheme 23). Saponification, followed by Curtius rearrangement and hydrogenation using customary conditions (see e.g., steps g and h of Scheme 23) could afford amine intermediate A-8, which could be converted to amide I-h by reacting with R$^1$CO$_2$H or R$^1$COCl, followed by removing the protecting group of ketone under customary conditions, such as step i of Scheme 23. Fluorination of amide I-h under customary conditions, such as DAST in DCM, could afford a compound of formula (I-i) where R$^3$ and R$^4$ are F. The reduction of the ketone of amide I-h using customary procedures (see e.g., step k of Scheme 23) could give an alcohol, such as a compound of formula (I-i) where R$^3$ is OH and R$^4$ is H. Fluorination of this alcohol using customary procedures, such as DAST in DCM, could yield a compound of formula (I-i) where R$^3$ is F and R$^4$ is H. Grignard Reaction of amide I-h with MeMgBr using customary procedures (see e.g., step 1 of Scheme 23) could afford a tertiary alcohol, such as a compound of formula (I-i) where R$^3$ is Me and R$^4$ is OH. In each instance of the compound of formula (I-h and I-i), R$^1$ and R$^2$ are as defined herein.

Scheme 23

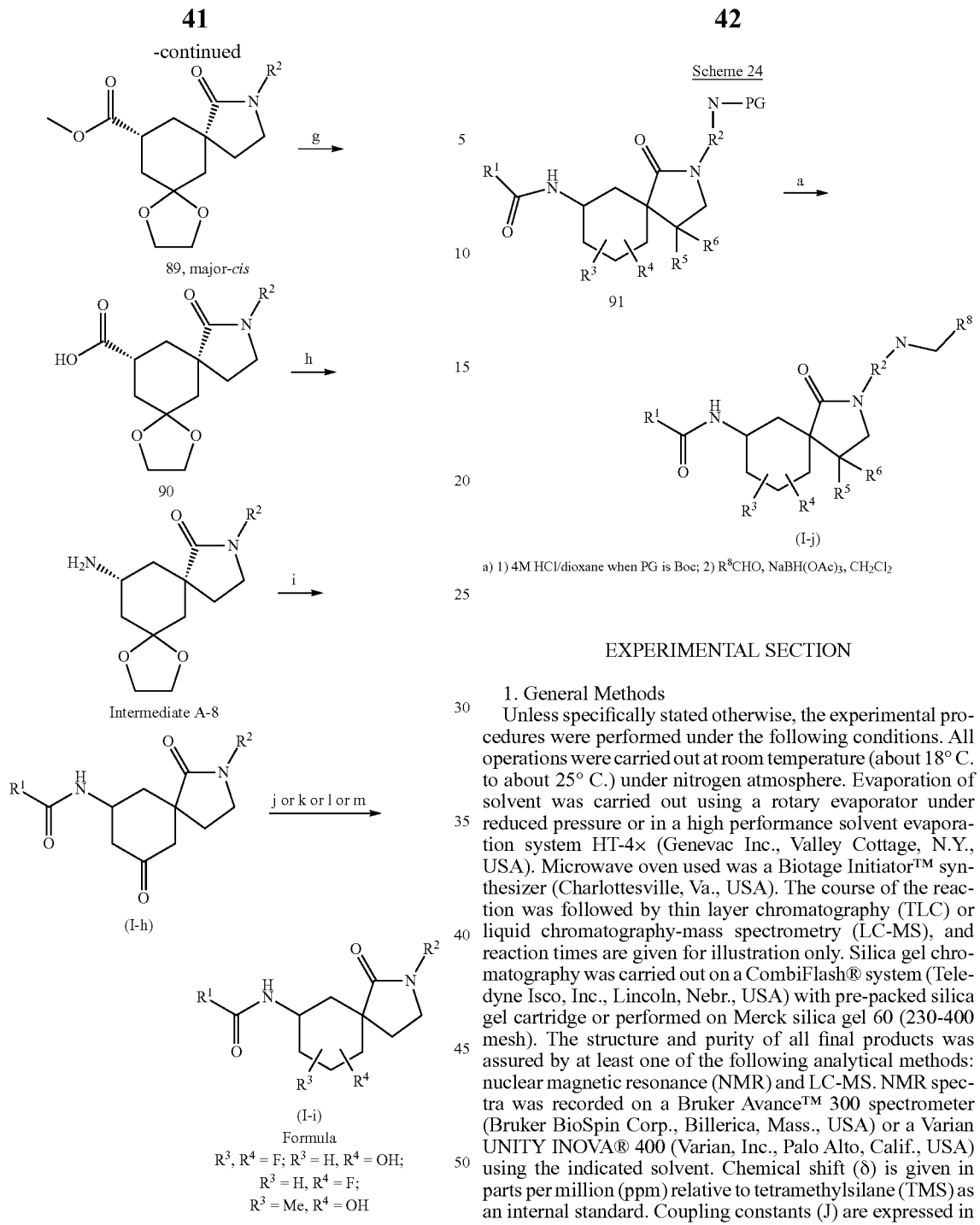

a) 1) 4M HCl/dioxane when PG is Boc; 2) R⁸CHO, NaBH(OAc)₃, CH₂Cl₂ a) 1) Py·SO₃, DMSO; 2) HOCH₂CH₂OH, pTSA, toluene, reflux; b) i-Pr₂NH, BuLi, DMPU, THF, allyl bromide, -78° C. to rt; c) O₃, DCM, Me₂S; d) R²NH₂, NaBH(OAc)₃, THF; e) i-PrMgCl, THF, 0° C.; f) NaH, EtOH, 0° C. to reflux or NaH, THF, rt; g) LiOH, THF; h) 1) DPPA, TEA, toluene, rt to 90° C.; 2) BnOH; 3) Pd/C, H₂, MeOH; i) 1) R¹COCl, TEA, DCM or R¹CO₂H, PyBOP, TEA, DCM; 2) THF, HCl, H₂O; j) DAST, DCM; k) NaBH4 or Red-Al, THF; l) 1) NaBH4 or Red-Al, THF; 2) DAST; m) RMgBr, THF A compound of formula (I-j) can be made via the processes outlined in Scheme 24. Removal of the protecting group Boc of compound 91 using customary procedures (see e.g., steps a in Scheme 24), followed by the reductive amination with aldehyde RCHO (R⁸: alkyl, cyclic alkyl, or H), and NaBH(OAc)₃ in CH₂Cl₂, could give a compound of formula (I-j), where $R^1$-$R^6$ are as defined herein.

EXPERIMENTAL SECTION

1. General Methods

Unless specifically stated otherwise, the experimental procedures were performed under the following conditions. All operations were carried out at room temperature (about 18° C. to about 25° C.) under nitrogen atmosphere. Evaporation of solvent was carried out using a rotary evaporator under reduced pressure or in a high performance solvent evaporation system HT-4× (Genevac Inc., Valley Cottage, N.Y., USA). Microwave oven used was a Biotage Initiator™ synthesizer (Charlottesville, Va., USA). The course of the reaction was followed by thin layer chromatography (TLC) or liquid chromatography-mass spectrometry (LC-MS), and reaction times are given for illustration only. Silica gel chromatography was carried out on a CombiFlash® system (Teledyne Isco, Inc., Lincoln, Nebr., USA) with pre-packed silica gel cartridge or performed on Merck silica gel 60 (230-400 mesh). The structure and purity of all final products was assured by at least one of the following analytical methods: nuclear magnetic resonance (NMR) and LC-MS. NMR spectra was recorded on a Bruker Avance™ 300 spectrometer (Bruker BioSpin Corp., Billerica, Mass., USA) or a Varian UNITY INOVA® 400 (Varian, Inc., Palo Alto, Calif., USA) using the indicated solvent. Chemical shift (δ) is given in parts per million (ppm) relative to tetramethylsilane (TMS) as an internal standard. Coupling constants (J) are expressed in hertz (Hz), and conventional abbreviations used for signal shape are: s=singlet; d=doublet; t=triplet; m=multiplet; br=broad; etc. Unless stated otherwise, mass spectra were obtained using electrospray ionization (ESMS) via either a Micromass® Platform II system or a Quattro Micro™ system (both from Waters Corp., Milford, Mass., USA) and (M+H)⁺ is reported.

General LC-MS Methods:

Method A: Mobile phase: A) water/acetonitrile (99/1) and 0.2% ammonium formate; B) acetonitrile. Gradient: 20-85% B from 0 to 1.7 min, 85% B from 1.7 to 1.84 min, 85-100% B from 1.84 to 1.85 min, 100% B from 1.85-1.99 min, 100-20% B from 1.99 to 2 min. Flow rate: 5.0 mL/min. Column: Inertsil® ODS-3, 50×4.6 mm, 3 μm particle size.

Method B: Mobile phase: A) water/acetonitrile (99/1) and 0.2% ammonium formate; B) acetonitrile. Gradient: 30-90% B from 0 to 1.7 min, 90% B from 1.7 to 1.84 min, 90-100% B from 1.84 to 1.85 min, 100% B from 1.85-1.99 min, 100-20% B from 1.99 to 2 min. Flow rate: 5.0 mL/min. Column: Inertsil® C8, 50×4.6 mm, 3 μm particle size.

Method C: Mobile phase: A) water/acetonitrile (99/1) and 0.2% ammonium formate; B) acetonitrile. Gradient: 10-85% B from 0 to 1.7 min, 85% B from 1.7 to 1.84 min, 85-100% B from 1.84 to 1.85 min, 100% B from 1.85-1.99 min, 100-20% B from 1.99 to 2 min. Flow rate: 5.0 mL/min. Column: Inertsil® C8, 50×4.6 mm, 3 μm particle size.

Method D: Mobile phase: A) water/acetonitrile (99/1) and 0.2% acetic acid; B) acetonitrile. Gradient: 0-30% B from 0 to 1.3 minutes, 30-85% B from 1.3 to 1.7 min, 85% B from 1.7-1.84 min, 85-100% B from 1.84 to 1.85 min, 100% B from 1.85 to 1.99 min, and 100-20% B from 1.99 to 2.00 min. Flow rate: 5.0 mL/min. Column: Inertsil® ODS-3, 50×4.6 mm, 3 μm particle size.

Method E: Mobile phase: A) water/acetonitrile (99/1) and 0.2% ammonium formate; B) acetonitrile. Gradient: 0-30% B from 0 to 1.3 minutes, 30-85% B from 1.3 to 1.7 min, 85% B from 1.7-1.84 min, 85-100% B from 1.84 to 1.85 min, 100% B from 1.85 to 1.99 min, and 100-20% B from 1.99 to 2.00 min. Flow rate: 5.0 mL/min. Column: Inertsil® ODS-3, 50×4.6 mm, 3 μm particle size.

2. Preparation of Intermediates of the Invention

Unless specified otherwise, all starting materials and reagents were obtained from commercial suppliers, such as Sigma-Aldrich (St. Louis, Mo., USA) and its subsidiaries, and used without further purification.

Intermediate 1

7-Amino-2-(3-chloro-phenyl)-2-aza-spiro[4.5]decan-1-one

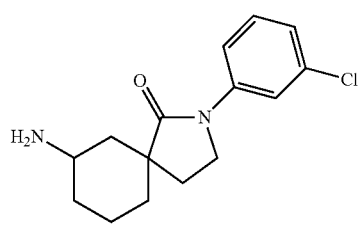 [SMILES: NC1CCCC2(CCN(c3cccc(Cl)c3)C2=O)C1]

Intermediate 1 was prepared via the process of Scheme 3, supra, as follows:

Step 1: 3-Oxo-cyclohexanecarboxylic acid ethyl ester

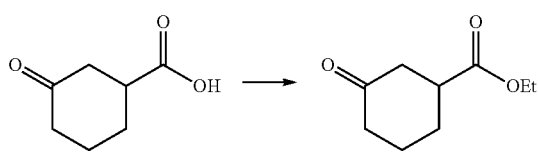 [SMILES: O=C1CCCC(C(=O)O)C1 ; CCOC(=O)C1CCCC(=O)C1]

To a round bottom flask was added 3-oxo-1-cyclohexanecarboxylic acid (3.85 g, 27.1 mmol), ethanol (7.91 mL), p-toluenesulfonic acid (0.097 g, 0.56 mmol) and toluene (65.9 mL). The mixture was refluxed with Dean-star trap overnight. The reaction mixture was cooled down and concentrated under reduced pressure to afford 4.61 g (100%) of the title compound, 3-oxo-cyclohexanecarboxylic acid ethyl ester, as a yellow oil, which was used in the next step without further purification.

Step 2:
7-Allyl-1,4-dioxa-spiro[4.5]decane-7-carboxylic acid ethyl ester

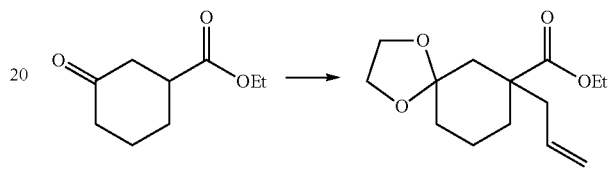

The residue obtained in step 1 was dissolved in toluene (100.0 mL). 1,2-ethanediol (3.02 mL, 54.2 mmol) was added. The mixture was refluxed with Dean-star trap overnight. The mixture was cooled down, diluted with ethyl acetate (60 mL), and washed sequentially with saturated $NaHCO_3$ (20 mL×2), water and brine. The organic layer was dried over $Na_2SO_4$ and concentrated under reduced pressure. The resulting residue was dried under high vacuum overnight to afford 4.50 g (78%) of protected ketone, 1,4-dioxa-spiro[4.5]dicane-7-carboxylic acid ethyl ester, as a yellow oil. $^1$H NMR (400 MHz, $CDCl_3$) δ 4.11 (q, J=7.1 Hz, 2H), 3.90-3.97 (m, 4H), 2.58 (tt, J=15.7, 3.8 Hz, 1H), 1.88-1.99 (m, 2H), 1.75-1.83 (m, 1H), 1.68-1.73 (m, 1H), 1.64 (t, J=2.6 Hz, 1H), 1.47-1.59 (m, 2H), 1.31-1.45 (m, 1H), 1.24 (t, J=7.2 Hz, 3H).

Then, to a round bottom flask was added N,N-diisopropylamine (3.97 mL, 28.4 mmol) and THF (22.1 mL). The mixture was cooled at −20° C. 1.6 M of n-butyllithium in hexane (15.8 mL) was added. The crude mixture was stirred at 0° C. for 30 min and then cooled down at −20° C., and 1,4-dioxa-spiro[4.5]dicane-7-carboxylic acid ethyl ester (4.50 g, 21.0 mmol) from step 1 was added dropwise. The mixture was stirred at 0° C. for 30 min, and then cooled at −20° C., and allyl bromide (2.00 mL, 23.1 mmol) was added. The mixture was warmed up to rt slowly and stirred at rt for 30 min. The reaction mixture was quenched with ice, diluted with ethyl acetate (60 mL), and washed sequentially with 1N aqueous HCl (5 mL), water and brine. The organic layer was dried over $Na_2SO_4$ and concentrated under reduced pressure to afford 4.30 g (81%) of the title compound, 7-allyl-1,4-dioxa-spiro[4.5]decane-7-carboxylic acid ethyl ester, as a yellow oil. It was used in the next step without further purification. $^1$H NMR (400 MHz, $CDCl_3$): δ5.64-5.74 (m, 1H), 4.97-5.05 (m, 2H), 4.05-4.17 (m, 2H), 3.82-3.99 (m, 4H), 2.34-2.41 (m, 1H), 2.27 (dt, J=13.6, 2.1 Hz, 1H), 2.08-2.16 (m, 2H), 1.76-

1.88 (m, 1H), 1.60-1.72 (m, 2H), 1.46-1.54 (m, 1H), 1.42 (d, J=13.6 Hz, 1H), 1.25 (t, J=7.1 Hz, 3H), 1.08-1.16 (m, 1H).

Step 3: 7-(2-Oxo-ethyl)-1,4-dioxa-spiro[4.5]decane-7-carboxylic acid ethyl ester

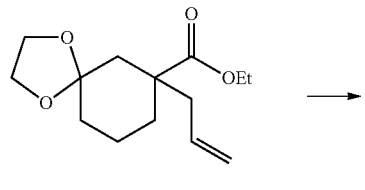

The title compound was prepared via two oxidation methods.

Method 1: Oxidation with OsO₄ and NaIO₄: 7-allyl-1,4-dioxa-spiro[4.5]dicane-7-carboxylic acid ethyl ester from step 2 (2.00 g, 7.86 mmol) was dissolved in THF (30.0 mL) and water (12.0 mL). Osmium tetraoxide (0.50 g, 1.97 mmol) was added, followed by the addition of sodium periodate (4.00 g, 18.7 mmol). The crude mixture was stirred at rt for 4 hrs and quenched with saturated aqueous sodium thiosulfate (100 mL). The mixture was stirred at rt for 30 min and diluted with ethyl acetate (150 mL). The organic layer was washed with water and brine, dried over Na₂SO₄ and concentrated under reduced pressure to afford 1.0 g (50%) of the title compound, 7-(2-oxo-ethyl)-1,4-dioxa-spiro[4.5]decane-7-carboxylic acid ethyl ester, as a yellow oil. It was used in the next step without further purification. ¹H NMR (400 MHz, CDCl₃): δ 9.71 (dd, J=2.0, 1.5 Hz, 1H), 4.08-4.23 (m, 2H), 3.83-3.96 (m, 4H), 2.95 (dd, J=17.0, 1.6 Hz, 1H), 2.68 (dd, J=17.1, 1.6 Hz, 1H), 2.17 (d, J=13.8 Hz, 1H), 1.43-2.00 (m, 7H), 1.26 (t, J=7.0 Hz, 3H).

Method 2: Ozonolysis: 7-Allyl-1,4-dioxa-spiro[4.5]decane-7-carboxylic acid ethyl ester from step 2 (4.1 g, 16 mmol) was dissolved in CH₂Cl₂ (100 mL). The solution was cooled at −78° C. Ozone generated with LG-7 (CD laboratory, ozone generator) was bubbled through the solution for 1.5 hrs until the solution turned light blue. Then oxygen was bubbled through until the solution turned to colorless. Dimethyl sulfide (11 mL, 150 mmol) was added at −78° C. The mixture was warmed up slowly to rt and stirred overnight. The crude mixture was quenched with water (30 mL), and the aqueous layer was extracted with CH₂Cl₂ (50 mL ×2). The combined organic layer was washed with water and brine, dried over Na₂SO₄, and concentrated under reduced pressure to afford 3.20 g (77%) of the title compound, 7-(2-oxo-ethyl)-1,4-dioxa-spiro[4.5]decane-7-carboxylic acid ethyl ester, as a yellow oil. It was used in the next step without further purification.

Step 4: 9-(3-Chloro-phenyl)-1,4-dioxa-9-aza-dispiro [4.1.4.3]tetradecan-8-one

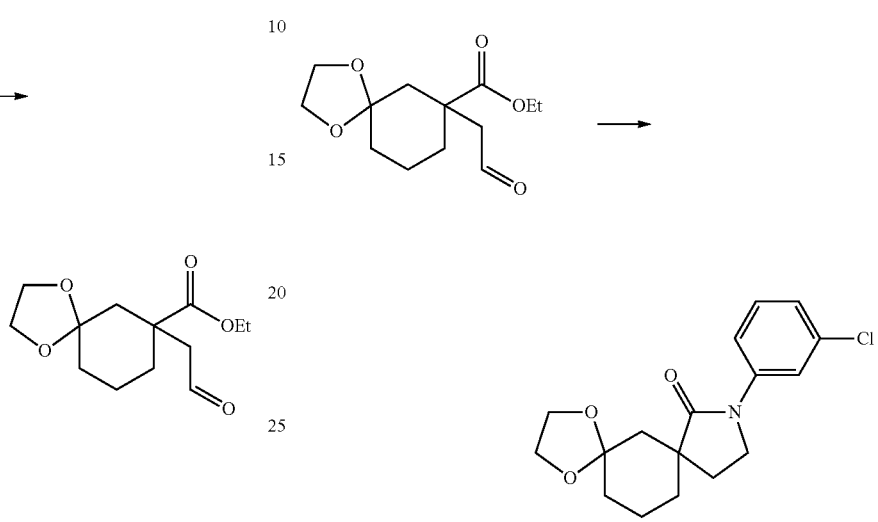

The residue obtained in step 3 (3.20 g, 12.5 mmol) was dissolved in THF (20.0 mL), m-chloroaniline (1.58 mL, 15.0 mmol) and 1 drop of acetic acid were added. The crude mixture was stirred at rt for 30 min. Then sodium triacetoxyborohydride (3.97 g, 18.7 mmol) was added. The mixture was stirred at rt for 24 hrs, then quenched with ice, and diluted with ethyl acetate (100 mL). The organic layer was washed sequentially with 1N aqueous NaOH (10 mL), water and brine, dried over Na₂SO₄, and concentrated under reduced pressure. The resulting residue was purified with silica gel chromatography (eluted with CH₂Cl₂ first, then MeOH/CH₂Cl₂: 1/9) to afford 7-[2-(3-chloro-phenylamino)-ethyl]-1,4-dioxa-spiro[4.5]decane-7-carboxylic acid ethyl ester (2.42 g, 53%), as a yellow oil. ¹H NMR (400 MHz, CDCl₃): δ 7.04 (t, J=8.1 Hz, 1H), 6.62-6.65 (m, 1H), 6.51 (t, J=1.9 Hz, 1H), 6.38-6.42 (m, 1H), 4.09-4.17 (m, 2H), 3.96-4.02 (m, 1H), 3.83-3.94 (m, 3H), 3.71 (bs, 1H), 3.10-3.18 (m, 1H), 2.97-3.04 (m, 1H), 2.30 (dt, J=13.6, 1.9 Hz, 1H), 2.14-2.22 (m, 1H), 1.99-2.07 (m, 1H), 1.81-1.92 (m, 1H), 1.52-1.75 (m, 4H), 1.49 (d, J=13.6 Hz, 1H), 1.17-1.28 (m, 4H). ESI-MS m/z: 368 (M+H)⁺.

This oil (2.42 g, 6.58 mmol) was dissolved in anhydrous THF (37.0 mL). The solution was cooled at 0° C., 2M of isopropylmagnesium chloride in THF (0.632 mL) was added dropwise. The mixture was stirred at 0° C. for 1 hr, then quenched with ice and diluted with ethyl acetate (80 mL). The organic layer was washed with water and brine, dried over Na₂SO₄, and concentrated under reduce pressure to afford 2.10 g (99%) of the title compound, 9-(3-chloro-phenyl)-1,4-dioxa-9-aza-dispiro[4.1.4.3]tetradecan-8-one, as a white solid, which was used in the next step without further purification. ESI-MS m/z: 322 (M+H)+.

Step 5: 2-(3-Chloro-phenyl)-2-aza-spiro[4.5]decane-1,7-dione

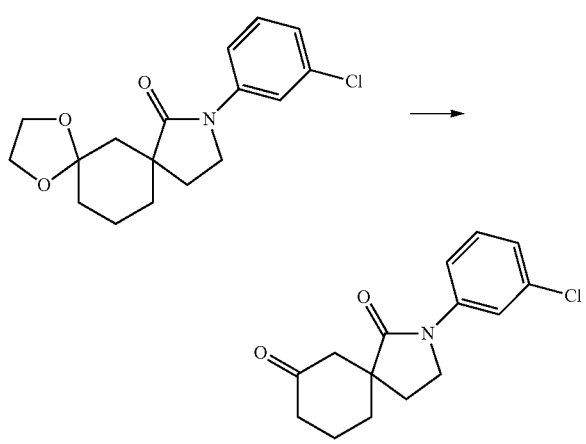

To a round bottom flask was added 9-(3-chloro-phenyl)-1,4-dioxa-9-aza-dispiro[4.1.4.3]tetradecan-8-one from step 4 (0.45 g, 0.84 mmol), THF (10.2 mL), and 2N aqueous HCl (7.0 mL). After stirring at rt overnight, the reaction mixture was diluted with ethyl acetate (60 mL). The organic layer was washed with water and brine, dried over Na$_2$SO$_4$, and concentrated under reduced pressure to afford 0.38 g (97%) of the title compound, 2-(3-chloro-phenyl)-2-aza-spiro[4.5]decane-1,7-dion, as a white solid, which was used in the next step without further purification. $^1$H NMR (400 MHz, CDCl$_3$): δ7.74 (t, J=2.0 Hz, 1H), 7.52 (ddd, J=8.3, 2.2, 1.0 Hz, 1H), 7.29 (t, J=8.1 Ha, 1H), 7.13 (ddd, J=8.1, 2.0, 1.0 Hz, 1H), 3.72-3.81 (m, 2H), 2.73 (dd, J=13.9, 1.0 Hz, 1H), 2.35-2.50 (m, 2H), 2.29 (dt, J=13.9, 1.7 Hz, 1H), 2.12-2.22 (m, 2H), 2.02-2.07 (m, 2H), 1.71-1.89 (m, 2H). ESI-MS m/z: 278 (M+H)+.

Step 6: 7-Amino-2-methyl-2-aza-spiro[4.5]decan-1-one

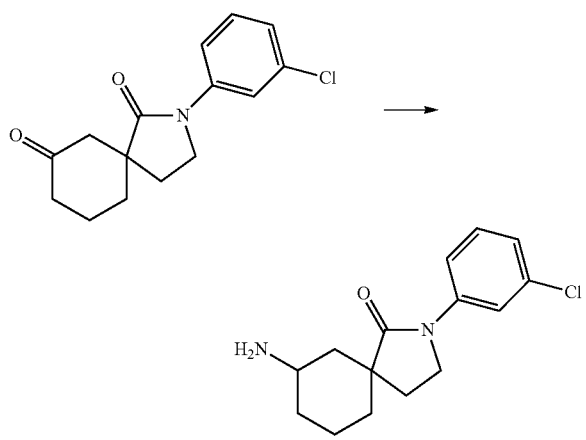

To a round bottom flask was added 2-(3-chloro-phenyl)-2-aza-spiro[4.5]decane-1,7-dione of step 5 (0.38 g, 1.35 mmol), methanol (4.92 mL), and ammonium acetate (1.25 g, 16.2 mmol). The mixture was stirred at rt for 1 hr. Sodium cyanoborohydride (0.085 g, 1.35 mmol) was then added. After stirring at rt for 2 hrs, the reaction mixture was quenched with ice and diluted with ethyl acetate (60 mL). The organic layer was washed with brine, dried over Na$_2$SO$_4$, and concentrated under reduced pressure to afford 0.35 g (94%) of the title compound, 7-amino-2-methyl-2-aza-spiro[4.5]decan-1-one, as a white solid. The title compound is a mixture of two diastereomers (trans/cis: 5/2; under LC-MS method C, the first peak with RT of 0.80 min was assigned as cis, and the second peak with RT of 0.83 min was assigned as trans.). ESI-MS m/z: 279 (M+H)+. It was used without further purification.

Intermediate 2 cis-7-Amino-2-(3-chloro-phenyl)-2-aza-spiro[4.5]decan-1-one

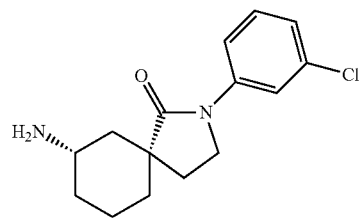 [SMILES: N[C@H]1CCC[C@]2(CCN(c3cccc(Cl)c3)C2=O)C1]

Intermediate 2 was made via the process of Scheme 4, supra, as follows:

Step 1: Cyclohexane-1,3-dicarboxylic acid diethyl ester

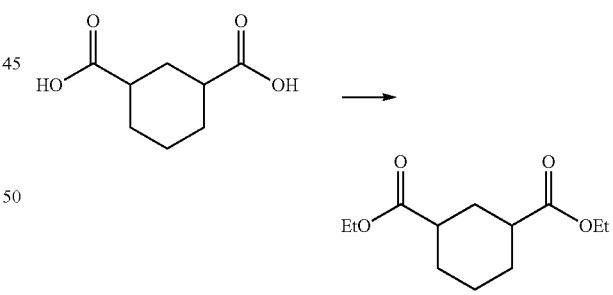

1,3-cyclohexanecarboxylic acid (60.0 g, 348.4 mmol, mixture of cis and trans) was dissolved in ethanol (600 mL). Concentrated sulfuric acid (10 mL) was added dropwise at rt. The mixture was refluxed for 5 hours and then cooled down to rt. The solvent was removed under reduced pressure, and the resulting residue was diluted with ethyl acetate (1500 mL). The organic layer was washed with cold saturated aqueous NaHCO$_3$ (400 mL) and brine (2×200 mL), dried over Na$_2$SO$_4$, and concentrated under reduced pressure to afford 77.4 g (97%) of the title compound, cyclohexane-1,3-dicarboxylic acid diethyl ester, as a colorless oil, which was used in the next step without further purification. $^1$H NMR (400

MHz, CDCl$_3$): δ4.01-4.22 (m, 4H), 2.67 (m, 1H), 2.31 (t, J=11.71 Hz, 1H), 1.30-2.25 (m, 8H), 1.20-1.31 (m, 6H).

Step 2: 1-Allyl-cyclohexane-1,3-dicarboxylic acid diethyl ester

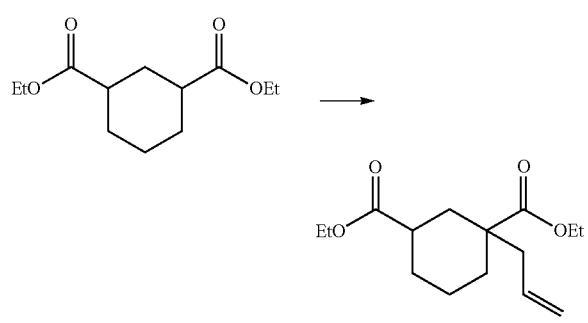

N,N-Diisopropylamine (31.8 mL, 227 mmol) was dissolved in anhydrous THF (260 mL), and then cooled to −78° C. BuLi in THF (1.6 M, 141.9 mL, 227 mmol) was added. The mixture was stirred at 0° C. for 30 min, then cooled down to −78° C. DMPU (97.7 mL, 810 mL) was added dropwise, followed by the addition of cyclohexane-1,3-dicarboxylic acid diethyl ester from step 1 (37.0 g, 162 mmol) in THF (60 mL). The mixture was stirred at −78° C. for 1 hr, allyl bromide (15.4 mL, 178 mmol) was then added. The mixture was warmed up slowly to rt. After stirring at rt overnight, the reaction mixture was quenched with ice-cold aqueous 1N HCl, and diluted with ethyl acetate (300 mL). The organic layer was washed with brine (2×200 mL), dried over Na$_2$SO$_4$, and concentrated under reduced pressure to give 43.5 g (quantitative yield) of the title compound, 1-allyl-cyclohexane-1,3-dicarboxylic acid diethyl ester, as an orange oil. $^1$H NMR (400 MHz, CDCl$_3$): δ5.66-5.77 (m, 1H), 5.00-5.06 (m, 2H), 4.08-4.19 (m, 4H), 2.50-1.31 (m, 11H), 1.30 (m, 6H).

Step 3: trans-1-(2-Oxo-ethyl)-cyclohexane-1,3-dicarboxylic acid diethyl ester

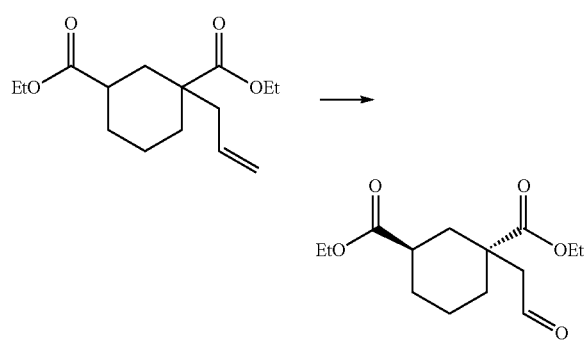

1-Allyl-cyclohexane-1,3-dicarboxylic acid diethyl ester of step 2 (38.0 g, 140 mmol) was dissolved in CH$_2$Cl$_2$ (500 mL) and MeOH (50 mL), and then cooled to −78° C. Ozone was bubbled through the solution for 6 h, then nitrogen was bubbled through for 20 min. Dimethylsulfide (104 mL, 1.4 mol) was added at −78° C. dropwise. The mixture was warmed up to rt and stirred at rt overnight. The reaction mixture was concentrated under reduced pressure. The resulting residue was purified by silica gel chromatography (hexanes/EtOAc, 85:15 to 80:20) to give 12.4 g (32%) of the title compound, trans-1-(2-oxo-ethyl)-cyclohexane-1,3-dicarboxylic acid diethyl ester, as a colorless oil. $^1$H NMR (400 MHz, CDCl$_3$): δ9.78 (dd, J=2.40 and 1.60 Hz, 1H), 4.20 (q, J=7.20 Hz, 2H), 4.10 (q, J=7.20 Hz, 2H), 2.70-2.48 (m, 4H), 2.20 (m, 1H), 2.00 (m, 1H), 1.75 (m, 1H), 1.60-1.22 (m, 10H). ESI-MS m/z: 271 (M+H)$^+$.

Step 4: trans-2-(3-Chloro-phenyl)-1-oxo-2-aza-spiro [4.5]decane-7-carboxylic acid ethyl ester

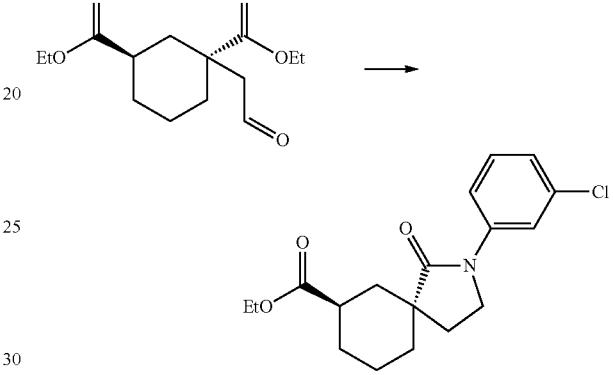

To a round bottom flask was added trans-1-(2-oxo-ethyl-cyclohexane-1,3-dicarboxylic acid diethyl ester from step 3 (9.63 g, 35.6 mmol), 1,2-dichloroethane (109 mL), m-chloroaniline (4.15 mL, 39.2 mmol) and acetic acid (0.05 mL). The reaction mixture was stirred at rt for 30 min. Sodium triacetoxyborohydride (9.00 g, 42.5 mmol) was added. After stirring at rt for 1 week, the reaction was quenched with ice, and diluted with ethyl acetate. The organic layer was washed with water and brine, dried over Na$_2$SO$_4$, and concentrated under reduced pressure. The resulting residue was purified by silica gel chromatography to afford trans-1-[2-(3-chloro-phenylamino)-ethyl]-cyclohexane-1,3-dicarboxylic acid diethyl ester (3.20 g, 23%). $^1$H NMR (300 MHz, CDCl$_3$): δ 7.05 (t, J=8.0 Hz, 1H), 6.64 (ddd, J=8.0, 2.0, 1.0 Hz, 1H), 6.51 (t, J=2.1 Hz, 1H), 6.40 (ddd, J=8.2, 2.3, 0.9 Hz, 1H), 4.08-4.19 (m, 4H), 3.74 (bs, 1H), 3.07-3.15 (m, 2H), 2.42-2.51 (m, 2H), 2.20-2.28 (m, 1H), 1.70-2.01 (m, 4H), 1.13-1.35 (m, 10H). ESI-MS m/z: 383 (M+H)$^+$.

This intermediate was dissolved in THF (68.0 mL), and cooled at 0° C. Isopropylmagnesium chloride (2M in THF, 6.28 mL) was added dropwise. After stirring at 0° C. for 1 hr, the reaction was quenched with ice-cold 1N aqueous HCl and diluted with ethyl acetate (60.0 mL). The organic layer was washed with water and brine, dried over Na$_2$SO$_4$, and concentrated under reduced pressure to afford 2.80 g (100%) of the title compound, trans-2-(3-chloro-phenyl)-1-oxo-2-aza-spiro[4.5]decane-7-carboxylic acid ethyl ester, which was used in the next step without further purification. $^1$H NMR (400 MHz, CDCl$_3$): δ 7.74 (t, J=2.0 Hz, 1H), 7.51 (ddd, J=8.3, 2.1, 1.0 Hz, 1H), 7.28 (t, J=8.2 Hz, 1H), 7.11 (ddd, J=7.9, 2.0, 0.9 Hz, 1H), 4.12 (q, J=7.0 Hz, 2H), 3.70-3.79 (m, 2H), 3.16-3.24 (m, 1H), 2.13-2.19 (m, 1H), 1.65-2.04 (m, 6H), 1.58-1.64 (m, 1H), 1.33-1.49 (m, 2H), 1.25 (t, J=7.2 Hz, 3H). ESI-MS m/z: 336 (M+H)$^+$.

Step 5: cis-2-(3-Chloro-phenyl)-1-oxo-2-aza-spiro[4.5]decane-7-carboxylic acid

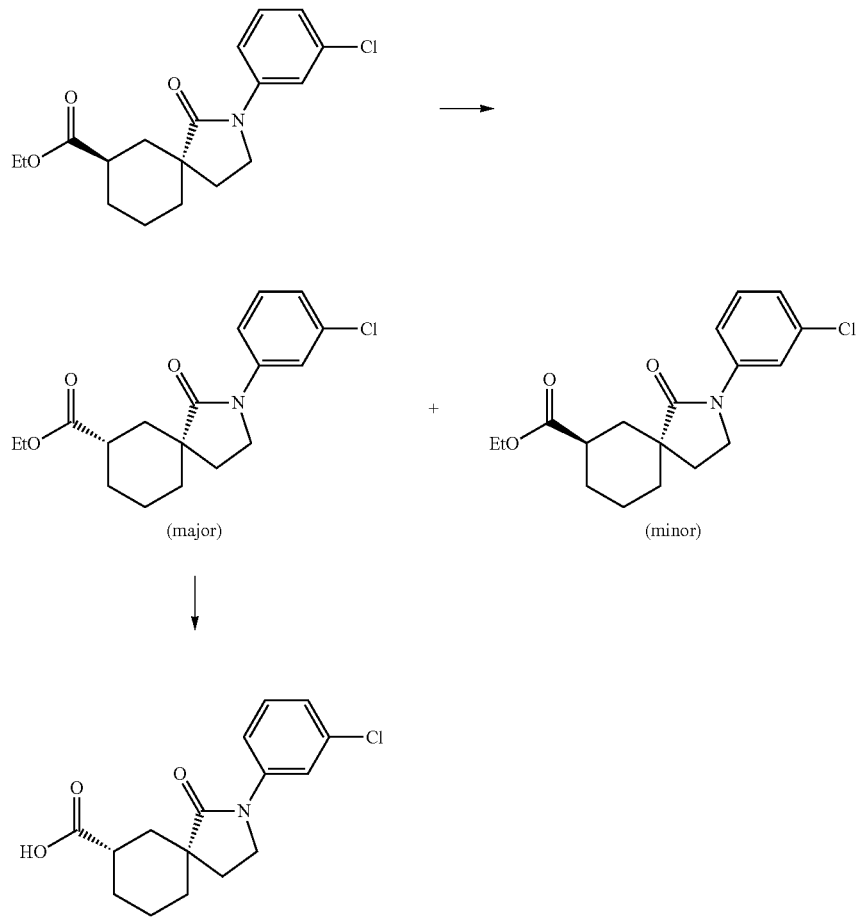 [SMILES: CCOC(=O)[C@@H]1CCC[C@]2(CCN(c3cccc(Cl)c3)C2=O)C1 ; CCOC(=O)[C@H]1CCC[C@]2(CCN(c3cccc(Cl)c3)C2=O)C1 ; CCOC(=O)[C@@H]1CCC[C@]2(CCN(c3cccc(Cl)c3)C2=O)C1 ; O=C(O)[C@H]1CCC[C@]2(CCN(c3cccc(Cl)c3)C2=O)C1]

Anhydrous ethanol (150 mL) was cooled at 0° C., and sodium hydride (0.68 g, 16.7 mmol) was added. After the mixture turned clear, trans-2-(3-chloro-phenyl)-1-oxo-2-aza-spiro[4.5]decane-7-carboxylix acid ethyl ester from step 4 (2.80 g, 8.34 mmol) in anhydrous ethanol (10.0 mL) was added. The mixture was refluxed for 3 hrs. Then it was cooled down to rt and concentrated under reduced pressure. Two peaks with same m/z (336) were observed on LC-MS (method B): The new peak with RT of 1.22 min was assigned as cis diastereomer, while the peak with RT of 1.33 min was the starting material, trans diastereomer. The residue was diluted with ethyl acetate (200 mL) and its pH was adjusted to 2 with 2N aqueous HCl. The organic layer was washed with brine, dried over Na$_2$SO$_4$, and concentrated under reduced pressure. The resulting residue was purified by silica gel chromatography to afford the desired cis ester as a white solid, which was then dissolved in THF (30.0 mL) and water (30.0 mL). Lithium hydroxide monohydrate (3.50 g, 83.4 mmol) was added. The mixture was stirred at rt overnight, and diluted with ethyl acetate (200 mL). The pH of mixture was adjusted to 2 with 2 N aqueous HCl. The organic layer was washed with brine, dried over Na$_2$SO$_4$, and concentrated under reduced pressure to afford 1.04 g (41%) of the title compound, cis-2-(3-chloro-phenyl)-1-oxo-2-aza-spiro[4.5]decane-7-carboxylic acid, as a white solid, which was used in the next step without further purification. ESI-MS m/z: 308 (M+H)$^+$. ESI-MS m/z: 306 (M–H)$^+$.

Step 6: cis-7-Amino-2-methyl-2-aza-spiro[4.5]decan-1-one

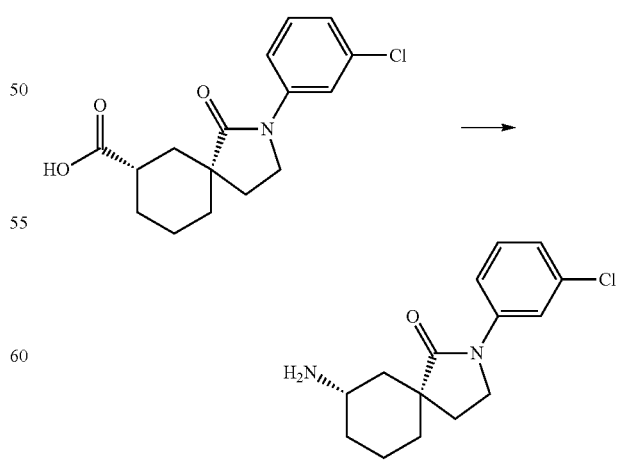

cis-2-(3-Chloro-phenyl)-1-oxo-2-aza-spiro[4.5]decane-7-carboxylic acid from step 6 (1.04 g, 3.41 mmol) was dissolved in toluene (17.9 mL), triethylamine (0.571 mL, 4.09 mmol) was added, followed by the addition of diphenylphosphonic azide (0.809 mL, 3.75 mmol). The mixture was stirred at rt for 1 h, and then heated at 90° C. for 2 hrs. The reaction mixture was cooled down to rt and poured into ice-cold aqueous 6N HCl (5.69 mL). After stirring at rt for 1 hr, the aqueous layer was separated. Aqueous HCl (1 M, 10.0 mL) was added into the organic layer, the mixture was stirred for 10 min, and the aqueous layer was separated. The combined aqueous layer was basified with solid $Na_2CO_3$ to pH 9, and extracted with $CH_2Cl_2$ (50 mL×2). The combined organic layer was dried over $Na_2SO_4$ and concentrated under reduced pressure. The residue was purified with RP-HPLC (Gradient: acetonitrile in water, 15-95% in 3.9 minutes with a cycle time of 5 min. Flow rate: 77 mL/min. Mobile phase additive: 10 mM of ammonium hydroxide. Column: Xbridge Prep C18 OBD (Waters Corp., Milford, Mass., USA), 19×50 mm, 5 um particle size) to afford 0.420 g (44%) of the title compound, cis-7-amino-2-methyl-1-aza-spiro[4.5]decan-1-one, as a white solid. LC/MS (method C): RT: 0.79 min; ESI-MS m/z: 279 $(M+H)^+$.

Intermediates 3 and 4

(5R,7R)-7-Amino-2-(3-chloro-phenyl)-2-aza-spiro[4.5]decan-1-one and (5S,7S)-7-Amino-2-(3-chloro-phenyl)-2-aza-spiro[4.5]decan-1-one Intermediate 3

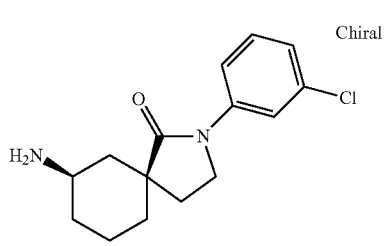

Intermediate 4

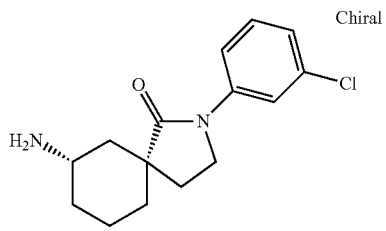

The racemic intermediate 2 (cis diastereomer) (420 mg) were resolved by HPLC (column: Chiralpak® OD (Diacel Chemical Industries, Inc., Osaka, Japan), 250×20 mm; mobile phase: 20% isopropanol, 80% hexane; flow rate: 14 mL/min; UV at 254 nm) to afford two enantiomers. The first peak (RT: 15.1 min) from the chiral HPLC was assigned as (5R,7R)-7-amino-2-(3-chloro-phenyl)-2-aza-spiro[4.5]decan-1-one (140 mg), and the second peak (RT: 20.7 min) from the chiral HPLC was assigned (5S,7S)-7-Amino-2-(3-chloro-phenyl)-2-aza-spiro[4.5]decan-1-one (120 mg).

Intermediate 5

7-Amino-2-(3-fluoro-phenyl)-2-aza-spiro[4.5]decan-1-one

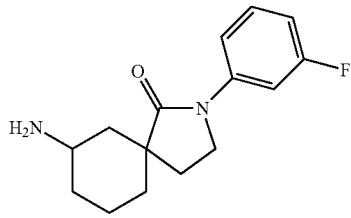 [SMILES: NC1CCCC2(CCN(c3cccc(F)c3)C2=O)C1]

Using the same experimental procedures described for intermediate 1, intermediate 5 was made from 12.5 mmol of 7-(2-Oxo-ethyl)-1,4-dioxa-spiro[4.5]decane-7-carboxylic acid ethyl ester and 15.0 mmol of 3-fluoroaniline; 1.30 g of crude title compound was obtained. The title compound is a mixture of cis and trans diastereoisomers (LC-MS (method C): RT 0.70 min (cis) and 0.73 min (trans); cis/trans: 1/2; purity (cis+trans) ($UV_{254}$): 94%). ESI-MS m/z: 263 $(M+H)^+$. It was used without further purification.

Intermediate 6 cis-7-Amino-2-(3-fluoro-phenyl)-2-aza-spiro[4.5]decan-1-one

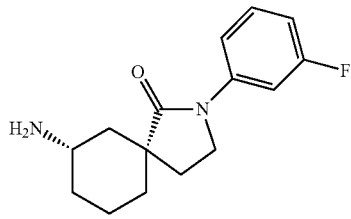 [SMILES: N[C@H]1CCC[C@]2(CCN(c3cccc(F)c3)C2=O)C1]

Using the same experimental procedures described in the synthesis of intermediate 2, intermediate 6 was made from 49.9 mmol of trans-1-(2-oxo-ethyl-cyclohexane-1,3-dicarboxylic acid diethyl ester and 59.9 mmol of m-fluoroaniline. As only a portion of an intermediate was used for the synthesis of the title compound, the amount and the yield obtained of the title compound are not provided. LC-MS (method C): RT: 0.70 min (cis); purity ($UV_{254}$): 95%. ESI-MS m/z: 263 $(M+H)^+$. It was used without further purification.

Intermediate 7

7-Amino-2-(6-methyl-pyridin-2-yl)-2-aza-spiro[4.5]decan-1-one

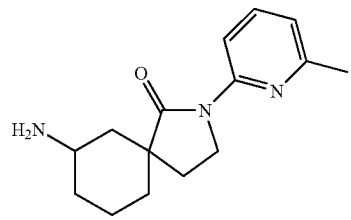 [SMILES: Cc1cccc(N2CCC3(CCCC(N)C3)C2=O)n1]

Using the same experimental procedures described in intermediate 1, intermediate 7 was made from 3.55 mmol of 7-(2-oxo-ethyl)-1,4-dioxa-spiro[4.5]decane-7-carboxylic acid ethyl ester and 3.91 mmol of 2-amino-6-methylpyridine. LC-MS (method D): RT: 0.84 min (cis and trans in one peak). ESI-MS m/z: 260 (M+H)$^+$. It was used without further purification.

Intermediate 8 cis-7-Amino-2-(6-methyl-pyridin-2-yl)-2-aza-spiro[4.5]decan-1-one

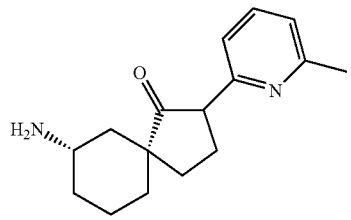

Using the same experimental procedures described in intermediate 2, intermediate 8 was made from 3.55 mmol of trans-1-(2-oxo-ethyl-cyclohexane-1,3-dicarboxylic acid diethyl ester and 3.91 mmol of 2-amino-6-methylpyridine LC-MS (method D): RT: 0.66 min; ESI-MS m/z: 260 (M+H)$^+$. It was used without further purification.

Intermediate 9 cis-7-Amino-2-(3-cyano-phenyl)-2-aza-spiro[4.5]decan-1-one

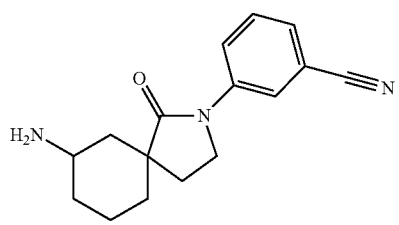 [SMILES: N#Cc1cccc(N2CCC3(CCCC(N)C3)C2=O)c1]

Using the same experimental procedures described in intermediate 1, intermediate 9 was made from 1.66 mmol of 7-(2-oxo-ethyl)-1,4-dioxa-spiro[4.5]decane-7-carboxylic acid ethyl ester and 1.99 mmol of 3-amino-benzonitrile, LC-MS (method A): two peaks were observed with RT of 0.40 min (cis) and 0.44 min (trans) respectively. ESI-MS m/z: 270 (M+H)$^+$. It was used without further purification.

Intermediate 10 cis-7-Amino-2-(2,4-dimethoxy-benzyl)-2-aza-spiro[4.5]decan-1-one hydrochloric acid salt

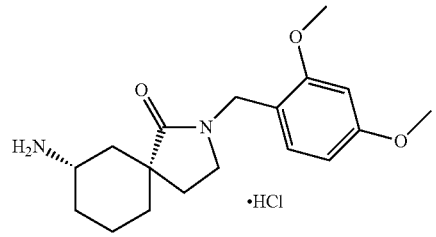 [SMILES: COc1ccc(CN2CC[C@]3(CCC[C@H](N)C3)C2=O)c(OC)c1 ; Cl]

Intermediate 10 was made via the process of Scheme 4, supra, as follows:

Step 1: Cyclohexane-1,3-dicarboxylic acid diethyl ester

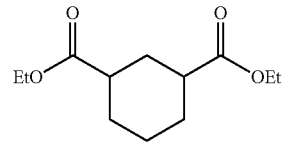

To a solution of 1,3-cyclohexanecarboxylic acid (340 g, 2.0 mol, mixture of cis/trans isomers) in ethanol (3.5 L), sulfuric acid (conc., 53 mL) was added dropwise at room temperature and the mixture was refluxed for 6.5 h. After cooling down, the solvent was removed, and the residue was diluted with ethyl acetate (1 L) and treated with cold aqueous NaOH until pH 9. The organic layer was washed with water, brine, dried with Na$_2$SO$_4$ and concentrated under vacuum to afford the title product (466 g, quant.) as a colorless oil, which was used in the next step without further purification.

Step 2: 1-Allyl-cyclohexane-1,3-dicarboxylic acid diethyl ester

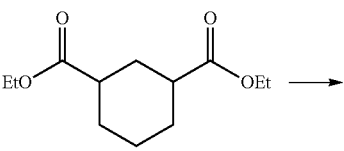

-continued

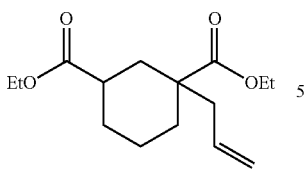

To a cooled solution (−78° C.) of N,N-diisopropylamine (272 mL, 1.94 mol) in anhydrous THF (1.4 L) was added n-BuLi (1.6 M in hexane, 1.21 L, 1.94 mol) over the period of one hour and 20 minutes. The mixture was stirred at 0° C. for one hour and again cooled down to −78° C. DMPU (834 mL, 6.92 mol) was added dropwise, followed by the addition of the solution of cyclohexane-1,3-dicarboxylic acid diethyl ester from step 1 (316 g, 1.38 mol) in THF (400 mL). The mixture was stirred at −78° C. for 2.5 hours, and then allyl bromide (132 mL, 1.52 mol) was added. The mixture was warmed up to rt slowly and stirred at rt overnight. The mixture was quenched with ice-cold aqueous HCl (1 N, 1 L), diluted with ethyl acetate (30 mL) and extracted. The organic layer was washed with water (4×1.5 L), brine, dried over Na₂SO₄ and concentrated under reduced pressure to afford 371 g of the title compound as a thick oil, which was used in the next step without further purification.

Step 3: 1-(2,3-dihydroxy-propyl)-cyclohexane-1,3-dicarboxylic acid diethyl ester

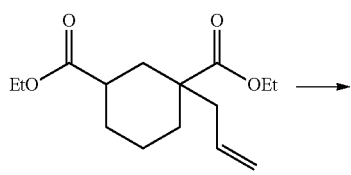

To a solution of 1-allyl-cyclohexane-1,3-dicarboxylic acid diethyl ester from step 2 (250 g, 0.93 mol) in t-butanol (2.3 L) and water (2.3 L) was added potassium ferricyanide (920 g, 2.79 mol), potassium carbonate (386 g, 2.79 mol), potassium osmate dihydrate (4.75 g, 13 mmol) and quinuclidine (0.073 g, 7.0 mmol). The resulting dark colored solution was stirred at rt overnight and then quenched with portion-wise addition of sodium sulfite (1.05 kg, 8.37 mol). After dilution with ethyl acetate, it was extracted, washed with water and brine, dried over Na₂SO₄, and concentrated under reduced pressure. The resulting residue (224 g) was used in the next step without delay and without further purification.

Step 4: trans-1-(2-oxo-ethyl)-cyclohexane-1,3-dicarboxylic acid diethyl ester

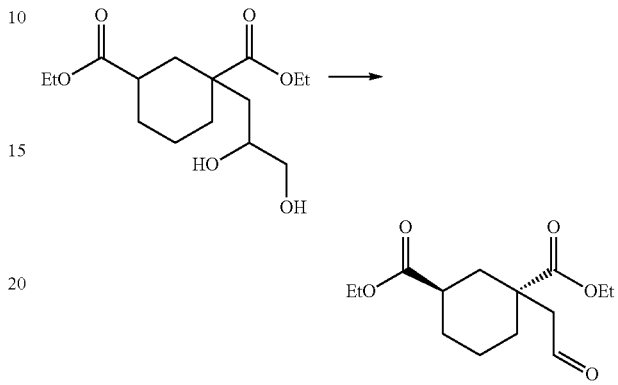

To a solution of 1-(2,3-dihydroxy-propyl)-cyclohexane-1,3-dicarboxylic acid diethyl ester from step 3 (224 g, 0.74 mol) in THF (0.74 L), t-butanol (1.48 L) and water (1.48 L) was added sodium bicarbonate (560 g, 6.66 mol), followed by the portion-wise addition of sodium periodate (475 g, 2.22 mol). The resulting white slurry was stirred at rt for two hours. The white solid was filtered off and washed with ethyl acetate. The organic layer of the filtrate was washed with a saturated aqueous solution of sodium sulfite, water and brine, dried over Na₂SO₄, and concentrated under reduced pressure. The resulting residue was purified by silica gel chromatography (20% ethyl acetate in hexane) to afford 87 g (35%, combined yield of steps 1 and 2) of the title compound as a thick oil.

Step 5: trans-1-[2-(3,5-dimethoxy-benzylamino)-ethyl]-cyclohexane-1,3-dicarboxylic acid diethyl ester

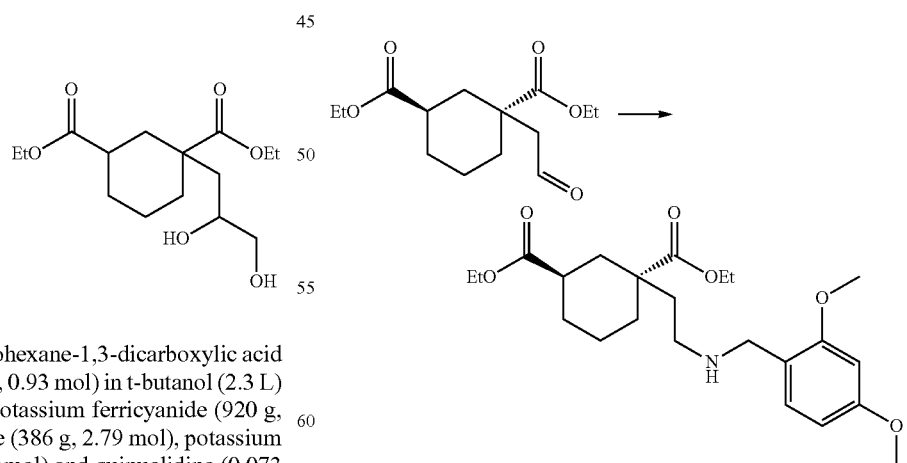

To a solution of trans-1-(2-oxo-ethyl)-cyclohexane-1,3-dicarboxylic acid diethyl ester from step 4 (89.0 g, 329 mmol) and 2,4-dimethoxybenzylamine (59.4 mL, 395 mmol) in 1,2-dichloroethane (659 mL) was added acetic acid (3.80 mL, 65.9 mmol). The mixture was stirred at room temperature for 1.5 hours. Then sodium triacetoxyborohydride (102.8 g, 461 mmol) was added portion-wise and stirred again at rt for 2.5 hours. The mixture was quenched with crushed ice, diluted with dichloromethane and extracted. The organic layer was washed with water and brine, dried over $Na_2SO_4$, and concentrated under reduced pressure. The resulting residue was purified by silica gel chromatography (Solvent: 10% methanol in ethyl acetate) to afford 58.2 g (42%) of the title compound, 1-[2-(3,5-dimethoxy-benzylamino)-ethyl]-cyclohexane-1,3-dicarboxylic acid diethyl ester, as a yellow gum. $^1$H NMR (400 MHz, CDCl$_3$): δ7.07-7.21 (m, 1 H), 6.34-6.60 (m, 3 H), 4.11 (q, J=7.0 Hz, 4 H), 3.68-3.91 (m, 8 H), 2.50-2.79 (m, 2 H), 2.27-2.50 (m, 2 H), 2.15 (d, J=12.9 Hz, 1 H), 1.97 (s, 2 H), 1.55-1.95 (m, 4 H), 1.00-1.45 (m, 8 H).

Step 6: cis-2-(2,4-dimethoxy-benzyl)-1-oxo-2-aza-spiro[4.5]decan-7-carboxylic acid

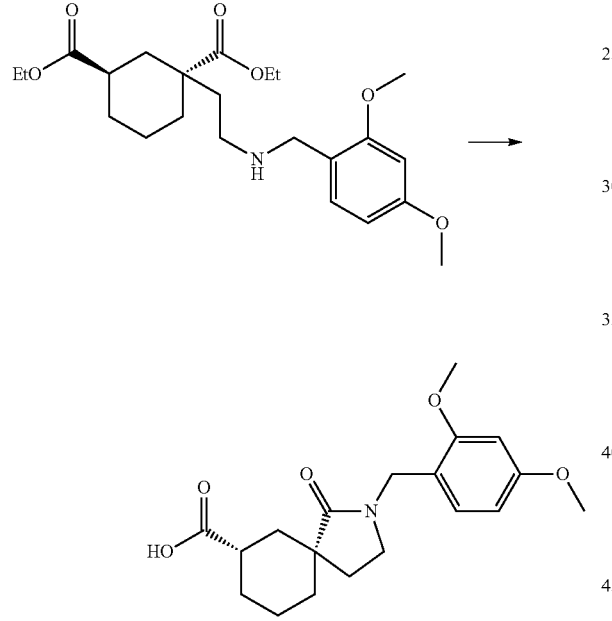

To a cooled (0° C.) ethanol (0.7 L) was added sodium hydride (60% in mineral oil, 16.2 g, 406 mmol) portion-wise. The mixture was stirred at rt for 30 min to get clear solution. Then a solution of 1-[2-(3,5-dimethoxy-benzylamino)-ethyl]-cyclohexane-1,3-dicarboxylic acid diethyl ester from step 5 (57.0 g, 135 mmol) in ethanol (0.7 L) was added slowly and the mixture was refluxed for 16 hours. The resulting mixture was concentrated under reduced pressure at rt and then diluted with ethyl acetate, washed with 1N HCl solution. The organic layer was washed with water and brine, dried over $Na_2SO_4$, and concentrated under reduced pressure. The residue was purified by silica gel chromatography (solvent: 10% methanol in dichloromethane) to yield 20.0 g (43%) of the title compound, cis-2-(2,4-dimethoxy-benzyl)-1-oxo-2-aza-spiro[4.5]decan-7-carboxylic acid. $^1$H NMR (400 MHz, CDCl$_3$) δ 6.98-7.13 (m, 1 H), 6.29-6.56 (m, 2 H), 4.21-4.56 (m, 2 H), 3.79 (d, J=5.1 Hz, 6 H), 2.82-3.33 (m, 2 H), 1.28-2.51 (m, 11 H).

Step 7: cis-7-amino-2-(2,4-dimethoxy-benzyl)-2-aza-spiro[4.5]decan-1-one

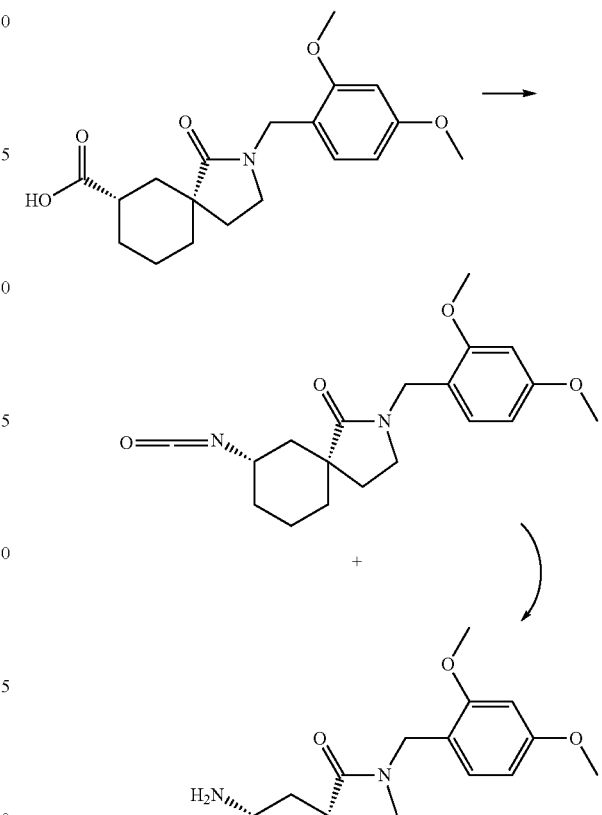

To a solution of cis-2-(2,4-dimethoxy-benzyl)-1-oxo-2-aza-spiro[4.5]decan-7-carboxylic acid from step 6 (20.0 g, 57.6 mmol) in toluene (290 mL) was added triethyl amine (9.63 mL, 69.1 mmol), followed by the addition of diphenyl phosphoryl azide (13.7 mL, 63.3 mL). The mixture was stirred at room temperature for 1.5 hours and then heated at 90° C. for three hours. The reaction mixture was cooled down to 0° C., treated with slow addition of HCl (6N, 50 mL), and stirred at rt for 1 hour. The resulting mixture was diluted with water and two layers were separated. The aqueous layer was cooled down to 0° C., neutralized with 40% aqueous KOH solution to pH ~7, then basicified with saturated NaHCO$_3$ and extracted with ethyl acetate, washed with brine, dried with Na$_2$SO$_4$ and concentrated to get 4.3 g of crude cis-7-amino-2-(2,4-dimethoxy-benzyl)-2-aza-spiro[4.5]decan-1-one. The organic layer was washed with water, brine, dried with Na$_2$SO$_4$ and concentrated. NMR of the resulting residue (35 g) showed that it was cis-2-(2,4-dimethoxy-benzyl)-7-isocyanato-2-aza-spiro[4.5]decan-1-one (contaminated with DPPA), which was not hydrolyzed. $^1$H NMR (400 MHz, CDCl$_3$) δ 1.02-1.97 (m, 10 H), 2.65-3.14 (m, 3 H), 3.68-3.82 (m, 6 H), 4.20 (d, 1 H), 4.39-4.52 (m, 1 H), 6.17-6.54 (m, 2 H), 6.83-7.09 (m, 1 H).

To a solution of cis-2-(2,4-dimethoxy-benzyl)-7-isocyanato-2-aza-spiro[4.5]decan-1-one (34.8 g, contaminated with DPPA) in THF (313 mL) was added HCl solution (6N, 103 mL) and stirred at rt for 14 hours. After cooling down to 0° C. it was basified with KOH (40%, until pH ~9) and extracted with EtOAc, washed with water, brine, dried with Na$_2$SO$_4$ and concentrated. Combined with the residue obtained previously from the aqueous layer, it was purified by chromatography using 10% methanol in dichloromethane to get 11.2 g (61%) of the title compound, as a white solid. $^1$H NMR (400 MHz, CDCl$_3$) δ 0.94-2.10 (m, 10 H), 2.67 (t, J=11.33 Hz, 1 H), 2.94-3.25 (m, 2 H), 3.71-3.84 (m, 6 H), 4.42 (s, 2 H), 6.26-6.59 (m, 2 H), 7.08 (d, J=8.21 Hz, 1 H)

Step 8: cis-7-Amino-2-(2,4-dimethoxy-benzyl)-2-aza-spiro[4.5]decan-1-one Hydrochloric acid salt

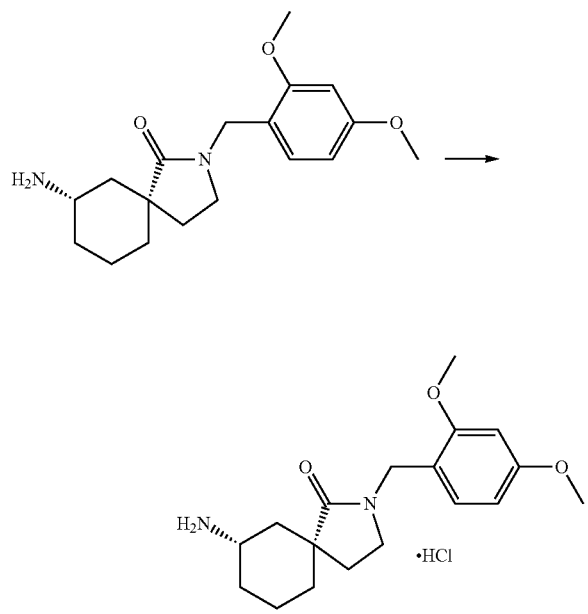

To a solution of free base cis-7-amino-2-(2,4-dimethoxy-benzyl)-2-aza-spiro[4.5]decan-1-one from step 8 (11.16 g, 35.04 mmol) in dichloromethane (100 mL) at 0° C. was added HCl solution (4 M in dioxane, 25 mL) and stirred at 0° C. for 30 minutes. The resulting white slurry was concentrated under reduced pressure at ~25-30° C. The white solid was dried under reduced pressure for 18 hours at room temperature to afford 12.73 g (quantitative yield) of the title compound, cis-7-amino-2-(2,4-dimethoxy-benzyl)-2-aza-spiro[4.5]decan-1-one hydrochloric acid salt. $^1$H NMR (400 MHz, DMSO-d$_6$): δ 1.09-2.21 (m, 10 H), 2.83-3.33 (m, 3 H), 3.75 (d, J=5.46 Hz, 6 H), 4.27 (s, 2 H), 6.48 (dd, J=8.39, 2.15 Hz, 1 H), 6.56 (d, J=2.34 Hz, 1 H), 6.97 (d, J=8.20 Hz, 1 H). MS: m/z 319.13 (M+H)$^+$. Elemental analysis: calculated for C$_{18}$H$_{26}$N$_2$O$_3$.HCl.0.5H$_2$O C, 59.41; H, 7.76; N, 7.70. Found: C, 59.41; H, 7.84; N, 17.81.

Step 7b: cis-7-amino-2-(2,4-dimethoxy-benzyl)-2-aza-spiro[4.5]decan-1-one hydrochloric acid salt Alternatively Step 7 can be carried out as described next, which eliminates Step 8.

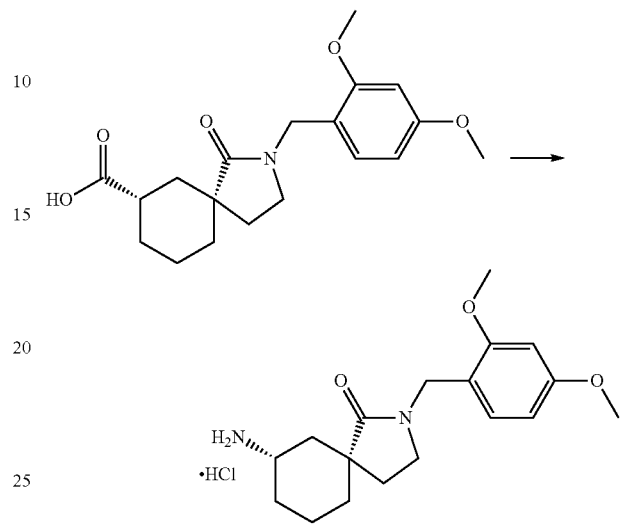

To a solution of cis-2-(2,4-dimethoxy-benzyl)-1-oxo-2-aza-spiro[4.5]decan-7-carboxylic acid from step 6 (20.0 g, 57.6 mmol) in toluene (300 mL) was added triethyl amine (9.63 mL, 69.1 mmol), followed by the addition of diphenyl phosphoryl azide (12.4 mL, 57.6 mmol). The mixture was stirred at room temperature for 2 hours and then heated at 90° C. for 3.5 hours. The reaction mixture was cooled down rt, and poured into ice-cold aqueous 6N HCl (120 mL). The mixture was stirred at rt overnight. The solid formed was filtered, washed with toluene (50 mL×2), and dried under oven to afford 16.6 g (81%) of the title compound cis-7-amino-2-(2,4-dimethoxy-benzyl)-2-aza-spiro[4.5]decan-1-one hydrochloric acid salt. $^1$H NMR (400 MHz, DMSO-d$_6$): δ 6.97 (d, J=8.20 Hz, 1 H), 6.56 (d, J=2.34 Hz, 1 H), 6.48 (dd, J=8.39, 2.15 Hz, 1 H), 4.27 (s, 2 H), 3.75 (d, J=5.46 Hz, 6 H), 2.83-3.33 (m, 3 H), 1.09-2.21 (m, 10 H). ESI-MS m/z: 319.13 (M+H)$^+$. Elemental analysis: calculated for C$_{18}$H$_{26}$N$_2$O$_3$.HCl.0.5H$_2$O C, 59.41; H, 7.76; N, 7.70. Found: C, 59.41; H, 7.84; N, 17.81. The aqueous layer of the filtrate was cooled down to 0° C., neutralized with solid K$_2$CO$_3$ to pH 7, extracted with CH$_2$Cl$_2$. The organic layer was washed with brine, dried over Na$_2$SO$_4$ and concentrated under reduced pressure to afford 1.4 g of free base cis-7-amino-2-(2,4-dimethoxy-benzyl)-2-aza-spiro[4.5]decan-1-one. $^1$H NMR (400 MHz, CDCl$_3$) δ 7.08 (d, J=8.2 Hz, 1 H), 6.26-6.59 (m, 2 H), 4.42 (s, 2 H), 3.71-3.84 (m, 6 H), 2.94-3.25 (m, 2 H), 2.67 (t, J=11.3 Hz, 1 H), 0.94-2.10 (m, 10 H). ESI-MS m/z: 319.13 (M+H)$^+$.

Intermediate 11

[cis-2-(4-Methoxy-benzyl)-1-oxo-2-aza-spiro[4.5]dec-7-yl]-carbamic acid tert-butyl ester

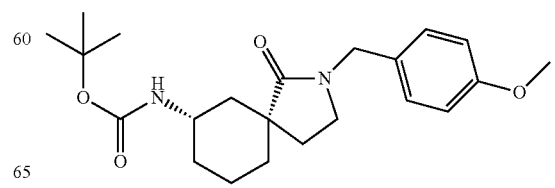

Step 1: trans-2-(4-Methoxy-benzyl)-1-oxo-2-aza-spiro[4.5]decane-7-carboxylic acid ethyl ester

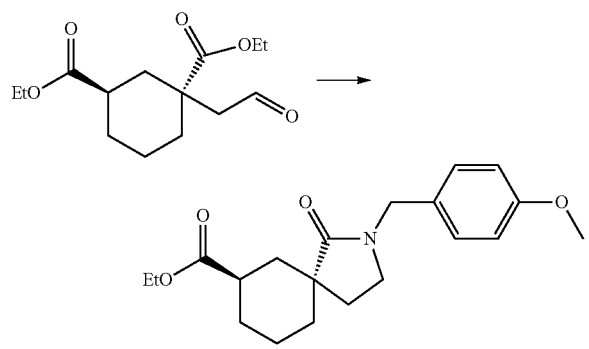

To a solution of trans-1-(2-oxo-ethyl)-cyclohexane-1,3-dicarboxylic acid diethyl ester from step 4 for intermediate 10 (4.36 g, 16.1 mmol) and 4-methoxybenzylamine (2.32 g, 16.9 mmol) in THF (100 mL) was added sodium triacetoxyborohydride (5.13 g, 24.2 mmol). The mixture was stirred at rt overnight and then quenched with cold saturated aqueous NaHCO$_3$. The aqueous layer was extracted with DCM (3×50 mL). The combined organic layers were concentrated under reduced pressure. The residue was dissolved in DCM, washed sequentially with 1N HCl (2×50 mL), saturated aqueous NaHCO$_3$ and brine, dried over MgSO$_4$, filtered, and concentrated under reduced pressure to give 5.10 g (91.6%) of the title compound, trans-2-(4-methoxy-benzyl)-1-oxo-2-aza-spiro[4.5]decane-7-carboxylic acid ethyl ester. $^1$H NMR (400 MHz, CDCl$_3$): δ 7.14 (d, J=8.6 Hz, 2H), 6.85 (d, J=8.7 Hz, 2H), 4.40 (d, J=14.5 Hz, 1H), 4.31 (d, J=14.5 Hz, 1H), 4.11 (q, J=7.2 Hz, 2H), 3.80 (s, 3H), 3.24 (tt, J=3.9, 10.9 Hz, 1H), 3.07-3.15 (m, 2H), 1.31-2.08 (m, 10H), 1.25 (t, J=7.1 Hz, 2H). ESI-MS m/z: 346 (M+H)$^+$. It was used in the next step without further purification.

Step 2: cis-2-(4-Methoxy-benzyl)-1-oxo-2-aza-spiro[4.5]decane-7-carboxylic acid ethyl ester

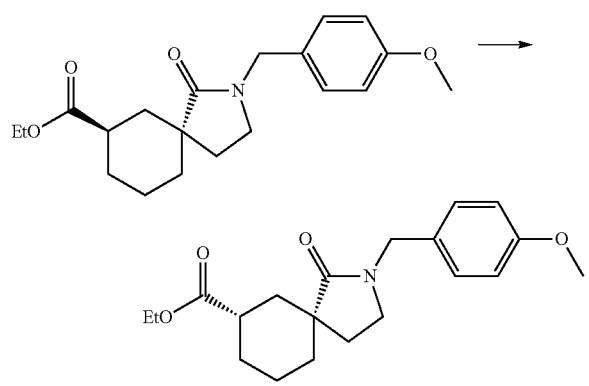

To a solution of trans-2-(4-methoxy-benzyl)-1-oxo-2-aza-spiro[4.5]decane-7-carboxylic acid ethyl ester from step 2 (5.10 g, 14.74 mmol) in anhydrous ethanol (80 mL) at 0° C. was added NaH (60% in mineral oil; 0.968 g) portion-wise. The reaction mixture was stirred at 65° C. overnight, then cooled to rt, and concentrated under reduced pressure. The residue was dissolved in water (20 mL) and the aqueous layer was extracted with DCM (3×30 mL). The combined organic layers were washed with saturated aqueous NaHCO$_3$ and brine, filtered, and concentrated under reduced pressure. The resulting residue was chromatographed on silica gel (0 to 50% ethyl acetate in hexanes) to give 2.56 g (46%) of the title compound, cis-2-(4-methoxy-benzyl)-1-oxo-2-aza-spiro[4.5]decane-7-carboxylic acid ethyl ester. $^1$H NMR (400 MHz, CDCl$_3$): δ 7.14 (d, J=8.6 Hz, 2H), 6.85 (d, J=8.7 Hz, 2H), 4.39 (s, 2H), 4.12 (q, J=7.1 Hz, 2H), 3.79 (s, 3H), 3.07-3.20 (m, 2H), 2.32 (tt, J=3.4, 12.6 Hz, 1H), 1.62-2.01 (m, 7H), 1.29-1.52 (m, 3H), 1.24 (t, J=7.1 Hz, 2H). ESI-MS m/z: 346 (M+H)$^+$.

The aqueous layer was acidified to ~pH2 with 1N HCl, extracted with DCM (3×30 mL). The combined organic layers were dried over MgSO4, filtered, and concentrated to give 0.79 g (15%) of 2-(4-methoxy-benzyl)-1-oxo-2-aza-spiro[4.5]decane-7-carboxylic acid as a mixture of two diastereomers.

Step 3: cis-2-(4-Methoxy-benzyl)-1-oxo-2-aza-spiro[4.5]decane-7-carboxylic acid

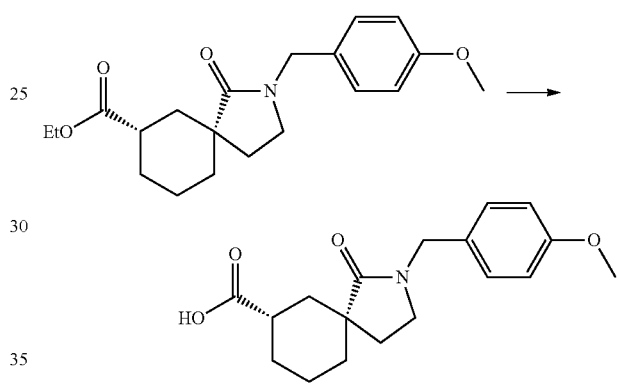

To a solution of cis-2-(4-methoxy-benzyl)-1-oxo-2-aza-spiro[4.5]decane-7-carboxylic acid ethyl ester from step 2 (1.76 g, 5.10 mmol) in THF (45 mL) was added 1.0 M of LiOH in water (15 mL) at rt. The reaction mixture was stirred at rt overnight and THF was evaporated under reduced pressure. The remaining aqueous layer was washed with ethyl ether (20 mL), acidified to pH2 with 1N HCl. The resulting precipitates were filtered, washed with water (3×), and dried under reduced pressure to give 1.4 g (87%) of the title compound, cis-2-(4-methoxy-benzyl)-1-oxo-2-aza-spiro[4.5]decane-7-carboxylic acid, as a white solid. $^1$H NMR (400 MHz, CDCl$_3$): δ 7.14 (d, J=8.6 Hz, 2H), 6.85 (d, J=8.7 Hz, 2H), 4.39 (s, 2H), 3.80 (s, 3H), 3.08-3.23 (m, 2H), 2.36 (tt, J=3.4, 12.4 Hz, 1H), 1.63-2.06 (m, 7H), 1.29-1.55 (m, 3H). ESI-MS m/z: 318 (M+H)$^+$.

Step 4: [cis-2-(4-Methoxy-benzyl)-1-oxo-2-aza-spiro[4.5]dec-7-yl]-carbamic acid tert-butyl ester

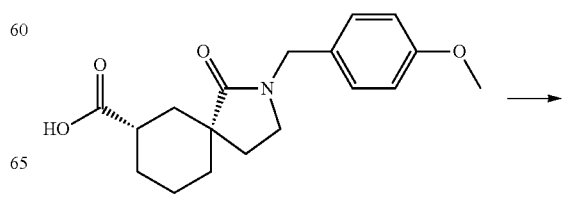

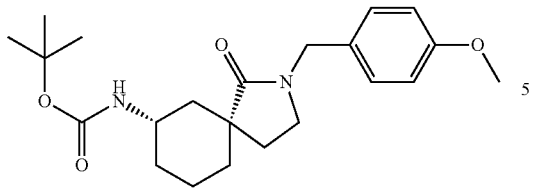

cis-2-(4-Methoxy-benzyl)-1-oxo-2-aza-spiro[4.5]decane-7-carboxylix acid from step 3 (0.510 g, 1.61 mmol) was dissolved in toluene (20.0 mL). Triethylamine (0.246 mL, 1.77 mmol) was added, followed by the addition of diphenylphosphonic azide (0.381 mL, 1.77 mmol). The reaction mixture was stirred at rt for 1 hr and then heated at 90° C. for 2 hours. The mixture was cooled to rt, tert-butyl alcohol (6.15 mL, 64.3 mmol) was added, and the mixture was then heated at 90° C. for 24 hrs. The reaction mixture was cooled down to rt and concentrated under reduced pressure. The resulting residue was diluted with ethyl acetate (100 mL), washed with saturated aqueous NaHCO$_3$, water and brine, dried over Na$_2$SO$_4$, and concentrated under reduced pressure. The residue was purified by silica gel chromatography (hexane/ethyl acetate: 30/70) to afford 0.50 g (80%) of the title compound, cis-2-(4-methoxy-benzyl)-1-oxo-2-aza-spiro[4.5]dec-7-yl]-carbamic acid tert-butyl ester. $^1$H NMR (400 MHz, CDCl$_3$): δ 7.13 (d, J=8.4 Hz, 2H), 6.85 (d, J=8.7 Hz, 2H), 4.71 (bs, 1H), 4.38 (m, 2H), 3.79 (s, 3H), 3.55 (bs, 1H), 3.07-3.18 (m, 2H), 1.35-1.98 (m, 18H), 1.13-1.22 (m, 1H). ESI-MS m/z: 389 (M+H)$^+$.

Intermediate 12

(cis-1-Oxo-2-aza-spiro[4.5]dec-7-yl)-carbamic acid tert-butyl ester

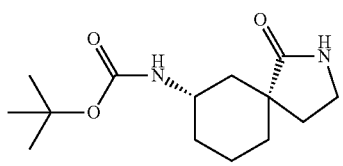 [SMILES: CC(C)(C)OC(=O)N[C@H]1CCC[C@]2(CCNC2=O)C1]

To a round bottom flask was added [cis-2-(4-methoxy-benzyl)-1-oxo-2-aza-spiro[4.5]dec-7-yl]-carbamic acid tert-butyl ester (intermediate 11) (0.500 g, 1.29 mmol,) and acetonitrile (25 mL). Ceric ammonium nitrate (2.12 g, 3.86 mmol) in water (10.0 mL) was added. The crude mixture was stirred at rt for one day and then diluted with CH$_2$Cl$_2$ (100 mL). The organic layer was washed with water and brine, dried with Na$_2$SO$_4$ and concentrated under reduced pressure. The residue was purified by silica gel chromatography (CH$_2$Cl$_2$/MeOH: 9/1) to afford 0.252 g (73%) of the title compound, cis-1-oxo-2-aza-spiro[4.5]dec-7-yl)-carbamic acid tert-butyl ester. $^1$H NMR (400 MHz, CDCl$_3$): δ 6.31 (bs, 1H), 4.66 (d, J=7.0 Hz, 1H), 3.48-3.60 (bs, 1H), 3.27-3.38 (m, 2H), 1.92-2.16 (m, 3H), 1.74-1.84 (m, 2H), 1.43-1.60 (m, 12H), 1.08-1.30 (m, 12H). ESI-MS m/z: 269 (M+H)$^+$.

Intermediate 12 was also made as follows:

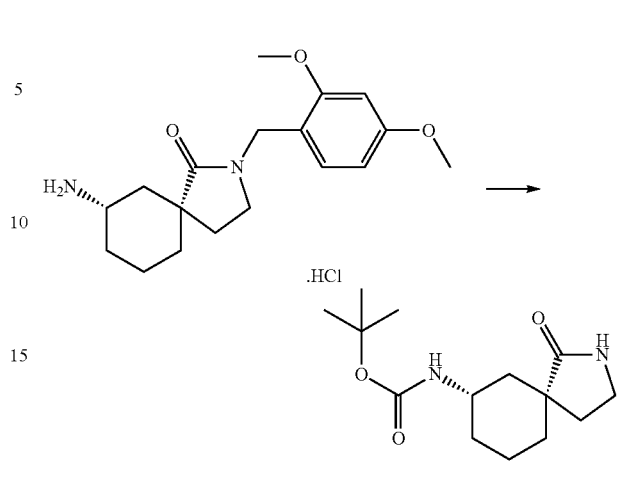

To a round bottom flask was added cis-7-amino-2-(2,4-dimethoxy-benzyl)-2-aza-spiro[4.5]decan-1-one HCl salt from step 8 for intermediate 10 (3.00 g, 8.46 mmol, intermediate 10) and trifluoroacetic acid (10.0 mL). The mixture was refluxed for 1.5 hrs, and then cooled down to rt and concentrated under reduced pressure. The resulting residue was diluted with CH$_2$Cl$_2$ (10 mL) and concentrated under reduced pressure. This procedure was repeated twice to remove excess trifluoroacetic acid. The resulting residue was dissolved in THF (20.0 mL), di-tert-butyldicarbonate (2.03 g, 9.30 mmol) and triethylamine (3.53 mL, 25.4 mmol) were added. After stirring at rt overnight, the reaction mixture was filtered through Celite®, and the filtrate was concentrated under reduced pressure to afford the title compound. LC-MS (method C): RT: 0.94 min. ESI-MS m/z: 269 (M+H)$^+$. It was used without further purification.

Intermediate 13 cis-2-(3-Fluoro-phenyl)-1-oxo-2-aza-spiro[4.5]dec-7-yl]-carbamic acid tert-butyl ester

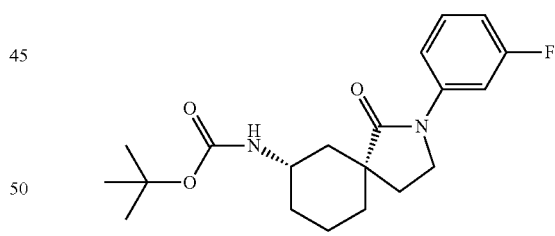

A mixture of (cis-1-oxo-2-aza-spiro[4.5]dec-7-yl)-carbamic acid tert-butyl ester (0.036 g, 0.13 mmol, intermediate 12), 3-fluoroiodobenzene (0.030 g, 0.13 mmol), copper(I) iodide (0.013 g, 0.067 mmol), potassium carbonate (0.037 g, 0.27 mmol) and N,N' dimethyl-ethane-1,2-diamine (0.012 g, 0.13 mmol) in 1,4-dioxane (2.0 mL, 26 mmol) was heated via microwave (Biotage) at 160° C. for 2 hours. The mixture was cooled to rt and passed through a layer of Celite®. The filtrate was concentrated under reduced pressure. The residue was purified with preparative TLC (hexane/ethyl acetate: 1/1) to afford 0.030 g (62%) of the title compound, cis-2-(3-fluorophenyl)-1-oxo-2-aza-spiro[4.5]dec-7-yl]-carbamic acid tert-butyl ester. $^1$H NMR (400 MHz, CDCl$_3$): δ 7.57 (dt, J=11.4, 2.3 Hz, 1H), 7.27-7.37 (m, 2H), 6.81-6.87 (m, 1H), 4.60 (bs, 1H), 3.71-3.82 (m, 2H), 3.58 (bs, 1H), 1.95-2.22 (m, 3H), 1.80-1.90 (m, 2H), 1.60-1.70 (m, 1H), 1.47-1.57 (m, 3H), 1.44 (s, 9H), 1.12-1.23 (m, 1H). ESI-MS m/z: 363 (M+H)⁺.

Intermediate 14 cis-[2-(6-Methyl-pyrazin-2-yl)-1-oxo-2-aza-spiro[4.5]dec-7-yl]-carbamic acid tert-butyl ester

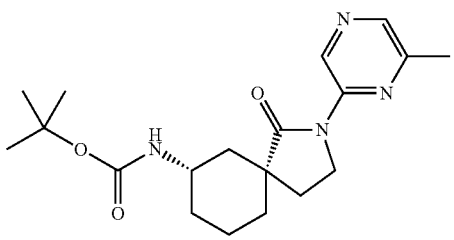 [SMILES: Cc1cncc(N2CC[C@]3(CCC[C@H](NC(=O)OC(C)(C)C)C3)C2=O)n1]

Using the same experimental procedures described for intermediate 13, intermediate 14 was made at 0.28 mmol reaction scale from intermediate 12 and 2-chloro-6-methylpyrazine, and 0.040 g (40%) of the title compound was obtained. $^1$H NMR (400 MHz, CDCl$_3$): δ9.51 (s, 1H), 8.18 (s, 1H), 4.57 (d, J=7.9 Hz, 1H), 3.90-4.05 (m, 2H), 3.59 (s, 1H), 2.49 (s, 3H), 1.96-2.22 (m, 3H), 1.81-1.93 (m, 2H), 1.47-1.69 (m, 4H), 1.44 (s, 9H), 1.17 (qd, J=12.4, 4.1 Hz, 1H). ESI-MS m/z: 361 (M+H)⁺.

Intermediate 15 cis-[2-(3,5-Difluoro-phenyl)-1-oxo-2-aza-spiro[4.5]dec-7-yl]-carbamic acid tert-butyl ester

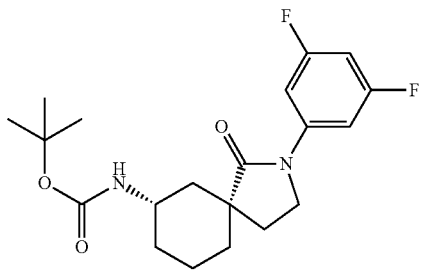 [SMILES: CC(C)(C)OC(=O)N[C@H]1CCC[C@]2(CCN(c3cc(F)cc(F)c3)C2=O)C1]

Using the same experimental procedures described for intermediate 13, intermediate 15 was made at 0.47 mmol reaction scale from intermediate 12 and 1-bromo-3,5-difluorobenzene, and 0.030 g (17%) of product was obtained. $^1$H NMR (400 MHz, CDCl$_3$) δ 7.29 (dd, J=9.8, 2.2 Hz, 2H), 6.59 (tt, J=8.9, 2.2 Hz, 1H), 4.54 (d, J=8.1 Hz, 1H), 3.68-3.79 (m, 2H), 3.58 (bs, 1H), 1.96-2.24 (m, 3H), 1.80-1.90 (m, 2H), 1.40-1.68 (m, 13H), 1.17 (qd, J=12.4, 4.0 Hz, 1H). ESI-MS m/z: 381 (M+H)⁺.

Intermediate 16 cis-[1-oxo-2-(6-trifluoromethyl-pyridin-2-yl)-2-aza-spiro[4.5]dec-7-yl]-carbamic acid tert-butyl ester

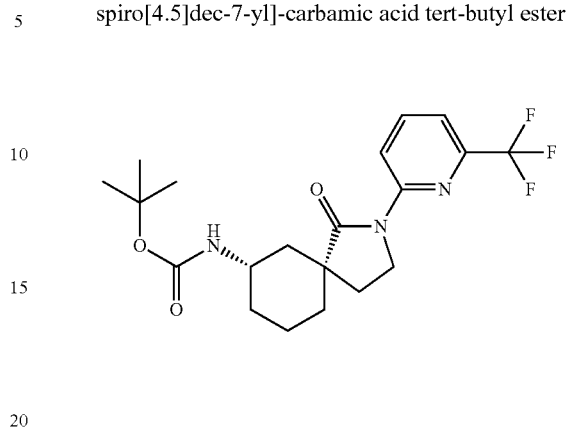

Using the same experimental procedures described for intermediate 13, intermediate 16 was made at 0.34 mmol reaction scale from intermediate 12 and 2-bromo-6-(trifluoromethyl)pyridine. LC-MS (Method C): RT: 1.66 min; ESI-MS m/z: 414 (M+H)⁺. It was used without further purification.

Intermediate 17 cis-2-(2-Methyl-pyrimidin-4-yl)-1-oxo-2-aza-spiro[4.5]dec-7-yl]carbamic acid tert-butyl ester

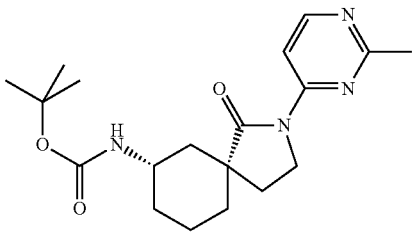 [SMILES: Cc1nccc(N2CC[C@]3(CCC[C@H](NC(=O)OC(C)(C)C)C3)C2=O)n1]

Intermediate 17 was prepared via the process of Scheme 2, supra, as follows:

A mixture of 4-chloro-2-methylpyrimidine (0.192 g, 1.49 mmol), (cis-1-oxo-2-aza-spiro[4.5]dec-7-yl)-carbamic acid tert-butyl ester (0.40 g, 1.49 mmol, intermediate 12), tris(dibenzylideneacetone)dipalladium(0) chloroform adduct (0.154 g, 0.149 mmol), dicesium carbonate (0.680 g, 2.09 mmol) and racemic BINAP (0.278 g, 0.447 mmol) in toluene (5.0 mL) was heated at 80° C. for 4 hours. The reaction mixture was cooled to rt. The catalyst was filtered off and the filtrate was concentrated under reduce pressure. The residue was purified by silica gel chromatography (0-30% ethyl acetate in hexane) to give 0.318 g (59%) of the title compound, cis-2-(2-methyl-pyrimidin-4-yl)-1-oxo-2-aza-spiro[4.5]dec-7-yl]carbamic acid tert-butyl ester, as a white solid. $^1$H NMR (400 MHz, CDCl$_3$) δ 8.49 (d, J=5.8 Hz, 2H), 8.17 (d, J=5.8 Hz, 1H), 4.52 (bs, 1H), 3.92-4.13 (m, 2H), 3.58 (bs, 1H), 2.64 (s, 3H), 1.97-2.17 (m, 3H), 1.80-1.92 (m, 2H), 1.47-1.63 (m, 4H), 1.44 (s, 9H), 1.11-1.22 (m, 1H). ESI-MS m/z: 361 (M+H)+.

Intermediate 18 cis-6-Methyl-pyridine-2-carboxylic acid (1-oxo-2-aza-spiro[4.5]dec-7-yl)-amide

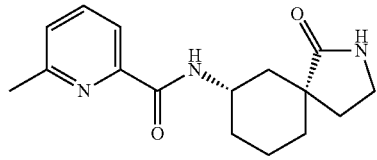 [SMILES: Cc1cccc(C(=O)N[C@H]2CCC[C@]3(CCNC3=O)C2)n1]

Route 1: Intermediate 18 was prepared via the process of Scheme 10, supra, as follows:

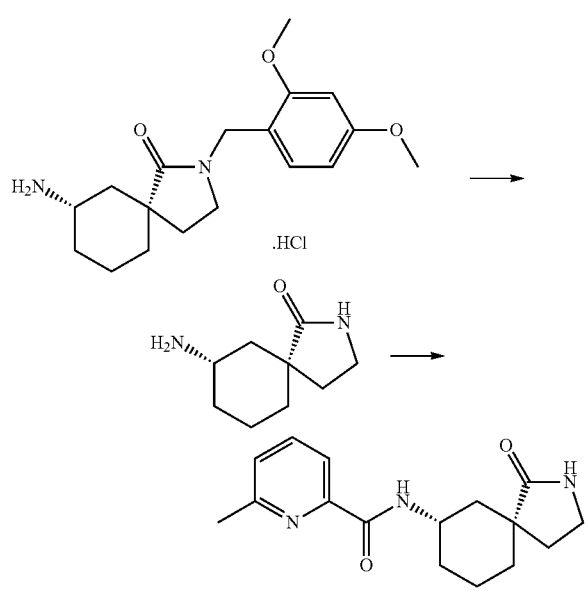

To a round bottom flask was added cis-7-amino-2-(2,4-dimethoxy-benzyl)-2-aza-spiro[4.5]decan-1-one HCl salt from step 8 for intermediate 10 (2.00 g, 5.64 mmol, intermediate 10) and trifluoroacetic acid (8.0 mL). The mixture was refluxed for 1.5 hrs, then cooled down to rt and concentrated under reduced pressure. The resulting residue was diluted with CH$_2$Cl$_2$ (10 mL) and concentrated under reduced pressure. This procedure was repeated twice to remove excess trifluoroacetic acid. The resulting residue was dissolved in CH$_2$Cl$_2$ (40.0 mL), 6-methylpicolinic acid (0.773 g, 5.64 mmol), and BOP (2.49 g, 5.64 mmol), and triethylamine (3.93 mL, 28.2 mmol) in CH$_2$Cl$_2$ (5.0 mL) were added. The reaction mixture was stirred at rt for 4 hours and then concentrated under reduced pressure. The residue was purified by silica gel chromatography (CH$_2$Cl$_2$/MeOH: 80/20) to afford 1.23 g (76%) of the title compound, cis-6-methyl-pyridine-2-carboxylic acid (1-oxo-2-aza-spiro[4.5]dec-7-yl)-amide, as a white solid. ESI-MS m/z: 288 (M+H)+.

Route 2: Intermediate 18 was also made via the process of Scheme 11, supra, as follows:

Step 1: cis-6-Methyl-pyridine-2-carboxylic acid [2-(4-methoxy-benzyl)-1-oxo-2-aza-Spiro[4.5]dec-7-yl]-amide

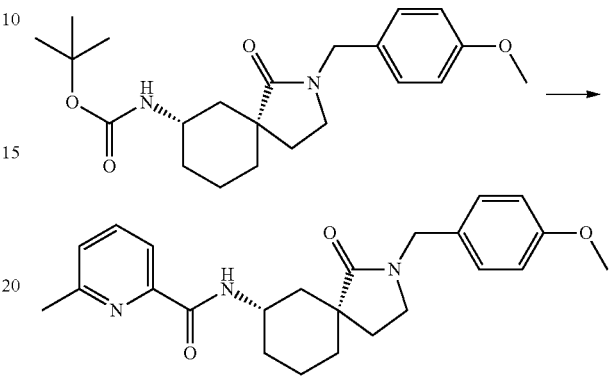

[cis-2-(4-methoxy-benzyl)-1-oxo-2-aza-spiro[4.5]dec-7-yl]-carbamic acid tert-butyl ester (0.50 g, 1.29 mmol, intermediate 11) was dissolved in CH$_2$Cl$_2$ (10.0 mL), and 4 M HCl/dioxane (3.2 mL) was added. The mixture was stirred at rt for 2 hrs and concentrated. The residue was dissolved in CH$_2$Cl$_2$ (20.0 mL), 6-methylpicolinic acid (0.176 g, 1.29 mmol), and BOP (0.569 g, 1.29 mmol), and triethylamine (0.538 mL, 3.86 mmol) in CH$_2$Cl$_2$ (5.0 mL) were added. The reaction mixture was stirred at rt for 4 hours and concentrated under reduced pressure. The residue was purified by silica gel chromatography (hexane/ethyl acetate: 3/7) to afford 0.48 g (91%) of the title compound, cis-6-methyl-pyridine-2-carboxylic acid [2-(4-methoxy-benzyl)-1-oxo-2-aza-spiro[4.5]dec-7-yl]-amide. $^1$H NMR (400 MHz, CDCl$_3$): δ 8.09 (d, J=8.6 Hz, 1H), 7.94 (d, J=7.1 Hz, 1H), 7.68 (t, J=7.6 Hz, 1H), 7.24 (d, J=7.4 Hz, 1H), 7.10-7.12 (m, 2H), 6.80-6.84 (m, 2H), 4.33-4.41 (m, 2H), 3.98-4.08 (m, 1H), 3.77 (s, 3H), 3.10-3.19 (m, 2H), 2.55 (s, 3H), 1.91-2.09 (m, 3H), 1.80-1.86 (m, 1H), 1.75-1.79 (m, 2H), 1.63-1.71 (m, 1H), 1.29-1.58 (m, 3H). ESI-MS m/z: 408 (M+H)+.

Step 2: cis-6-Methyl-pyridine-2-carboxylic acid (1-oxo-2-aza-spiro[4.5]dec-7-yl)-amide

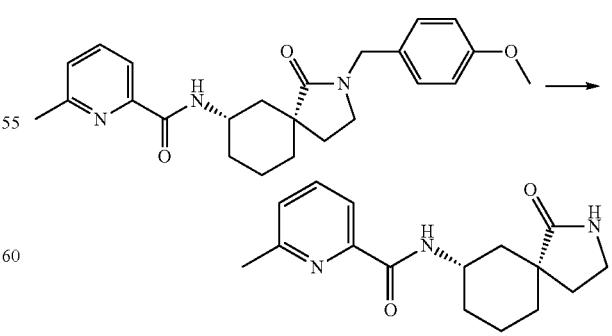

To a round bottom flask was added cis-6-methyl-pyridine-2-carboxylic acid [2-(4-methoxy-benzyl)-1-oxo-2-aza-spiro[4.5]dec-7-yl]-amide from step 1 (0.480 g, 1.18 mmol), acetonitrile (18.3 mL), and ceric ammonium nitrate (1.94 g, 3.53 mmol) in water (7.2 mL). The reaction mixture was stirred at rt for one day and then diluted with CH$_2$Cl$_2$ (100 mL). The organic layer was washed with water and brine, dried over Na$_2$SO$_4$, and concentrated under reduced pressure. The residue was purified by silica gel chromatography (CH$_2$Cl$_2$/MeOH: 4/1) to afford 0.210 g (61%) of title compound, cis-6-methyl-pyridine-2-carboxylic acid (1-oxo-2-aza-spiro[4.5]dec-7-yl)-amide, as a white solid. $^1$H NMR (400 MHz, CDCl$_3$) δ 8.08 (d, J=8.6 Hz, 1H), 7.96 (d, J=7.6 Hz, 1H), 7.70 (t, J=7.7 Hz, 1H), 7.25 (d, J=7.6 Hz, 1H), 6.23 (s, 1H), 4.00-4.10 (m, 1H), 3.30-3.39 (m, 2H), 2.56 (s, 3H), 2.15-2.23 (m, 1H), 2.07-2.14 (m, 2H), 1.81-1.87 (m, 2H), 1.70 (t, J=12.4 Hz, 1H), 1.48-1.64 (m, 3H), 1.30-1.38 (m, 1H). ESI-MS m/z: 288 (M+H)$^+$.

Route 3: Intermediate 18 was also made from cis-7-amino-2-(2,4-dimethyoxy-benzyl)-2-aza-spiro[4.5]decan-1-one (intermediate 10).

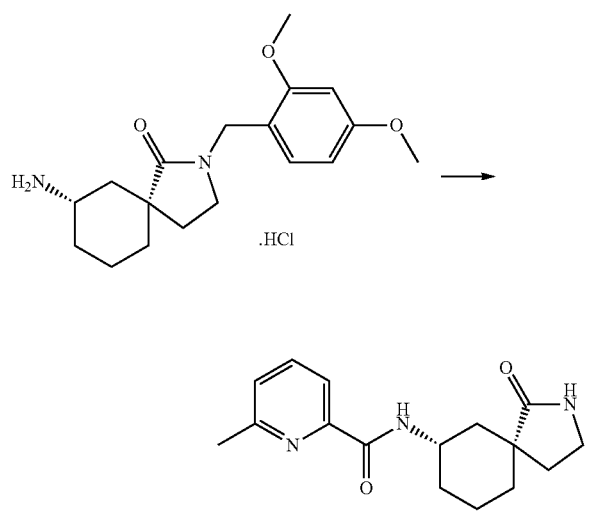

To a solution of 7-amino-2-(2,4-dimethyoxy-benzyl)-2-aza-spiro[4.5]decan-1-one HCl salt from step 8 for intermediate 10 (0.20 g, 0.63 mmol) in CH$_2$Cl$_2$ (9.37 mL) was added 6-methyl-pyridine-2-carboxylic acid (0.095 g, 0.691 mmol) and PyBOP (0.360 g, 0.691 mmol), followed by triethylamine (0.306 mL, 2.20 mmol). The reaction mixture was stirred at rt overnight and then transferred to a 125-mL reparatory funnel with CH$_2$Cl$_2$ (30 mL). The organic layer was washed with saturated NH$_4$Cl, saturated NaHCO$_3$ and brine, dried over Na$_2$SO$_4$, filtered, and concentrated under reduced pressure. The residue was purified by silica gel chromatography (0 to 50% ethyl acetate in methylene chloride) to give cis-6-methyl-pyridine-2-carboxylic acid [2-2,4-dimethoxy-benzyl)-1-oxo-2-aza-spiro[4.5]dec-7-yl]-amide, which was then heated in TFA (0.537 mL) to reflux for 1 hr. The reaction mixture was cooled to rt and concentrated. The residue was dissolved in CH$_2$Cl$_2$, washed with saturated NaHCO$_3$ and brine, dried over MgSO$_4$, and concentrated under reduced pressure to give 0.15 g (83%) of the title compound, cis-6-methyl-pyridine-2-carboxylic acid (1-oxo-2-aza-spiro[4.5]dec-7-yl)-amide, which was used in the next step without further purification. ESI-MS m/z: 288 (M+H)$^+$.

Route 4: Intermediate 18 was also made via the process of Scheme 11, supra, as follows:

Step 1: cis-7-Amino-2-(4-methoxy-benzyl)-2-aza-spiro[4.5]decan-1-one

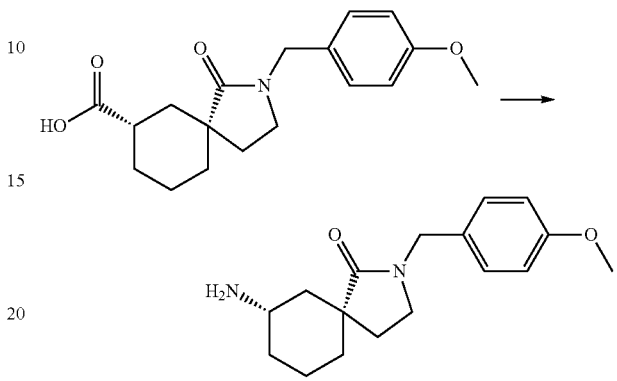

cis-2-(4-Methoxy-benzyl)-1-oxo-2-aza-spiro[4.5]decane-7-carboxylic acid from step 3 for intermediate 11 (1.52 g, 4.79 mmol) was dissolved in toluene (22.0 mL). Triethylamine (0.801 mL, 5.75 mmol) was added, followed by the addition of diphenylphosphonic azide (1.14 mL, 5.27 mmol). The reaction mixture was stirred at rt for 1 hr and then heated at 90° C. for 2 hrs. The mixture was cooled to rt and was added slowly to ice-cold 6.0 M of HCl in water (8.0 mL). The resulting biphasic mixture was stirred vigorously at rt for 1 hr. The aqueous layer was separated, diluted with water (50 mL), and basified with solid Na$_2$CO$_3$ to pH 10. The mixture was extracted with CH$_2$Cl$_2$ (2×50 mL). The combined organic layers were dried over Na$_2$SO$_4$, filtered, and concentrated under reduced pressure to give 1.38 g of the title compound, cis-7-amino-2-(4-methoxy-benzyl)-2-aza-spiro[4.5]decan-1-one, which was used for the next step without further purification. $^1$H NMR (300 MHz, CDCl$_3$) δ7.1 (d, J=8.7 Hz, 2H), 6.83 (d, J=8.7 Hz, 2H), 4.44 (d, J=14.5 Hz, 1H), 4.23 (d, J=14.5 Hz, 1H), 3.00-3.14 (m, 2H), 2.83-2.98 (br, 1H), 1.25-1.94 (m, 10H). ESI-MS m/z: 289 (M+H)$^+$.

Step 2: cis-6-Methyl-pyridine-2-carboxylic acid [2-(4-methoxy-benzyl)-1-oxo-2-aza-spiro[4.5]dec-7-yl]-amide

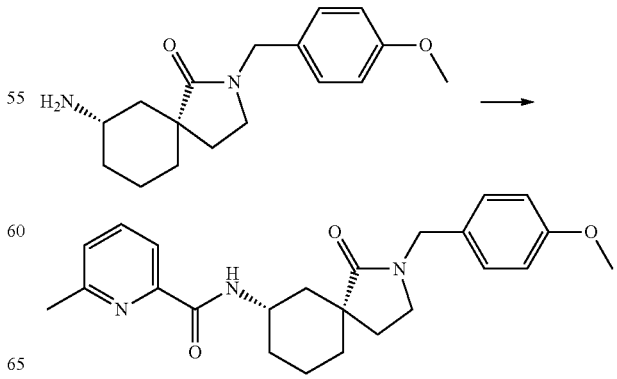

To a solution of cis-7-amino-2-(2,4-dimethyoxy-benzyl)-2-aza-spiro[4.5]decan-1-one from step 1 (675 mg, 2.34 mmol) in CH$_2$Cl$_2$ (34.9 mL) was added 6-methylpyridine-2-carboxylic acid (353 mg, 2.57 mmol) and PyBOP (1.34 g, 2.57 mmol), followed by triethylamine (1.14 mL, 8.19 mmol). The reaction mixture was stirred at rt overnight and then transferred to a 125-mL separatory funnel with CH$_2$Cl$_2$ (30 mL). The organic layer was washed with saturated aqueous NH$_4$Cl, saturated aqueous NaHCO$_3$ and brine, dried over Na$_2$SO$_4$, filtered, and concentrated under reduced pressure. The residue was purified by CombiFlash® system (12 g silica gel cartridge; gradient: 0 to 50% ethyl acetate in hexanes over 10 min, then 50% ethyl acetate in hexanes for 20 min) to give 0.62 g (65%) of the title compound, cis-6-methyl-pyridine-2-carboxylic acid [2-(4-methoxy-benzyl)-1-oxo-2-aza-spiro[4.5]dec-7-yl]-amide. $^1$H NMR (400 MHz, CDCl$_3$): δ 8.10 (d, J=8.4 Hz, 1H), 7.96 (d, J=7.6 Hz, 1H), 7.71 (t, J=7.7 Hz, 1H), 7.26 (d, J=7.4 Hz, 1H), 7.13 (d, J=8.6 Hz, 1H), 6.84 (d, J=8.6 Hz, 1H), 4.39 (s, 2H), 3.99-4.11 (m, 1H), 3.79 (s, 3H), 3.10-3.22 (m, 2H), 2.57 (s, 3H), 1.64-2.14 (m, 7H), 1.30-1.56 (m, 3H). ESI-MS m/z: 408 (M+H)$^+$.

Step 3: cis-6-Methyl-pyridine-2-carboxylic acid ((5S,7S)-1-oxo-2-aza-spiro[4.5]dec-7-yl)-amide

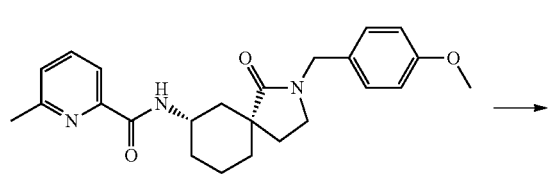

Using the same experimental procedures described in the synthesis of intermediate 18 in route 2 (step 2), intermediate 18 also was made at 1.52 mmol reaction scale from cis-6-methyl-pyridine-2-carboxylic acid [2-(4-methoxy-benzyl)-1-oxo-2-aza-spiro[4.5]dec-7-yl]-amide from route 4 (step 2), and 0.37 g (55%) of the title compound was obtained by CombiFlash® system (4 g silica gel cartridge; gradient: 0 to 10% MeOH with 2N NH$_3$ in DCM over 8 min, then 10% MeOH with 2N NH$_3$ in DCM for 8 min). ESI-MS m/z: 288 (M+H)$^+$.

Intermediate 19 cis-3-Fluoro-N-((5S,7S)-1-oxo-2-aza-spiro[4.5]dec-7-yl)-benzamide

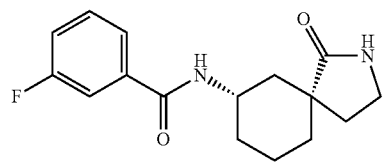 [SMILES: O=C(N[C@H]1CCC[C@]2(CCNC2=O)C1)c1cccc(F)c1]

Using the same experimental procedures described in route 1 for intermediate 18, intermediate 19 was made at 1.19 mmol reaction scale from intermediate 10 and 3-fluorobenzoic acid and purified by silica gel chromatography (CH$_2$Cl$_2$/MeOH: 10/1) to afford 0.145 g (42%) of the title compound. LC-MS (method C): RT: 0.86 min; ESI-MS m/z: 291 (M+H)$^+$.

Using the same experimental procedures described in route 2 for intermediate 18, intermediate 19 was also made from 0.643 mmol of [cis-2-(4-methoxy-benzyl)-1-oxo-2-aza-spiro[4.5]dec-7-yl]-carbamic acid tert-butyl ester and 0.643 mmol of 3-fluorobenzoic acid. $^1$H NMR (400 MHz, CDCl$_3$) δ 8.45 (bs, 1H), 7.59-7.68 (m, 2H), 7.35-7.42 (m, 1H), 7.13-7.19 (m, 1H), 6.22 (bs, 1H), 4.29-4.38 (m, 1H), 3.35-3.45 (m, 2H), 2.09-2.18 (m, 1H), 1.97-2.04 (m, 1H), 1.39-1.93 (m, 8H). ESI-MS m/z: 291 (M+H)$^+$.

Using the same experimental procedures described in route 3 for intermediate 18, intermediate 19 was also made from 2.82 mmol of intermediate 10 and 2.82 mmol of 3-fluorobenzoic acid. LC-MS (method C): RT: 0.86 min; ESI-MS m/z: 291 (M+H)$^+$. It was used without further purification.

Intermediate 20 cis-2-Methyl-pyrimidine-4-carboxylic acid (1-oxo-2-aza-spiro[4.5]dec-7-yl)-amide

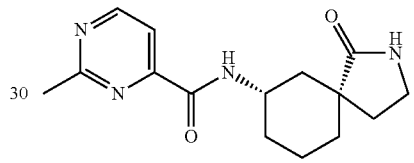

Using the same experimental procedures described in route 1 for intermediate 18, intermediate 20 was made at 2.82 mmol reaction scale from intermediate 10 and 2-methyl-pyrimidine-4-carboxylic acid, and purified by RP-HPLC purification system (Gradient: acetonitrile in water, 12-95% in 3.5 minutes with a cycle time of 5 min. A shallow gradient between 18-42% of acetonitrile was used between 0.6-3.1 min to separate close-eluting impurities. Flow rate: 100 mL/min. Mobile phase additive: 39 mM of ammonium acetate. Column: Inertsil® C18, 30×50 mm, 5 μm particle size (GL Sciences, Tokyo, Japan)) to afford 0.330 g (41%) of the title compound. LC-MS (method C): RT: 0.63 min; ESI-MS m/z: 289 (M+H).

Intermediate 21 cis-Pyridine-2-carboxylic acid (1-oxo-2-aza-spiro[4.5]dec-7-yl)-amide

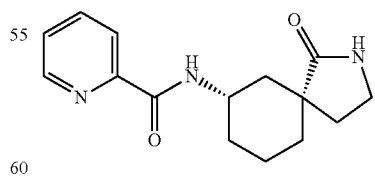

Using the same experimental procedures described in route 1 for intermediate 18, intermediate 21 was made at 2.82 mmol reaction scale from intermediate 10 and picolinic acid, and purified by chromatography (CH$_2$Cl$_2$/MeOH: 4/1) to afford 0.420 g (54%) of the title compound. LC-MS (method C): retention time RT: 0.72 min; ESI-MS m/z: 274 (M+H)$^+$.

Intermediate 22 cis-Pyrimidine-4-carboxylic acid (1-oxo-2-aza-spiro[4.5]dec-7-yl)-amide

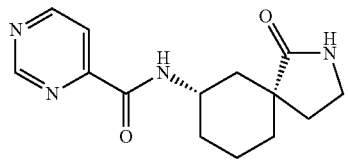 [SMILES: O=C(N[C@H]1CCC[C@]2(CCNC2=O)C1)c1ccncn1]

Using the same experimental procedures described in route 1 for intermediate 18, intermediate 22 was made at 0.71 mmol reaction scale from intermediate 10 and pyrimidine-4-carboxylic acid, and purified by chromatography (CH$_2$Cl$_2$/MeOH: 4/1) to afford 0.045 g (23%) of the title compound. LC-MS (method D): RT: 1.15 min; ESI-MS m/z: 275 (M+H)$^+$.

Intermediate 23 cis-2-Methyl-N-(1-oxo-2-aza-spiro[4.5]dec-7-yl)-isonicotinamide

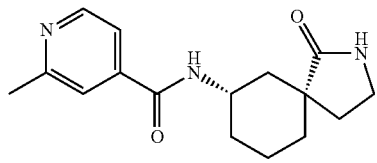 [SMILES: Cc1cc(C(=O)N[C@H]2CCC[C@]3(CCNC3=O)C2)ccn1]

Using the same experimental procedures described in route 1 for intermediate 18, intermediate 23 was made at 2.82 mmol reaction scale from intermediate 10 and 2-methylisonicotinic acid, and purified on a RP-HPLC/MS purification system (Gradient: acetonitrile in water, 12-95% in 3.0 minutes with a cycle time of 5 min. A shallow gradient between 13-30% of acetonitrile was used between 0.5-2.0 min to separate close-eluting impurities. Flow rate: 100 mL/min. Mobile phase additive: 39 mM of ammonium acetate. Column: Inertsil® C18, 30×50 mm, 5 um particle size (GL Sciences)) to afford 0.300 g (37%) of the title compound was obtained. LC-MS (method C): RT: 0.66 min; ESI-MS m/z: 288 (M+H)$^+$.

Intermediate 24 cis-9-Amino-7,7-difluoro-2-(3-fluoro-phenyl)-2-aza-spiro[4.5]decan-1-one

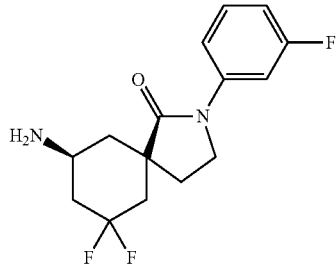

Intermediate 24 was prepared via the process of Scheme 6, supra, as follows:

Step 1: 5-Hydroxy-cyclohexane-1,3-dicarboxylic acid dimethyl ester

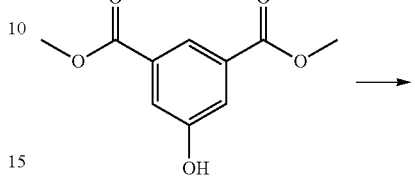

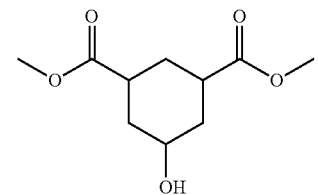

To a solution of dimethyl-5-hydroxyisophthalate (3.50 g, 16.6 mmol) in methanol (60.0 mL) was added 5% rhodium on alumina (0.80 g) at 0° C., followed by acetic acid (0.60 mL, 10.6 mmol). The reaction mixture was shaken under hydrogen (55 psi) at room temperature overnight and then filtered through Celite® and concentrated under reduced pressure. The residue was purified by CombiFlash® system (12 g silica gel cartridge; gradient: 0 to 50% ethyl acetate in DCM over 30 min) to give 3.00 g (83%) of the title compound, 5-hydroxy-cyclohexane-1,3-dicarboxylic acid dimethyl ester. $^1$H NMR (400 MHz, CDCl$_3$): δ 3.56-3.78 (m, 7H), 2.15-2.51 (m, 5H), 1.25-1.66 (m, 3 H).

Step 2: 5-Oxo-cyclohexane-1,3-dicarboxylic acid dimethyl ester

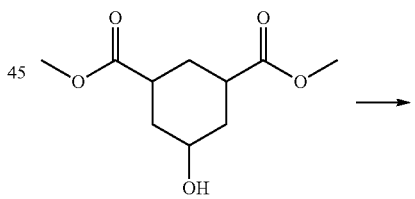

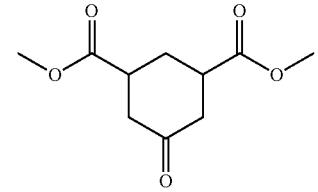

To a mixture of 5-hydroxy-cyclohexane-1,3-dicarboxylic acid dimethyl ester from step 1 (3.00 g, 13.9 mmol) and triethylamine (5.80 mL, 41.6 mmol) in dimethyl sulfoxide (6.00 mL, 84.5 mmol) and DCM (0.60 mL, 9.36 mmol) was added portion-wise sulfur trioxide-pyridine complex (5.08 g, 31.9 mmol) at 10° C. The reaction mixture was stirred at room temperature for 2 hrs and then quenched with water (50 mL). The aqueous layer was extracted with EtOAc (3×50 mL). The combined organic layers were washed with brine (2×40 mL)

and concentrated under reduced pressure. The residue was purified by CombiFlash® system (gradient: 0 to 50% ethyl acetate in DCM over 30 min) to give 2.2 g (74%) the title compound, 5-oxo-cyclohexane-1,3-dicarboxylic acid dimethyl ester. $^1$H NMR (400 MHz, CDCl$_3$): δ 3.72 (s, 6H), 2.61-2.75 (m, 2H), 2.31-2.47 (m, 3H), 1.83 (ddt, J=2.9, 13.5, 34.4 Hz, 2H), 1.53 (q, J=13.2 Hz, 1H).

Step 3: 5,5-Difluoro-cyclohexane-1,3-dicarboxylic acid dimethyl ester

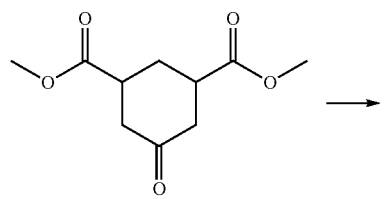

To a solution of diethylaminosulfur trifluoride (3.45 mL, 26.1 mmol) in DCM (30.0 mL) at 0° C. was added a solution of 5-oxo-cyclohexane-1,3-dicarboxylic acid dimethyl ester (2.80 g, 13.1 mmol) in DCM (26.0 mL), followed by addition of ethanol (0.15 mL, 2.61 mmol). The reaction mixture was stirred at room temperature overnight and then quenched carefully with cold saturated aqueous NaHCO$_3$. The aqueous layer was extracted with DCM (×3). The combined organic layers were washed with brine, dried over Na$_2$SO$_4$, filtered, and concentrated under reduced pressure. The residue was purified by CombiFlash® system (12 g silica gel cartridge; gradient: 0 to 30% ethyl acetate in DCM over 19 min, then 30% ethyl acetate in DCM for 5 min) to give 2.5 g (81%) of the title compound, 5,5-difluoro-cyclohexane-1,3-dicarboxylic acid dimethyl ester. $^1$H NMR (400 MHz, CDCl$_3$): δ 3.73 (s, 6H), 2.70-2.80 (m, 2H), 2.60-2.68 (m, 2H), 2.44-2.55 (m, 3H), 1.92 (q, J=13.5 Hz, 1H).

Step 4: 1-Allyl-5,5-difluoro-cyclohexane-1,3-dicarboxylic acid dimethyl ester

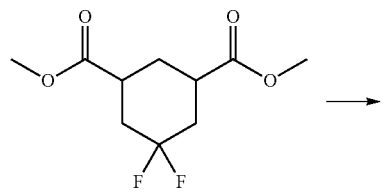

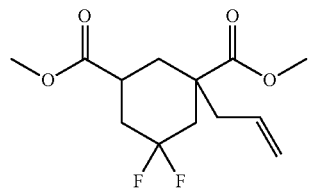

Using the same experimental procedures described in step 2 for intermediate 2, starting from 5,5-difluoro-cyclohexane-1,3-dicarboxylic acid dimethyl ester (10.6 mmol), 2.5 g (86%) of the title compound was obtained. $^1$H NMR (400 MHz, CDCl$_3$): δ 5.57-5.73 (m, 1H), 5.02-5.17 (m, 2H), 3.64-3.77 (m, 6H), 1.58-3.05 (m, 9H).

Step 5: trans-5,5-Difluoro-1-(2-oxo-ethyl)-cyclohexane-1,3-dicarboxylic acid dimethyl ester

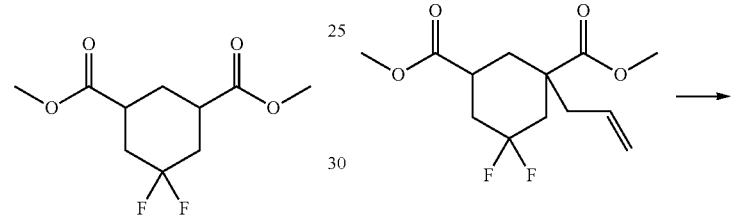

Using the same experimental procedures described in step 3 for intermediate 2, starting from 1-allyl-5,5-difluoro-cyclohexane-1,3-dicarboxylic acid dimethyl ester (7.24 mmol), 1.3 g (65%) of the title compound was obtained. $^1$H NMR (400 MHz, CDCl$_3$): δ 9.68 (dd, J=1.2, 2.1 Hz, 1H), 3.69-3.77 (m, 6H), 2.95-3.25 (m, 1H), 2.84 (dd, J=0.9, 16.9 Hz, 1H), 2.63-2.75 (m, 2H), 2.56 (dd, J=2.1, 16.9 Hz, 1H), 2.34-2.45 (m, 1H), 1.72-1.90 (m, 2H), 1.37 (t, J=13 Hz, 1H).

Step 6: trans-5,5-Difluoro-1-[2-(3-fluoro-phenylamino)-ethyl]-cyclohexane-1,3-dicarboxylic acid dimethyl ester

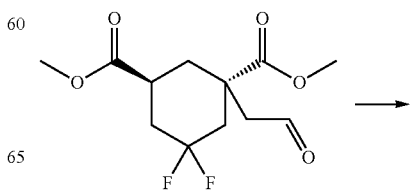

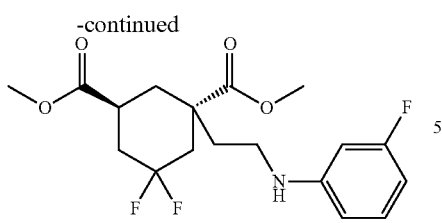

Using the same experimental procedures described in step 4 for intermediate 2, starting from trans-5,5-difluoro-1-(2-oxo-ethyl)-cyclohexane-1,3-dicarboxylic acid dimethyl ester (4.67 mmol), 1.32 g (75%) of the title compound was obtained. $^1$H NMR (400 MHz, CDCl$_3$): δ 7.04-7.13 (m, 1H), 6.18-6.48 (m, 3H), 3.65-3.79 (m, 6H), 2.96-3.27 (m, 3H), 2.62-2.82 (m, 2H), 2.32-2.45 (m, 2H), 2.06-2.15 (m, 1H), 1.57-2.93 (m, 3H), 1.20-1.33 (m, 1H). ESI-MS m/z: 374 (M+H)$^+$.

Step 7: trans-9,9-Difluoro-2-(3-fluoro-phenyl)-1-oxo-2-aza-spiro[4.5]decane-7-carboxylic acid methyl ester

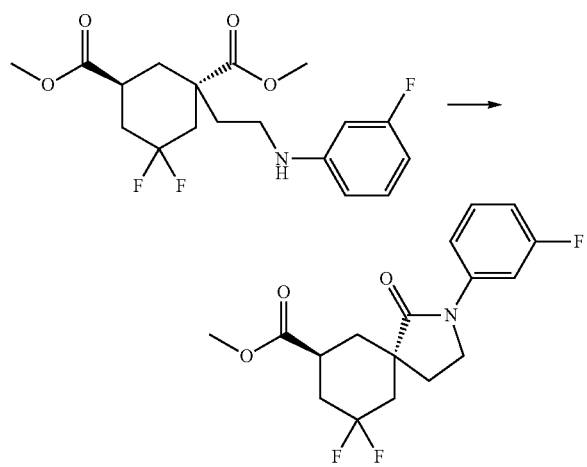

Using the same experimental procedures described in step 4 of intermediate 2, starting from trans-5,5-difluoro-1-[2-(3-fluoro-phenylamino)-ethyl]-cyclohexane-1,3-dicarboxylic acid dimethyl ester (3.51 mmol), 0.55 g of the title compound was obtained. LC-MS (Method A): retention time RT: 1.29 min; ESI-MS m/z: 342 (M+H)$^+$. It was used without further purification.

Step 8: cis-9,9-Difluoro-2-(3-fluoro-phenyl)-1-oxo-2-aza-spiro[4.5]decane-7-carboxylic acid

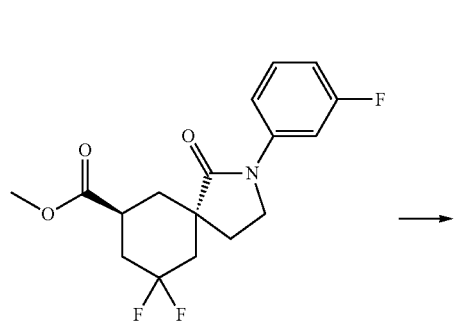

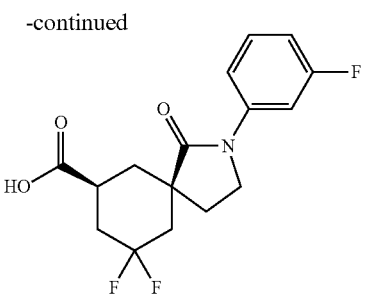

Using the same experimental procedures described in step 5 for intermediate 2, starting from 5,5-difluoro-1-[2-(3-fluoro-phenylamino)-ethyl]-cyclohexane-1,3-dicarboxylic acid dimethyl ester (1.02 mmol), 0.27 g (80%) of the title compound was obtained. During the epimerization, all ester was hydrolyzed to a desired acid. LC-MS (Method A): RT: 0.70 min; purity (UV$_{254}$): 91%; ESI-MS m/z: 328 (M+H)$^+$. It was used without further purification.

Step 9: cis-9-Amino-7,7-difluoro-2-(3-fluoro-phenyl)-2-aza-spiro[4.5]decan-1-one

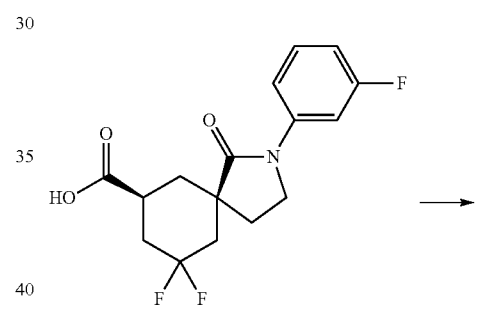

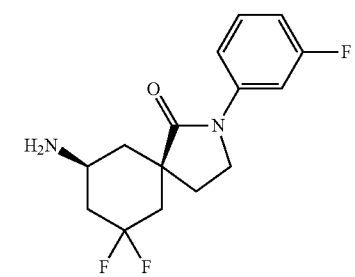

Using the same experimental procedures described in step 7 for intermediate 2, starting from 5,5-difluoro-1-[2-(3-fluoro-phenylamino)-ethyl]-cyclohexane-1,3-dicarboxylic acid dimethyl ester (0.37 mmol), a small amount of crude title compound was obtained and used without measuring the amount obtained and without further purification. ESI-MS m/z: 299 (M+H)$^+$.

Intermediate 25 cis-9-Amino-2-(2,4-dimethoxy-benzyl)-7,7-difluoro-2-aza-spiro[4.5]decan-1-one

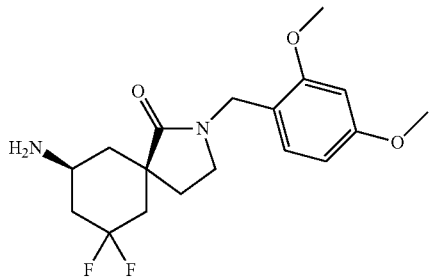 [SMILES: COc1ccc(CN2CC[C@]3(C[C@H](N)CC(F)(F)C3)C2=O)c(OC)c1]

Intermediate 25 was made via the process of Scheme 6, supra, as follows:

Step 1: trans-2-(2,4-Dimethoxy-benzyl)-9,9-difluoro-1-oxo-2-aza-spiro[4.5]decane-7-carboxylic acid methyl ester

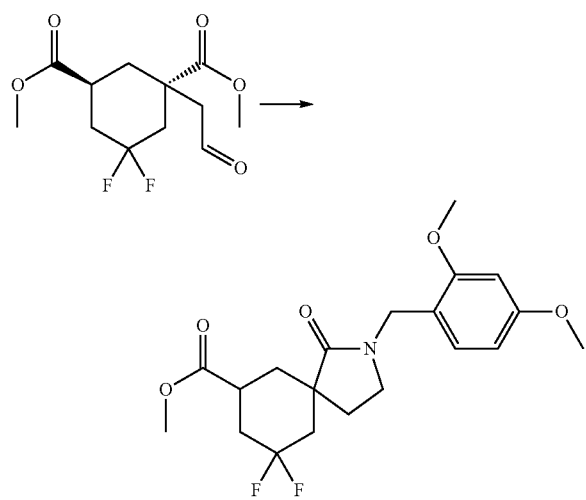

To a solution of trans-5,5-difluoro-1-(2-oxo-ethyl)-cyclohexane-1,3-dicarboxylic acid dimethyl ester (4.00 g, 14.4 mmol) and 2,4-dimethoxybenzylamine (2.40 g, 14.4 mmol) in THF (50.0 mL) was added sodium triacetoxyborohydride (4.56 g, 21.5 mmol) was added portion-wise and stirred at rt overnight. The mixture was quenched with cold saturated NaHCO$_3$. The aqueous laser was extracted with EtOAc (3×30 mL). The combined organic layers were washed with saturated NaHCO$_3$ and brine, dried over MgSO$_4$, filtered, and concentrated under reduced pressure. The resulting residue was purified by silica gel chromatography (Solvent: 50% ethyl acetate in hexanes) to afford 1.8 g (32%) of the title compound, trans-2-(2,4-Dimethoxy-benzyl)-9,9-difluoro-1-oxo-2-aza-spiro[4.5]decane-7-carboxylic acid methyl ester. $^1$H NMR (400 MHz, CDCl$_3$): δ 7.12-7.07 (m, 1H), 6.47-6.40 (m, 2H), 4.52 (d, J=14.3 Hz, 1 H), 4.32 (d, J=14.3 Hz, 1 H), 3.80 (s, 3H), 3.79 (s, 3H), 3.70 (s, 3H), 3.48-3.38 (m, 1H), 3.12 (dd, J=7.5, 5.9 Hz, 2H), 2.41-1.67 (m, 8H). ESI-MS m/z: 398 (M+H)$^+$.

Step 2: cis-2-(2,4-Dimethoxy-benzyl)-9,9-difluoro-1-oxo-2-aza-spiro[4.5]decane-7-carboxylic acid methyl ester

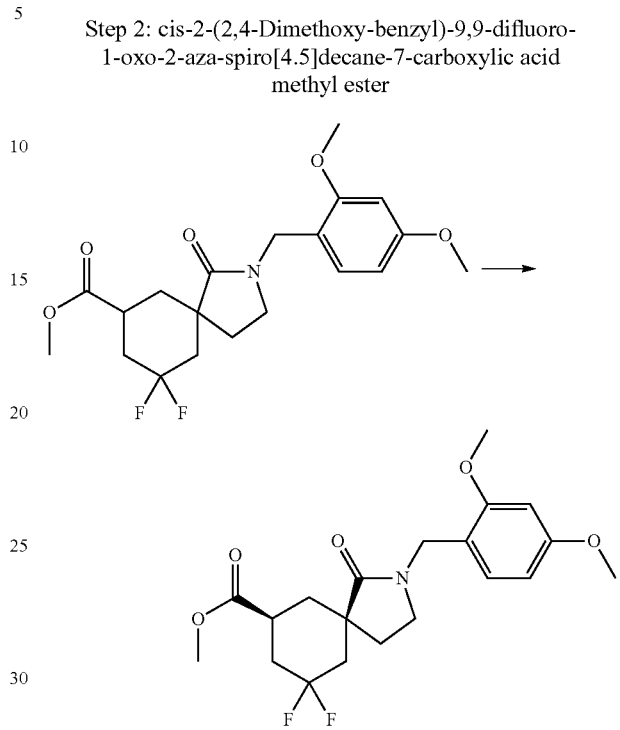

To a solution of trans-2-(2,4-Dimethoxy-benzyl)-9,9-difluoro-1-oxo-2-aza-spiro[4.5]decane-7-carboxylic acid methyl ester (1.80 g, 4.53 mmol) in MeOH (20.0 mL) was added NaH (200 mg, 5.00 mmol, 60% in mineral oil) at 0° C. The reaction mixture was stirred at room temperature overnight and quenched with ice. The aqueous layer was extracted with DCM (3×30 mL). The combined organic layers were washed with brine and concentrated. The resulting residue was purified by silica gel chromatography (Solvent: 30% ethyl acetate in hexanes) to afford 1.25 g (69%) of the title compound, cis-2-(2,4-Dimethoxy-benzyl)-9,9-difluoro-1-oxo-2-aza-spiro[4.5]decane-7-carboxylic acid methyl ester. $^1$H NMR (400 MHz, CDCl$_3$): δ7.08 (d, J=8.9 Hz, 1 H), 6.46-6.42 (m, 2H), 4.48 (d, J=14.4 Hz, 1 H), 4.37 (d, J=14.3 Hz, 1 H), 3.80 (s, 3H), 3.79 (s, 3H), 3.70 (s, 3H), 3.19-3.11 (m, 2H), 2.78-1.74 (m, 9H). ESI-MS m/z: 398 (M+H)$^+$.

Step 3: cis-2-(2,4-Dimethoxy-benzyl)-9,9-difluoro-1-oxo-2-aza-spiro[4.5]decane-7-carboxylic acid

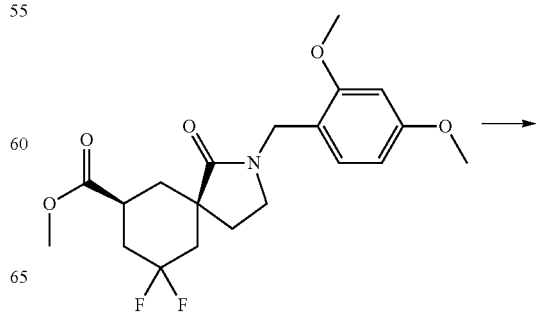

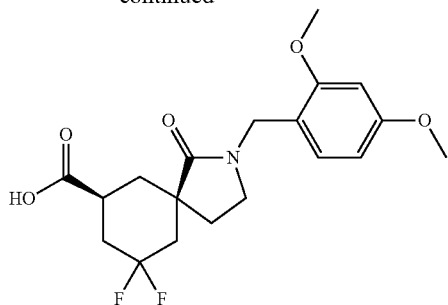

The solution of cis-2-(2,4-Dimethoxy-benzyl)-9,9-difluoro-1-oxo-2-aza-spiro[4.5]decane-7-carboxylic acid methyl ester (1.25 g, 3.14 mmol) and LiOH (0.239 g, 10.0 mmol) in water (10 mL) and THF (30 mL) was stirred at room temperature overnight and concentrated. The aqueous layer was acidified with 1N HCl up to pH2 and extracted with DCM (3×30 mL). The combined organic layers were dried over MgSO$_4$, filtered, and concentrated under reduced pressure to yield 1.42 g of the title compound, cis-2-(2,4-dimethoxy-benzyl)-1-oxo-2-aza-spiro[4.5]decan-7-carboxylic acid, which was used for the next step without further purification. ESI-MS m/z: 384 (M+H)$^+$.

Step 4: cis-9-Amino-2-(2,4-dimethoxy-benzyl)-7,7-difluoro-2-aza-spiro[4.5]decan-1-one

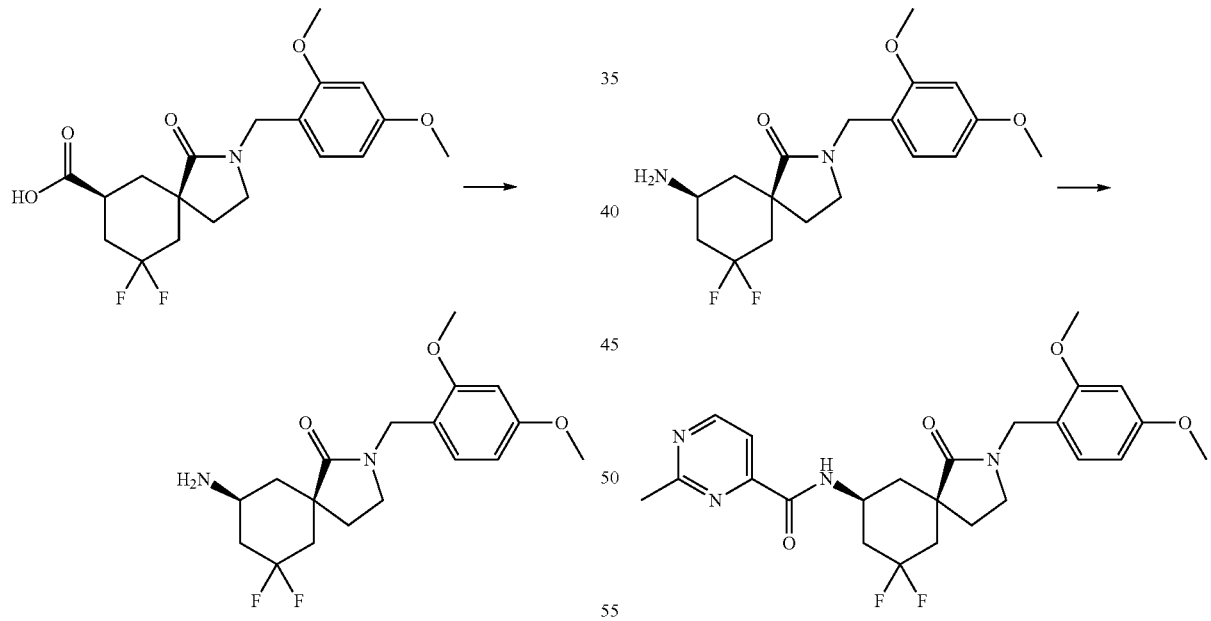

To a solution of cis-2-(2,4-dimethoxy-benzyl)-1-oxo-2-aza-spiro[4.5]decan-7-carboxylic acid (0.700 g, 1.82 mmol) in toluene (15 mL) was added triethylamine (0.34 mL, 2.5 mmol), followed by the addition of diphenyl phosphoryl azide (0.47 mL, 2.2 mmol). The mixture was stirred at room temperature for 1 hour and then heated at 90° C. for 2 hours. The reaction mixture was cooled down to room temperature, then was added slowly to ice-cold HCl (6N, 10 mL). The resulting mixture was stirred vigorously at room temperature for 2 hours. Two layers were separated. The aqueous layer was basified with solid NaCO$_3$ to pH ~10 and extracted with DCM (3×30 mL). The combined organic layers were washed with brine, dried over Na2SO4, filtered, and concentrated to give 0.4 g of the title compound, cis-9-amino-2-(2,4-dimethoxy-benzyl)-7,7-difluoro-2-aza-spiro[4.5]decan-1-one, which was used for the next step without further purification. ESI-MS m/z: 355 (M+H)$^+$.

Intermediate 26 cis-2-Methyl-pyrimidine-4-carboxylic acid (9,9-difluoro-1-oxo-2-aza-spiro[4.5]dec-7-yl)-amide

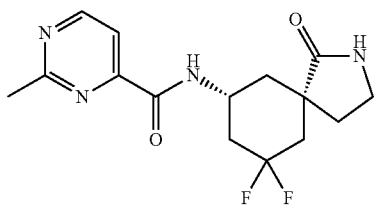 [SMILES: Cc1nccc(C(=O)N[C@H]2CC(F)(F)C[C@]3(CCNC3=O)C2)n1]

Intermediate 26 was prepared via the process of Scheme 13, supra, as follows:

Step 1: cis-2-Methyl-pyrimidine-4-carboxylic acid [2-(2,4-dimethoxy-benzyl)-9,9-difluoro-1-oxo-2-aza-spiro[4.5]dec-7-yl]-amide

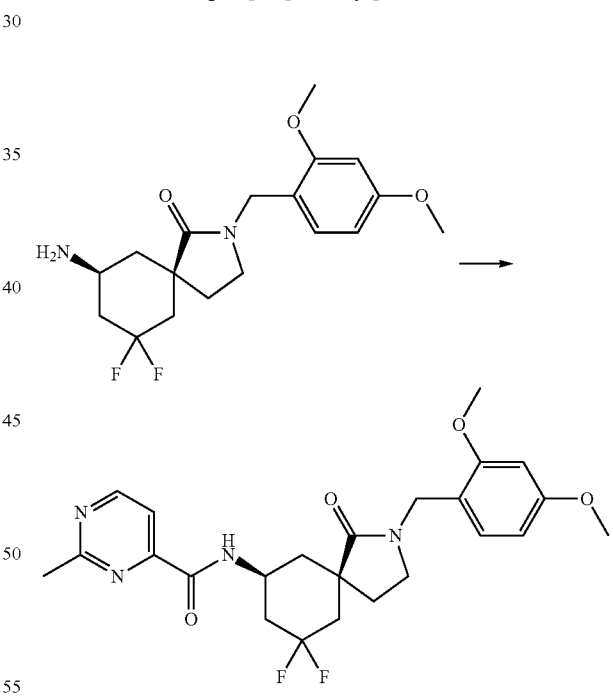

To a solution of 2-methylpyridine-4-carboxylic acid (171 mg, 1.24 mmol) in CH$_2$Cl$_2$ (15 mL) was added EDCI (263 mg, 1.69 mmol) and HOBT (152 mg, 1.13 mmol) at 0° C., followed by the addition of cis-9-amino-2-(2,4-dimethoxy-benzyl)-7,7-difluoro-2-aza-spiro[4.5]decan-1-one (400 mg, 1.13 mmol) The reaction mixture was stirred at rt overnight and then diluted with CH$_2$Cl$_2$ (30 mL). The organic layer was washed with saturated aqueous NaHCO$_3$ and brine and concentrated under reduced pressure. The residue was purified by CombiFlash® system (12 g silica gel cartridge; gradient: 0 to 2% MeOH (2N NH$_3$) in CH$_2$Cl$_2$ over 10 min) to give 0.4 g (70%) of the title compound, cis-2-Methyl-pyrimidine-4-carboxylic acid [2-(2,4-dimethoxy-benzyl)-9,9-difluoro-1-oxo-2-aza-spiro[4.5]dec-7-yl]-amide. $^1$H NMR (400 MHz, CDCl$_3$): δ8.89 (d, J=5.0 Hz, 1 H), 8.00 (d, J=8.6 Hz, 1 H), 7.90 (d, J=5.1 Hz, 1 H), 7.10 (d, J=8.7 Hz, 1 H), 6.48-6.43 (m, 2H), 4.45 (s, 2H), 4.44-4.34 (m, 1H), 3.82 (s, 3H), 2.81 (s, 3H), 3.25-3.20 (m, 2H), 2.80 (s, 3H), 2.66-2.53 (m, 1H), 2.37-1.72 (m, 7H). ESI-MS m/z: 475 (M+H)$^+$.

Step 2: cis-2-Methyl-pyrimidine-4-carboxylic acid (9,9-difluoro-1-oxo-2-aza-spiro[4.5]dec-7-yl)-amide

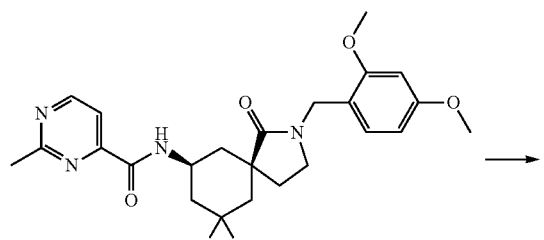

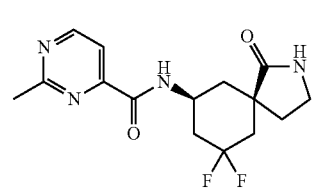

Using the same experimental procedures described in the synthesis of intermediate 18 in route 2 (step 2), intermediate 18 also was made at 0.8 mmol reaction scale from cis-2-Methyl-pyrimidine-4-carboxylic acid [2-(2,4-dimethoxy-benzyl)-9,9-difluoro-1-oxo-2-aza-spiro[4.5]dec-7-yl]-amide, and 0.3 g of the title compound was obtained, which was used for the next step without further purification. ESI-MS m/z: 325 (M+H)$^+$.

Intermediate 27 cis-6-Methyl-pyridine-2-carboxylic acid (9,9-difluoro-1-oxo-2-aza-Spiro[4.5]dec-7-yl)-amide

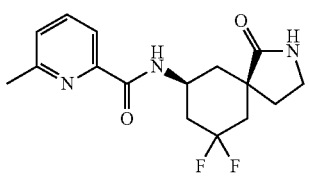 [SMILES: Cc1cccc(C(=O)N[C@@H]2CC(F)(F)C[C@@]3(CCNC3=O)C2)n1]

Using the same experimental procedures described in the synthesis of intermediate 26, intermediate 27 was also made from 0.635 mmol of cis-9-amino-2-(2,4-dimethoxy-benzyl)-7,7-difluoro-2-aza-spiro[4.5]decan-1-one and 0.698 mmol of 2-methylpicolinic acid. $^1$H NMR (400 MHz, CDCl$_3$) δ 8.09 (d, J=8.4 Hz, 1 H), 7.98 (d, J=7.6 Hz, 1 H), 7.73 (t, J=7.7 Hz, 1 H), 7.29 (d, J=7.8 Hz, 1 H), 5.55 (s, 1H), 4.52-4.36 (m, 1H), 3.44-3.33 (m, 2H), 2.66-2.58 (m, 1H), 2.57 (s, 3H), 2.34-1.64 (m, 7H). ESI-MS m/z: 324 (M+H)$^+$.

Intermediate 28 cis-Pyridine-2-carboxylic acid (9,9-difluoro-1-oxo-2-aza-spiro[4.5]dec-7-yl)-amide

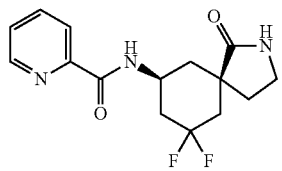 [SMILES: O=C(N[C@@H]1CC(F)(F)C[C@@]2(CCNC2=O)C1)c1ccccn1]

Using the same experimental procedures described in the synthesis of intermediate 26, intermediate 19 was also made from 0.254 mmol of cis-9-amino-2-(2,4-dimethoxy-benzyl)-7,7-difluoro-2-aza-spiro[4.5]decan-1-one and 0.305 mmol of pyridine-2-carbonyl chloride. ESI-MS m/z: 310 (M+H)$^+$. It was used without further purification.

Intermediate 29 cis-N-(9,9-Difluoro-1-oxo-2-aza-spiro[4.5]dec-7-yl)-3-fluoro-benzamide

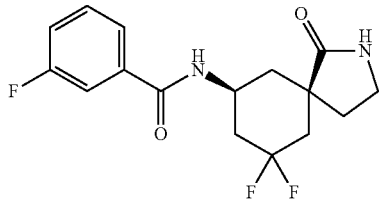 [SMILES: O=C(N[C@@H]1CC(F)(F)C[C@@]2(CCNC2=O)C1)c1cccc(F)c1]

Using the same experimental procedures described in the synthesis of intermediate 26, intermediate 29 was also made from 1.29 mmol of cis-9-amino-2-(2,4-dimethoxy-benzyl)-7,7-difluoro-2-aza-spiro[4.5]decan-1-one and 1.6 mmol of 3-fluorobenzoyl chloride. ESI-MS m/z: 327 (M+H)$^+$. It was used without further purification.

Intermediate 30 cis-13-Amino-9-(3,5-difluoro-phenyl)-1,4-dioxa-9-aza-dispiro[4.1.4.3]tetradecan-8-one

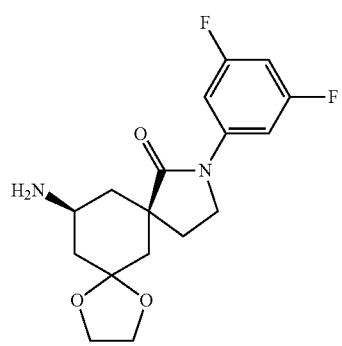 [SMILES: N[C@@H]1CC2(C[C@@]3(CCN(c4cc(F)cc(F)c4)C3=O)C1)OCCO2]

Intermediate 30 was prepared via the process of Scheme 23, supra, as follows:

Step 1: 1,4-Dioxa-spiro[4.5]decane-7,9-dicarboxylic acid dimethyl ester

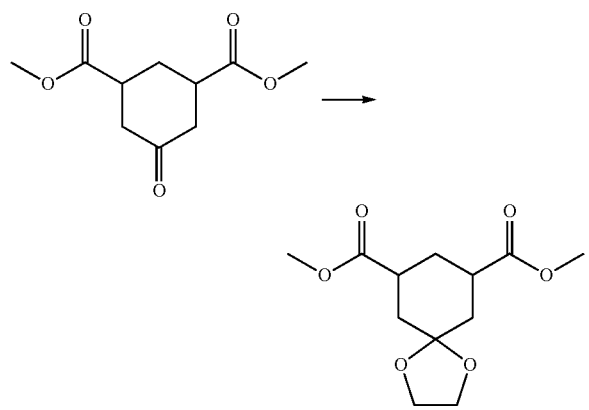

A solution of 5-oxocyclohexane-1,3-dicarboxylic acid dimethyl ester (22.8 g, 106.4 mmol), ethylene glycol (13.3 g, 215 mmol) and p-toluenesulfonic acid monohydrate (0.22 g, 1.3 mmol) in toluene (230 mL), in a flask fitted with Dean-Stark trap was heated under reflux for 5 h. The reaction was cooled to room temperature, water was added and the mixture was extracted with ethyl acetate. Organic layer was separated, washed with NaHCO$_3$ solution and brine, dried over anhydrous Na$_2$SO$_4$ and concentrated under reduced pressure to give an oil, which was triturated with hexane and left in the fridge overnight. The precipitated solid was filtered and dried under vacuum to provide 17.1 (63%) g of the title compound, 1,4-Dioxa-spiro[4.5]decane-7,9-dicarboxylic acid dimethyl ester as a white solid. $^1$HNMR (400 MHz, CDCl$_3$), δ: 3.95 (m, 4H), 3.7 (s, 6H), 2.72-2.62 (m, 3H), 2.32-2.22 (m, 1H), 2.02-1.96 (m, 2H), 1.6-1.4 (m, 3H).

Step 2: 7-Allyl-1,4-dioxa-spiro[4.5]decane-7,9-dicarboxylic acid dimethyl ester

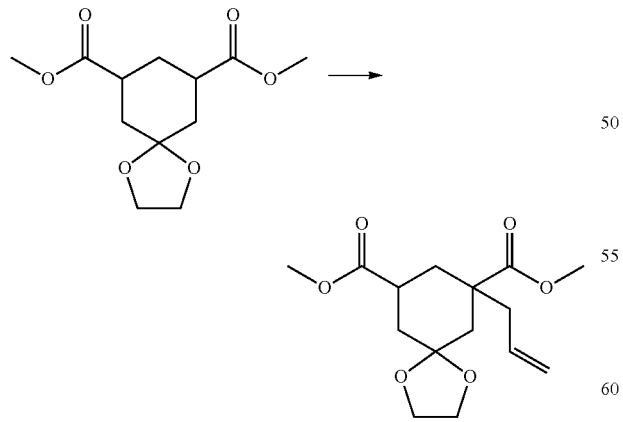

A 1.6 M hexane solution of n-BuLi (101 mL, 161 mmol) was added to the stirred anhydrous THF (300 mL) at −78° C., followed by diisopropylamine (16.2 g, 161 mmol). The reaction mixture was stirred at −78° C. for 15 min and at 0° C. for 1 h. The mixture was re-cooled to −78° C., 1,3-dimethyl-3,4,5,6-tetrahydro-2-(1H)-pyrimidinone (DMPO) (48 g, 372 mmol) was added slowly, and the resultant white suspension was stirred for 30 min. A solution of 1,4-dioxaspiro[4.5]decane-7,9-dicarboxylic acid dimethyl ester (32 g, 124 mmol) in THF (100 mL) was added, the light yellowish solution was stirred for 30 min, then allyl bromide (16.6 g, 137 mmol) was added, the reaction mixture was allowed to warm to room temperature and left stirring at room temperature overnight. The reaction was quenched with saturated aqueous NH$_4$Cl solution and extracted with ethyl acetate; the organic extracts were combined and washed with water, brine, dried over anhydrous Na$_2$SO$_4$ and concentrated under reduced pressure to give 40 g of crude product as viscous oil. Purification by flash column chromatography on silica gel (hexane-chloroform-ethyl acetate 8:1:1) gave 23.8 g (65%) of the title compound, 1-allyl-5,5-difluoro-cyclohexane-1,3-dicarboxylic acid dimethyl ester as colorless oil. $^1$H NMR (400 MHz, CDCl$_3$), δ: 5.7-5.6 (m, 1H), 5.10-5.00 (m, 2H), 4.0-3.8 (m, 4H), 3.68 (s, 6H), 3.08-2.98 (m, 1H), 2.5-2.3 (m, 2H), 2.15-2.08 (m, 1H), 1.98-1.92 (m, 1H), 1.65-1.58 (m, 1H), 1.45-1.38 (m, 1H), 1.28-1.18 (m, 1H). ES MS: 299.2 (M+1)$^+$.

Step 3: trans-7-(2-Oxo-ethyl)-1,4-dioxa-spiro[4.5]decane-7,9-dicarboxylic acid dimethyl ester

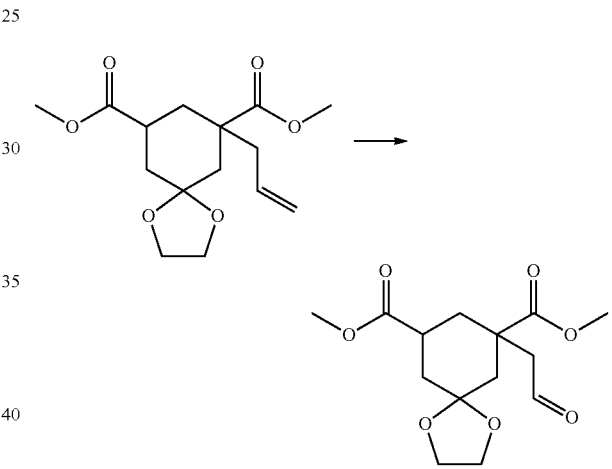

Using the same experimental procedures described in step 3 for intermediate 2, starting from 1-allyl-5,5-difluoro-cyclohexane-1,3-dicarboxylic acid dimethyl ester (5.00 g, 16.8 mmol), 5.5 g of the title compound was obtained, which was used for the next step without further purification. $^1$H NMR (400 MHz, CDCl$_3$): δ 9.78-9.69 (m, 1H), 4.04-3.68 (m, 10H), 3.26-3.15 (m, 1H), 2.78-1.31 (m, 8H).

Step 4: trans-7-[2-(3,5-Difluoro-phenylamino)-ethyl]-1,4-dioxa-spiro[4.5]decane-7,9-dicarboxylic acid dimethyl ester

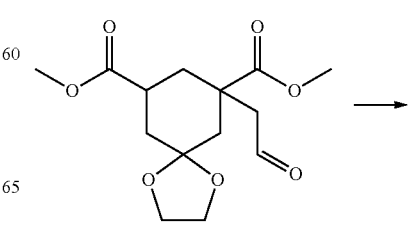

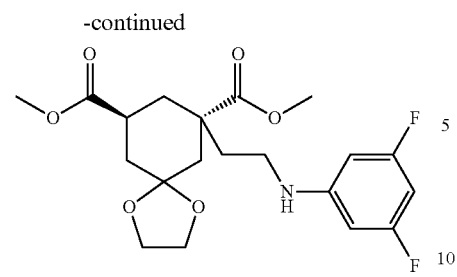

Using the same experimental procedures described in step 4 for intermediate 2, starting from trans-5,5-difluoro-1-(2-oxo-ethyl)-cyclohexane-1,3-dicarboxylic acid dimethyl ester (1.80 g, 5.99 mmol) and 3,5-difluoroaniline (0.772 g, 5.98 mmol), 0.835 g (75%) of the title compound was obtained. $^1$H NMR (400 MHz, CDCl$_3$): δ 6.23 (br, 3H), 4.04-3.74 (m, 6H), 3.72 (s, 3H), 3.70 (s, 3H), 3.29-2.97 (m, 3H), 2.62-1.18 (m, 6H). ESI-MS m/z: 414 (M+H)$^+$.

Step 5: trans-9-(3,5-Difluoro-phenyl)-8-oxo-1,4-dioxa-9-aza-dispiro[4.1.4.3]tetradecane-13-carboxylic acid methyl ester

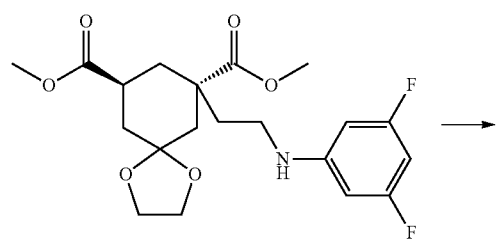

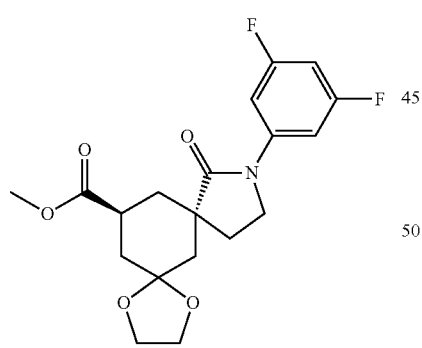

Using the same experimental procedures described in step 4 of intermediate 2, starting from trans-5,5-difluoro-1-[2-(3-fluoro-phenylamino)-ethyl]-cyclohexane-1,3-dicarboxylic acid dimethyl ester (0.835 g, 2.02 mmol), 0.7 g (99%) of the title compound was obtained. $^1$H NMR (400 MHz, CDCl$_3$): δ 7.38-7.30 (m, 2H), 6.64-6.57 (m, 1H), 3.98-3.91 (m, 4H), 3.81-3.67 (m, 5H), 3.32-3.23 (m, 1H), 2.41-1.63 (m, 8H). ESI-MS m/z: 382 (M+H)$^+$.

Step 6: cis-9-(3,5-Difluoro-phenyl)-8-oxo-1,4-dioxa-9-aza-dispiro[4.1.4.3]tetradecane-13-carboxylic acid methyl ester

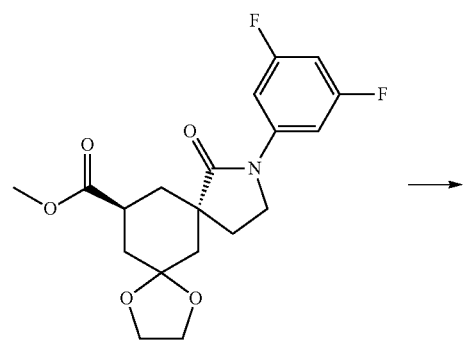

To a solution of trans-9-(3,5-Difluoro-phenyl)-8-oxo-1,4-dioxa-9-aza-dispiro[4.1.4.3]tetradecane-13-carboxylic acid methyl ester (0.68 g, 1.78 mmol) in THF (10 mL) was added NaH (60% in mineral oil, 93 mg, 2.3 mmol) at 0° C. The reaction mixture was stirred at room temperature overnight, cooled to 0° C., and quenched with ice. The aqueous layer was extracted with EtOAc (3×20 mL). The combined organic layer was washed with brine and concentrated. Purification by flash column chromatography on silica gel (gradient: 0 to 50% EtOAc in hexanes) gave 0.553 g (81%) of the title compound was obtained. $^1$H NMR (400 MHz, CDCl$_3$): δ 7.32-7.27 (m, 2H), 6.63-6.56 (m, 1H), 3.99-3.69 (m, 4H), 3.74-3.70 (m, 2H), 3.69 (s, 3H), 2.82-2.72 (m, 1H), 2.44-2.35 (m, 1H), 2.16-1.60 (m, 7H). ESI-MS m/z: 382 (M+H)$^+$.

Step 7: cis-9-(3,5-Difluoro-phenyl)-8-oxo-1,4-dioxa-9-aza-dispiro[4.1.4.3]tetradecane-13-carboxylic acid

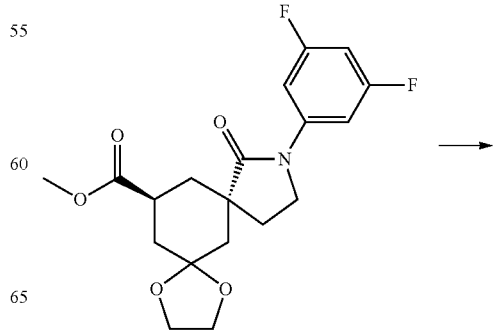

-continued

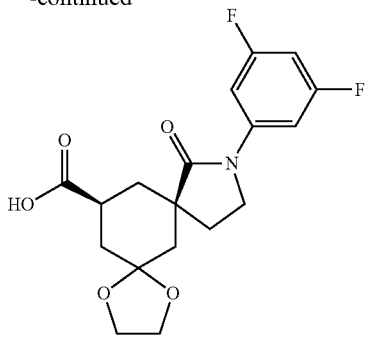

Using the same experimental procedures described in step 5 for intermediate 2, starting from cis-9-(3,5-Difluoro-phenyl)-8-oxo-1,4-dioxa-9-aza-dispiro[4.1.4.3]tetradecane-13-carboxylic acid methyl ester (0.553 g, 1.45 mmol), 0.447 g (84%) of the title compound was obtained. It was used without further purification. ESI-MS m/z: 368 (M+H)$^+$.

Step 8: cis-13-Amino-9-(3,5-difluoro-phenyl)-1,4-dioxa-9-aza-dispiro[4.1.4.3]tetradecan-8-one

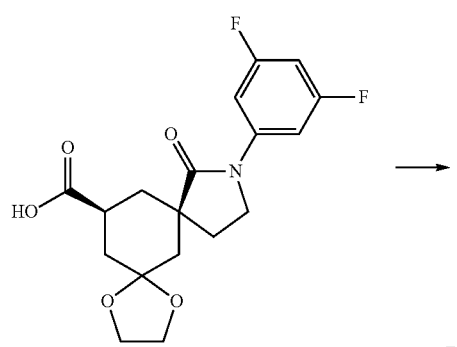

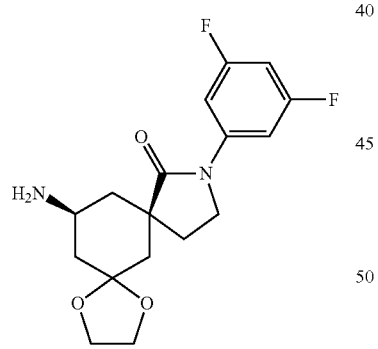

To a solution of cis-9-(3,5-Difluoro-phenyl)-8-oxo-1,4-dioxa-9-aza-dispiro[4.1.4.3]tetradecane-13-carboxylic acid (0.447 g, 1.22 mmol) in toluene (15 mL) was added triethylamine (0.24 mL, 1.58 mmol), followed by the addition of diphenyl phosphoryl azide (0.31 mL, 1.46 mmol). The mixture was stirred at room temperature for 1 hour and then heated at 90° C. for 2 hours. The reaction mixture was cooled down to room temperature, then benzyl alcohol (0.263 g, 2.43 mmol) was added. The resulting mixture was heated at 90° C. overnight. The solvent was concentrated and the residue was purified by flash column chromatography on silica gel (0 to 70% EtOAc in hexanes) to give 0.4 g of Cbz-protected intermediate, which was dissolved in MeOH (80 mL) and passed through H-Cube® (Pd/C 10%, 10 bar, 25° C., flow rate 0.5 mL/min). The resulting mixture was concentrated to give 0.3 g (70% over 2 steps) of the title compound. It was used for the next step without further purification. $^1$H NMR (400 MHz, CDCl$_3$): δ 7.33-7.28 (m, 2H), 6.65-6.58 (m, 1H), 4.04-3.91 (m, 4H), 3.78-3.69 (m, 2H), 3.40-3.29 (m, 1H), 2.45-1.37 (m, 8H). ESI-MS m/z: 339 (M+H)$^+$.

Intermediate 31 cis-13-Amino-9-(3-fluoro-phenyl)-1,4-dioxa-9-aza-dispiro[4.1.4.3]tetradecan-8-one

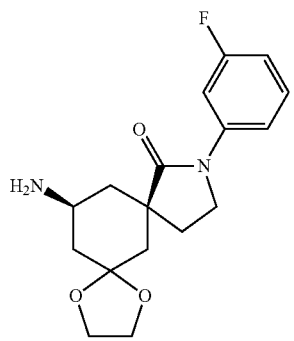 [SMILES: N[C@@H]1CC2(C[C@@]3(CCN(c4cccc(F)c4)C3=O)C1)OCCO2]

Using the same experimental procedures described in the synthesis of intermediate 30, intermediate 31 was also made from 9.30 mmol of cis-9-(3-fluoro-phenyl)-8-oxo-1,4-dioxa-9-aza-dispiro[4.1.4.3]tetradecane-13-carboxylic acid. ESI-MS m/z: 321 (M+H)$^+$.

Intermediate 32 cis-Thiazole-2-carboxylic acid (1-oxo-2-aza-spiro[4.5]dec-7-yl)-amide

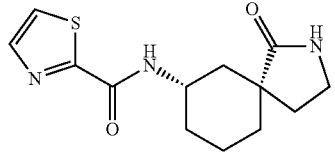 [SMILES: O=C(N[C@H]1CCC[C@]2(CCNC2=O)C1)c1nccs1]

Into a vial was added intermediate 10 (90 mg, 0.2 mmol), triethylamine (76 mg, 0.75 mmol) and methylene chloride (5.0 mL). The mixture was cooled in ice bath. Thiazole-2-carbonyl chloride (56 mg, 0.38 mmol) was then added. After stirring at rt for 2 hrs, the mixture was then washed with saturated sodium bicarbonate, dried over Na$_2$SO$_4$, and concentrated under reduced pressure to afford thiazole-2-carboxylic acid [2-(2,4-dimethoxy-benzyl)-1-oxo-2-aza-spiro[4.5]dec-7-yl]-amide (60 mg, 60%). $^1$H NMR (300 MHz, CDCl$_3$): δ7.86 (d, J=3.1 Hz, 1H), 7.69-7.79 (m, 1H), 7.54 (d, J=3.1 Hz, 1H), 7.04-7.10 (m, 1H), 6.38-6.46 (m, 2H), 4.35-4.50 (m, 2H), 4.00-4.18 (m, 1H), 3.79 (s 3H), 3.78 (s, 3H), 3.12-3.20 (m, 2H), 1.24-2.05 (m, 10H). ESI-MS m/z: 429 (M+H)$^+$. The residue obtained above was treated with TFA (1.0 mL), and heated at 60° C. for 3 hrs. The mixture was then partitioned into dichloromethane and saturated sodium bicarbonate, and the organic layer was dried over sodium sulfate and concentrated in vacuo to give the title compound cis- Thiazole-2-carboxylic acid (1-oxo-2-aza-spiro[4.5]dec-7-yl)-amide. ESI-MS m/z: 280 (M+H)+ (Method A, RT: 0.57). It was used in next step without further purification.

Intermediate 33 cis-7-Amino-2-(3,5-difluoro-phenyl)-2-aza-spiro [4.5]decan-1-one Hydrochloric acid salt

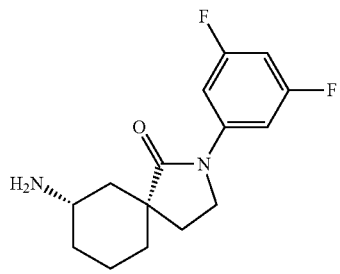 [SMILES: N[C@H]1CCC[C@]2(CCN(c3cc(F)cc(F)c3)C2=O)C1]

Step 1: trans-1-[2-(3,5-Difluorophenylamino)-ethyl]-cyclohexane-1,3-dicarboxylic acid diethyl ester

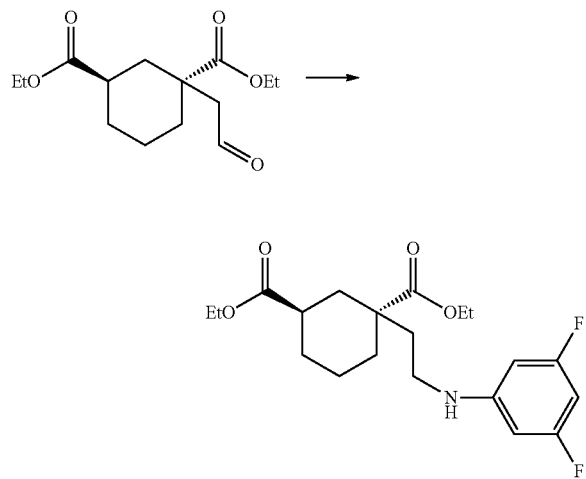

To a solution of trans-1-(2-oxo-ethyl)-cyclohexane-1,3-dicarboxylic acid diethyl ester (86.4 g, 320 mmol) in 1,2-dichloroethane (640 mL) was added acetic acid (3.66 mL, 64.0 mmol) followed by the slow addition of a solution of 3,5-difluoroaniline (57.8 g, 448 mmol) in 1,2-dichloroethane (320 mL). The mixture was stirred at room temperature for 1.5 h, then cooled to 0° C., sodium triacetoxyborohydride (94.8 g, 447 mmol) was added portionwise, and stirring continued at room temperature for 14 h. The mixture was cooled to 0° C. and quenched with crushed ice and extracted with dichloromethane. The organic layer was separated, washed with water, brine, dried with $Na_2SO_4$ and concentrated under vacuum. The residue was purified by column chromatography on silica gel (hexane/EtOAc:4/1) to give 110.8 g (90%) of the title compound as transparent oil. $^1$H NMR (400 MHz, $CDCl_3$) δ 5.85-6.23 (m, 4 H), 4.01-4.24 (m, 4 H), 3.81 (t, J=5.7 Hz, 2 H), 2.97-3.21 (m, 2 H), 2.36-2.56 (m, 2 H), 2.24 (d, J=11.7 Hz, 1 H), 1.62-2.03 (m, 4 H), 1.02-1.42 (m, 8 H).

Step 2: cis-2-(3,5-Difluorophenyl)-1-oxo-2-aza-spiro [4.5]decane-7-carboxylic acid ethyl ester To a cooled (0° C.) solution of trans-1-[2-(3,5-Difluorophenylamino)-ethyl]-cyclohexane-1,3-dicarboxylic acid diethyl ester (110.8 g, 289 mmol) in ethanol (725 mL), sodium hydride (60% in mineral oil, 34.7 g, 867 mmol) was added portionwise, and the reaction mixture was stirred at room temperature for 4 h, then refluxed for 15 h. The resulting mixture was concentrated under vacuum at room temperature, diluted with ethyl acetate, cooled to 0° C. and treated with a 6 N HCl solution until pH ~4. The organic layer was washed with water, brine, dried with $Na_2SO_4$ and concentrated. The residue was purified by column chromatography on silica gel (hexane/EtOAc:3/1) to give 32.7 g (33.5%) of the title compound as a yellow gum. $^1$H NMR (400 MHz, $CDCl_3$) δ 7.23-7.38 (m, 2 H), 6.59 (tt, J=8.7, 2.2 Hz, 1 H), 4.12 (q, J=7.0 Hz, 2 H), 3.66-3.80 (m, 2 H), 2.27-2.50 (m, 0 H), 1.95-2.14 (m, 4 H), 1.77-1.94 (m, 3 H), 1.62-1.76 (m, 1 H), 1.34-1.53 (m, 2 H), 1.25 (t, J=7.0 Hz, 3 H).

Together with cis-2-(3,5-difluorophenyl)-1-oxo-2-aza-spiro[4.5]decane-7-carboxylic acid ethyl ester, trans-2-(3,5-difluorophenyl)-1-oxo-2-aza-spiro[4.5]decane-7-carboxylic acid ethyl ester (12.5 g, 13%), cis-2-(3,5-difluorophenyl)-1-oxo-2-aza-spiro[4.5]decane-7-carboxylic acid (11.0 g, 12%) and trans-2-(3,5-difluorophenyl)-1-oxo-2-aza-spiro[4.5]decane-7-carboxylic acid (7.97 g, 9%) were isolated, all yellow gums as well. trans-2-(3,5-Difluorophenyl)-1-oxo-2-aza-spiro[4.5]decane-7-carboxylic acid ethyl ester: $^1$H NMR (400 MHz, $CDCl_3$) δ 7.23-7.33 (m, 2 H), 6.52-6.64 (m, 1 H), 4.12 (q, J=7.0 Hz, 2 H), 3.65-3.76 (m, 2 H), 3.10-3.26 (m, 1 H), 2.10-2.19 (m, 1 H), 1.84-2.08 (m, 5 H), 1.52-1.75 (m, 2 H), 1.28-1.50 (m, 2 H), 1.22 (t, J=7.0 Hz, 3 H).

cis-2-(3,5-Difluorophenyl)-1-oxo-2-aza-spiro[4.5]decane-7-carboxylic acid: $^1$H NMR (400 MHz, $CDCl_3$) δ 7.22-7.36 (m, 2 H), 6.52-6.67 (m, 1 H), 3.66-3.81 (m, 2 H), 2.34-2.52 (m, 1 H), 2.00-2.18 (m, 3 H), 1.78-1.99 (m, 3 H), 1.32-1.76 (m, 4 H).

trans-2-(3,5-Difluorophenyl)-1-oxo-2-aza-spiro[4.5]decane-7-carboxylic acid: $^1$H NMR (400 MHz, $CDCl_3$) δ 7.20-7.37 (m, 2 H), 6.58 (tt, J=8.8, 2.34 Hz, 1 H), 3.60-3.81 (m, 2

H), 3.13-3.37 (m, 1 H), 2.19 (dd, J=13.5, 4.10 Hz, 1 H), 1.84-2.12 (m, 5 H), 1.16-1.78 (m, 4 H).

Step 3: cis-2-(3,5-Difluorophenyl)-1-oxo-2-aza-spiro[4.5]decane-7-carboxylic acid

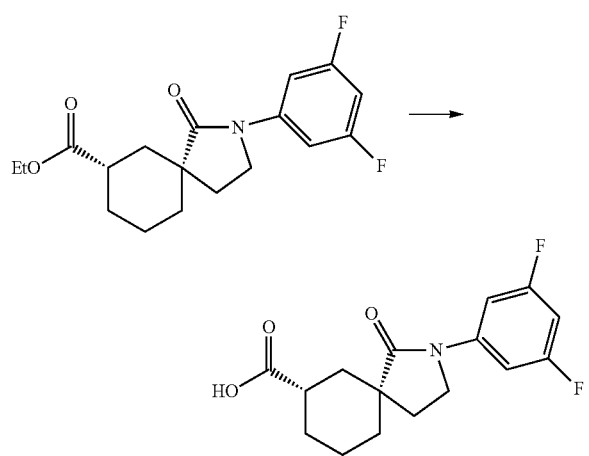

To a solution of cis-2-(3,5-Difluorophenyl)-1-oxo-2-aza-spiro[4.5]decane-7-carboxylic acid ethyl ester (31.7 g, 94.0 mmol) in THF (376 mL) and water (376 mL) was added solid anhydrous lithium hydroxide (22.5 g, 9.40 mmol). The resulting slurry was stirred at room temperature for 15 h, then cooled to 0° C., treated with 4 N HCl until pH~5 (slow addition), and extracted with ethyl acetate. The organic layer was separated, washed with water, brine, dried with Na$_2$SO$_4$ and concentrated under vacuum to give 27.8 g of the title compound as sticky gum, which was used in the next step without further purification. $^1$H NMR (400 MHz, CHLOROFORM-d) δ 7.22-7.36 (m, 2 H), 6.52-6.67 (m, 1 H), 3.66-3.81 (m, 2 H), 2.34-2.52 (m, 1 H), 2.00-2.18 (m, 3 H), 1.78-1.99 (m, 3 H), 1.32-1.76 (m, 4 H).

Step 4: cis-7-Amino-2-(3,5-difluorophenyl)-2-aza-spiro[4.5]decan-1-one HCl salt (Ref.: 09-057-7)

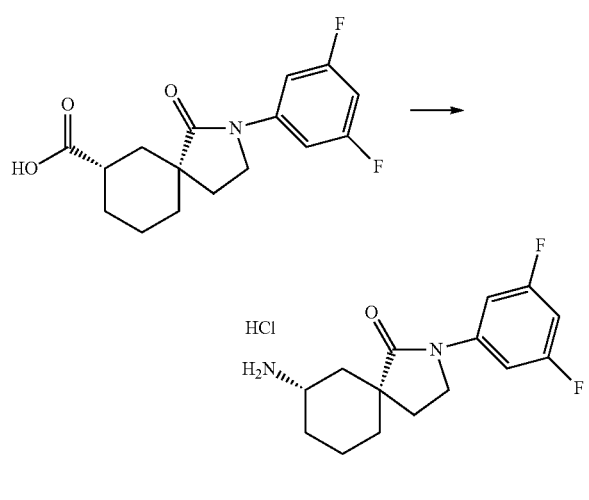

To a suspension of cis-2-(3,5-Difluorophenyl)-1-oxo-2-aza-spiro[4.5]decane-7-carboxylic acid (5.53 g, 17.9 mmol) in toluene (90 mL) at room temperature, triethylamine (2.98 mL, 21.4 mmol) was added, followed by diphenylphosphoryl azide (3.86 mL, 17.9 mmol), and the mixture was stirred at room temperature for 2 h. After that the reaction mixture was heated at 90° C. for 3.5 h, then cooled to 0° C., treated with 6 N HCl (10 mL, slow addition!), and stirring continued at room temperature for 14 h. The resulting white precipitate was filtered, washed with toluene and dried under vacuum to give 5.05 g (89%) of the title compound as a white solid.

$^1$H NMR (400 MHz, DMSO-d$_6$) δ 7.42-7.54 (m, 2 H), 7.00 (tt, J=9.2, 2.30 Hz, 1 H), 3.73-3.81 (m, 2 H), 3.04-3.17 (m, 1 H), 1.87-2.20 (m, 3 H), 1.83 (d, J=11.7 Hz, 1 H), 1.68-1.78 (m, 1 H), 1.63 (t, J=12.5 Hz, 1 H), 1.39-1.57 (m, 2 H), 1.22-1.38 (m, 2 H), MS: m/z 281.19 (M+H)$^+$. HPLC: 96.45%. Analysis: calculated for C$_{15}$H$_{18}$N$_2$O.HCl.0.65 H$_2$O: C, 54.85; H, 6.23; N, 8.53. Found: C, 54.84; H, 6.06; N, 8.79.

Intermediate 34

7-Amino-2-(1-methyl-1H-pyrazol-3-yl)-2-aza-spiro[4.5]decan-1-one

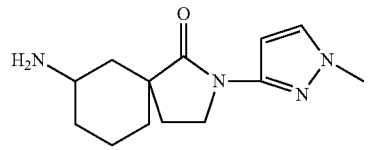 [SMILES: Cn1ccc(N2CCC3(CCCC(N)C3)C2=O)n1]

Using the similar experimental procedures described in intermediate 33, intermediate 34 hydrochloric acid salt was made from 3.7 mmol of trans-1-(2-oxo-ethyl-cyclohexane-1,3-dicarboxylic acid diethyl ester and 3.7 mmol of 1-methyl-1H-pyrazol-3-amine. The intermediate 34 hydrochloric acid salt was basified with sodium hydroxide to afford the title compound which is a mixture of two diastereomers (cis/trns: 7/2; under LC-MS method E, the first peak with RT of 1.06 min was assigned as cis, and the second peak with RT of 1.10 min was assigned as trans.). ESI-MS m/z: 249 (M+H)$^+$. It was used without further purification.

Intermediate 35

4-[7-(3-Fluoro-benzoylamino)-1-oxo-2-aza-spiro[4.5]dec-2-yl]-piperidine-1-carboxylic acid tert-butyl ester

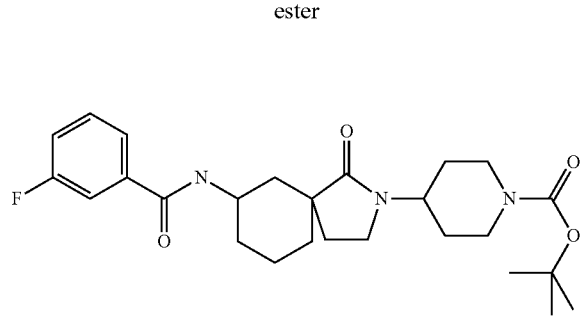

Step 1: 4-(7-Benzyloxycarbonylamino-1-oxo-2-aza-spiro[4.5]dec-2-yl)-piperidine-1-carboxylic acid tert-butyl ester

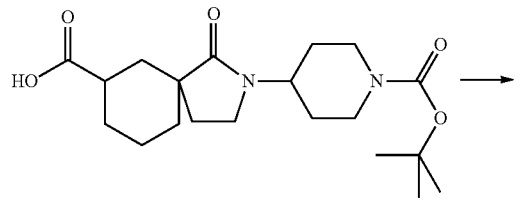

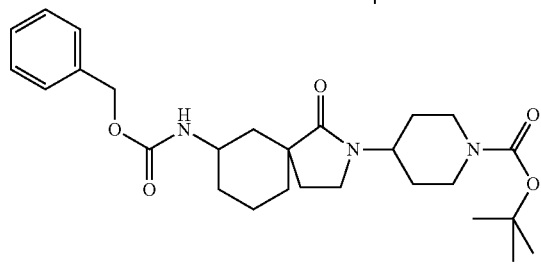

Using the same experimental procedures described in the synthesis of intermediate 10, 2-(1-tert-Butoxycarbonyl-piperidin-4-yl)-1-oxo-2-aza-spiro[4.5]decane-7-carboxylic acid (mixture of cis and trans diastereomers) was made from 7.40 mmol of 1-(2-oxo-ethyl)-cyclohexane-1,3-dicarboxylic aid diethyl ester and 7.40 mmol of 4-amino-1-Boc-piperidine. 2-(1-tert-Butoxycarbonyl-piperidin-4-yl)-1-oxo-2-aza-spiro[4.5]decane-7-carboxylic acid (1.24 g, 3.25 mmol) was dissolved in toluene (20.0 mL), triethylamine (0.54 mL, 3.90 mmol) was added, followed by the addition of diphenylphosphonic azid (0.70 mL, 3.25 mmol). The mixture was stirred at rt for 1.5 hrs, and then heated at 90° C. for 2 hrs. Benzyl alcohol (2.0 mL, 19.5 mmol) was added, and the mixture was heated at 90° C. overnight. The mixture was cooled down, concentrated under reduce pressure to afford 0.85 g (54%) of the title compound which is a mixture of two diastereomers (cis/trns: 1/1; under LC-MS method C, the first peak with RT of 1.56 min was assigned as cis, and the second peak with RT of 1.59 min was assigned as trans.). ESI-MS m/z: 486 (M+H)+.

Step 2: 4-(7-Amino-1-oxo-2-aza-spiro[4.5]dec-2-yl)-piperidine-1-carboxylic acid tert-butyl ester

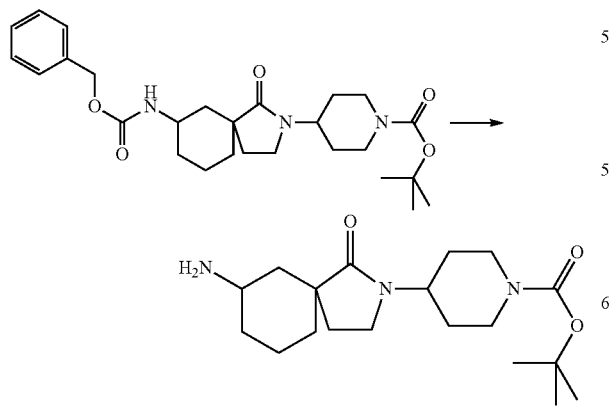

4-(7-Benzyloxycarbonylamino-1-oxo-2-aza-spiro[4.5]dec-2-yl)-piperidine-1-carboxylic acid tert-butyl ester (0.75 g, 1.54 mmol) in methanol (50.0 mL) was shaken under hydrogenated at 50 psi and rt for 2.5 hrs. The catalyst was filtered off, and the filtrate was concentrated to afford 0.42 g (77%) of the title compound. LC-MS (method C): RT: 0.94 min; ESI-MS m/z: 352 (M+H)+. It was used in the next step without further purification.

Step 3: 4-[7-(3-Fluoro-benzoylamino)-1-oxo-2-aza-spiro[4.5]dec-2-yl]-piperidine-1-carboxylic acid tert-butyl ester

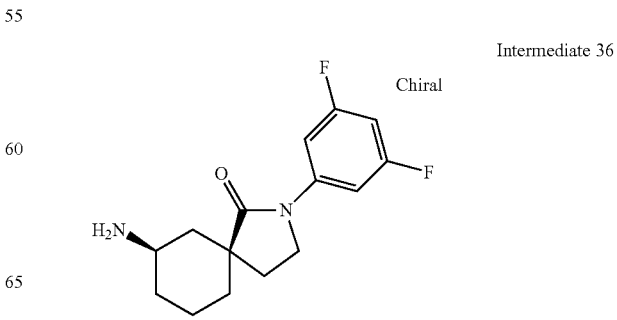

4-(7-Amino-1-oxo-2-aza-spiro[4.5]dec-2-yl)-piperidine-1-carboxylic acid tert-butyl ester (0.20 g, 0.57 mmol), 3-fluorobenzoic acid (0.080 g, 0.56 mmol), BOP (0.252 g, 0.57 mmol), and triethylamine (0.115 g, 1.14 mmol) in methylene chloride (5.0 mL) was stirred at rt overnight. The mixture was concentrated, and the resulting residue was purified with chromatography (ethyl acetate) to afford the title compound which is a mixture of two diastereomers (cis/trans: 3/2; under LC-MS method C, the first peak with RT of 1.47 min was assigned as cis, and the second peak with RT of 1.50 min was assigned as trans.). 1H NMR (400 MHz, CDCl3) δ 8.5 (s, 0.6 H), 7.60-7.68 (m, 1H), 7.36-7.50 (m, 2H), 7.14-7.20 (m, 1H), 5.92 (d, J=6.8 Hz, 0.4 H), 4.55-4.65 (m, 0.4 H), 4.04-4.38 (m, 3.6H), 3.20-3.30 (m, 2H), 2.71-2.86 (m, 2H), 1.28-2.25 (m, 23H). ESI-MS m/z: 474 (M+H)+.

Intermediates 36 and 37

(5R,7R)-7-Amino-2-(3,5-difluoro-phenyl)-2-aza-spiro[4.5]decan-1-one and (5S,7S)-7-Amino-2-(3,5-difluoro-phenyl)-2-aza-spiro[4.5]decan-1-one Intermediate 36

-continued

Intermediate 37

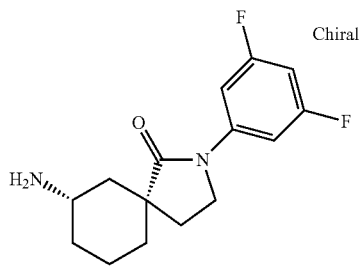

The racemic intermediate 33 (cis diastereomer) (650 mg) were resolved by HPLC (column: Chiralpak® IC (Chiral Technologies, Inc.), 150×30 mm, 5 µM particle size; mobile phase: 30% isopropanol, 70% $CO_2$; flow rate: 100 g/min; UV at 254 nm) to afford two enantiomers. The first peak (RT: 3.18 min) from the chiral HPLC was assigned as (5S,7S)-7-amino-2-(3,5-difluoro-phenyl)-2-aza-spiro[4.5]decan-1-one (270 mg), and the second peak (RT: 6.92 min) from the chiral HPLC was assigned (5R,7R)-7-Amino-2-(3,5-difluoro-phenyl)-2-aza-spiro[4.5]decan-1-one (250 mg).

Intermediate 38 cis-7-Amino-2-(6-(4-fluorophenyl)pyrimidin-4-yl)-2-azaspiro[4.5]decan-1-one

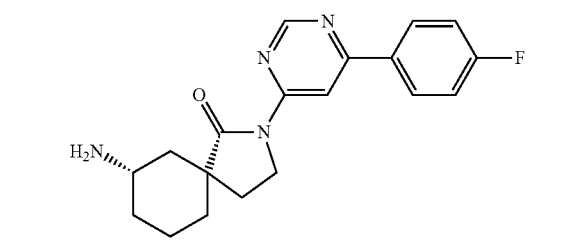

Steps 1-4: trans-ethyl 2-(6-(4-fluorophenyl)pyrimidin-4-yl)-1-oxo-2-azaspiro[4.5]decane-7-carboxylate

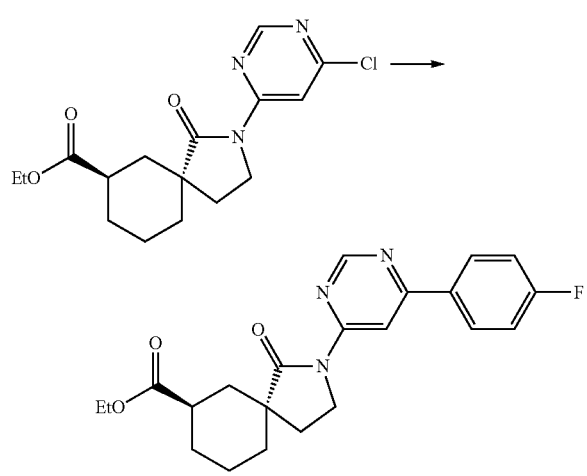

Using analogous procedures as described in the synthesis of intermediate 2 (steps 1 to 4), trans-ethyl 2-(6-chloropyrimidin-4-yl)-1-oxo-2-azaspiro[4.5]decane-7-carboxylate was made from 219 mmol of 1,3-cyclohexanecarboxylic acid.

Step 5: trans-ethyl 2-(6-(4-fluorophenyl)pyrimidin-4-yl)-1-oxo-2-azaspiro[4.5]decane-7-carboxylate To a de-oxygenated solution of trans-ethyl 2-(6-chloropyrimidin-4-yl)-1-oxo-2-azaspiro[4.5]decane-7-carboxylate (6.75 g, 20.03 mmol), 4-fluorobenzeneboronic acid (3.35 g, 24.04 mmol) and cesium carbonate (13 g, 40.06 mmol) in 1,4-dioxane (180 mL) was added $Pd_2(dba)_3$ (1.1 g, 1.2 mmol) and $P(^tBu)_3$ (1M in THF, 2.4 mL, 2.4 mmol) under argon atmosphere. The reaction mass mixture heated at reflux for 4 h. The reaction mixture was filtered through a bed of Celite® and the filtrate was concentrated. The crude residue was purified by combiflash column chromatography to afford 7.2 g (90.5%) of trans-ethyl 2-(6-(4-fluorophenyl)pyrimidin-4-yl)-1-oxo-2-azaspiro[4.5]decane-7-carboxylate. ESI-MS m/z: 398 $(M+H)^+$.

Steps 6-7: cis-7-Amino-2-(6-(4-fluorophenyl)pyrimidin-4-yl)-2-azaspiro[4.5]decan-1-one Using analogous procedures as described in the synthesis of intermediate 2 (steps 5 and 6), intermediate 38 was made from 5.03 mmol of trans-ethyl 2-(6-(4-fluorophenyl)pyrimidin-4-yl)-1-oxo-2-azaspiro[4.5]decane-7-carboxylate. ESI-MS m/z: 341 $(M+H)^+$.

3. Preparation of Compounds of the Invention

Unless specified otherwise, all starting materials and reagents were obtained from commercial suppliers, such as Sigma-Aldrich Corp. (St. Louis, Mo., USA) and its subsidiaries, and used without further purification. Unless indicated as the absolute stereochemistry, the stereochemistry of compounds of the invention has been assigned arbitrarily when indicated, such as for di-fluoro-cyclohexane-spirolactam compounds of formula (I).

Example 1 and Example 2 trans-Pyridine-2-carboxylic acid [2-(3-chloro-phenyl)-1-oxo-2-aza-spiro[4.5]dec-7-yl]amide and cis-pyridine-2-carboxylic acid [2-(3-chloro-phenyl)-1-oxo-2-aza-spiro[4.5]dec-7-yl]-amide, respectively Example 1

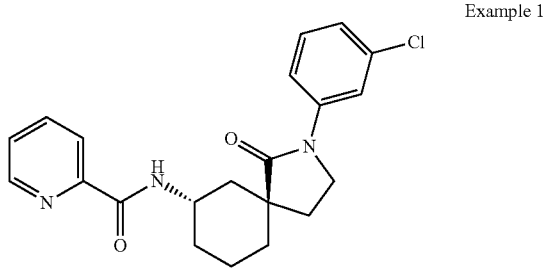

-continued

Example 2

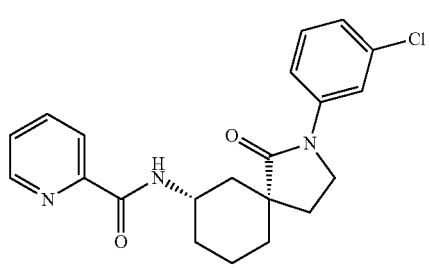

Example 1 and Example 2 were prepared from intermediate 1 via the process of Scheme 1, supra, as follows:

7-Amino-2-(3-chloro-phenyl)-2-aza-spiro[4.5]decan-1-one (0.140 g, 0.502 mmol, intermediate 1) was dissolved in CH$_2$Cl$_2$ (2.0 mL), picolinic acid (0.068 g, 0.552 mmol), and BOP (0.244 g, 0.552 mmol), and triethylamine (0.31 mL, 2.21 mmol) in CH$_2$Cl$_2$ (1.0 mL) were added. The reaction mixture was stirred at rt overnight and then concentrated under reduced pressure. The resulting residue was purified by preparative TLC (hexane/ethyl acetate: 1/2) to afford two diastereomers. The less polar one was assigned as trans, Example 1 (0.097 g, 51%), and the polar one was assigned as cis, Example 2 (0.043 g, 22%). Trans diastereomer (Example 1): $^1$H NMR (400 MHz, CDCl$_3$): δ 8.54 (ddd, J=4.8, 1.7, 1.1 Hz, 1H), 8.20 (dt, J=7.6, 1.1 Hz, 1H), 8.02 (d, J=7.6 Hz, 1H), 7.84 (td, J=7.8, 1.7 Hz, 1H), 7.72 (t, J=2.0, 1.0 Hz, 1H), 7.55 (ddd, J=8.3, 2.1, 1.0 Hz, 1H), 7.42 (ddd, J=7.6, 4.8, 1.2 Hz, 1H), 7.27 (t, J=8.0 Hz, 1H), 7.10 (ddd, J=7.9, 2.1, 1.0 Hz, 1H), 4.63-4.71 (m, 1H), 3.67-3.80 (m, 2H), 2.32 (dd, J=13.3, 4.3 Hz, 1H), 2.01-2.14 (m, 3H), 1.86-1.92 (m, 1H), 1.70-1.77 (m, 2H), 1.63 (dd, J=13.4, 8.6 Hz, 1H), 1.45-1.58 (m, 2H). ESI-MS m/z: 384 (M+H)$^+$. Cis diastereomer (Example 2): $^1$H NMR (400 MHz, CDCl$_3$): δ 8.55 (ddd, J=4.8, 1.7, 1.0 Hz, 1H), 8.19 (dt, J=7.8, 1.1 Hz, 1H), 8.05 (d, J=8.7 Hz, 1H), 7.84 (td, J=7.5, 1.5 Hz, 1H), 7.73 (t, J=2.0, 1.0 Hz, 1H), 7.55 (ddd, J=7.7, 2.2, 1.0 Hz, 1H), 7.42 (ddd, J=7.5, 4.7, 1.2 Hz, 1H), 7.28 (t, J=8.1 Hz, 1H), 7.11 (ddd, J=8.1, 2.0, 1.0 Hz, 1H), 4.07-4.18 (m, 1H), 3.74-3.84 (m, 2H), 2.23-2.30 (m, 1H), 2.09-2.19 (m, 2H), 1.88-1.98 (m, 2H), 1.69-1.79 (m, 2H), 1.65-1.65 (m, 2H), 1.34-1.44 (m, 1H). ESI-MS m/z: 384 (M+H)$^+$.

Example 5 and Example 6

Pyridine-2-carboxylic acid [(5R,7R)-2-(3-chloro-phenyl)-1-oxo-2-aza-spiro[4.5]dec-7-yl]-amide and pyridine-2-carboxylic acid [(5S,7S)-2-(3-chloro-phenyl)-1-oxo-2-aza-spiro[4.5]dec-7-yl]-amide Example 5
Chiral

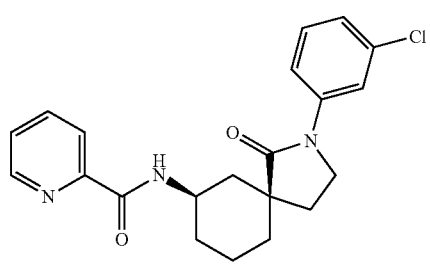

Example 6
Chiral

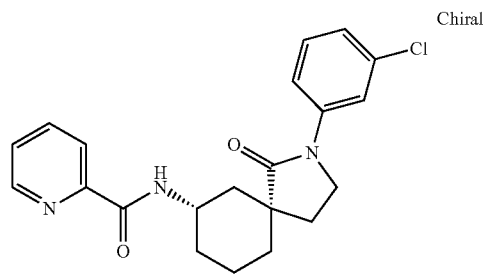

The racemic Example 2 (30 mg) were resolved by HPLC (column: Chiralpak® AD (Diacel), 250×20 mm; mobile phase: 20% isopropanol, 79.9% hexane, 0.1% diethylamine; flow rate: 14 mL/min; UV at 254 nm) to afford two enantiomers. The first peak from chiral HPLC was assigned as Example 5, pyridine-2-carboxylic acid [(5R,7R)-2-(3-chloro-phenyl)-1-oxo-2-aza-spiro[4.5]-dec-7-yl]amide (8 mg), and the second peak from chiral HPLC was assigned as Example 6, pyridine-2-carboxylic acid [(5S,7S)-2-(3-chloro-phenyl)-1-oxo-2-aza-spiro[4.5]-dec-7-yl]amide (7 mg).

Example 5

$^1$H NMR (400 MHz, CDCl$_3$): δ 8.55 (ddd, J=4.8, 1.7, 1.0 Hz, 1H), 8.19 (dt, J=7.8, 1.1 Hz, 1H), 8.05 (d, J=8.7 Hz, 1H), 7.84 (td, J=7.5, 1.5 Hz, 1H), 7.73 (t, J=2.0, 1.0 Hz, 1H), 7.55 (ddd, J=7.7, 2.2, 1.0 Hz, 1H), 7.42 (ddd, J=7.5, 4.7, 1.2 Hz, 1H), 7.28 (t, J=8.1 Hz, 1H), 7.11 (ddd, J=8.1, 2.0, 1.0 Hz, 1H), 4.07-4.18 (m, 1H), 3.74-3.84 (m, 2H), 2.23-2.30 (m, 1H), 2.09-2.19 (m, 2H), 1.88-1.98 (m, 2H), 1.69-1.79 (m, 2H), 1.65-1.65 (m, 2H), 1.34-1.44 (m, 1H). ESI-MS m/z: 384 (M+H)$^+$.

Example 6

$^1$H NMR (400 MHz, CDCl$_3$): δ 8.55 (ddd, J=4.8, 1.7, 1.0 Hz, 1H), 8.19 (dt, J=7.8, 1.1 Hz, 1H), 8.05 (d, J=8.7 Hz, 1H), 7.84 (td, J=7.5, 1.5 Hz, 1H), 7.73 (t, J=2.0, 1.0 Hz, 1H), 7.55 (ddd, J=7.7, 2.2, 1.0 Hz, 1H), 7.42 (ddd, J=7.5, 4.7, 1.2 Hz, 1H), 7.28 (t, J=8.1 Hz, 1H), 7.11 (ddd, J=8.1, 2.0, 1.0 Hz, 1H), 4.07-4.18 (m, 1H), 3.74-3.84 (m, 2H), 2.23-2.30 (m, 1H), 2.09-2.19 (m, 2H), 1.88-1.98 (m, 2H), 1.69-1.79 (m, 2H), 1.65-1.65 (m, 2H), 1.34-1.44 (m, 1H). ESI-MS m/z: 384 (M+H)$^+$.

In an analogous manner to Examples 1 and 2, Examples 3-4 and 12-14 in Table 1 (below) were made from commercially available 6-methyl-pyridine-2-carboxylic acid, 6-methyl-pyrazine-2-carboxylic acid, pyrazine-2-carboxylic acid, and 1-methyl-1H-pyrazole-3-carboxylic acid at 0.14 to 0.22 mmol reaction scales.

In a similar manner to Examples 1 and 2, Examples 17-22 in Table 1 were made at 0.22 mmol reaction scales from intermediate 5 and commercially available 6-methyl-pyridine-2-carboxylic acid, picolinic acid, and 6-methyl-pyrazine-2-carboxylic acid In a similar manner to Examples 1 and 2, Example 19 in Table 1 also was made at a 7.62 mmol reaction scale from commercially available picolinic acid and intermediate 6.

In a similar manner to Example 1 and 2, Examples 7-8 and 23-24 in Table 1 were made at 0.11-0.22 mmol reaction scales from intermediate 7 and commercially available picolinic acid, 3-chlorobenzoic acid, 6-methyl-pyridine-2-carboxylic acid, and 3-fluorobenzoic acid, respectively.

In a similar manner to Example 1 and 2, Example 27 in Table 1 was made at a 1.24 mmol reaction scale from commercially available 3-fluorobenzoic acid and intermediate 8.

Example 27

$^1$H NMR (300 MHz, CDCl$_3$) δ 8.16 (d, J=8.3 Hz, 1H), 7.77 (br, 1H), 7.66-7.55 (m, 3H), 7.41 (dt, J=5.7, 8.3 Hz, 1H), 7.23-7.14 (m, 1H), 6.91 (d, J=7.4 Hz, 1H), 4.39-4.24 (m, 1H), 4.18-3.97 (m, 2H), 2.48 (s, 3H), 2.18-1.47 (m, 10H). ESI-MS m/z: 382 (M+H)$^+$.

In a similar manner to Example 1 and 2, Examples 9-11 and 15-16 in Table 1 were made at a 0.19 mmol reaction scale from intermediate 9 and commercially available picolinic acid, 6-methyl-pyridine-2-carboxylic acid, 6-methyl-pyrazine-2-carboxylic acid, 3-fluorobenzoic acid, and 3-chloroorobenzoic acid, respectively.

Example 15

$^1$H NMR (400 MHz, CDCl$_3$): δ8.02-8.04 (m, 1H), 7.89-7.93 (m, 1H), 7.28-7.60 (m, 5H), 7.16-7.22 (m, 1H), 4.23-4.34 (m, 1H), 3.78-3.89 (m, 2H), 1.75-2.27 (m, 7H), 1.50-1.70 (m, 3H). ESI-MS m/z: 392 (M+H)$^+$.

In a similar manner to Examples 1 and 2, Example 158 in Table 1 was made at 0.2 mmol reaction scale from intermediate 34 and commercially available 3-fluorobenzoic acid.

Example 158

$^1$H NMR (400 MHz, CDCl$_3$): δ 8.20 (bs, 0.8H), 7.60-7.69 (m, 1.6H), 7.44-7.51 (m, 0.4H), 7.35-7.42 (m, 1H), 7.25-7.29 (m, 1H), 7.13-7.20 (m, 1H), 6.80-6.83 (m, 1H), 5.99 (d, J=7.0 Hz, 0.2 H), 4.65-4.75 (m, 0.2H), 4.30-4.40 (m, 0.8H), 3.80-3.95 (m, 5H), 1.35-2.34 (m, 10H). ESI-MS m/z: 371 (M+H)$^+$.

In a similar manner to Examples 1 and 2, Example 86-88 in Table 1 was made at 0.81 mmol reaction scale from intermediate 38 and commercially available 6-methyl-pyrazine-2-carboxylic acid, 6-methyl-pyridine-2-carboxylic acid and 3-fluorobenzoic acid.

Example 30 cis-Pyridine-2-carboxylic acid [2-(4-fluoro-pyridin-2-yl)-1-oxo-2-aza-spiro[4.5]dec-7-yl]-amide

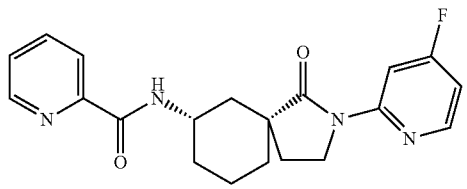 [SMILES: O=C(N[C@H]1CCC[C@]2(CCN(c3cc(F)ccn3)C2=O)C1)c1ccccn1]

Example 30 was prepared from intermediate 21 via the process of Scheme 2, supra, as follows:

cis-Pyridine-2-carboxylic acid (1-oxo-2-aza-spiro[4.5]dec-7-yl)-amide (60.0 mg, 0.22 mmol, intermediate 21), 2-chloro-4-fluoropyridine (28.8 mg, 0.219 mmol), potassium carbonate (60.6 mg, 0.438 mmol), copper(I) iodide (41.7 mg, 0.219 mmol), and (1R,2R)—N,N'-dimethyl-cyclohexane-1,2-diamine (31.2 mg, 0.219 mmol) in 1,4-dioxane (3.00 mL) were placed in a sealed-tube. The reaction mixture was heated at 80° C. overnight. The crude mixture was cooled to rt and diluted with DCM (50 mL). The organic layer was washed with ammonia water/water (1:1, 2×15 mL) and brine, dried over MgSO$_4$, filtered, and concentrated under reduced pressure. The residue was purified by CombiFlash® system (4 g silica gel cartridge; gradient: 0 to 40% ethyl acetate in DCM) to afford 24 mg (30%) of the title compound, cis-Pyridine-2-carboxylic acid [2-(4-fluoro-pyridin-2-yl)-1-oxo-2-aza-spiro [4.5]dec-7-yl]-amide. $^1$H NMR (400 MHz, CDCl$_3$) δ 8.55 (ddd, J=1.0, 1.7, 4.8 Hz, 1H), 8.30 (dd, J=8.8, 5.7 Hz, 1H), 8.25 (dd, J=11.6, 2.3 Hz, 1H), 8.18 (dt, J=7.8, 1.0 Hz, 1H), 8.06 (br d, J=8.2 Hz, 1H), 7.84 (td, J=6.0, 2.3 Hz, 1H), 6.79 (ddd, J=7.8, 5.7, 2.3 Hz, 1H), 3.97-4.20 (m, 3H), 2.09-2.27 (m, 3H), 1.56-2.01 (m, 6H), 1.33-1.46 (m, 1H). ESI-MS m/z: 369 (M+H)$^+$.

In an analogous manner to Example 30, Examples 31-32, 34, and 63-64 in Table 1 (below) were made at 0.21-0.49 mmol reaction scales from intermediate 18 and commercially available heteroaryl halides; 2-chloro-5-fluoropyridine, 2-chloro-4-fluoropyridine, 2-chloro-4-methylpyrimidine, 5-bromo-2-methylpyridine, and 3-bromo-5-fluoropyridine, respectively.

Example 31

$^1$H NMR (400 MHz, CDCl$_3$) δ 8.47 (dd, J=9.2, 4.1 Hz, 1H), 8.24-8.31 (m, 1H), 8.22 (d, J=3.0 Hz, 1H), 8.03 (d, J=7.7 Hz, 1H), 7.77 (t, J=7.7 Hz, 1H), 7.45 (ddd, J=9.2, 7.7, 3.0 Hz, 1H), 7.31 (d, J=7.7 Hz, 1H), 3.96-4.21 (m, 3H), 2.62 (s, 3H), 2.10-2.28 (m, 3H), 1.58-2.02 (m, 6H), 1.36-1.51 (m, 1H). ESI-MS m/z: 383 (M+H)$^+$.

Example 32

$^1$H NMR (400 MHz, CDCl$_3$) δ 8.24 (dd, J=8.8, 5.7 Hz, 1H), 8.19 (dd, J=2.3, 11.7 Hz, 1H), 8.12 (br d, J=7.4 Hz, 1H), 7.92 (d, J=7.7 Hz, 1H), 7.66 (t, J=7.7 Hz, 1H), 7.21 (d, J=8.4 Hz, 1H), 6.73 (ddd, J=7.8, 5.7, 2.3 Hz, 1H), 3.90-4.12 (m, 3H), 2.52 (s, 3H), 2.02-2.20 (m, 3H), 1.46-1.94 (m, 6H), 1.27-1.41 (m, 1H). ESI-MS m/z: 383 (M+H)$^+$.

Example 34

$^1$H NMR (400 MHz, CDCl$_3$) δ 8.37 (d, J=5.0 Hz, 1H), 8.06 (br d, J=7.0 Hz, 1H), 7.84 (d, J=7.7 Hz, 1H), 7.58 (t, J=7.7 Hz, 1H), 7.12 (d, J=7.9 Hz, 1H), 6.73 (d, J=5.0 Hz, 1H), 3.76-4.01 (m, 3H), 2.54 (s, 3H), 2.35 (s, 3H), 1.92-2.08 (m, 3H), 1.37-1.84 (m, 6H), 1.19-1.31 (m, 1H). ESI-MS m/z: 380 (M+H)$^+$.

Example 63

$^1$H NMR (400 MHz, CDCl$_3$) δ 8.60 (d, J=2.6 Hz, 1H), 8.14 (dd, J=2.6, 8.5 Hz, 1H), 8.11 (br d, J=8.6 Hz, 1H), 7.97 (d, J=7.6 Hz, 1H), 7.71 (t, J=7.7 Hz, 1H), 7.26 (d, J=7.2 Hz, 1H), 7.17 (d, J=8.6 Hz, 1H), 4.06-4.18 (m, 1H), 3.77-3.88 (m, 2H), 2.57 (s, 3H), 2.54 (s, 3H), 2.09-2.34 (m, 3H), 1.59-1.99 (m, 6H), 1.33-1.47 (m, 1H). ESI-MS m/z: 379 (M+H)$^+$.

Example 64

$^1$H NMR (400 MHz, CDCl$_3$) δ 8.51 (br, 1H), 8.22-8.29 (m, 2H), 8.12 (br d, J=8.4 Hz, 1H), 7.97 (d, J=7.6 Hz, 1H), 7.71 (t, J=7.7 Hz, 1H), 7.27 (d, J=7.4 Hz, 1H), 4.06-4.19 (m, 1H), 3.78-3.91 (m, 2H), 2.57 (s, 3H), 2.10-2.37 (m, 3H), 1.88-1.98 (m, 2H), 1.53-1.84 (m, 4H), 1.34-1.48 (m, 1H). ESI-MS m/z: 383 (M+H)$^+$.

In a similar manner to Example 30, Examples 35-37 in Table 1 (below) were made at a 0.55 mmol reaction scale from intermediate 19 and commercially available heteroaryl halides; 2-chloro-5-fluoropyridine, 2-chloro-4-fluoropyridine, and 2-chloro-4-methylpyrimidine, respectively.

Example 35

$^1$H NMR (400 MHz, CDCl$_3$) δ 8.45 (dd, J=4.1, 9.2 Hz, 1H), 8.24 (d, J=3.0 Hz, 1H), 7.57-7.64 (m, 2H), 7.40-7.51 (m, 2H), 7.18-7.25 (m, 1H), 4.28-4.40 (m, 1H), 3.98-4.16 (m, 2H), 2.04-2.22 (m, 2H), 1.81-1.98 (m, 5H), 1.53-1.67 (m, 3H). ESI-MS m/z: 386 (M+H)$^+$.

Example 36

$^1$H NMR (400 MHz, CDCl$_3$) δ 8.25 (dd, J=5.7, 8.8 Hz, 1H), 8.18 (dd, J=11.6, 2.3 Hz, 1H), 7.47-7.56 (m, 2H), 7.35 (td, J=8.1, 5.6 Hz, 1H), 7.09-7.16 (m, 1H), 6.76 (ddd, J=7.8, 5.7, 2.3 Hz, 1H), 4.18-4.29 (m, 1H), 3.91-4.11 (m, 2H), 1.96-2.13 (m, 2H), 1.71-1.89 (m, 5H), 1.44-1.59 (m, 3H). ESI-MS m/z: 386 (M+H)$^+$.

Example 37

$^1$H NMR (400 MHz, CDCl$_3$) δ 8.57 (d, J=5.0 Hz, 1H), 7.57-7.65 (m, 2H), 7.42 (td, J=8.1, 5.6 Hz, 1H), 7.16-7.23 (m, 1H), 6.95 (d, J=5.0 Hz, 1H), 4.27-4.38 (m, 1H), 3.99-4.18 (m, 2H), 2.55 (s, 3H), 2.04-2.22 (m, 2H), 1.87-1.95 (m, 5H), 1.54-1.68 (m, 3H). ESI-MS m/z: 383 (M+H)$^+$.

In a similar manner to Example 30, Example 57 in Table 1 (below) was made at a 0.22 mmol reaction scale from intermediate 20 and commercially available 2-chloro-5-fluoropyridine.

Example 57

$^1$H NMR (400 MHz, CDCl$_3$) δ 8.85 (d, J=5.0 Hz, 1H), 8.44 (dd, J=9.2, 4.1 Hz, 1H), 8.20 (d, J=3.0 Hz, 1H), 8.08 (br d, J=8.6 Hz, 1H), 7.89 (d, J=4.9 Hz, 1H), 7.44 (ddd, J=9.2, 7.6, 3.0 Hz, 1H), 3.95-4.19 (m, 3H), 2.78 (s, 3H), 2.08-2.24 (m, 3H), 1.58-1.98 (m, 6H), 1.35-1.47 (m, 1H). ESI-MS m/z: 384 (M+H)$^+$.

In a similar manner to Example 30, Examples 29, 33 and 74 in Table 1 (below) were made at 0.22-0.44 mmol reaction scales from intermediate 21 and commercially available heteroaryl halides: 2-chloro-4-methylpyrimidine, 2-chloro-5-fluoropyridine, and 3-bromo-5-fluoropyridine, respectively.

Example 33

$^1$H NMR (400 MHz, CDCl$_3$) δ 8.55-8.60 (m, 1H), 8.47 (dd, J=9.4, 4.0 Hz, 1H), 8.19-8.24 (m, 2H), 8.11 (br d, J=8.1 Hz, 1H), 7.89 (td, J=7.7, 1.7 Hz, 1H), 7.42-7.49 (m, 2H), 3.98-4.21 (m, 3H), 2.11-2.29 (m, 3H), 1.59-2.02 (m, 6H), 1.36-1.48 (m, 1H). ESI-MS m/z: 369 (M+H)$^+$.

Example 74

$^1$H NMR (400 MHz, CDCl$_3$) δ 8.56-8.60 (m, 1H), 8.54 (br, 1H), 8.26-8.33 (m, 2H), 8.17-8.22 (m, 1H), 8.07 (br d, J=8.8 Hz, 1H), 7.87 (td, J=7.7, 1.7 Hz, 1H), 7.45 (ddd, J=7.6, 4.8, 1.2 Hz, 1H), 4.09-4.21 (m, 1H), 3.81-3.95 (m, 2H), 2.20-2.40 (m, 2H), 2.11-2.18 (m, 1H), 1.90-2.03 (m, 2H), 1.56-1.83 (m, 4H), 1.37-1.49 (m, 1H). ESI-MS m/z: 369 (M+H)$^+$.

Example of 42 cis-6-Methyl-pyridine-2-carboxylic acid [2-(3,5-difluoro-phenyl)-1-oxo-2-aza-spiro[4.5]dec-7-yl]-amide

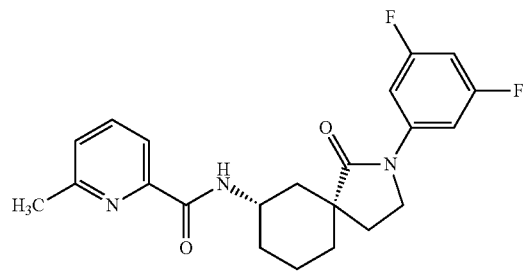 [SMILES: Cc1cccc(C(=O)N[C@H]2CCC[C@]3(CCN(c4cc(F)cc(F)c4)C3=O)C2)n1]

Example 42 was prepared from intermediate 18 via the process of Scheme 2, supra, as follows:

cis-6-Methyl-pyridine-2-carboxylic acid (1-oxo-2-aza-spiro[4.5]dec-741)-amide (0.450 g, 1.56 mmol, intermediate 18), (1-bromo-3,5-difluoro-benzene (0.363 g, 1.88 mmol), potassium carbonate (0.649 g, 4.70 mmol) and N—N' dimethyl-ethane-1,2-diamine (0.138 g, 1.56 mmol) in 1,4-dioxane (15.0 mL) were heated in a microwave synthesizer (Biotage) at 160° C. for 2 hours. The reaction mixture was cooled to rt and filtered through a layer of Celite®. The filtrate was concentrated under reduced pressure and the resulting residue was purified on a reversed phase liquid chromatography/mass spectrometry (RP-HPLC/MS) purification system (Gradient: acetonitrile in water, 28-95% in 3.6 minutes with a cycle time of 5 min. A shallow gradient between 40-70% of acetonitrile was used between 0.75-3.4 min to separate close-eluting impurities. Flow rate: 100 mL/min. Mobile phase additive: 39 mM of ammonium acetate. Column: Inertsil® C18, 30×50 mm, 5 um particle size (GL Sciences)) to afford 0.120 g (20%) of the title compound, cis-6-methyl-pyridine-2-carboxylic acid [2-(3,5-difluoro-phenyl)-1-oxo-2-aza-spiro[4.5]dec-7-yl]-amide as a white solid. $^1$H NMR (400 MHz, CDCl$_3$): δ 8.12 (d, J=8.1 Hz, 1H), 7.97 (d, J=7.6 Hz, 1H), 7.71 (t, J=7.8 Hz, 1H), 7.29-7.32 (m, 2H), 7.20 (d, J=7.8 Hz, 1H), 6.59 (tt, J=8.8, 2.2 Hz, 1H), 4.06-4.16 (m, 1H), 3.71-3.81 (m, 2H), 2.57 (s, 3H), 2.23-2.30 (m, 1H), 2.10-2.19 (m, 2H), 1.88-1.96 (m, 2H), 1.78 (t, J=12.4 Hz, 1H), 1.68-1.76 (m, 1H), 1.54-1.65 (m, 2H), 1.35-1.45 (m, 1H). ESI-MS m/z: 400 (M+H)$^+$.

The racemic Example 42 (220 mg, accumulated by repeating the above reaction one more time) were resolved by HPLC (column: Chiralpak® AD, 250×20 mm; mobile phase: 25% isopropanol, 75% hexane; flow rate: 14 mL/min; UV at 254 nm) to afford two enantiomers. The first peak from the chiral HPLC was assigned as Example 67, 6-methyl-pyridine-2-carboxylic acid [(5R,7R)-2-(3,5-difluoro-phenyl)-1-oxo-2-aza-spiro[4.5]-dec-7-yl]amide (106 mg), and the second peak from the chiral HPLC was assigned as Example 81, 6-methyl-pyridine-2-carboxylic acid [(5S,7S)-2-(3,5-difluoro-phenyl)-1-oxo-2-aza-spiro[4.5]-dec-7-yl]amide (93 mg).

Example 67

$^1$H NMR (400 MHz, CDCl$_3$): δ 8.12 (d, J=8.1 Hz, 1H), 7.97 (d, J=7.6 Hz, 1H), 7.71 (t, J=7.8 Hz, 1H), 7.29-7.32 (m,

2H), 7.20 (d, J=7.8 Hz, 1H), 6.59 (tt, J=8.8, 2.2 Hz, 1H), 4.06-4.16 (m, 1H), 3.71-3.81 (m, 2H), 2.57 (s, 3H), 2.23-2.30 (m, 1H), 2.10-2.19 (m, 2H), 1.88-1.96 (m, 2H), 1.78 (t, J=12.4 Hz, 1H), 1.68-1.76 (m, 1H), 1.54-1.65 (m, 2H), 1.35-1.45 (m, 1H). ESI-MS m/z: 400 (M+H)$^+$.

Example 81

$^1$H NMR (400 MHz, CDCl$_3$): δ 8.12 (d, J=8.1 Hz, 1H), 7.97 (d, J=7.6 Hz, 1H), 7.71 (t, J=7.8 Hz, 1H), 7.29-7.32 (m, 2H), 7.20 (d, J=7.8 Hz, 1H), 6.59 (tt, J=8.8, 2.2 Hz, 1H), 4.06-4.16 (m, 1H), 3.71-3.81 (m, 2H), 2.57 (s, 3H), 2.23-2.30 (m, 1H), 2.10-2.19 (m, 2H), 1.88-1.96 (m, 2H), 1.78 (t, J=12.4 Hz, 1H), 1.68-1.76 (m, 1H), 1.54-1.65 (m, 2H), 1.35-1.45 (m, 1H). ESI-MS m/z: 400 (M+H)$^+$.

In an analogous manner to Example 42, Examples 43-52 and 71-72 in Table 1 (below) were made at 0.07-1.56 mmol reaction scales from intermediate 18 and commercially available 6-bromo-pyridine-2-carbonitrile, 1-fluoro-4-iodo-benzene, 2-bromo-pyridine, bromobenzene, 1-iodo-3-methyl-benzene, 2-bromo-4-methylpyridine, 2-bromo-5-methylpyridine, 2-bromo-3-methylpyridine, 1-fluoro-2-iodobenzene, 4-bromo-2-methylpyridine, 3-bromo-5-methylpyridine, and 1-bromo-3-methoxybenzene, respectively.

Example 43

$^1$H NMR (400 MHz, CDCl$_3$) δ 8.70 (dd, J=0.8, 8.7 Hz, 1H), 8.10 (d, J=8.5 Hz, 1H), 8.00-7.96 (m, 1H), 7.79 (dd, J=7.4, 8.7 Hz, 1H), 7.71 (t, J=7.7 Hz, 1H), 7.43 (dd, J=0.8, 7.4 Hz, 1H), 7.29-7.25 (m, 1H), 4.18-3.97 (m, 3H), 2.57 (s, 3H), 2.28-1.34 (m, 10H). ESI-MS m/z: 390 (M+H)$^+$.

Example 44

$^1$H NMR (400 MHz, CDCl$_3$): δ8.11 (d, J=8.6 Hz, 1H), 7.97 (d, J=8.5 Hz, 1H), 7.71 (t, J=7.6 Hz, 1H), 7.57-7.63 (m, 2H), 7.26 (d, J=7.6 Hz, 1H), 7.02-7.08 (m, 2H), 4.06-4.17 (m, 1H), 3.74-3.83 (m, 2H), 2.57 (s, 3H), 2.22-2.30 (m, 1H), 2.10-2.19 (m, 2H), 1.86-1.97 (m, 2H), 1.54-1.83 (m, 4H), 1.34-1.45 (m, 1H). ESI-MS m/z: 382 (M+H)$^+$.

Example 45

$^1$H NMR (400 MHz, CDCl$_3$) δ 8.41 (d, J=8.5 Hz, 1H), 8.38-8.35 (m, 1H), 8.13 (d, J=8.5 Hz, 1H), 7.98 (d, J=7.7 Hz, 1H), 7.74-7.66 (m, 2H), 7.26 (d, J=7.4 Hz, 1H), 7.06-7.01 (m, 2H), 4.18-3.97 (m, 3H), 2.57 (s, 3H), 2.28-1.34 (m, 10H). ESI-MS m/z: 365 (M+H)$^+$.

Example 46

$^1$H NMR (400 MHz, CDCl$_3$) δ 8.12 (d, J=8.4 Hz, 1H), 7.97 (d, J=7.6 Hz, 1H), 7.71 (t, J=7.7 Hz, 1H), 7.67-7.62 (m, 2H), 7.39-7.34 (m, 1H), 7.26 (d, J=7.5 Hz, 1H), 7.17-7.11 (m, 1H), 4.18-4.06 (m, 1H), 3.87-3.76 (m, 2H), 2.57 (s, 3H), 2.30-1.33 (m, 10H). ESI-MS m/z: 364 (M+H)$^+$.

Example 47

$^1$H NMR (400 MHz, CDCl$_3$) δ 8.13 (d, J=8.5 Hz, 1H), 7.97 (d, J=7.6 Hz, 1H), 7.71 (t, J=7.7 Hz, 1H), 7.51 (br, 1H), 7.39 (d, J=8.2 Hz, 1H), 7.28-7.22 (m, 2H), 6.96 (d, J=7.5 Hz, 1H), 4.18-4.06 (m, 1H), 3.86-3.74 (m, 2H), 2.57 (s, 3H), 2.36 (s, 3H), 2.28-1.34 (m, 10H). ESI-MS m/z: 378 (M+H)$^+$.

Example 48

$^1$H NMR (400 MHz, CDCl$_3$) δ 8.25 (s, 1H), 8.21 (d, J=5.1 Hz, 1H), 8.14 (d, J=6.6 Hz, 1H), 7.98 (d, J=7.6 Hz, 1H), 7.71 (t, J=7.7 Hz, 1H), 7.26 (d, J=7.3 Hz, 1H), 6.89-6.85 (m, 1H), 4.19-3.97 (m, 3H), 2.57 (s, 3H), 2.36 (s, 3H), 2.24-1.33 (m, 10H). ESI-MS m/z: 379 (M+H)$^+$.

In a similar manner to Examples 67 and 81, Examples 25, 28, 73, 80, 82, 95, 147, 148, 152, and 156 in Table 1 (below) were separated from their corresponding racemates: Example 19, 27, 31, 44, 76, 78, 65, 58, 84, and 41 by chiral HPLC, respectively.

Example 25

$^1$H NMR (400 MHz, CDCl$_3$): δ8.54-8.56 (m, 1H), 8.16-8.19 (m, 1H), 8.04 (d, J=8.3 Hz, 1H), 7.84 (td, J=7.9, 1.7 Hz, 1H), 7.58 (dt, J=11.3, 2.0 Hz, 1H), 7.40-7.44 (m, 1H), 7.28-7.37 (m, 2H), 6.81-6.87 (m, 1H), 4.07-4.18 (m, 1H), 3.74-3.85 (m, 2H), 2.23-2.30 (m, 1H), 2.08-2.19 (m, 2H), 1.87-1.98 (m, 2H), 1.55-1.80 (m, 4H), 1.34-1.44 (m, 1H). ESI-MS m/z: 368 (M+H)$^+$.

Example 28

$^1$H NMR (300 MHz, CDCl$_3$) δ 8.16 (d, J=8.3 Hz, 1H), 7.77 (br, 1H), 7.66-7.55 (m, 3H), 7.41 (dt, J=5.7, 8.3 Hz, 1H), 7.23-7.14 (m, 1H), 6.91 (d, J=7.4 Hz, 1H), 4.39-4.24 (m, 1H), 4.18-3.97 (m, 2H), 2.48 (s, 3H), 2.18-1.47 (m, 10H). ESI-MS m/z: 382 (M+H)$^+$.

Example 73

$^1$H NMR (400 MHz, CDCl$_3$) δ 8.47 (dd, J=4.0, 9.3 Hz, 1H), 8.22 (d, J=3.0 Hz, 1H), 8.16 (br d, J=8.5 Hz, 1H), 8.01 (d, J=7.7 Hz, 1H), 7.74 (t, J=7.7 Hz, 1H), 7.45 (ddd, J=9.2, 7.7, 3.0 Hz, 1H), 7.29 (d, J=6.8 Hz, 1H), 3.97-4.21 (m, 3H), 2.60 (s, 3H), 2.11-2.28 (m, 3H), 1.56-2.01 (m, 6H), 1.35-1.48 (m, 1H). ESI-MS m/z: 383 (M+H)$^+$.

Example 80

$^1$H NMR (400 MHz, CDCl$_3$): δ8.11 (d, J=8.6 Hz, 1H), 7.97 (d, J=8.5 Hz, 1H), 7.71 (t, J=7.6 Hz, 1H), 7.57-7.63 (m, 2H), 7.26 (d, J=7.6 Hz, 1H), 7.02-7.08 (m, 2H), 4.06-4.17 (m, 1H), 3.74-3.83 (m, 2H), 2.57 (s, 3H), 2.22-2.30 (m, 1H), 2.10-2.19 (m, 2H), 1.86-1.97 (m, 2H), 1.54-1.83 (m, 4H), 1.34-1.45 (m, 1H). ESI-MS m/z: 382 (M+H)$^+$.

Example 82

$^1$H NMR (400 MHz, CDCl$_3$): δ8.85 (d, J=5.0 Hz, 1H), 8.12 (d, J=8.3 Hz, 1H), 7.89 (d, J=4.3 Hz, 1H), 7.28-7.34 (m, 2H), 6.59 (tt, J=8.8, 2.3 Hz, 1H), 4.07-4.17 (m, 1H), 3.73-3.82 (m, 2H), 2.78 (s, 3H), 2.06-2.28 (m, 3H), 1.89-1.96 (m, 2H), 1.55-1.85 (m, 4H), 1.37-1.48 (m, 1H). ESI-MS m/z: 401 (M+H)$^+$.

Example 95

$^1$H NMR (400 MHz, CDCl$_3$): δ 8.56 (d, J=5.0 Hz, 1H), 8.20 (bs, 1H), 7.60 (bs, 1H), 7.54-7.59 (m, 1H), 7.49-7.52 (m, 1H), 7.30-7.34 (m, 2H), 6.84-6.90 (m, 1H), 4.28-4.38 (m, 1H), 3.76-3.90 (m, 2H), 2.59 (s, 3H), 2.14-2.23 (m, 1H), 1.82-2.12 (m, 6H), 1.48-1.64 (m, 3H). ESI-MS m/z: 382 (M+H)$^+$.

Example 147

$^1$H NMR (400 MHz, CDCl$_3$): δ8.51 (d, J=6.0 Hz, 1H), 8.17 (d, J=5.8 Hz, 1H), 7.80-7.86 (m, 2H), 7.06-7.15 (m, 3H), 4.23-4.33 (m, 1H), 3.94-4.16 (m, 2H), 2.65 (s, 3H), 2.04-2.20 (m, 2H), 1.75-1.96 (m, 5H), 1.49-1.65 (m, 3H). ESI-MS m/z: 383 (M+H)$^+$.

Example 148

$^1$H NMR (400 MHz, CDCl$_3$): δ8.49 (d, J=6.5 Hz, 1H), 8.16 (d, J=5.8 Hz, 1H), 7.82 (t, J=2.0 Hz, 1H), 7.67-7.71 (m, 1H), 7.43-7.47 (m, 1H), 7.28-7.39 (m, 2H), 4.21-4.32 (m, 1H), 3.94-4.15 (m, 2H), 2.64 (s, 3H), 2.04-2.19 (m, 2H), 1.76-1.98 (m, 5H), 1.47-1.66 (m, 3H). ESI-MS m/z: 399 (M+H)$^+$.

Example 152

$^1$H NMR (400 MHz, CDCl$_3$) δ 8.49 (d, J=5.9 Hz, 1H), 8.16-8.19 (m, 1H), 7.60-7.63 (m, 1H), 7.55-7.59 (m, 1H), 7.29-7.35 (m, 2H), 6.75 (s, 1H), 4.19-4.29 (m, 1H), 4.07-4.15 (m, 1H), 3.98-4.02 (m, 1H), 2.65 (s, 3H), 2.40 (s, 3H), 2.04-2.22 (m, 2H), 1.85-2.04 (m, 3H), 1.71-1.81 (m, 2H), 1.39-1.65 (m, 3H). ESI-MS m/z: 379 (M+H)$^+$.

Example 156

$^1$H NMR (400 MHz, CDCl$_3$) δ 8.65 (d, J=8.5 Hz, 1H), 8.10 (d, J=8.5 Hz, 1H), 7.98 (d, J=7.6 Hz, 1H), 7.84 (t, J=7.8 Hz, 1H), 7.71 (t, J=7.7 Hz, 1H), 7.40 (d, J=7.4 Hz, 1H), 7.26 (d, J=7.5 Hz, 1H), 4.18-4.02 (m, 3H), 2.57 (s, 3H), 2.28-1.33 (m, 10H). ESI-MS m/z: 433 (M+H)$^+$.

In a similar manner to Example 42, Examples 26, 53, 130, 132-136, 138-139, and 142 in Table 1 (below) were made at 0.03-1.0 mmol reaction scales from intermediate 19 and commercially available heteroaryl halides: 2-bromo-pyridine, 6-bromo-pyridine-2-carbonitrile, 1-iodo-3-methoxy-benzene, (3-iodo-phenyl)-dimethyl-amine, 1-iodo-4-methoxy-benzene, 4-[3-(3-bromo-phenyl)-propyl]-morpholine, 1-bromo-3-fluoro-5-methoxy-benzene, 2-(3-iodo-phenoxy)-1-pyrrolidin-1-yl-ethanone, (4-iodo-phenyl)-dimethyl-amine, 2-bromo-thiazole, and 3-fluoro-5-iodo-benzonitrile, respectively.

Example 130

$^1$H NMR (400 MHz, CDCl$_3$): δ8.05-7.83 (m, br, 1H), 7.66-7.58 (m, 2H), 7.46 (t, J=2.3 Hz, 1H), 7.42-7.35 (m, 1H), 7.27-7.23 (m, 1H), 7.20-7.13 (m, 1H), 7.10-7.05 (m, 1H), 6.74-6.70 (m, 1H), 4.39-4.28 (m, 1H), 3.91-3.74 (m, 5H), 2.22-1.46 (m, 10H), ESI-MS m/z: 397 (M+H)$^+$.

Example 132

$^1$H NMR (400 MHz, CDCl$_3$): δ 8.32 (s, br, 1H), 7.71-7.60 (m, 2H), 7.40-7.32 (m, 2H), 7.24-7.11 (m, 2H), 6.73-6.67 (m, 1H), 6.58-6.53 (m, 1H), 4.41-4.30 (m, 1H), 3.93-3.73 (m, 2H), 2.96 (s, 6H), 2.19-2.45 (m, 10H). ESI-MS m/z: 401 (M+H)$^+$.

Example 133

$^1$H NMR (400 MHz, CDCl$_3$): δ 8.08-7.86 (m, 1H), 7.65-7.57 (m, 2H), 7.53-7.48 (m, 2H), 7.41-7.35 (m, 1H), 7.19-7.13 (m, 1H), 6.92-6.88 (m, 2H), 4.40-4.27 (m, 1H), 3.87-3.70 (m, 5H), 2.21-1.46 (m, 10H). ESI-MS m/z: 397 (M+H)$^+$.

Example 134

$^1$H NMR (300 MHz, CDCl$_3$): δ 7.96-7.75 (m, 1H), 7.68-7.55 (m, 3H), 7.46-7.27 (m, 3H), 7.24-7.11 (m, 1H), 7.00 (m, 1H), 4.44-4.26 (m, 1H), 3.97-3.65 (m, 6H), 2.77-1.47 (m, 20H). ESI-MS m/z: 494 (M+H)$^+$.

Example 135

$^1$H NMR (300 MHz, CDCl$_3$): δ7.82-7.55 (m, 3H), 7.45-7.34 (m, 1H), 7.22-7.13 (m, 2H), 7.04-6.95 (m, 1H), 6.49-6.39 (m, 1H), 4.39-4.24 (m, 1H), 3.87-3.71 (m, 5H), 2.24-1.46 (m, 10H). ESI-MS m/z: 415 (M+H)$^+$.

Example 136

$^1$H NMR (400 MHz, CDCl$_3$): δ 7.93-7.71 (m, br, 1H), 7.66-7.56 (m, 2H), 7.43-7.35 (m, 2H), 7.28-7.26 (m, 1H), 7.22-7.13 (m, 2H), 6.79-6.75 (m, 1H), 4.63 (s, 2H), 4.36-4.25 (m, br, 1H), 3.90-3.74 (m, 2H), 3.51 (t, J=6.8 Hz, 4H), 2.22-1.48 (m, 14H). ESI-MS m/z: 494 (M+H)$^+$.

Example 138

$^1$H NMR (400 MHz, CDCl$_3$): δ 8.50-8.07 (m, br, 1H), 7.69-7.60 (m, 2H), 7.48-7.34 (m, 3H), 7.21-7.13 (m, 1H), 6.74 (d, J=8.7 Hz, 2H), 4.43-4.29 (m, 1H), 3.91-3.67 (m, 2H), 2.95 (m, 6H), 2.22-1.46 (m, 10H). ESI-MS m/z: 410 (M+H)$^+$.

Example 139

$^1$H NMR (400 MHz, CDCl$_3$): δ 7.65-7.56 (m, 2H), 7.50 (d, J=3.5 Hz, 1H), 7.45-7.38 (m, 2H), 7.22-7.16 (m, 1H), 7.05-(d, J=3.5 Hz, 1H), 4.39-4.29 (m, 1H), 4.24-4.05 (m, 2H), 2.32-2.12 (m, 2H), 1.98-1.55 (m, 8H). ESI-MS m/z: 374 (M+H)$^+$.

Example 142

$^1$H NMR (400 MHz, CDCl$_3$): δ7.89-7.84 (m, 1H), 7.75 (s, br, 1H), 7.59-7.52 (m, 2H), 7.46-7.38 (m, 1H), 7.23-7.07 (m, 3H), 4.32-4.20 (m, 1H), 3.85-3.77 (m, 2H), 2.30-1.45 (m, 10H). ESI-MS m/z: 410 (M+H)$^+$.

In a similar manner to Example 42, Examples 59-61, 76 and 141 in Table 1 (below) were made at 0.03-4.16 mmol reaction scales from intermediate 20 and commercially 2-chloro-6-methylpyrazine, 3-iodo-benzonitrile, 2-bromo-6-trifluoromethyl-pyridine, 1,3-difluoro-5-iodo-benzene, and 1-bromo-3-fluoro-5-methoxy-benzene, respectively.

Example 141

$^1$H NMR (400 MHz, CDCl$_3$): δ 8.88 (s, br, 1H), 8.20-8.06 (m, 1H), 7.91 (s, br, 1H), 7.15 (s, br, 1H), 7.09-7.04 (m, 1H), 6.46-6.41 (m, 1H), 4.19-4.07 (m, 1H), 3.85-3.75 (m, 5H), 2.81 (s, 3H), 2.30-1.36 (m, 10H). ESI-MS m/z: 413 (M+H)$^+$.

In a similar manner to Example 42, Example 75 in Table 1 (below) was made at a 0.11 mmol reaction scale from intermediate 21 and commercially available 4-iodo-1,2-difluoro-benzene.

In a similar manner to Example 42, Example 79 in Table 1 (below) was made at a 0.13 mmol reaction scale from intermediate 22 and commercially available 1-bromo-3,5-difluoro-benzene.

In a similar manner to Example 42, Example 78 in Table 1 (below) was made at a 1.04 mmol reaction scale from intermediate 23 and commercially available 1-iodo-3-fluoro-benzene.

In a similar manner to Example 42, Example 137 in Table 1 (below) was made at a 0.1 mmol reaction scale from intermediate 32 and commercially available 1-iodo-3-fluoro-benzene.

Example 137

¹H NMR (400 MHz, CDCl₃): δ 7.86 (d, J=3.1 Hz, 1H), 7.60-7.57 (m, 1H), 7.56 (d, J=3.1 Hz, 1H), 7.44 (d, br, J=8 Hz, 1H), 7.38-7.28 (m, 2H), 6.87-6.81 (m, 1H), 4.18-4.04 (m, 1H), 3.85-3.75 (m, 2H), 2.27-1.35 (m, 10H). ESI-MS m/z: 374.0 (M+H)⁺.

Example 62 cis-6-methyl-pyridine-2-carboxylic acid [2-(2-methyl-pyrimidin-4-yl)-1-oxo-2-aza-spiro[4.5]dec-7-yl]-amide

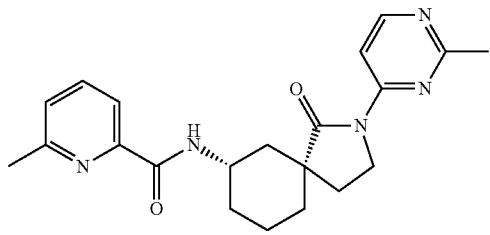

Example 62 was prepared from intermediate 18 via the process of Scheme 2, supra, as follows: 4-Chloro-2-methylpyrimidine (0.019 g, 0.148 mmol), cis-6-methyl-pyridine-2-carboxylic acid (1-oxo-2-aza-spiro[4.5]dec-7-yl)-amide (0.047 g, 0.162 mmol, intermediate 18), dicesium carbonate (0.067 g, 0.206 mmol), tris(dibenzylideneacetone)dipalladium(0) chloroform adduct (0.031 g, 0.030 mmol), and racemic BINAP (0.055 g, 0.089 mmol) in toluene (1.0 mL) were heated at 80° C. for 6 hours. The crude mixture was cooled down to rt, and the catalyst was filtered off. The filtrate was concentrated under reduced pressure, and the resulting residue was purified on a RP-HPLC/MS purification system (Gradient: acetonitrile in water, 24-95% in 3.6 minutes with a cycle time of 5 min. A shallow gradient between 40-68% of acetonitrile was used between 0.75-3.4 min to separate close-eluting impurities. Flow rate: 100 mL/min. Mobile phase additive: 48 mM of ammonium formate. Column: Inertsil® C8, 30×50 mm, 5 um particle size (GL Sciences)) to afford 0.032 g (57%) of the title compound, cis-6-methyl-pyridine-2-carboxylic acid [2-(2-methyl-pyrimidin-4-yl)-1-oxo-2-aza-spiro[4.5]dec-7-yl]-amide as a white solid. ¹H NMR (400 MHz, CDCl₃): δ 8.47 (d, J=5.8 Hz, 1H), 8.17 (d, J=5.8 Hz, 1H), 8.09 (d, J=8.9 Hz, 1H), 7.96 (d, J=8.3 Hz, 1H), 7.70 (t, J=7.6 Hz, 1H), 7.25 (d, J=7.6 Hz, 1H), 3.94-4.16 (m, 3H), 2.63 (s, 3H), 2.55 (s, 3H), 2.09-2.24 (m, 3H), 1.86-1.97 (m, 2H), 1.77 (t, J=12.4 Hz, 1H), 1.57-1.69 (m, 3H), 1.33-1.42 (m, 1H). ESI-MS m/z: 380 (M+H)⁺.

In a similar manner to Example 62, Example 65 and 66, 150 and 151 in Table 1 (below) were made at 2.81 mmol reaction scale from intermediate 19 and commercially available 4-chloro-2-methyl-pyrimidine and 4-bromo-2-methylpyridine, 4-chloro-2-trifluoromethyl-pyrimidine, and 4-chloro-2,6-dimethyl-pyrimidine, respectively.

Example 65

¹H NMR (400 MHz, CDCl₃): δ 8.51 (d, J=6.0 Hz, 1H), 8.17 (d, J=5.8 Hz, 1H), 7.80-7.86 (m, 2H), 7.06-7.15 (m, 3H), 4.23-4.33 (m, 1H), 3.94-4.16 (m, 2H), 2.65 (s, 3H), 2.04-2.20 (m, 2H), 1.75-1.96 (m, 5H), 1.49-1.65 (m, 3H). ESI-MS m/z: 383 (M+H)⁺.

Example 66

¹H NMR (400 MHz, CDCl₃): δ 8.42 (s, 1H), 7.51-7.60 (m, 3H), 7.36-7.43 (m, 2H), 7.29 (bs, 1H), 7.15-7.21 (m, 1H), 4.22-4.31 (m 1H), 3.78-3.83 (m, 2H), 2.54 (s, 3H), 2.06-2.25 (m, 2H), 1.75-1.96 (m, 5H), 1.46-1.63 (m, 3H). ESI-MS m/z: 382 (M+H)⁺.

Example 151

¹H NMR (400 MHz, CDCl₃) δ 8.73 (d, J=6.1 Hz, 1H), 8.54 (d, J=5.8 Hz, 1H), 7.50-7.57 (m, 2H), 7.37-7.44 (m, 1H), 7.16-7.22 (m, 1H), 6.96 (s, 1H), 4.14-4.29 (m, 2H), 3.99-4.07 (m, 1H), 2.10-2.25 (m, 2H), 1.74-2.01 (m, 5H), 1.44-1.67 (m, 3H). ESI-MS m/z: 437 (M+H)⁺.

Example 152

¹H NMR (400 MHz, CDCl₃) δ 8.01 (s, 1H), 7.51-7.59 (m, 2H), 7.32-7.40 (m, 2H), 7.12-7.19 (m, 1H), 4.19-4.29 (m, 1H), 4.04-4.11 (m, 1H), 3.96-3.99 (m, 1H), 2.58 (s, 3H), 2.43 (s, 3H), 2.01-2.16 (m, 2H), 1.73-1.93 (m, 5H), 1.45-1.62 (m, 3H). ESI-MS m/z: 397 (M+H)⁺.

In a similar manner to Example 62, Example 140 in Table 1 (below) was made at 0.1 mmol reaction scale from intermediate 32 and commercially available 4-chloro-2-methyl-pyrimidine.

Example 140

¹H NMR (400 MHz, CDCl₃): δ8.50 (s, br, 1H), 8.19 (d, J=5.8 Hz, 1H), 7.86 (d, J=3.0 Hz, 1H), 7.57 (d, J=3.0 Hz, 1H), 7.43-7.35 (m, 1H), 3.94-4.18 (m, 3H), 2.64 (s, 3H), 1.35-2.23 (m, 10H). ESI-MS m/z: 372 (M+H)⁺.

Example 76 cis 2-Methyl-pyrimidine-4-carboxylic acid [2-(3,5-difluoro-phenyl)-1-oxo-2-aza-spiro[4.5]dec-7-yl]-amide

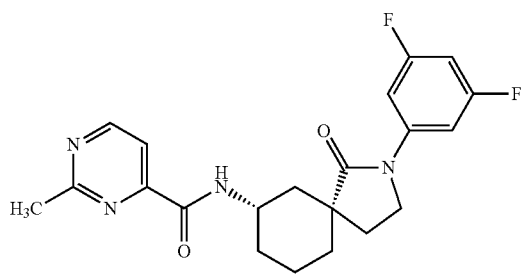 [SMILES: Cc1nccc(C(=O)N[C@H]2CCC[C@]3(CCN(c4cc(F)cc(F)c4)C3=O)C2)n1]

Example 76 was also prepared from intermediate 33 via the process of Scheme 1, supra, as follows:

In a round-bottom flask was charged with cis-7-amino-2-(3,5-difluoro-phenyl)-2-aza-spiro[4.5]decan-1-one. HCl (10.8 g, 34.1 mmol), 2-methylpyrimidine-4-carboxylic acid (4.71 g, 34.1 mmol), and BOP (15.1 g, 34.1 mmol). Methylene chloride (218 mL) was added, and the mixture was cooled at 0° C. Triethylamine (14.2 mL, 102 mmol) was added dropwise. The mixture was warmed up to rt and stirred at rt overnight. The mixture was diluted with methylene chloride (100 mL) and water (50 mL). The aqueous layer was extracted with $CH_2Cl_2$ (100 mL). The combined organic layer was washed with brine, dried over $Na_2SO_4$ and concentrated under reduced pressure. The residue obtained was crystallized from ethyl acetate to afford 8.8 g (77%) of the title compound cis 2-Methyl-pyrimidine-4-carboxylic acid [2-(3,5-difluoro-phenyl)-1-oxo-2-aza-spiro[4.5]dec-7-yl]-amide: $^1$H NMR (400 MHz, $CDCl_3$): δ8.85 (d, J=5.0 Hz, 1H), 8.10 (d, J=8.1 Hz, 1H), 7.89 (d, J=5.4 Hz, 1H), 7.28-7.35 (m, 2H), 6.60 (tt, J=8.8, 2.5 Hz, 1H), 4.07-4.18 (m, 1H), 3.74-3.80 (m, 2H), 2.79 (s, 3H), 2.07-2.28 (m, 3H), 1.89-1.97 (m, 2H), 1.55-1.85 (m, 4H), 1.37-1.48 (m, 1H). ESI-MS m/z: 401 $(M+H)^+$.

In a similar manner to Example 76, Example 143-146 in Table 1 (below) were made at 0.05-0.07 mmol reaction scales from intermediate 33 and commercially available thiazole-2-carbonyl chloride, 2-methyl-thiazole-4-carboxylic acid, pentanoyl, and butyryl chloride, respectively.

Example 143

$^1$H NMR (400 MHz, $CDCl_3$): δ7.86 (d, J=3.1 Hz, 1H), 7.56 (d, J=3.1 Hz, 1H), 7.39 (d, br J=8.0 Hz, 1H), 7.28-7.32 (m, 2H), 6.62-6.55 (m, 1H), 4.06-4.17 (m, 1H), 3.72-3.81 (m, 2H), 1.35-2.28 (m, 10H). ESI-MS m/z: 392 $(M+H)^+$.

Example 144

$^1$H NMR (400 MHz, $CDCl_3$): δ7.91 (s, 1H), 7.27-7.37 (m, 3H), 6.54-6.61 (m, 1H), 4.03-4.15 (m, 1H), 3.70-3.80 (m, 2H), 2.70 (s, 3H), 1.30-2.29 (m, 10H). ESI-MS m/z: 406 $(M+H)^+$.

Example 145

$^1$H NMR (400 MHz, $CDCl_3$): δ 7.27-7.31 (m, 2H), 6.56-6.63 (m, 1H), 5.83 (m, 1H), 3.93-4.05 (m, 1H), 3.70-3.79 (m, 2H), 1.22-2.23 (m, 16H), 0.91 (m, 3H). ESI-MS m/z: 365 $(M+H)^+$.

Example 146

$^1$H NMR (400 MHz, $CDCl_3$): δ 7.26-7.30 (m, 2H), 6.56-6.62 (m, 1H), 5.97 (s, 1H), 3.95-4.06 (m, 1H), 3.71-3.80 (m, 2H), 1.21-2.25 (m, 14H), 0.93 (t, J=7.4 Hz, 3H). ESI-MS m/z: 351 $(M+H)^+$.

Example 78 cis-N-[2-(3-Fluoro-phenyl)-1-oxo-2-aza-spiro[4.5]dec-7-yl]-2-methyl-isonicotinamide

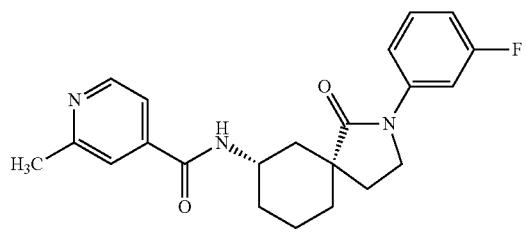

Example 78 was also prepared from intermediate 13 as follows:

[2-(3-fluoro-phenyl)-1-oxo-2-aza-spiro[4.5]dec-7-yl]-carbamic acid tert-butyl ester (0.010 g, 0.028 mmol, intermediate 13) was dissolved in methylene chloride (1.0 mL), 4M of hydrogen chloride in 1,4-dioxane (0.7 mL) was added. The mixture was stirred at rt overnight and then concentrated under reduced pressure. The resulting residue was dissolved in methylene chloride (1.0 mL). Triethylamine (0.015 mL, 0.11 mmol) was added, followed by the addition of 2-methylisonicotinic acid (0.005 g, 0.033 mmol) and BOP (0.015 g, 0.033 mmol). The mixture was stirred at rt for 4 hours and concentrated under reduced pressure. The residue was purified on a RP-HPLC/MS purification system (Gradient: acetonitrile in water, 24-95% in 3.6 minutes with a cycle time of 5 min. A shallow gradient between 28-56% of acetonitrile was used between 0.75-3.3 min to separate close-eluting impurities. Flow rate: 100 mL/min. Mobile phase additive: 48 mM of ammonium formate. Column: Inertsil® C18, 30×50 mm, 5 um particle size (GL Sciences)) to afford 0.008 g (80%) of the title compound, cis-N-[2-(3-fluoro-phenyl)-1-oxo-2-aza-spiro[4.5]dec-7-yl]-2-methyl-isonicotin-amide as a white solid. $^1$H NMR (400 MHz, $CDCl_3$): δ 8.56 (d, J=5.0 Hz, 1H), 8.20 (bs, 1H), 7.60 (bs, 1H), 7.54-7.59 (m, 1H), 7.49-7.52 (m, 1H), 7.30-7.34 (m, 2H), 6.84-6.90 (m, 1H), 4.28-4.38 (m, 1H), 3.76-3.90 (m, 2H), 2.59 (s, 3H), 2.14-2.23 (m, 1H), 1.82-2.12 (m, 6H), 1.48-1.64 (m, 3H). ESI-MS m/z: 382 $(M+H)^+$.

In an analogous manner to Example 78, Examples 68-70, 77 and 93-94 in Table 1 were made at 0.03-0.16 mmol reaction scales from intermediate 13 and commercially available 5-fluoro-pyridine-2-carboxylic acid, 2-methyl-pyrimidine-4-carboxylic acid, pyrimidine-4-carboxylic acid, isonicotinic acid, 2-methylisonicotinic acid, 6-hydroxymethyl-pyridine-2-carboxylic acid, and 6-trifluoromethyl-pyridine-2-carboxylic acid, respectively.

Example 68

$^1$H NMR (400 MHz, $CDCl_3$): δ 8.38 (d, J=3.0 Hz, 1H), 8.19-8.23 (m, 1H), 7.89 (d, J=8.1 Hz, 1H), 7.50-7.60 (m, 2H), 7.28-7.38 (m, 2H), 6.81-6.87 (m, 1H), 4.05-4.16 (m, 1H), 3.75-3.85 (m, 2H), 2.06-2.29 (m, 3H), 1.87-1.97 (m, 2H), 1.33-1.80 (m, 5H). ESI-MS m/z: 386 $(M+H)^+$.

Example 69

$^1$H NMR (400 MHz, $CDCl_3$): δ 8.85 (d, J=3.8 Hz, 1H), 8.12 (d, J=8.3 Hz, 1H), 7.89 (d, J=5.0 Hz, 1H), 7.56-7.61 (m, 1H), 7.28-7.37 (m, 2H), 6.82-6.88 (m, 1H), 4.07-4.18 (m, 1H), 3.77-3.83 (m, 2H), 2.78 (s, 3H), 2.05-2.27 (m, 3H), 1.37-1.96 (m, 7H). ESI-MS m/z: 383 $(M+H)^+$.

In a similar manner to Example 78, Examples 38-40 in Table 1 were made at a 0.06 mmol reaction scale from intermediate 14 and commercially available carboxylic acids: 3-fluorobenzoic acid, picolinic acid and 6-methyl-pyridine-2-carboxylic acid, respectively.

Example 38

$^1$H NMR (400 MHz, $CDCl_3$) δ 9.53 (s 1H), 8.22 (s, 1H), 7.63-7.56 (m, 2H), 7.46-7.39 (m, 1H), 7.23-7.16 (m, 1H), 4.38-4.27 (m, 1H), 4.16-3.93 (m, 2H), 2.50 (s, 3H), 2.23-1.52 (m, 10H). ESI-MS m/z: 383 $(M+H)^+$.

In a similar manner to Example 78, Examples 54-56 in Table 1 were made at a 0.03 mmol reaction scale from intermediate 15 and commercially available carboxylic acids:

picolinic acid, 6-methyl-pyrazine-2-carboxylic acid and pyrazine-2-carboxylic acid, respectively.

Example 54

¹H NMR (400 MHz, CDCl₃) δ8.54-8.57 (m, 1H), 8.15-8.19 (m, 1H), 8.05 (d, J=8.3 Hz, 1H), 7.82-7.87 (m, 1H), 7.40-7.45 (m, 1H), 7.27-7.34 (m, 2H), 6.55-6.62 (m, 1H), 4.07-4.18 (m, 1H), 3.71-3.82 (m, 2H), 2.23-2.31 (m, 1H), 2.07-2.20 (m, 2H), 1.87-1.98 (m, 2H), 1.34-1.80 (m, 5H). ESI-MS m/z: 386 (M+H)⁺.

Example 55

¹H NMR (400 MHz, CDCl₃) δ 9.18 (s, 1H), 8.61 (s, 1H), 7.92 (d, J=8.5 Hz, 1H), 7.27-7.34 (m, 1H), 6.56-6.63 (m, 1H), 4.09-4.20 (m, 1H), 3.73-3.81 (m, 2H), 2.61 (s, 3H), 2.07-2.29 (m, 3H), 1.89-1.96 (m, 2H), 1.35-1.83 (m, 5H). ESI-MS m/z: 401 (M+H)⁺.

In a similar manner to Example 78, Example 41 in Table 1 was made at 0.05 mmol reaction scale from intermediate 16 and commercially available 6-methyl-pyridine-2-carboxylic acid.

Example 41

¹H NMR (400 MHz, CDCl₃) δ8.65 (d, J=8.5 Hz, 1H), 8.10 (d, J=8.5 Hz, 1H), 7.98 (d, J=7.6 Hz, 1H), 7.84 (t, J=7.8 Hz, 1H), 7.71 (t, J=7.7 Hz, 1H), 7.40 (d, J=7.4 Hz, 1H), 7.26 (d, J=7.5 Hz, 1H), 4.18-4.02 (m, 3H), 2.57 (s, 3H), 2.28-1.33 (m, 10H). ESI-MS m/z: 433 (M+H)⁺.

In a similar manner to Example 78, Examples 58, 84-85, 89-92, 96 and 149 in Table 1 were made at 0.04-0.08 mmol reaction scales from intermediate 17 and commercially available carboxylic acids: 3-chlorobenzoic acid, 3-methyl-benzoic acid, 3,5-difluorobenzoic acid, 4-fluorobenzoic acid, 3,4-difluorobenzoic acid, 2-fluorobenzoic acid, 2-methyl-isonicotinic acid, 6-trifluoromethyl-pyridine-2-carboxylic acid and 5-fluoro-pyridine-2-carboxylix acid, respectively.

Example 58

¹H NMR (400 MHz, CDCl₃): δ 8.49 (d, J=6.5 Hz, 1H), 8.16 (d, J=5.8 Hz, 1H), 7.82 (t, J=2.0 Hz, 1H), 7.67-7.71 (m, 1H), 7.43-7.47 (m, 1H), 7.28-7.39 (m, 2H), 4.21-4.32 (m, 1H), 3.94-4.15 (m, 2H), 2.64 (s, 3H), 2.04-2.19 (m, 2H), 1.76-1.98 (m, 5H), 1.47-1.66 (m, 3H). ESI-MS m/z: 399 (M+H)⁺.

Example 84

¹H NMR (400 MHz, CDCl₃) δ 8.49 (d, J=5.9 Hz, 1H), 8.16-8.19 (m, 1H), 7.60-7.63 (m, 1H), 7.55-7.59 (m, 1H), 7.29-7.35 (m, 2H), 6.75 (s, 1H), 4.19-4.29 (m, 1H), 4.07-4.15 (m, 1H), 3.98-4.02 (m, 1H), 2.65 (s, 3H), 2.40 (s, 3H), 2.04-2.22 (m, 2H), 1.85-2.04 (m, 3H), 1.71-1.81 (m, 2H), 1.39-1.65 (m, 3H). ESI-MS m/z: 379 (M+H)⁺.

Example 85

¹H NMR (400 MHz, CDCl₃) δ8.53 (d, J=5.8 Hz, 1H), 8.18 (d, J=6.1 Hz, 1H), 7.62 (s, 1H), 7.35-7.40 (m, 2H), 6.91-6.98 (m, 1H), 4.31 (m, 1H), 4.09-4.18 (m, 1H), 3.94-4.03 (m, 1H), 2.65 (s, 3H), 2.02-2.18 (m, 2H), 1.50-1.93 (m, 8H). ESI-MS m/z: 401 (M+H)⁺.

Example 89

¹H NMR (400 MHz, CDCl₃) δ8.52 (d, J=6.0 Hz, 1H), 8.17 (d, J=6.0 Hz, 1H), 7.80-7.86 (m, 2H), 7.09-7.15 (m, 3H), 4.22-4.32 (m, 1H), 4.09-4.16 (m, 1H), 3.94-4.02 (m, 1H), 2.65 (s, 3H), 2.05-2.20 (m, 2H), 1.44-2.00 (m, 8H). ESI-MS m/z: 383 (M+H)⁺.

Example 149

¹H NMR (400 MHz, CDCl₃): δ8.48 (d, J=5.9 Hz, 1H), 8.37 (d, J=2.8 Hz, 1H), 8.16-8.22 (m, 2H), 7.86 (d, J=8.6 Hz, 1H), 7.50-7.55 (m, 1H), 4.04-4.15 (m, 2H), 3.94-4.02 (m, 1H), 2.63 (s, 3H), 2.07-2.24 (m, 3H), 1.86-1.97 (m, 2H), 1.56-1.78 (m, 4H), 1.34-1.42 (m, 1H). ESI-MS m/z: 384 (M+H)⁺.

Example 83 cis-6-methyl-pyridine-2-carboxylic acid (2-benzyl-1-oxo-2-aza-spiro[4.5]dec-7-yl)-amide

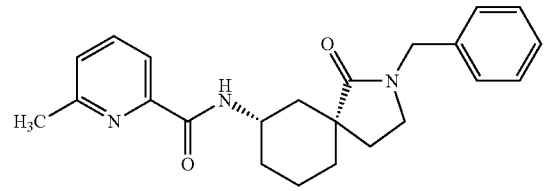 [SMILES: Cc1cccc(C(=O)N[C@H]2CCC[C@]3(CCN(Cc4ccccc4)C3=O)C2)n1]

Example 83 was prepared from intermediate 18 via the process of Scheme 2, supra, as follows:

To a solution of cis-6-Methyl-pyridine-2-carboxylic acid (1-oxo-2-aza-spiro[4.5]dec-741)-amide (0.100 g, 0.348 mmol, intermediate 18) in anhydrous THF (5.0 mL) at 0° C. was added sodium hydride (0.015 g, 0.383 mmol). The reaction mixture was stirred at 0° C. for 30 mins, benzyl bromide (0.041 mL, 0.348 mmol) was then added dropwise. The mixture was stirred at rt overnight, then quenched with water and diluted with ethyl acetate (100 mL). The organic layer was washed with brine, dried over Na₂SO₄, and concentrated under reduced pressure. The resulting residue was purified by silica gel chromatography (hexane/ethyl acetate: 100/0 to 0/100) to afford 0.115 g (88%) of the title compound, cis-6-methyl-pyridine-2-carboxylic acid (2-benzyl-1-oxo-2-aza-spiro[4.5]dec-7-yl)-amide, as a white solid. ¹H NMR (400 MHz, CDCl₃): δ 8.11 (d, J=8.6 Hz, 1H), 7.97 (d, J=7.5 Hz, 1H), 7.70 (t, J=7.5 Hz, 1H), 7.18-7.33 (m, 6H), 4.45 (m, 2H), 4.01-4.11 (m, 1H), 3.14-3.22 (m, 2H), 2.57 (s, 3H), 1.95-2.12 (m, 4H), 1.70-1.89 (m, 3H), 1.67-1.76 (m, 1H), 1.52-1.60 (m, 1H), 1.45-1.50 (m, 1H), 1.32-1.42 (m, 1H). ESI-MS m/z: 378 (M+H)⁺.

In a similar manner to Example 83, Examples 153-155 in Table 1 was made at 0.11 mmol reaction scale from intermediate 18 and commercially available iodomethane, iodoethane, and 1-iodopropane, respectively.

Example 153

¹H NMR (400 MHz, CDCl₃): δ8.08 (d, J=8.6 Hz, 1H), 7.95 (d, J=8.1 Hz, 1H), 7.69 (t, J=7.9 Hz, 1H), 7.25 (d, J=7.8 Hz, 1H), 3.99-4.12 (m, 1H), 3.28-3.33 (m, 2H), 2.84 (s, 3H), 2.55 (s, 3H), 1.95-2.14 (m, 3H), 1.26-1.87 (m, 7H). ESI-MS m/z: 302 (M+H)⁺.

Example 154

¹H NMR (400 MHz, CDCl₃): δ8.08 (d, J=8.6 Hz, 1H), 7.95 (d, J=7.3 Hz, 1H), 7.69 (t, J=8.7 Hz, 1H), 7.24 (d, J=8.9 Hz, 1H), 4.00-4.11 (m, 1H), 3.25-3.37 (m, 4H), 2.55 (s, 3H), 2.04-2.13 (m, 2H), 1.94-2.02 (m, 1H), 1.26-1.87 (m, 7H), 1.09 (t, J=7.3 Hz, 3H). ESI-MS m/z: 316 (M+H)⁺.

Example 155

¹H NMR (400 MHz, CDCl₃): δ8.07 (d, J=8.4 Hz, 1H), 7.95 (d, J=7.6 Hz, 1H), 7.69 (t, J=7.6 Hz, 1H), 7.25 (d, J=8.6 Hz, 1H), 4.00-4.11 (m, 1H), 3.20-3.33 (m, 4H), 2.55 (s, 3H), 2.04-2.12 (m, 2H), 1.95-2.02 (m, 1H), 1.25-1.87 (m, 9H), 0.87 (t, J=7.4 Hz, 3H). ESI-MS m/z: 330 (M+H)⁺.

Example 97 cis-Pyridine-2-carboxylic acid [9,9-difluoro-2-(3-fluoro-phenyl)-1-oxo-2-aza-spiro[4.5]dec-7-yl]-amide

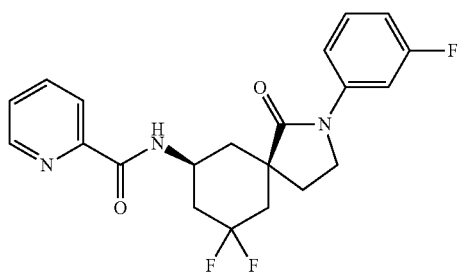 [SMILES: O=C(N[C@@H]1CC(F)(F)C[C@@]2(CCN(c3cccc(F)c3)C2=O)C1)c1ccccn1]

Example 97 was prepared from intermediate 24 via the process of Scheme 1, supra, as follows:

To a solution of crude cis-7-amino-2-(4-methoxy-benzyl)-2-aza-spiro[4.5]decan-1-one, which was prepared from 5,5-difluoro-1-[2-(3-fluoro-phenylamino)-ethyl]-cyclohexane-1,3-dicarboxylic acid dimethyl ester (0.37 mmol), and triethylamine (0.141 mL, 1.01 mmol) in DCM (3.37 mL) was added pyridine-2-carbonyl chloride.HCl (57.3 mg, 0.322 mmol) at 0° C. The reaction mixture was stirred at rt overnight, and then diluted with DCM (50 mL), washed with saturated aqueous NaHCO₃ and brine, dried over MgSO₄, filtered, and concentrated under reduced pressure. The residue was purified on a reversed phase liquid chromatography/mass spectrometry (RP-HPLC/MS) purification system (Gradient: acetonitrile in water, 27-95% in 3.6 minutes with a cycle time of 5 min. A shallow gradient between 38-68% of acetonitrile was used between 0.75-3.3 minutes. Flow rate: 100 mL/min. Mobile phase additive: 48 mM of ammonium formate. Column: Inertsil® C8, 30×50 mm, 5 um particle size (GL Sciences)) to give 27 mg of the title compound, pyridine-2-carboxylic acid [9,9-difluoro-2-(3-fluoro-phenyl)-1-oxo-2-aza-spiro[4.5]dec-7-yl]-amide. ¹H NMR (400 MHz, CDCl₃): δ 8.57 (d, J=4.8 Hz, 1H), 8.27 (br d, J=7.9 Hz, 1H), 8.23 (d, J=7.8 Hz, 1H), 7.94 (dt, J=7.7, 1.6 Hz, 1H), 7.49-7.60 (m, 2H), 7.31-7.38 (m, 2H), 6.85-6.91 (m, 1H), 4.40-4.56 (m, 1H), 3.77-3.91 (m, 2H), 2.55-2.69 (m, 1H), 2.24-2.44 (m, 3H), 2.07-2.16 (m, 2H), 1.93 (ddt, J=3.4, 12.8, 34.1 Hz, 1H), 1.73 (t, J=12.7 Hz, 1H). ESI-MS m/z: 404 (M+H)⁺.

Examples 98, 99, 101 and Example 102

Pyridine-2-carboxylic acid [(5R,7S)-9,9-difluoro-2-(3-fluoro-phenyl)-1-oxo-2-aza-spiro[4.5]dec-7-yl]-amide; Pyridine-2-carboxylic acid [(5S,7R)-9,9-difluoro-2-(3-fluoro-phenyl)-1-oxo-2-aza-spiro[4.5]dec-7-yl]-amide; Pyridine-2-carboxylic acid [(5S,7S)-9,9-difluoro-2-(3-fluoro-phenyl)-1-oxo-2-aza-spiro[4.5]dec-7-yl]-amide; and Pyridine-2-carboxylic acid [(5R,7R)-9,9-difluoro-2-(3-fluoro-phenyl)-1-oxo-2-aza-spiro[4.5]dec-7-yl]-amide, respectively Examples 101 and 102 were made via the process of Scheme 1 from pyridine-2-carbonyl chloride and intermediate A-3 (R² is 3-fluorophenyl) which may be made from trans-9,9-difluoro-2-(3-fluoro-phenyl)-1-oxo-2-aza-spiro[4,5]decane-7-carboxylic acid methyl ester (step 7 of intermediate 24) via steps i and j in Scheme 6, supra.

A mixture of Example 97 and trans-diastereomers, Examples 101-102, was resolved by HPLC (column: Chiralpak® AD, 250×20 mm (Diacel); mobile phase: 15% isopropanol in hexane; flow rate: 14 mL/min; UV at 254 nm) to give two enantiomers of each diastereomer. The first peak from chiral HPLC was arbitrarily assigned as Example 99, pyridine-2-carboxylic acid [(5S,7R)-9,9-difluoro-2-(3-fluoro-phenyl)-1-oxo-2-aza-spiro[4.5]dec-7-yl]-amide, the second peak from chiral HPLC was arbitrarily assigned as Example 101, pyridine-2-carboxylic acid [(5S,7S)-9,9-difluoro-2-(3-fluoro-phenyl)-1-oxo-2-aza-spiro[4.5]dec-7-yl]-amide, the third peak from chiral HPLC was arbitrarily assigned as Example 98, pyridine-2-carboxylic acid [(5R,7S)-9,9-difluoro-2-(3-fluoro-phenyl)-1-oxo-2-aza-spiro[4.5]dec-7-yl]-amide, and the fourth peak from chiral HPLC was arbitrarily assigned as Example 102, pyridine-2-carboxylic acid [(5R,7R)-9,9-difluoro-2-(3-fluoro-phenyl)-1-oxo-2-aza-spiro[4.5]dec-7-yl]-amide.

Example 98

¹H NMR (400 MHz, CDCl₃): δ 8.57 (d, J=4.8 Hz, 1H), 8.27 (br d, J=7.9 Hz, 1H), 8.23 (d, J=7.8 Hz, 1H), 7.94 (dt, J=7.7, 1.6 Hz, 1H), 7.49-7.60 (m, 2H), 7.31-7.38 (m, 2H), 6.85-6.91 (m, 1H), 4.40-4.56 (m, 1H), 3.77-3.91 (m, 2H), 2.55-2.69 (m, 1H), 2.24-2.44 (m, 3H), 2.07-2.16 (m, 2H), 1.93 (ddt, J=3.4, 12.8, 34.1 Hz, 1H), 1.73 (t, J=12.7 Hz, 1H). ESI-MS m/z: 404 (M+H)⁺.

Example 99

¹H NMR (400 MHz, CDCl₃): δ 8.57 (d, J=4.8 Hz, 1H), 8.27 (br d, J=7.9 Hz, 1H), 8.23 (d, J=7.8 Hz, 1H), 7.94 (dt, J=7.7, 1.6 Hz, 1H), 7.49-7.60 (m, 2H), 7.31-7.38 (m, 2H), 6.85-6.91 (m, 1H), 4.40-4.56 (m, 1H), 3.77-3.91 (m, 2H), 2.55-2.69 (m, 1H), 2.24-2.44 (m, 3H), 2.07-2.16 (m, 2H), 1.93 (ddt, J=3.4, 12.8, 34.1 Hz, 1H), 1.73 (t, J=12.7 Hz, 1H). ESI-MS m/z: 404 (M+H)⁺.

Example 100: cis-2-[2-(3-chloro-phenyl)-1-oxo-2-aza-spiro[4.5]dec-7-yl]-2,3-dihydro-isoindol-1-one

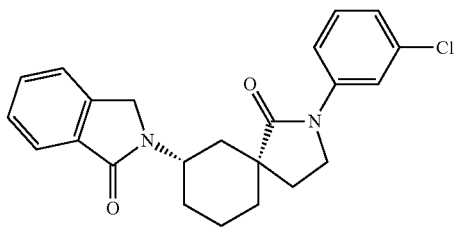 [SMILES: O=C1c2ccccc2CN1[C@H]1CCC[C@]2(CCN(c3cccc(Cl)c3)C2=O)C1]

Example 100 was prepared from intermediate 1 via the process of Scheme 21, supra, as follows:

A mixture of 7-Amino-2-(3-chloro-phenyl)2-aza-spiro[4.5]decan-1-one (0.080 g, 0.287 mmol, intermediate 1), methyl 2-formylbenzoate (0.047 g, 0.287 mmol), sodium triacetoxyborohydride (0.061 g, 0.287 mmol) and one drop of acetic acid in 1,2-dichloroethane (2.0 mL) was stirred at rt overnight. The reaction mixture was quenched with ice and diluted with ethyl acetate (20.0 mL). The organic layer was washed with water and brine, dried with Na₂SO₄, and concentrated under reduced pressure. The residue was purified by preparative TLC (ethyl acetate) to afford 0.013 g (12%) of the title compound, cis-2-[2-(3-chloro-phenyl)-1-oxo-2-aza-spiro[4.5]dec-7-yl]-2,3-dihydro-isoindol-1-one as well as 0.032 g (28%) of the trans diastereomer. The less polar spot on the TLC plate was assigned as trans, and the polar spot was assigned as cis, Example 100. ¹H NMR (400 MHz, CDCl₃): δ 7.82-7.85 (m, 1H), 7.74 (t, J=2.2 Hz, 1H), 7.44-7.56 (m, 4H), 7.28 (t, J=8.2 Hz, 1H), 7.12 (ddd, J=8.1, 2.1, 1.1 Hz), 4.41-4.49 (m, 1H), 4.38 (s, 2H), 3.75-3.84 (m, 2H), 2.18-2.34 (m, 2H), 1.91-2.04 (m, 3H), 1.55-1.75 (m, 5H). ESI-MS m/z: 395 (M+H)⁺.

(1S,4R)-4,7,7-Trimethyl-3-oxo-2-oxa-bicyclo[2.2.1]heptane-1-carboxylic acid [(5R,7R)-2-(3-chloro-phenyl)-1-oxo-2-aza-spiro[4.5]dec-7-yl]-amide

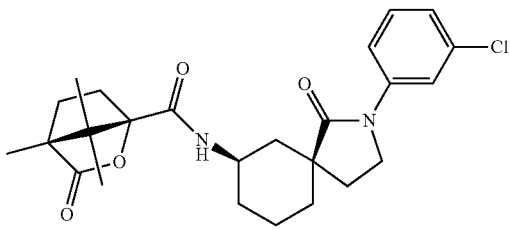 [SMILES: CC1(C)[C@@]2(C)CC[C@]1(C(=O)N[C@@H]1CCC[C@@]3(CCN(c4cccc(Cl)c4)C3=O)C1)OC2=O]

To determine the absolute stereochemistry of the compounds of the invention, (1S,4R)-4,7,7-trimethyl-3-oxo-2-oxa-bicyclo[2.2.1]heptane-1-carboxylic acid [(5R,7R)-2-(3-chloro-phenyl)-1-oxo-2-aza-spiro[4.5]dec-7-yl]-amide was made from intermediate 3 via the process of Scheme 1, supra, as follows:

(5R,7R)-7-amino-2-(3-chloro-phenyl)-2-aza-spiro[4.5]decan-1-one (0.130 g, 0.467 mmol, intermediate 3) was dissolved in methylene chloride (10.0 mL). Triethylamine (0.0708 g, 0.699 mmol) was added, followed by the addition of (1S)-(–)-camphanic acid chloride (0.101 g, 0.466 mmol).

The mixture was stirred at rt for 1 hr and concentrated under reduced pressure. The residue was purified by silica gel chromatography (ethyl acetate) to afford 0.20 g (93%) of the title compound as a white solid. ¹H NMR (400 MHz, CDCl₃): δ 7.72 (t, J=2.0 Hz, 1H), 7.57 (ddd, J=8.3, 2.4, 1.0 Hz, 1H), 7.29 (t, J=8.1 Hz, 1H), 7.12 (ddd, J=8.0, 2.0, 1.1 Hz, 1H), 6.46 (d, J=8.1 Hz, 1H), 3.90-4.00 (m, 1H), 3.73-3.84 (m, 2H), 2.48-2.56 (m, 1H), 2.08-2.15 (m, 2H), 1.86-1.98 (m, 5H), 1.63-1.72 (m, 2H), 1.50-1.61 (m, 4H), 1.27-1.35 (m, 1H), 1.11 (s, 3H), 1.08 (s, 3H), 0.87 (s, 3H). ESI-MS m/z: 459 (M+H)⁺.

A single crystal of (1S,4R)-4,7,7-trimethyl-3-oxo-2-oxa-bicyclo[2.2.1]heptane-1-carboxylic acid [(5R,7R)-2-(3-chloro-phenyl)-1-oxo-2-aza-spiro[4.5]dec-7-yl]-amide was grown in methanol and its absolute structure was determined and confirmed by X-ray.

In a similar manner to (1S,4R)-4,7,7-trimethyl-3-oxo-2-oxa-bicyclo[2.2.1]heptane-1-carboxylic acid [(5R,7R)-2-(3-chloro-phenyl)-1-oxo-2-aza-spiro[4.5]dec-7-yl]-amide, (1S,4R)-4,7,7-trimethyl-3-oxo-2-oxa-bicyclo[2.2.1]heptane-1-carboxylic acid [(5R,7R)-2-(3,5-difluoro-phenyl)-1-oxo-2-aza-spiro[4.5]dec-7-yl]-amide was made at 0.54 mmol reaction scale from intermediate 36 and (1S)-(–)-camphanic acid. A single crystal of (1S,4R)-4,7,7-trimethyl-3-oxo-2-oxa-bicyclo[2.2.1]heptane-1-carboxylic acid [(5R,7R)-2-(3,5-difluoro-phenyl)-1-oxo-2-aza-spiro[4.5]dec-7-yl]-amide was grown in methanol and its absolute structure was determined and confirmed by X-ray.

Example 129 cis-2-Methyl-pyrimidine-4-carboxylic acid [9,9-difluoro-2-(3-fluoro-phenyl)-1-oxo-2-aza-spiro[4.5]dec-7-yl]-amide

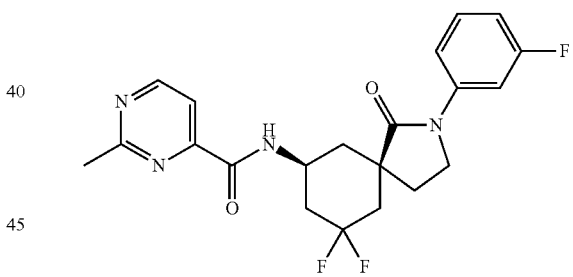

Example 129 was prepared from intermediate 26 via the process of Scheme 2, supra, as follows:

cis-2-Methyl-pyrimidine-4-carboxylic acid (9,9-difluoro-1-oxo-2-aza-spiro[4.5]dec-7-yl)-amide (300 mg, 0.6 mmol), 3-fluoroiodobenzene (287 mg, 1.29 mmol), potassium carbonate (179 mg, 1.29 mmol), copper(I) iodide (190 mg, 0.647 mmol), and (1R,2R)—N,N'-dimethyl-cyclohexane-1,2-diamine (92 mg, 0.65 mmol) in 1,4-dioxane (10 mL) were placed in a sealed-tube. The reaction mixture was heated at 100° C. overnight. The crude mixture was cooled to rt and diluted with DCM (50 mL). The organic layer was washed with ammonia water/water (1:1, 2×20 mL) and brine, dried over MgSO₄, filtered, and concentrated under reduced pressure. The residue was purified by CombiFlash® system (25 g silica gel cartridge; gradient: 0 to 50% ethyl acetate in DCM) to afford 135 mg (35%) of the title compound, cis-2-Methyl-pyrimidine-4-carboxylic acid [9,9-difluoro-2-(3-fluoro-phenyl)-1-oxo-2-aza-spiro[4.5]dec-7-yl]-amide. ¹H NMR (400 MHz, CDCl₃) δ 8.81 (d, J=5.0, 1H), 7.94 (d, J=8.2, 1H), 7.83

(d, J=5.0, 1H), 7.52-7.46 (m, 1H), 7.29-7.24 (m, 2H), 6.84-6.78 (m, 1H), 4.46-4.32 (m, 1H), 3.83-3.71 (m, 2H), 2.62-2.50 (m, 1H), 2.35-1.74 (m, 6H), 1.69 (t, J=12.8, 1H). ESI-MS m/z: 404 (M+H)$^+$.

Mixture of two enantiomers of Example 129 was resolved by HPLC (column: Chiralpak®AD, 250×20 mm (Diacel); mobile phase: 15% isopropanol in hexane; flow rate: 14 mL/min; UV at 254 nm) to give two enantiomers. The first peak from chiral HPLC was arbitrarily assigned as Example 103, 2-methyl-pyrimidine-4-carboxylic acid [(5S,7R)-9,9-difluoro-2-(3-fluoro-phenyl)-1-oxo-2-aza-spiro[4.5]dec-7-yl]-amide, and the second peak from chiral HPLC was arbitrarily assigned as Example 104, 2-methyl-pyrimidine-4-carboxylic acid [(5R,7S)-9,9-difluoro-2-(3-fluoro-phenyl)-1-oxo-2-aza-spiro[4.5]dec-7-yl]-amide.

In an analogous manner to Example 129, Example 105 in Table 1 (below) was made at 0.216 mmol reaction scale from intermediate 26 and commercially available 3,5-difluoroiodobenzene.

In an analogous manner to Example 129, Examples 106 and 110-112 Table 1 (below) were made at 0.097-0.233 mmol reaction scales from intermediate 28 and commercially available 4-fluoroiodobenzene, 3,5-difluoroiodobenzene, 2-chloro-5-fluoropyridine, 4-chloro-2-methylpyrimidine, respectively.

In an analogous manner to Example 129, Examples 107-109 in Table 1 (below) were made at 0.093-0.233 mmol reaction scales from intermediate 27 and commercially 3-fluoroiodobenzene, 4-chloro-2-methylpyrimidine, 2-chloro-5-fluoropyridine, respectively.

In an analogous manner to Example 129, Example 128 in Table 1 (below) was made at 0.214 mmol reaction scale from intermediate 29 and commercially available 4-chloro-2-methylpyrimidine.

In a similar manner to Examples 103 and 104, Examples 110, 109, and 128 in Table 1 (below) were separated into their corresponding enantiomers: Example 113 (1$^{st}$ peak) and 114 (2$^{nd}$ peak), 120 (1$^{st}$ peak) and 121 (2$^{nd}$ peak), and 127 (1$^{st}$ peak) by chiral HPLC, respectively.

Example 103

$^1$H NMR (400 MHz, CDCl$_3$) δ 8.81 (d, J=5.0, 1H), 7.94 (d, J=8.2, 1H), 7.83 (d, J=5.0, 1H), 7.52-7.46 (m, 1H), 7.29-7.24 (m, 2H), 6.84-6.78 (m, 1H), 4.46-4.32 (m, 1H), 3.83-3.71 (m, 2H), 2.62-2.50 (m, 1H), 2.35-1.74 (m, 6H), 1.69 (t, J=12.8, 1H). ESI-MS m/z: 404 (M+H)$^+$.

Example 104

$^1$H NMR (400 MHz, CDCl$_3$) δ 8.81 (d, J=5.0, 1H), 7.94 (d, J=8.2, 1H), 7.83 (d, J=5.0, 1H), 7.52-7.46 (m, 1H), 7.29-7.24 (m, 2H), 6.84-6.78 (m, 1H), 4.46-4.32 (m, 1H), 3.83-3.71 (m, 2H), 2.62-2.50 (m, 1H), 2.35-1.74 (m, 6H), 1.69 (t, J=12.8, 1H). ESI-MS m/z: 404 (M+H)$^+$.

Example 105

$^1$H NMR (400 MHz, CDCl$_3$) δ 8.82 (d, J=5.0, 1H), 8.57 (d, J=5.0, 1H), 7.84 (d, J=5.0, 1H), 7.23-7.15 (m, 2H), 6.59-6.51 (m, 1H), 4.77-4.70 (m, 1H), 3.71-3.57 (m, 2H), 2.74 (s, 3H), 2.40-1.97 (m, 8H). ESI-MS m/z: 437 (M+H)$^+$.

Example 106

$^1$H NMR (400 MHz, CDCl$_3$) δ 8.58-8.55 (m, 1H), 8.22-8.18 (m, 1H), 8.10 (d, J=8.4 Hz, 1H), 7.89 (dt, J=7.7, 1.7 Hz, 1H), 7.63-7.57 (m, 2H), 7.51-7.46 (m, 1H), 7.13-7.06 (m, 2H), 4.57-4.43 (m, 1H), 3.92-3.75 (m, 2H), 2.70-1.81 (m, 7H), 1.73 (t, J=12.8, 1H). ESI-MS m/z: 404 (M+H)$^+$.

Example 107

$^1$H NMR (400 MHz, CDCl$_3$) δ 8.14 (d, J=8.4 Hz, 1H), 8.00 (d, J=7.6 Hz, 1H), 7.75 (t, J=7.7 Hz, 1H), 7.61-7.56 (m, 1H), 7.37-7.33 (m, 2H), 7.31 (d, J=7.6 Hz, 1H), 6.92-6.86 (m, 1H), 4.55-4.43 (m, 1H), 3.93-3.78 (m, 2H), 2.70-2.60 (m, 1H), 2.58 (s, 3H), 2.45-1.84 (m, 6H), 1.75 (t, J=12.7 Hz, 1H). ESI-MS m/z: 418 (M+H)$^+$.

Example 108

$^1$H NMR (400 MHz, CDCl$_3$) δ 8.51 (d, J=5.8 Hz, 1H), 8.14 (d, J=5.9 Hz, 1H), 8.11 (d, J=8.6 Hz, 1H), 7.73 (t, J=7.7 Hz, 1H), 7.29 (d, J=7.7 Hz, 1H), 4.54-4.42 (m, 1H), 4.19-3.95 (m, 2H), 2.65 (s, 3H), 2.63-2.59 (m, 1H), 2.56 (s, 3H), 2.40-1.82 (m, 6H), 1.72 (t, J=12.7 Hz, 1H). ESI-MS m/z: 416 (M+H)$^+$.

Example 109

$^1$H NMR (400 MHz, CDCl$_3$) δ 8.41 (dd, J=9.4, 4.0 Hz, 1H), 8.23 (d, J=3.0 Hz, 1H), 8.13 (d, J=8.6 Hz, 1H), 8.00 (d, J=7.7 Hz, 1H), 7.75 (t, J=7.7 Hz, 1H), 7.50-7.44 (m, 1H), 7.31 (d, J=7.5 Hz, 1H), 4.56-4.45 (m, 1H), 4.18-3.98 (m, 2H), 2.71-2.61 (m, 1H), 2.58 (s, 3H), 2.43-1.83 (m, 6H), 1.76 (t, J=12.8 Hz, 1H). ESI-MS m/z: 419 (M+H)$^+$.

Example 110

$^1$H NMR (400 MHz, CDCl$_3$) δ 8.56 (d, J=3.9 Hz, 1H), 8.19 (d, J=7.6 Hz, 1H), 8.08 (d, J=7.2 Hz, 1H), 7.89 (t, J=7.7 Hz, 1H), 7.50-7.45 (m, 1H), 7.33-7.28 (m, 2H), 6.64 (tt, J=8.8, 2.2 Hz, 1H), 4.56-4.43 (m, 1H), 3.89-3.76 (m, 2H), 2.69-2.58 (m, 1H), 2.46-1.82 (m, 6H), 1.71 (t, J=12.7 Hz, 1H). ESI-MS m/z: 422 (M+H)$^+$.

Example 111

$^1$H NMR (400 MHz, CDCl$_3$) δ 8.53 (d, J=4.6 Hz, 1H), 8.41 (dd, J=9.2, 4.0 Hz, 1H), 8.23 (d, J=3.0 Hz, 1H), 8.20 (d, J=7.9 Hz, 1H), 8.07 (d, J=8.4 Hz, 1H), 7.88 (dt, J=7.8, 1.6 Hz, 1H), 7.50-7.44 (m, 2H), 4.56-4.45 (m, 1H), 4.17-3.98 (m, 2H), 2.71-2.60 (m, 1H), 2.42-1.81 (m, 6H), 1.74 (t, J=12.7 Hz, 1H). ESI-MS m/z: 405 (M+H)$^+$.

Example 112

$^1$H NMR (400 MHz, CDCl$_3$) δ 8.58-8.51 (m, 2H), 8.22-8.16 (m, 2H), 8.08 (d, J=8.3 Hz, 1H), 7.92-7.86 (m, 1H), 7.50-7.45 (m, 1H), 4.56-4.43 (m, 1H), 4.22-3.97 (m, 2H), 2.69 (s, 3H), 2.67-2.60 (m, 1H), 2.43-1.82 (m, 6H), 1.71 (t, J=12.6 Hz, 1H). ESI-MS m/z: 402 (M+H)$^+$.

Example 113

$^1$H NMR (400 MHz, CDCl$_3$) δ 8.56 (d, J=3.9 Hz, 1H), 8.19 (d, J=7.6 Hz, 1H), 8.08 (d, J=7.2 Hz, 1H), 7.89 (t, J=7.7 Hz, 1H), 7.50-7.45 (m, 1H), 7.33-7.28 (m, 2H), 6.64 (tt, J=8.8, 2.2 Hz, 1H), 4.56-4.43 (m, 1H), 3.89-3.76 (m, 2H), 2.69-2.58 (m, 1H), 2.46-1.82 (m, 6H), 1.71 (t, J=12.7 Hz, 1H). ESI-MS m/z: 422 (M+H)$^+$.

Example 114

$^1$H NMR (400 MHz, CDCl$_3$) δ 8.56 (d, J=3.9 Hz, 1H), 8.19 (d, J=7.6 Hz, 1H), 8.08 (d, J=7.2 Hz, 1H), 7.89 (t, J=7.7 Hz,

1H), 7.50-7.45 (m, 1H), 7.33-7.28 (m, 2H), 6.64 (tt, J=8.8, 2.2 Hz, 1H), 4.56-4.43 (m, 1H), 3.89-3.76 (m, 2H), 2.69-2.58 (m, 1H), 2.46-1.82 (m, 6H), 1.71 (t, J=12.7 Hz, 1H). ESI-MS m/z: 422 (M+H)+.

Example 120

$^1$H NMR (400 MHz, CDCl$_3$) δ 8.53 (d, J=5.9 Hz, 1H), 8.15 (d, J=5.8 Hz, 1H), 7.54-7.39 (m, 3H), 7.26-7.20 (m, 1H), 6.26 (d, J=7.9 Hz, 1H), 4.58-4.47 (m, 1H), 4.19-4.01 (m, 2H), 2.67 (s, 3H), 2.65-2.56 (m, 1H), 2.40-2.07 (m, 5H), 1.96-1.78 (m, 1H), 1.67 9t, J=12.3, 1H). ESI-MS m/z: 419 (M+H)+.

Example 121

$^1$H NMR (400 MHz, CDCl$_3$) δ 8.53 (d, J=5.9 Hz, 1H), 8.15 (d, J=5.8 Hz, 1H), 7.54-7.39 (m, 3H), 7.26-7.20 (m, 1H), 6.26 (d, J=7.9 Hz, 1H), 4.58-4.47 (m, 1H), 4.19-4.01 (m, 2H), 2.67 (s, 3H), 2.65-2.56 (m, 1H), 2.40-2.07 (m, 5H), 1.96-1.78 (m, 1H), 1.67 9t, J=12.3, 1H). ESI-MS m/z: 419 (M+H)+.

Example 127

$^1$H NMR (400 MHz, CDCl$_3$) δ 8.41 (dd, J=9.4, 4.0 Hz, 1H), 8.23 (d, J=3.0 Hz, 1H), 8.13 (d, J=8.6 Hz, 1H), 8.00 (d, J=7.7 Hz, 1H), 7.75 (t, J=7.7 Hz, 1H), 7.50-7.44 (m, 1H), 7.31 (d, J=7.5 Hz, 1H), 4.56-4.45 (m, 1H), 4.18-3.98 (m, 2H), 2.71-2.61 (m, 1H), 2.58 (s, 3H), 2.43-1.83 (m, 6H), 1.76 (t, J=12.8 Hz, 1H). ESI-MS m/z: 419 (M+H)+.

Example 128

$^1$H NMR (400 MHz, CDCl$_3$) δ 8.53 (d, J=5.9 Hz, 1H), 8.15 (d, J=5.8 Hz, 1H), 7.54-7.39 (m, 3H), 7.26-7.20 (m, 1H), 6.26 (d, J=7.9 Hz, 1H), 4.58-4.47 (m, 1H), 4.19-4.01 (m, 2H), 2.67 (s, 3H), 2.65-2.56 (m, 1H), 2.40-2.07 (m, 5H), 1.96-1.78 (m, 1H), 1.67 9t, J=12.3, 1H). ESI-MS m/z: 419 (M+H)+.

Example 115 cis-2-Methyl-pyrimidine-4-carboxylic acid [2-(3,5-difluoro-phenyl)-1,9-dioxo-2-aza-spiro[4.5]dec-7-yl]-amide

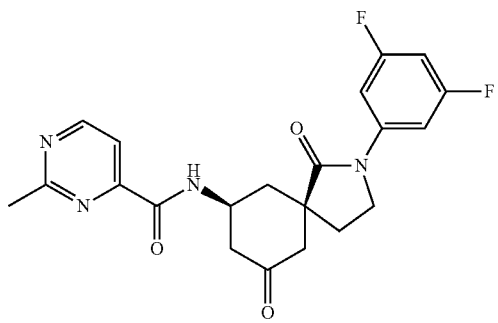 [SMILES: Cc1nccc(C(=O)N[C@@H]2CC(=O)C[C@@]3(CCN(c4cc(F)cc(F)c4)C3=O)C2)n1]

Example 115 was prepared from intermediate 30 via the process of Scheme 23, supra, as follows:
To a solution of cis-13-amino-9-(3,5-difluoro-phenyl)-1,4-dioxa-9-aza-dispiro[4.1.4.3]tetradecan-8-one (300 mg, 0.887 mmol) and 2-methylpyrimidine-4-carboxylic acid (128 mg, 1.05 mmol) in DCM (6 mL) was added PYBOP (508 mg, 0.975 mmol) and triethylamine (0.27 mL, 1.95 mmol). The reaction mixture was stirred at room temperature overnight and concentrated. The residue was chromatographed on silica gel (0 to 70% EtOAc in hexanes) to give an intermediate (300 mg), which was dissolved in THF (5 mL), followed by the addition of 3.0 M HCl in water (5 mL). The reaction mixture was stirred at room temperature overnight and concentrated. The residue was suspended in DCM (20 mL) and quenched with saturated aqueous NaHCO$_3$. The aqueous layer was extracted with DCM (2×20 mL). The combined organic layers were concentrated. The residue was chromatographed on silica gel (0 to 80% EtOAc in hexanes) to give 190 mg (49% over 2 steps) of the title compound, cis-2-Methyl-pyrimidine-4-carboxylic acid [2-(3,5-difluoro-phenyl)-1,9-dioxo-2-aza-spiro[4.5]dec-7-yl]-amide. $^1$H NMR (400 MHz, CDCl$_3$) δ 8.90 (d, J=5.0 Hz, 1H), 8.29 (d, J=8.4 Hz, 1H), 7.90 (d, J=5.0 Hz, 1H), 7.33-7.29 (m, 2H), 6.65 (tt, J=8.7, 2.2 Hz, 1H), 4.62-4.50 (m, 1H), 3.88-3.80 (m, 2H), 2.96-2.76 (m, 5H), 2.59 (dd, J=13.6, 11.4 Hz, 1H), 2.44-2.09 (m, 5H). ESI-MS m/z: 415 (M+H)+.

In an analogous manner to Example 115, Example 124 in Table 1 (below) was made at 1.15 mmol reaction scale from intermediate 31 and commercially available 6-methylpicolinic acid.

Example 124

$^1$H NMR (400 MHz, CDCl$_3$) δ 8.32 (d, J=8.6 Hz, 1H), 8.00 (d, J=7.7 Hz, 1H), 7.75 (t, J=7.7 Hz, 1H), 7.62-7.57 (m, 1H), 7.37-7.30 (m, 3H), 6.93-6.87 (m, 1H), 4.61-4.49 (m, 1H), 3.92-3.81 (m, 2H), 2.96-2.90 (m, 1H), 2.81 (d, J=14.1 Hz, 1H), 2.61 (s, 3H), 2.56 (d, J=12.9 Hz, 1H), 2.43-2.07 (m, 5H). ESI-MS m/z: 396 (M+H)+.

Example 123 cis-3-Fluoro-N-[2-(3-fluoro-phenyl)-1,9-dioxo-2-aza-spiro[4.5]dec-7-yl]-benzamide

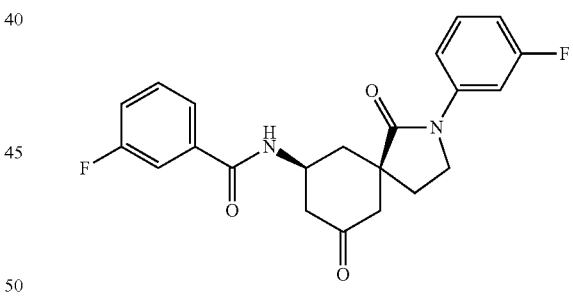

Example 123 was prepared from intermediate 31 via the process of Scheme 23, supra, as follows:
To a solution of cis-13-amino-9-(3-fluoro-phenyl)-1,4-dioxa-9-aza-dispiro[4.1.4.3]tetradecan-8-one (370 mg, 1.15 mmol) and triethylamine (0.40 mL, 2.9 mmol) in DCM (10 mL) was added 3-fluorobenzoyl chloride (220 mg, 1.38 mmol) at −78° C. The reaction mixture was stirred at room temperature overnight and diluted with DCM (50 mL). The organic layer was washed with saturated NaHCO$_3$ and brine, dried over MgSO$_4$, filtered, and concentrated. The residue was chromatographed on silica gel (gradient: 0 to 70% EtOAc in hexanes) to give an intermediate (300 mg), which was dissolved in THF (5 mL), followed by the addition of 3.0 M HCl in water (5 mL). The reaction mixture was stirred at room temperature overnight and concentrated. The residue was suspended in DCM (20 mL) and quenched with saturated aqueous NaHCO₃. The aqueous layer was extracted with DCM (2×20 mL). The combined organic layers were concentrated. The residue was chromatographed on silica gel (0 to 80% EtOAc in hexanes) to give 162 mg (21% over 2 steps) of the title compound, cis-3-Fluoro-N-[2-(3-fluoro-phenyl)-1,9-dioxo-2-aza-spiro[4.5]dec-7-yl]-benzamide. ¹H NMR (400 MHz, CDCl₃) δ 7.61-7.51 (m, 3H), 7.45 (d, J=8.4 Hz, 1H), 7.43-7.33 (m, 3H), 7.24-7.18 (m, 1H), 6.95-6.89 (m, 1H), 4.85-4.74 (m, 1H), 3.95-3.83 (m, 2H), 2.86 (dd, J=14.6, 5.6 Hz, 1H), 2.80 (d, J=14.3 Hz, 1H), 2.60 (dd, J=14.6, 7.6 Hz, 1H), 2.46 (d, J=14.3 Hz, 1H), 2.33-2.11 (m, 4H). ESI-MS m/z: 399 (M+H)⁺.

Example 116 cis-2-Methyl-pyrimidine-4-carboxylic acid [2-(3,5-difluorophenyl)-9-hydroxy-1-oxo-2-aza-spiro[4.5]dec-7-yl]-amide

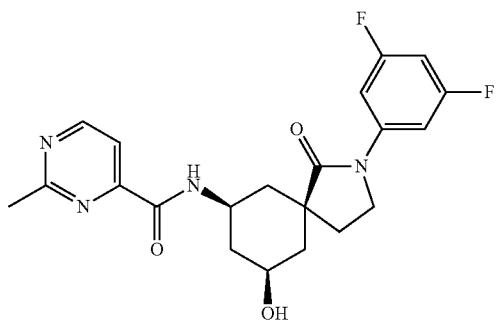 [SMILES: Cc1nccc(C(=O)N[C@@H]2C[C@H](O)C[C@@]3(CCN(c4cc(F)cc(F)c4)C3=O)C2)n1]

Example 117 trans-2-Methyl-pyrimidine-4-carboxylic acid [2-(3,5-difluorophenyl)-9-hydroxy-1-oxo-2-aza-spiro[4.5]dec-7-yl]-amide

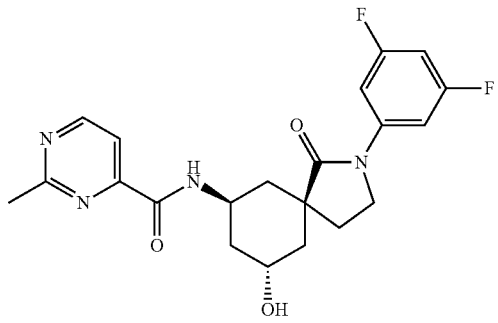 [SMILES: Cc1nccc(C(=O)N[C@@H]2C[C@@H](O)C[C@@]3(CCN(c4cc(F)cc(F)c4)C3=O)C2)n1]

Route 1: Examples 116 and 117 were prepared from Example 115 via the process of Scheme 23, supra, as follows:

The reaction mixture of cis-2-methyl-pyrimidine-4-carboxylic acid [2-(3,5-difluoro-phenyl)-1,9-dioxo-2-aza-spiro[4.5]dec-7-yl]-amide (40 mg, 0.0965 mmol) and sodium borohydride (7.3 mg, 0.193 mmol) in THF (3 mL) was stirred at room temperature for 4 hours. The reaction mixture was quenched with water and extracted with DCM (3×10 mL). The combined organic layers were dried over MgSO₄, filtered, and concentrated. The residue was purified by HPLC to afford two diastereomers. The first peak from the HPLC (purified on a reversed phase liquid chromatography/mass spectrometry (RP-HPLC/MS) purification system. Gradient: acetonitrile in water, 18-95% in 3.6 minutes with a cycle time of 5 min. A shallow gradient between 23-46% of acetonitrile was used between 0.6-3.0 min to separate close-eluting impurities. Flow rate: 100 mL/min. Mobile phase additive: 48 mM of ammonium formate. Column: Inertsil C8, 30×50 mm, 5 um particle size) was assigned as Example 116, cis-2-Methyl-pyrimidine-4-carboxylic acid [2-(3,5-difluorophenyl)-9-hydroxy-1-oxo-2-aza-spiro[4.5]dec-7-yl]-amide (4 mg), and the second peak from the HPLC was assigned as Example 117, trans-2-Methyl-pyrimidine-4-carboxylic acid [2-(3,5-difluorophenyl)-9-hydroxy-1-oxo-2-aza-spiro[4.5]dec-7-yl]-amide (6 mg).

Example 116

¹H NMR (400 MHz, CDCl₃) δ 8.89 (d, J=5.0 Hz, 1H), 8.08 (d, J=8.6 Hz, 1H), 7.90 (d, J=5.0 Hz, 1H), 7.33-7.29 (m, 2H), 6.67-6.60 (m, 1H), 4.30-4.17 (m, 1H), 4.01-4.17 (m, 1H), 3.90-3.74 (m, 2H), 2.80 (s, 3H), 2.51-2.42 (m, 1H), 2.29-2.11 (m, 2H), 2.01-1.44 (m, 5H). ESI-MS m/z: 417 (M+H)⁺.

Example 117

¹H NMR (400 MHz, CDCl₃) δ 8.88 (d, J=5.0 Hz, 1H), 8.53 (d, J=2.2 Hz, 1H), 7.90 (d, J=4.9 Hz, 1H), 7.39-7.30 (m, 2H), 6.67-6.58 (m, 1H), 4.72-4.59 (m, 1H), 4.57-4.44 (m, 1H), 3.88-3.74 (m, 2H), 2.82 (s, 3H), 2.53-2.35 (m, 2H), 2.16-1.72 (m, 6H). ESI-MS m/z: 417 (M+H)⁺.

Route 2: Example 117 was also made, as follows:

To a solution of cis-2-methyl-pyrimidine-4-carboxylic acid [2-(3,5-difluoro-phenyl)-1,9-dioxo-2-aza-spiro[4.5]dec-7-yl]-amide (20 mg, 0.048 mmol) THF (3 mL) was added 1.0 M of L-Selectride in THF (0.1 mL, 0.1 mmol) at −78° C. The reaction mixture was stirred at −78° C. for 1 h and quenched with ice. The aqueous layer was extracted with DCM (3×10 mL). The combined organic layers were dried over MgSO4, filtered, and concentrated. The residue was purified by HPLC to give 5 mg (25%) of the title compound.

In an analogous manner (route 2) to Example 117, Example 125 in Table 1 (below) was made at 0.176 mmol reaction scale from Example 123.

Example 125

¹H NMR (400 MHz, CDCl₃) δ 8.64 (br s, 1H), 7.62-7.46 (m, 3H), 7.39-7.25 (m, 3H), 7.15-7.08 (m, 1H), 6.87-6.80 (m, 1H), 4.69-4.61 (m, 1H), 4.30-4.21 (m, 1H), 3.89-3.70 (m, 2H), 2.26-2.01 (m, 4H), 1.81 (dq, J=14.4, 4.6 Hz, 2H), 1.64 (dq, J=9.7, 4.0 Hz, 1H), 1.45 (dq, J=13.4, 9.4 Hz, 1H). ESI-MS m/z: 401 (M+H)⁺.

In an analogous manner (route 2) to Example 117, Example 126 in Table 1 (below) was made at 0.114 mmol reaction scale from Example 124.

Example 126

¹H NMR (400 MHz, CDCl₃) δ 8.40 (d, J=8.3 Hz, 1H), 8.00 (d, J=7.5 Hz, 1H), 7.73 (t, J=7.7 Hz, 1H), 7.67-7.61 (m, 1H), 7.39-7.29 (m, 2H), 6.90-6.84 (m, 1H), 4.72-4.60 (m, 1H), 4.53-4.48 (m, 1H), 3.88-3.77 (m, 2H), 2.60 (s, 3H), 2.53-2.40 (m, 2H), 2.21-2.00 (m, 3H), 1.83-1.73 (m, 3H). ESI-MS m/z: 398 (M+H)⁺.

Example 119 cis-2-Methyl-pyrimidine-4-carboxylic acid [2-(3,5-difluoro-phenyl)-9-hydroxy-9-methyl-1-oxo-2-aza-spiro[4.5]dec-7-yl]-amide

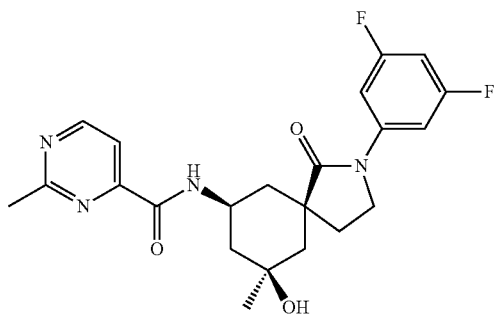 [SMILES: Cc1nccc(C(=O)N[C@@H]2C[C@](C)(O)C[C@@]3(CCN(c4cc(F)cc(F)c4)C3=O)C2)n1]

Example 118 trans-2-Methyl-pyrimidine-4-carboxylic acid [2-(3,5-difluoro-phenyl)-9-hydroxy-9-methyl-1-oxo-2-aza-spiro[4.5]dec-7-yl]-amide Examples 119 and 118 were prepared from Example 115 via the process of Scheme 23, supra, as follows:

To a solution of cis-2-methyl-pyrimidine-4-carboxylic acid [2-(3,5-difluoro-phenyl)-1,9-dioxo-2-aza-spiro[4.5]dec-7-yl]-amide (30 mg, 0.0724 mmol) in THF (3 mL) was added 3.0M of methylmagnesium bromide in ether (0.05 mL) at −78° C. The reaction mixture was stirred at −78° C. for 1 h and quenched with water. The aqueous layer was extracted with DCM (3×10 mL). The combined organic layers were dried over MgSO₄, filtered, and concentrated. The residue was purified by RP-HPLC/MS purification system (gradient: acetonitrile in water, 24-95% in 3.6 minutes with a cycle time of 5 min. A shallow gradient between 26-56% of acetonitrile was used between 0.75-3.4 min to separate close-eluting impurities. Flow rate: 100 mL/min. Mobile phase additive: 48 mM of ammonium formate. Column: Inertsil® C8, 30×50 mm, 5 um particle size) to afford two diastereomers. The first peak from the HPLC was assigned as Example 119, cis-2-methyl-pyrimidine-4-carboxylic acid [2-(3,5-difluoro-phenyl)-9-hydroxy-9-methyl-1-oxo-2-aza-spiro[4.5]dec-7-yl]-amide (2 mg), and the second peak from the HPLC was assigned as Example 118, trans-2-Methyl-pyrimidine-4-carboxylic acid [2-(3,5-difluoro-phenyl)-9-hydroxy-9-methyl-1-oxo-2-aza-spiro[4.5]dec-7-yl]-amide (3 mg).

Example 118

¹H NMR (400 MHz, CDCl₃) δ 8.88 (d, J=4.6 Hz, 1H), 7.95 (d, J=8.8 Hz, 1H), 7.91 (d, J=4.8 Hz, 1H), 7.35-7.29 (m, 2H), 6.65-6.58 (m, 1H), 4.64-4.52 (m, 1H), 3.84-3.71 (m, 2H), 2.78 (s, 3H), 2.60-2.41 (m, 2H), 2.18-2.00 (m, 2H), 1.92 (d, J=14.2, 1H), 1.74-1.54 (m, 3H), 1.38 (s, 3H). ESI-MS m/z: 431 (M+H)⁺.

Example 119

¹H NMR (400 MHz, CDCl₃) δ 8.88 (d, J=4.6 Hz, 1H), 7.95 (d, J=8.8 Hz, 1H), 7.91 (d, J=4.8 Hz, 1H), 7.35-7.29 (m, 2H), 6.65-6.58 (m, 1H), 4.64-4.52 (m, 1H), 3.84-3.71 (m, 2H), 2.78 (s, 3H), 2.60-2.41 (m, 2H), 2.18-2.00 (m, 2H), 1.92 (d, J=14.2, 1H), 1.74-1.54 (m, 3H), 1.38 (s, 3H). ESI-MS m/z: 431 (M+H)⁺.

Example 122 trans-2-Methyl-pyrimidine-4-carboxylic acid [2-(3,5-difluoro-phenyl)-9-fluoro-1-oxo-2-aza-spiro[4.5]dec-7-yl]-amide

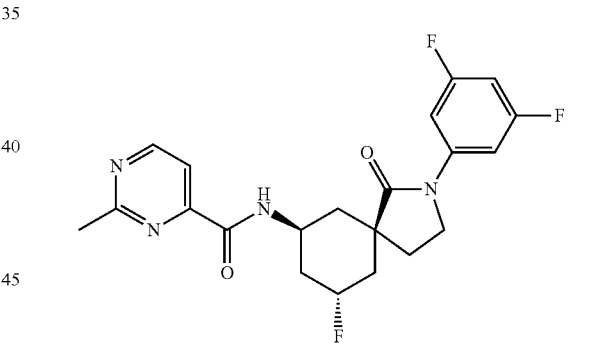

Example 122 was prepared from Example 117 via the process of Scheme 23, supra, as follows:

To a solution of trans-2-Methyl-pyrimidine-4-carboxylic acid [2-(3,5-difluorophenyl)-9-hydroxy-1-oxo-2-aza-spiro[4.5]dec-7-yl]-amide (crude, <0.121 mmol) in DCM (5 mL) was added DAST (20.3 µL, 0.154 mmol) at 0° C. The reaction mixture was stirred at room temperature overnight and quenched with saturated aqueous NaHCO₃. The aqueous layer was extracted with DCM. The combined organic layers were washed with brine, dried over Na₂SO₄, filtered, and concentrated. The residue was chromatographed on silica gel (0 to 70% EtOAc in hexanes) to give 2 mg of the title compound, trans-2-methyl-pyrimidine-4-carboxylic acid [2-(3,5-difluoro-phenyl)-9-fluoro-1-oxo-2-aza-spiro[4.5]dec-7-yl]-amide. ¹H NMR (400 MHz, CDCl₃) δ 8.79 (d, J=5.0 Hz, 1H), 8.00 (d, J=8.5 Hz, 1H), 7.82 (t, J=5.0 Hz, 1H), 7.26-7.21 (m, 1H), 6.54 (tt, J=8.8, 2.2 Hz, 1H), 5.22-5.05 (m, 1H), 4.55-4.43

(m, 1H), 3.79-3.66 (m, 2H), 2.71 (s, 3H), 2.45-2.25 (m, 3H), 2.09-1.92 (m, 3H), 1.74-1.54 (m, 2H). ESI-MS m/z: 419 (M+H)$^+$.

Example 131 cis-3-Fluoro-N-[2-(3-hydroxy-phenyl)-1-oxo-2-aza-spiro[4.5]dec-7-yl]-benzamide

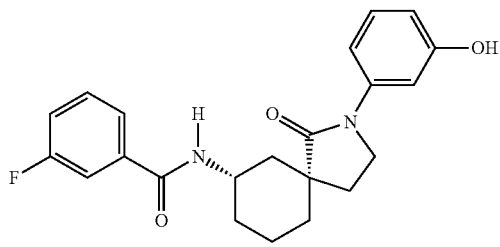 [SMILES: O=C(N[C@H]1CCC[C@]2(CCN(c3cccc(O)c3)C2=O)C1)c1cccc(F)c1]

Example 131 was made from Example 130 via the process of Scheme 22 (step c), supra, as follows:

Into a vial containing cis 3-fluoro-N—[-2-(3-methoxy-phenyl)-1-oxo-2-aza-spiro[4.5]dec-7-yl]-benzamide (150 mg, 0.38 mmol) was added 20 mL of dichloromethane. The solution was cooled at −70° C. 2 mL of 2 M boron tribromide in dichloromethane was added, and the mixture was slowly warmed up to rt and stirred at rt for 40 hrs.

The reaction was quenched with cold water and the organic layer was separated. The precipitate was extracted with DCM and ethyl acetate. The organic extracts were combined, dried over sodium sulfate and purified on a reversed phase liquid chromatography/mass spectrometry (RP-HPLC/MS) purification system (Gradient: acetonitrile in water, 25-95% in 3.6 minutes with a cycle time of 5 min. A shallow gradient between 27-56% of acetonitrile was used between 0.75-3.4 min to separate close-eluting impurities. Flow rate: 100 mL/min. Mobile phase additive: 48 mM of ammonium acetate. Column: Inertsil® C18, 30×50 mm, 5 um particle size (GL Sciences)) to afford 50 mg (26%) of the title compound. $^1$H NMR (400 MHz, CDCl$_3$): δ7.60-7.52 (m, 3H), 7.43-7.36 (m, 1H), 7.26-7.14 (m, 2H), 6.99-6.95 (m, 1H), 6.70-6.66 (m, 1H), 6.58 (s, br, 1H), 4.31-4.20 (m, 1H), 3.84-3.75 (m, 2H), 2.24-1.44 (m, 10H). ESI-MS m/z: 383.0 (M+H)$^+$.

Example 157

3-Fluoro-N-[2-(1-methyl-piperidin-4-yl)-1-oxo-2-aza-spiro[4.5]dec-7-yl]-benzamide

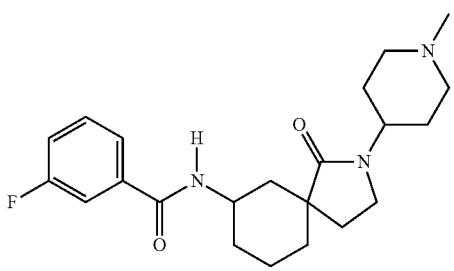 [SMILES: CN1CCC(N2CCC3(CCCC(NC(=O)c4cccc(F)c4)C3)C2=O)CC1]

Example 157 was made from intermediate 35 via the process of Scheme 24, supra, as follows:

4-[7-(3-Fluoro-benzoylamino)-1-oxo-2-aza-spiro[4.5]dec-2-yl]-piperidine-1-carboxylic acid 0tert-butyl ester (0.135 g, 0.285 mmol) was dissolved in CH$_2$Cl$_2$ (2.0 mL). 4 M of Hydrogen chloride in 1,4-dioxane (1.0 mL) was added, the mixture was stirred at rt overnight. The mixture was concentrated under reduced pressure to afford a mixture of two diastereomers (cis/trans: 3/2; under LC-MS method C, the first peak with RT of 0.77 min was assigned as cis, and the second peak with RT of 0.81 min was assigned as trans.). ESI-MS m/z: 374 (M+H)$^+$. It was used in the next step without further purification. 3-Fluoro-N-(1-oxo-2-piperidin-4-yl-2-aza-spiro[4.5]dec-7-yl)-benzamide (0.050 g, 0.13 mmol) was dissolved in CH$_2$Cl$_2$ (2.3 mL), formaldehyde (0.011 g, 0.13 mmol, 37% aqueous solution) was added, followed by the addition of sodium triacetoxyborohydride (0.043 g, 0.20 mmol). The mixture was stirred at rt overnight, and then quenched with ice. The mixture was diluted with CH$_2$Cl$_2$ (20 mL). The organic layer was washed with brine, dried over Na$_2$SO$_4$ and concentrated under reduced pressure. The resulting residue was purified on RP-HPLC/MS) (Gradient: acetonitrile in water, 5-95% in 2.5 minutes with a cycle time of 5 min. A shallow gradient between 5-20% of acetonitrile was used between 0.5-2.0 min. Flow rate: 77 mL/min. Mobile phase additive: 84 mM of ammonium formate. Column: SunFire C18, 19×50 mm, 5 um particle size) to afford 0.011 g (21%) of the title compound 3-fluoro-N-[2-(1-methyl-piperidin-4-yl)-1-oxo-2-aza-spiro[4.5]dec-7-yl]-benzamide. $^1$H NMR (400 MHz, CDCl$_3$) δ 8.5 (s, 0.6H), 7.60-7.69 (m, 1H), 7.36-7.50 (m, 2H), 7.14-7.20 (m, 1H), 5.92 (d, J=6.8 Hz, 0.4 H), 4.55-4.65 (m, 0.4 H), 4.27-4.37 (m, 0.6 H), 3.91-4.01 (m, 1H), 3.21-3.34 (m, 2H), 2.85-2.95 (m, 2H), 2.29 (s, 1.8 H), 2.28 (s, 1.2H), 1.30-2.24 (m, 16H). ESI-MS m/z: 388 (M+H)$^+$.

Example 159

2-Methyl-6-oxo-1,6-dihydro-pyrimidine-4-carboxylic acid [(5R,7R)-2-(3,5-difluoro-phenyl)-1-oxo-2-aza-spiro[4.5]dec-7-yl]amide

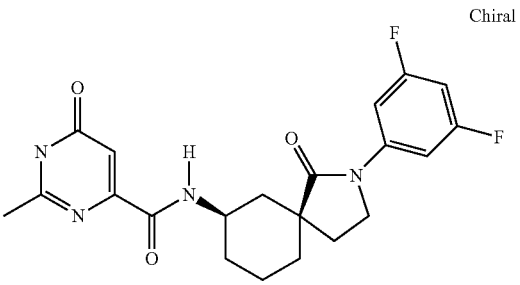 [SMILES: Cc1nc(C(=O)N[C@@H]2CCC[C@@]3(CCN(c4cc(F)cc(F)c4)C3=O)C2)cc(=O)[nH]1]

Example 159 was made from intermediate 36 via the process of Scheme 1, supra, as follows:

To a solution of intermediate 36 (5R,7R)-7-amino-2-(3,5-difluoro-phenyl)-2-aza-spiro[4.5]decan-1-one (80 mg, 0.28 mmol), triethylamine (0.16 mL, 1.14 mmol) in DMF (2.0 mL) was added 6-hydroxy-2-methyl-pyrimidine-4-carboxylix acid (49 mg, 0.32 mmol), HOBt (51 mg, 0.38 mmol) and EDCI (73 mg, 0.38 mmol). The mixture was stirred at rt overnight. The solvent was removed with Genevac, and the resulting residue was purified with spectrometry (RP-HPLC/MS) purification system (Gradient: acetonitrile in water, 25-95% in 3.9 minutes with a cycle time of 5 min. Flow rate:

100 mL/min. Mobile phase additive: 48 mM of ammonium formate. Column: Inertsil C18, 30×50 mm, 5 um particle size) to afford 26 mg (22%) of the title compound 2-methyl-6-oxo-1,6-dihydro-pyrimidine-4-carboxylic acid [(5R,7R)-2-(3,5-difluoro-phenyl)-1-oxo-2-aza-spiro[4.5]dec-7-yl]amide. $^1$H NMR (400 MHz, CDCl$_3$) δ 13.0 (bs, 1H), 7.94 (d, J=8.4 Hz, 1H), 7.25-7.32 (m, 2H), 7.14 (s, 1H), 6.56-6.63 (m, 1H), 4.02-4.12 (m, 1H), 3.73-3.80 (m, 2H), 2.52 (s, 3H), 2.04-2.26 (m, 3H), 1.86-1.95 (m, 2H), 1.34-1.80 (m, 5H). ESI-MS m/z: 417 (M+H)$^+$.

TABLE 1

Spirolactam derivatives

| Example No | STRUCTURE | CHEMICAL NAME | LC-MS |
|---|---|---|---|
| 1 | 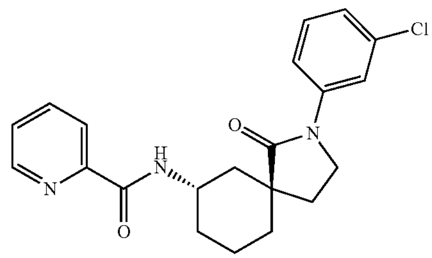 [SMILES: O=C(N[C@H]1CCC[C@@]2(CCN(c3cccc(Cl)c3)C2=O)C1)c1ccccn1] | trans-Pyridine-2-carboxylic acid [2-(3-chloro-phenyl)-1-oxo-2-aza-spiro[4.5]dec-7-yl]-amide | Method: C RT: 1.46 Calcd. Mass: 383 m/z (M + H): 384 |
| 2 | 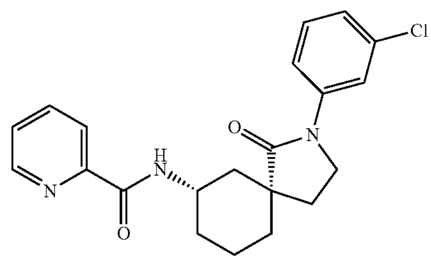 [SMILES: O=C(N[C@H]1CCC[C@]2(CCN(c3cccc(Cl)c3)C2=O)C1)c1ccccn1] | cis-Pyridine-2-carboxylic acid [2-(3-chloro-phenyl)-1-oxo-2-aza-spiro[4.5]dec-7-yl]-amide | Method: C RT: 1.39 Calcd. Mass: 383 m/z (M + H): 384 |
| 3 | 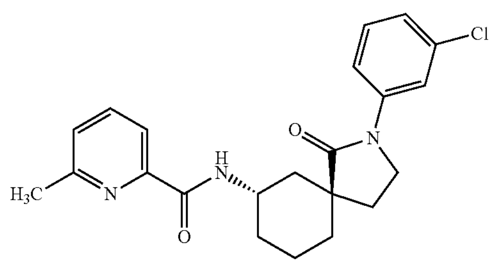 [SMILES: Cc1cccc(C(=O)N[C@H]2CCC[C@@]3(CCN(c4cccc(Cl)c4)C3=O)C2)n1] | trans-6-Methyl-pyridine-2-carboxylic acid [2-(3-chloro-phenyl)-1-oxo-2-aza-spiro [4.5]dec-7-yl]-amide | Method: C RT: 1.54 Calcd. Mass: 397 m/z (M + H): 398 |
| 4 | 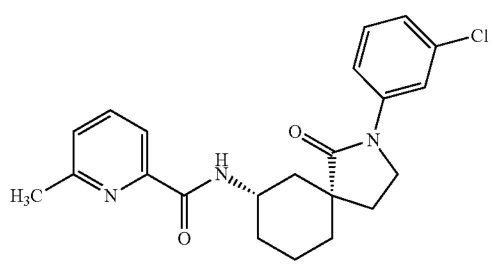 [SMILES: Cc1cccc(C(=O)N[C@H]2CCC[C@]3(CCN(c4cccc(Cl)c4)C3=O)C2)n1] | cis-6-Methyl-pyridine-2-carboxylic acid [2-(3-chloro-phenyl)-1-oxo-2-aza-spiro[4.5]dec-7-yl]-amide | Method: C RT: 1.47 Calcd. Mass: 397 m/z (M + H): 398 |
| 5 | Chiral | Pyridine-2-carboxylic acid [(5R,7R)-2-(3-chloro-phenyl)-1-oxo-2-aza-spiro [4.5]dec-7-yl]amide | Method: C RT: 1.38 Calcd. Mass: 383 m/z (M + H): 384 |

TABLE 1-continued

Spirolactam derivatives

| Example No | STRUCTURE | CHEMICAL NAME | LC-MS |
|---|---|---|---|
| 6 | (Chiral) | Pyridine-2-carboxylic acid [(5S,7S)-2-(3-chloro-phenyl)-1-oxo-2-aza-spiro[4.5]dec-7-yl]amide | Method: C<br>RT: 1.38<br>Calcd. Mass: 383<br>m/z (M + H): 384 |
| 7 | 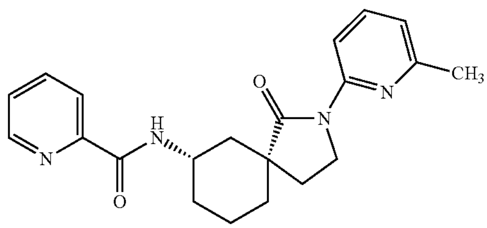 [SMILES: Cc1cccc(N2CC[C@]3(CCC[C@H](NC(=O)c4ccccn4)C3)C2=O)n1] | cis-Pyridine-2-carboxylic acid [2-(6-methyl-pyridin-2-yl)-1-oxo-2-aza-spiro [4.5]dec-7-yl]-amide | Method: C<br>RT: 1.26<br>Calcd. Mass: 364<br>m/z (M + H): 365 |
| 8 | 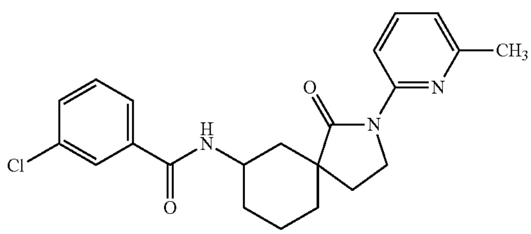 [SMILES: Cc1cccc(N2CCC3(CCCC(NC(=O)c4cccc(Cl)c4)C3)C2=O)n1] | 3-Chloro-N-[2-(6-methyl-pyridin-2-yl)-1-oxo-2-aza-spiro[4.5]dec-7-yl]-benzamide | Method: C<br>RT: 1.49<br>Calcd. Mass: 397<br>m/z (M + H): 398 |
| 9 | 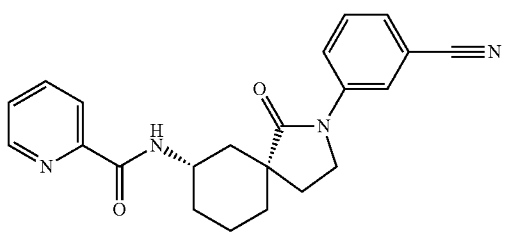 [SMILES: N#Cc1cccc(N2CC[C@]3(CCC[C@H](NC(=O)c4ccccn4)C3)C2=O)c1] | cis-Pyridine-2-carboxylic acid [2-(3-cyano-phenyl)-1-oxo-2-aza-spiro[4.5]dec-7-yl]-amide | Method: C<br>RT: 1.20<br>Calcd. Mass: 374<br>m/z (M + H): 375 |
| 10 | 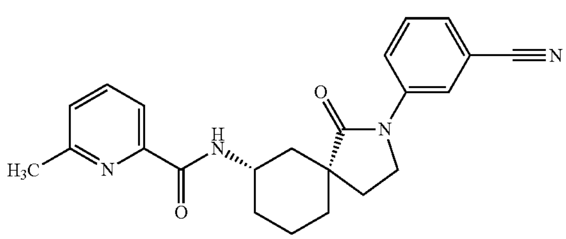 [SMILES: Cc1cccc(C(=O)N[C@H]2CCC[C@]3(CCN(c4cccc(C#N)c4)C3=O)C2)n1] | cis-6-Methyl-pyridine-2-carboxylic acid [2-(3-cyano-phenyl)-1-oxo-2-aza-spiro [4.5]dec-7-yl]-amide | Method: C<br>RT: 1.30<br>Calcd. Mass: 388<br>m/z (M + H): 389 |
| 11 | 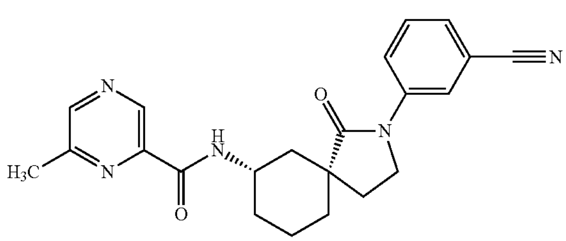 [SMILES: Cc1cncc(C(=O)N[C@H]2CCC[C@]3(CCN(c4cccc(C#N)c4)C3=O)C2)n1] | cis-6-Methyl-pyrazine-2-carboxylic acid [2-(3-cyano-phenyl)-1-oxo-2-aza-spiro [4.5]dec-7-yl]-amide | Method: C<br>RT: 1.15<br>Calcd. Mass: 389<br>m/z (M + H): 390 |

TABLE 1-continued

Spirolactam derivatives

| Example No | STRUCTURE | CHEMICAL NAME | LC-MS |
|---|---|---|---|
| 12 | 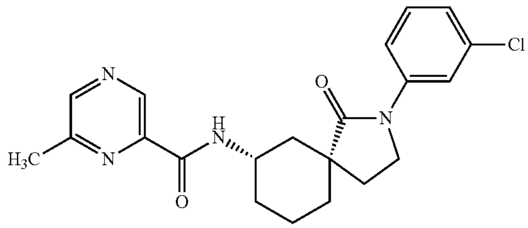 [SMILES: Cc1cncc(C(=O)N[C@H]2CCC[C@]3(CCN(c4cccc(Cl)c4)C3=O)C2)n1] | cis-6-Methyl-pyrazine-2-carboxylic acid [2-(3-chloro-phenyl)-1-oxo-2-aza-spiro[4.5]dec-7-yl]-amide | Method: C<br>RT: 1.33<br>Calcd. Mass: 398<br>m/z (M + H): 399 |
| 13 | 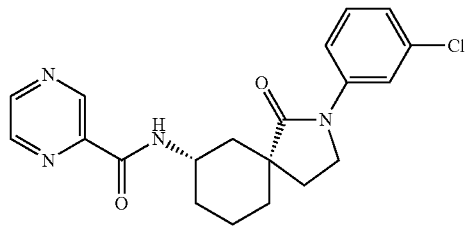 [SMILES: O=C(N[C@H]1CCC[C@]2(CCN(c3cccc(Cl)c3)C2=O)C1)c1cnccn1] | cis-Pyrazine-2-carboxylic acid [2-(3-chloro-phenyl)-1-oxo-2-aza-spiro[4.5]dec-7-yl]-amide | Method: C<br>RT: 1.23<br>Calcd. Mass: 384<br>m/z (M + H): 385 |
| 14 | 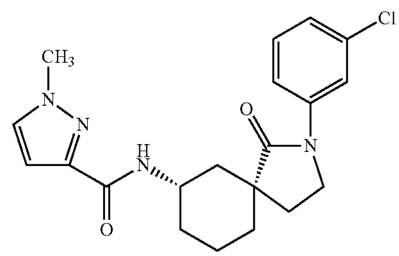 [SMILES: Cn1ccc(C(=O)N[C@H]2CCC[C@]3(CCN(c4cccc(Cl)c4)C3=O)C2)n1] | cis-1-Methyl-1H-pyrazole-3-carboxylic acid [2-(3-chloro-phenyl)-1-oxo-2-aza-spiro[4.5]dec-7-yl]-amide | Method: C<br>RT: 1.21<br>Calcd. Mass: 386<br>m/z (M + H): 387 |
| 15 | 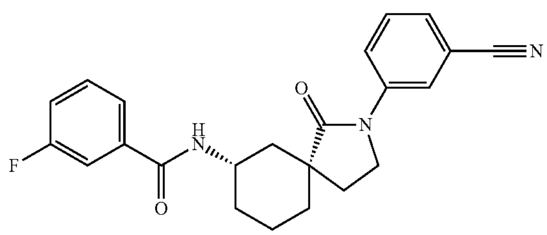 [SMILES: N#Cc1cccc(N2CC[C@]3(CCC[C@H](NC(=O)c4cccc(F)c4)C3)C2=O)c1] | cis-N-[2-(3-Cyano-phenyl)-1-oxo-2-aza-spiro[4.5]dec-7-yl]-3-fluoro-benzamide | Method: C<br>RT: 1.30<br>Calcd. Mass: 391<br>m/z (M + H): 392 |
| 16 | 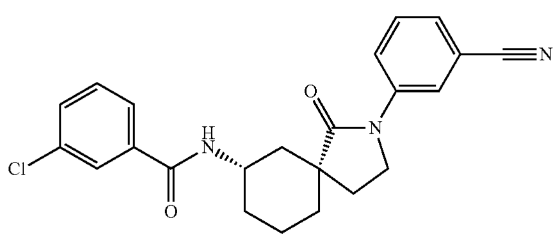 [SMILES: N#Cc1cccc(N2CC[C@]3(CCC[C@H](NC(=O)c4cccc(Cl)c4)C3)C2=O)c1] | cis-N-[2-(3-Cyano-phenyl)-1-oxo-2-aza-spiro[4.5]dec-7-yl]-3-chloro-benzamide | Method: C<br>RT: 1.40<br>Calcd. Mass: 407<br>m/z (M + H): 408 |
| 17 | 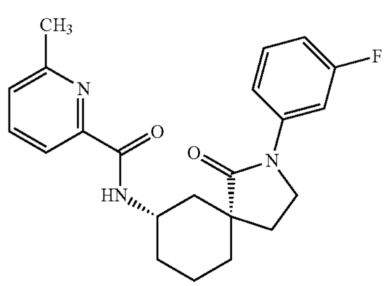 [SMILES: Cc1cccc(C(=O)N[C@H]2CCC[C@]3(CCN(c4cccc(F)c4)C3=O)C2)n1] | cis-6-Methyl-pyridine-2-carboxylic acid [2-(3-fluoro-phenyl)-1-oxo-2-aza-spiro[4.5]dec-7-yl]-amide | Method: B<br>RT: 1.00<br>Calcd. Mass: 381<br>m/z (M + H): 382 |

TABLE 1-continued

Spirolactam derivatives

| Example No | STRUCTURE | CHEMICAL NAME | LC-MS |
|---|---|---|---|
| 18 | 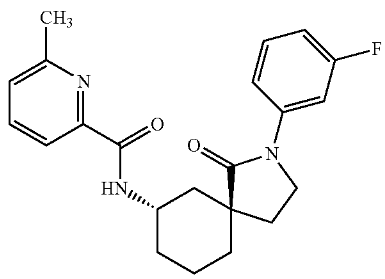 [SMILES: Cc1cccc(C(=O)N[C@H]2CCC[C@@]3(CCN(c4cccc(F)c4)C3=O)C2)n1] | trans-6-Methyl-pyridine-2-carboxylic acid [2-(3-fluoro-phenyl)-1-oxo-2-aza-spiro [4.5]dec-7-yl]-amide | Method: B<br>RT: 1.10<br>Calcd. Mass: 381<br>m/z (M + H): 382 |
| 19 | 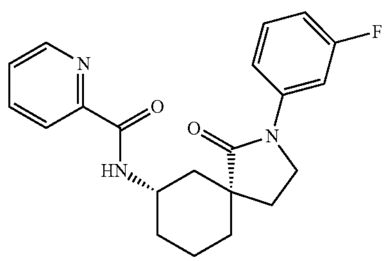 [SMILES: O=C(N[C@H]1CCC[C@]2(CCN(c3cccc(F)c3)C2=O)C1)c1ccccn1] | cis-Pyridine-2-carboxylic acid [2-(3-fluoro-phenyl)-1-oxo-2-aza-spiro[4.5]dec-7-yl]-amide | Method: B<br>RT: 0.82<br>Calcd. Mass: 367<br>m/z (M + H): 368 |
| 20 | 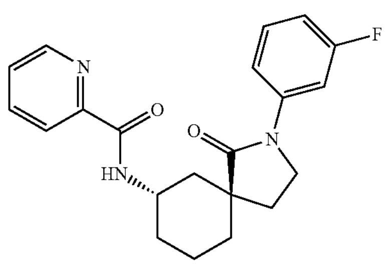 [SMILES: O=C(N[C@H]1CCC[C@@]2(CCN(c3cccc(F)c3)C2=O)C1)c1ccccn1] | trans-Pyridine-2-carboxylic acid [2-(3-fluoro-phenyl)-1-oxo-2-aza-spiro [4.5]dec-7-yl]amide | Method: B<br>RT: 0.95<br>Calcd. Mass: 367<br>m/z (M + H): 368 |
| 21 | 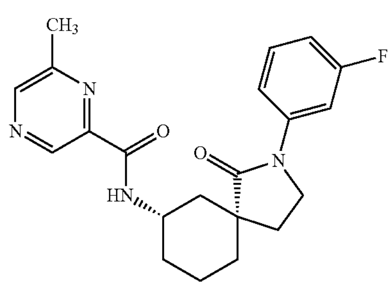 [SMILES: Cc1cncc(C(=O)N[C@H]2CCC[C@]3(CCN(c4cccc(F)c4)C3=O)C2)n1] | cis-6-Methyl-pyrazine-2-carboxylic acid [2-(3-fluoro-phenyl)-1-oxo-2-aza-spiro [4.5]dec-7-yl]-amide | Method: B<br>RT: 0.84<br>Calcd. Mass: 382<br>m/z (M + H): 383 |
| 22 | 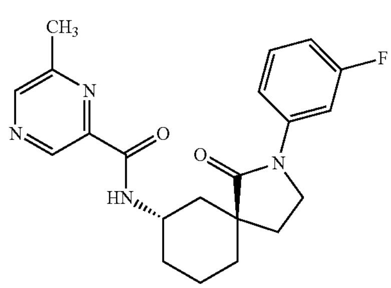 [SMILES: Cc1cncc(C(=O)N[C@H]2CCC[C@@]3(CCN(c4cccc(F)c4)C3=O)C2)n1] | trans-6-Methyl-pyrazine-2-carboxylic acid[2-(3-fluoro-phenyl)-1-oxo-2-aza-spiro [4.5]dec-7-yl]-amide | Method: B<br>RT: 0.89<br>Calcd. Mass: 382<br>m/z (M + H): 383 |

TABLE 1-continued

Spirolactam derivatives

| Example No | STRUCTURE | CHEMICAL NAME | LC-MS |
| --- | --- | --- | --- |
| 23 | 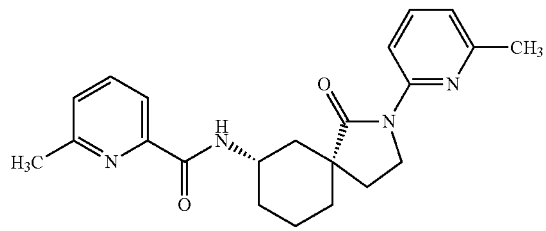 | cis-6-Methyl-pyridine-2-carboxylic acid [2-(6-methyl-pyridin-2-yl)-1-oxo-2-aza-spiro[4.5]dec-7-yl]-amide | Method: C<br>RT: 1.38<br>Calcd. Mass: 378<br>m/z (M + H): 379 |
| 24 | 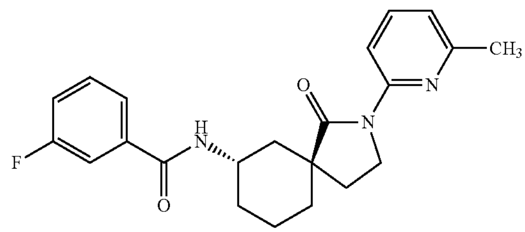 [SMILES: Cc1cccc(N2CC[C@@]3(CCC[C@H](NC(=O)c4cccc(F)c4)C3)C2=O)n1] | trans-3-Fluoro-N-[2-(6-methyl-pyridin-2-yl)-1-oxo-2-aza-spiro[4.5]dec-7-yl]-benzamide | Method: C<br>RT: 1.43<br>Calcd. Mass: 381<br>m/z (M + H): 382 |
| 25 | Chiral | Pyridine-2-carboxylic acid [(5R,7R)-2-(3-fluoro-phenyl)-1-oxo-2-aza-spiro[4.5]dec-7-yl]amide | Method: C<br>RT: 1.30<br>Calcd. Mass: 367<br>m/z (M + H): 368 |
| 26 | 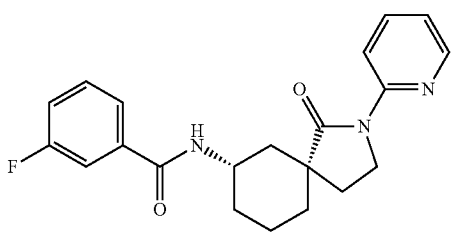 [SMILES: O=C(N[C@H]1CCC[C@]2(CCN(c3ccccn3)C2=O)C1)c1cccc(F)c1] | 3-Fluoro-N-(1-oxo-2-pyridin-2-yl-2-aza-spiro[4.5]dec-7-yl)-benzamide | Method: C<br>RT: 1.26<br>Calcd. Mass: 367<br>m/z (M + H): 368 |
| 27 | 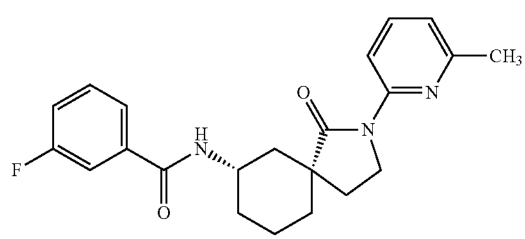 [SMILES: Cc1cccc(N2CC[C@]3(CCC[C@H](NC(=O)c4cccc(F)c4)C3)C2=O)n1] | cis-3-Fluoro-N-[2-(6-methyl-pyridin-2-yl)-1-oxo-2-aza-spiro[4.5]dec-7-yl]-benzamide | Method: C<br>RT: 1.39<br>Calcd. Mass: 381<br>m/z (M + H): 382 |
| 28 | Chiral | 3-Fluoro-N-[(5R,7R)-2-(6-methyl-pyridin-2-yl)-1-oxo-2-aza-spiro[4.5]dec-7-yl]-benzamide | Method: C<br>RT: 1.38<br>Calcd. Mass: 381<br>m/z (M + H): 382 |

TABLE 1-continued

Spirolactam derivatives

| Example No | STRUCTURE | CHEMICAL NAME | LC-MS |
|---|---|---|---|
| 29 | 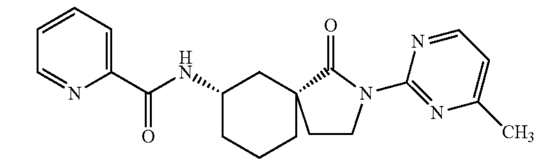 [SMILES: Cc1ccnc(N2CC[C@]3(CCC[C@H](NC(=O)c4ccccn4)C3)C2=O)n1] | cis-Pyridine-2-carboxylic acid [2-(4-methyl-pyrimidin-2-yl)-1-oxo-2-aza-spiro [4.5]dec-7-yl]-amide | Method: A RT: 0.75 Calcd. Mass: 365 m/z (M + H): 366 |
| 30 | 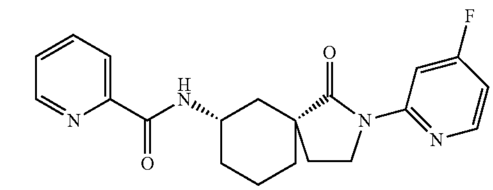 | cis-Pyridine-2-carboxylic acid [2-(4-fluoro-pyridin-2-yl)-1-oxo-2-aza-spiro [4.5]dec-7-yl]amide | Method: A RT: 1.16 Calcd. Mass: 368 m/z (M + H): 369 |
| 31 | 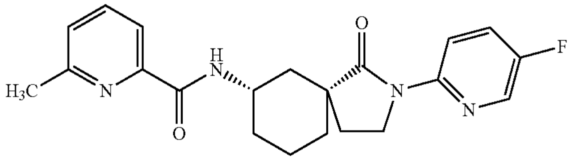 [SMILES: Cc1cccc(C(=O)N[C@H]2CCC[C@]3(CCN(c4ccc(F)cn4)C3=O)C2)n1] | cis-6-Methyl-pyridine-2-carboxylic acid [2-(5-fluoro-pyridin-2-yl)-1-oxo-2-aza-spiro[4.5]dec-7-yl]-amide | Method: A RT: 1.28 Calcd. Mass: 382 m/z (M + H): 383 |
| 32 | 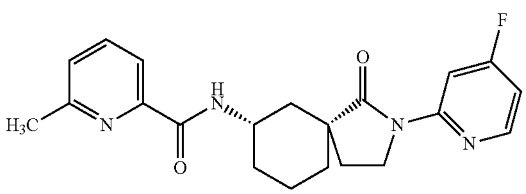 [SMILES: Cc1cccc(C(=O)N[C@H]2CCC[C@]3(CCN(c4cc(F)ccn4)C3=O)C2)n1] | cis-6-Methyl-pyridine-2-carboxylic acid [2-(4-fluoro-pyridin-2-yl)-1-oxo-2-aza-spiro[4.5]dec-7-yl]-amide | Method: A RT: 1.30 Calcd. Mass: 382 m/z (M + H): 383 |
| 33 | 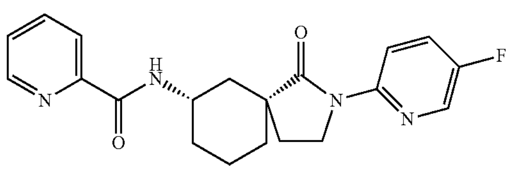 [SMILES: O=C(N[C@H]1CCC[C@]2(CCN(c3ccc(F)cn3)C2=O)C1)c1ccccn1] | cis-Pyridine-2-carboxylic acid [2-(5-fluoro-pyridin-2-yl)-1-oxo-2-aza-spiro [4.5]dec-7-yl]-amide | Method: A RT: 1.15 Calcd. Mass: 368 m/z (M + H): 369 |
| 34 | 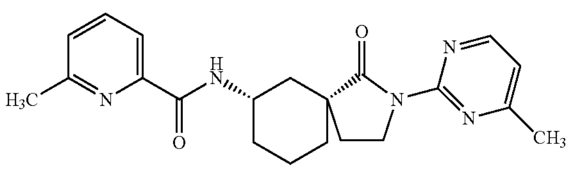 | cis-6-Methyl-pyridine-2-carboxylic acid [2-(4-methyl-pyrimidin-2-yl)-1-oxo-2-aza-spiro[4.5]dec-7-yl]-amide | Method: A RT: 0.88 Calcd. Mass: 379 m/z (M + H): 380 |
| 35 | 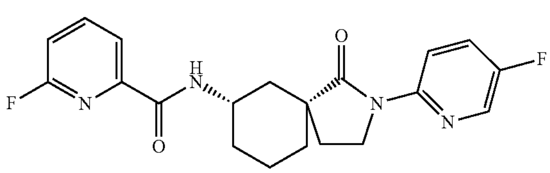 [SMILES: O=C(N[C@H]1CCC[C@]2(CCN(c3ccc(F)cn3)C2=O)C1)c1cccc(F)n1] | cis-3-Fluoro-N-[2-(5-fluoro-pyridin-2-yl)-1-oxo-2-aza-spiro[4.5]dec-7-yl]-benzamide | Method: A RT: 1.28 Calcd. Mass: 385 m/z (M + H): 386 |
| 36 | 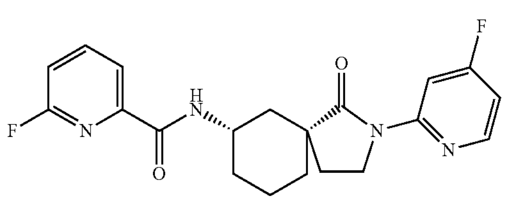 [SMILES: O=C(N[C@H]1CCC[C@]2(CCN(c3cc(F)ccn3)C2=O)C1)c1cccc(F)n1] | cis-3-Fluoro-N-[2-(4-fluoro-pyridin-2-yl)-1-oxo-2-aza-spiro[4.5]dec-7-yl]-benzamide | Method: A RT: 1.28 Calcd. Mass: 385 m/z (m + H): 386 |

TABLE 1-continued

Spirolactam derivatives

| Example No | STRUCTURE | CHEMICAL NAME | LC-MS |
|---|---|---|---|
| 37 | 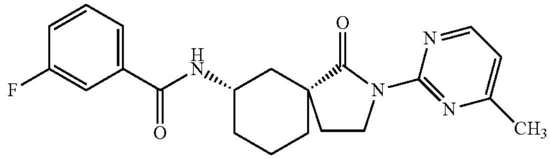 [SMILES: Cc1ccnc(N2CC[C@]3(CCC[C@H](NC(=O)c4cccc(F)c4)C3)C2=O)n1] | cis-3-Fluoro-N-[2-(4-methyl-pyrimidin-2-yl)-1-oxo-2-aza-spiro[4.5]dec-7-yl]-benzamide | Method: A<br>RT: 0.92<br>Calcd. Mass: 382<br>m/z (M + H): 383 |
| 38 | 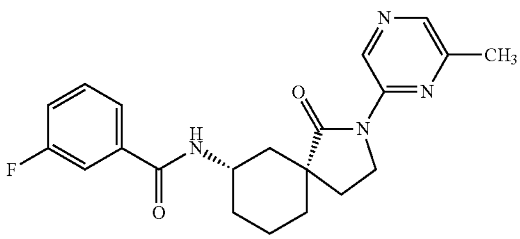 [SMILES: Cc1cncc(N2CC[C@]3(CCC[C@H](NC(=O)c4cccc(F)c4)C3)C2=O)n1] | cis-3-Fluoro-N-[2-(6-methyl-pyrazin-2-yl)-1-oxo-2-aza-spiro[4.5]dec-7-yl]-benzamide | Method: C<br>RT: 1.25<br>Calcd. Mass: 382<br>m/z (M + H): 383 |
| 39 | 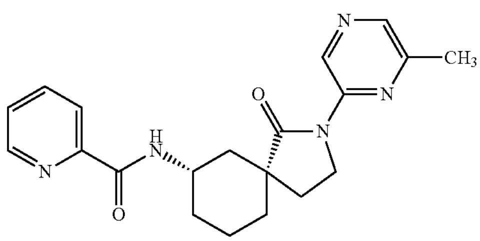 [SMILES: Cc1cncc(N2CC[C@]3(CCC[C@H](NC(=O)c4ccccn4)C3)C2=O)n1] | cis-Pyridine-2-carboxylic acid [2-(6-methyl-pyrazin-2-yl)-1-oxo-2-aza-spiro [4.5]dec-7-yl]-amide | Method: C<br>RT: 1.10<br>Calcd. Mass: 365<br>m/z (M + H): 366 |
| 40 | 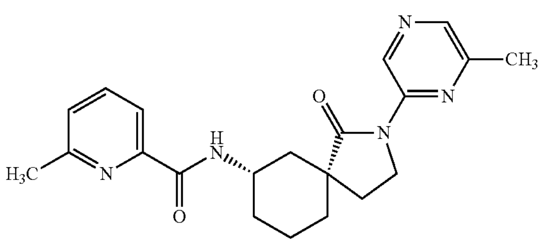 | cis-6-Methyl-pyridine-2-carboxylic acid [2-(6-methyl-pyrazin-2-yl)-1-oxo-2-aza-spiro[4.5]dec-7-yl]-amide | Method: C<br>RT: 1.25<br>Calcd. Mass: 379<br>m/z (M + H): 380 |
| 41 | 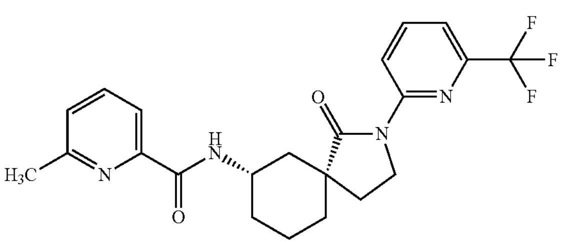 [SMILES: Cc1cccc(C(=O)N[C@H]2CCC[C@]3(CCN(c4cccc(C(F)(F)F)n4)C3=O)C2)n1] | cis-6-Methyl-pyridine-2-carboxylic acid [1-oxo-2-(6-trifluoromethyl-pyridin-2-yl)-2-aza-spiro[4.5]dec-7-yl]-amide | Method: C<br>RT: 1.59<br>Calcd. Mass: 432<br>m/z (M + H): 433 |
| 42 | 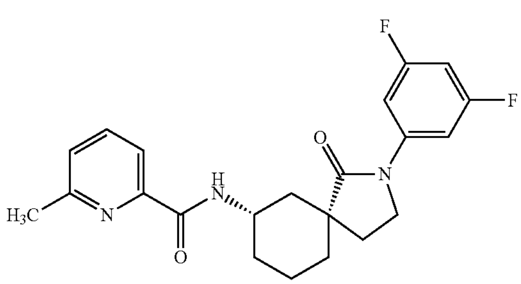 | cis-6-Methyl-pyridine-2-carboxylic acid [2-(3,5-difluoro-phenyl)-1-oxo-2-aza-spiro[4.5]dec-7-yl]-amide | Method: C<br>RT: 1.48<br>Calcd. Mass: 399<br>m/z (M + H): 400 |

TABLE 1-continued

Spirolactam derivatives

| Example No | STRUCTURE | CHEMICAL NAME | LC-MS |
|---|---|---|---|
| 43 | 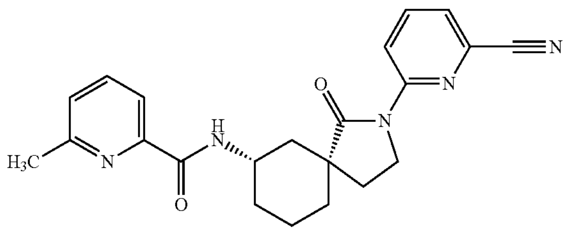 [SMILES: Cc1cccc(C(=O)N[C@H]2CCC[C@]3(CCN(c4cccc(C#N)n4)C3=O)C2)n1] | cis-6-Methyl-pyridine-2-carboxylic acid [2-(6-cyano-pyridin-2-yl)-1-oxo-2-aza-spiro[4.5]dec-7-yl]-amide | Method: C<br>RT: 1.38<br>Calcd. Mass: 389<br>m/z (M + H): 390 |
| 44 | 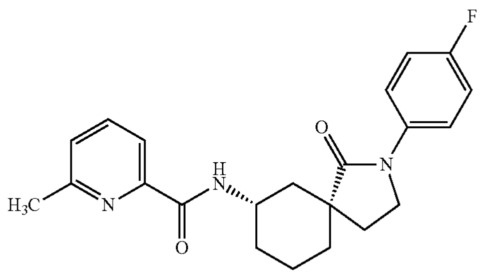 [SMILES: Cc1cccc(C(=O)N[C@H]2CCC[C@]3(CCN(c4ccc(F)cc4)C3=O)C2)n1] | cis-6-Methyl-pyridine-2-carboxylic acid [2-(4-fluoro-phenyl)-1-oxo-2-aza-spiro[4.5]dec-7-yl]-amide | Method: C<br>RT: 1.36<br>Calcd. Mass: 381<br>m/z (M + H): 382 |
| 45 | 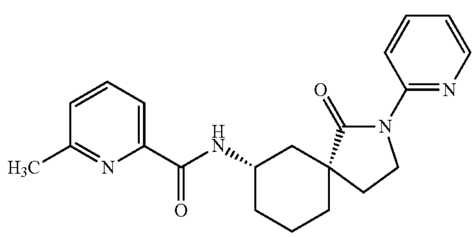 [SMILES: Cc1cccc(C(=O)N[C@H]2CCC[C@]3(CCN(c4ccccn4)C3=O)C2)n1] | 6-Methyl-pyridine-2-carboxylic acid (1-oxo-2-pyridin-2-yl-2-aza-spiro[4.5]dec-7-yl)-amide | Method: C<br>RT: 1.26<br>Calcd. Mass: 364<br>m/z (M + H): 365 |
| 46 | 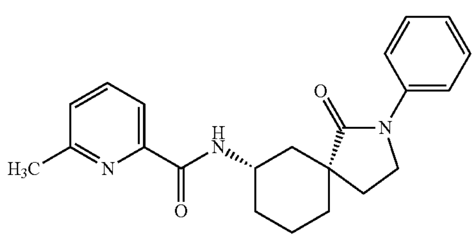 [SMILES: Cc1cccc(C(=O)N[C@H]2CCC[C@]3(CCN(c4ccccc4)C3=O)C2)n1] | cis-6-Methyl-pyridine-2-carboxylic acid (1-oxo-2-phenyl-2-aza-spiro[4.5]dec-7-yl)-amide | Method: C<br>RT: 1.32<br>Calcd. Mass: 363<br>m/z (M + H): 364 |
| 47 | 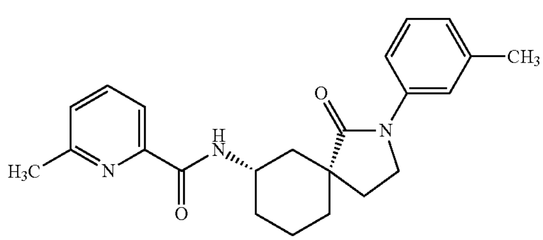 | cis-6-Methyl-pyridine-2-carboxylic acid (1-oxo-2-m-tolyl-2-aza-spiro[4.5]dec-7-yl)-amide | Method: C<br>RT: 1.41<br>Calcd. Mass: 377<br>m/z (M + H): 378 |
| 48 | 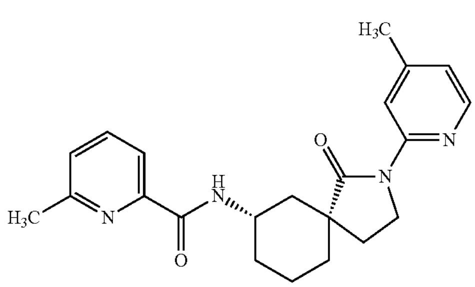 [SMILES: Cc1ccnc(N2CC[C@]3(CCC[C@H](NC(=O)c4cccc(C)n4)C3)C2=O)c1] | cis-6-Methyl-pyridine-2-carboxylic acid [2-(4-methyl-pyridin-2-yl)-1-oxo-2-aza-spiro[4.5]dec-7-yl]-amide | Method: C<br>RT: 1.33<br>Calcd. Mass: 378<br>m/z (M + H): 379 |

TABLE 1-continued

Spirolactam derivatives

| Example No | STRUCTURE | CHEMICAL NAME | LC-MS |
|---|---|---|---|
| 49 | 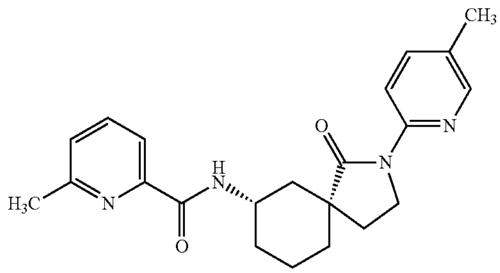 | cis-6-Methyl-pyridine-2-carboxylic acid [2-(5-methyl-pyridin-2-yl)-1-oxo-2-aza-spiro[4.5]dec-7-yl]-amide | Method: C RT: 1.33 Calcd. Mass: 378 m/z (M + H): 379 |
| 50 | 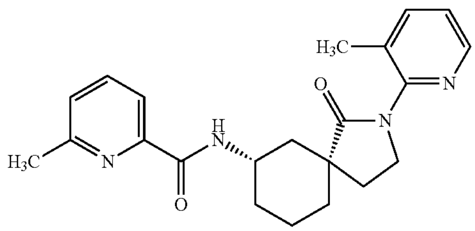 [SMILES: Cc1cccc(C(=O)N[C@H]2CCC[C@]3(CCN(c4ncccc4C)C3=O)C2)n1] | cis-6-Methyl-pyridine-2-carboxylic acid [2-(3-methyl-pyridin-2-yl)-1-oxo-2-aza-spiro[4.5]dec-7-yl]-amide | Method: C RT: 1.10 Calcd. Mass: 378 m/z (M + H): 379 |
| 51 | 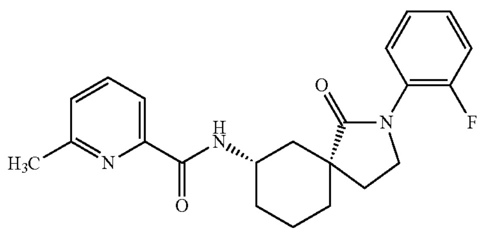 [SMILES: Cc1cccc(C(=O)N[C@H]2CCC[C@]3(CCN(c4ccccc4F)C3=O)C2)n1] | cis-6-Methyl-pyridine-2-carboxylic acid [2-(2-fluoro-phenyl)-1-oxo-2-aza-spiro[4.5]dec-7-yl]-amide | Method: C RT: 1.27 Calcd. Mass: 381 m/z (M + H): 382 |
| 52 | 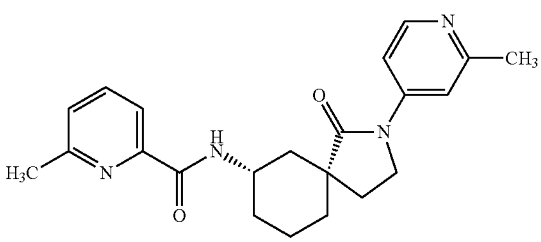 | cis-6-Methyl-pyridine-2-carboxylic acid [2-(2-methyl-pyridin-4-yl)-1-oxo-2-aza-spiro[4.5]dec-7-yl]-amide | Method: C RT: 1.15 Calcd. Mass: 378 m/z (M + H): 379 |
| 53 | 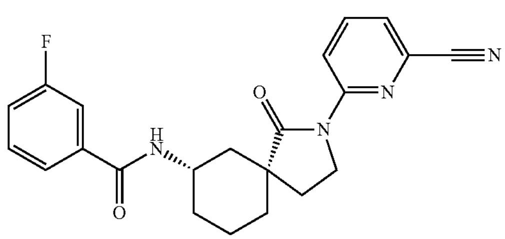 [SMILES: N#Cc1cccc(N2CC[C@]3(CCC[C@H](NC(=O)c4cccc(F)c4)C3)C2=O)n1] | cis-N-[2-(6-Cyano-pyridin-2-yl)-1-oxo-2-aza-spiro[4.5]dec-7-yl]-3-fluoro-benzamide | Method: C RT: 1.34 Calcd. Mass: 392 m/z (M + H): 393 |
| 54 | 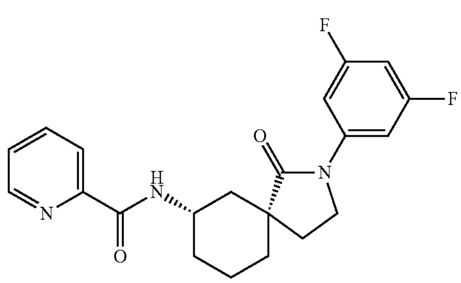 [SMILES: O=C(N[C@H]1CCC[C@]2(CCN(c3cc(F)cc(F)c3)C2=O)C1)c1ccccn1] | cis-Pyridine-2-carboxylic acid [2-(3,5-difluoro-phenyl)-1-oxo-2-aza-spiro [4.5]dec-7-yl] amide | Method: C RT: 1.39 Calcd. Mass: 385 m/z (M + H): 386 |

TABLE 1-continued

Spirolactam derivatives

| Example No | STRUCTURE | CHEMICAL NAME | LC-MS |
|---|---|---|---|
| 55 | 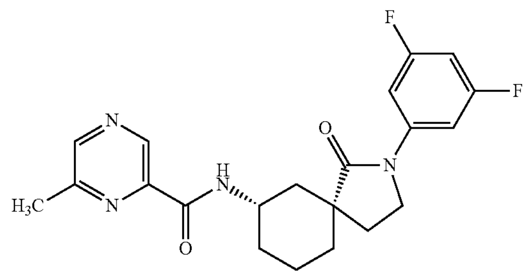 | cis-6-Methyl-pyrazine-2-carboxylic acid [2-(3,5-difluoro-phenyl)-1-oxo-2-aza-spiro [4.5]dec-7-yl]-amide | Method: C<br>RT: 1.34<br>Calcd. Mass: 400<br>m/z (M + H): 401 |
| 56 | 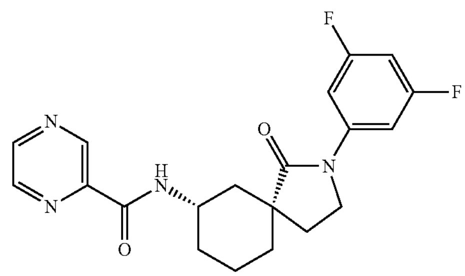 [SMILES: O=C(N[C@H]1CCC[C@]2(CCN(c3cc(F)cc(F)c3)C2=O)C1)c1cnccn1] | cis-Pyrazine-2-carboxylic acid [2-(3,5-difluoro-phenyl)-1-oxo-2-aza-spiro [4.5]dec-7-yl]-amide | Method: C<br>RT: 1.26<br>Calcd. Mass: 386<br>m/z (M + H): 387 |
| 57 | 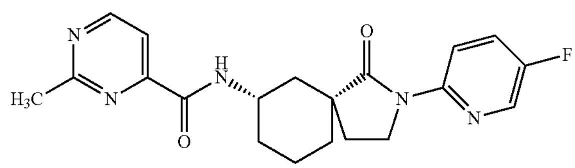 [SMILES: Cc1nccc(C(=O)N[C@H]2CCC[C@]3(CCN(c4ccc(F)cn4)C3=O)C2)n1] | cis-2-Methyl-pyrimidine-4-carboxylic acid [2-(5-fluoro-pyridin-2-yl)-1-oxo-2-aza-spiro [4.5]dec-7-yl]amide | Method: A<br>RT: 1.04<br>Calcd. Mass: 383<br>m/z (M + H): 384 |
| 58 | 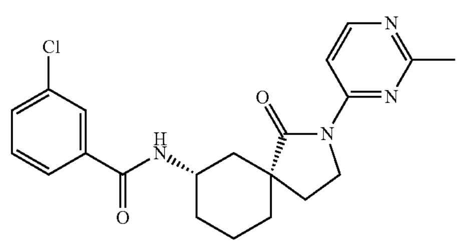 [SMILES: Cc1nccc(N2CC[C@]3(CCC[C@H](NC(=O)c4cccc(Cl)c4)C3)C2=O)n1] | cis-3-Chloro-N-2-(2-methyl-pyrimidin-4-yl)-1-oxo-2-aza-spiro[4.5]dec-7-yl]benzamide | Method: C<br>RT: 1.32<br>Calcd. Mass: 398<br>m/z (M + H): 399 |
| 59 | 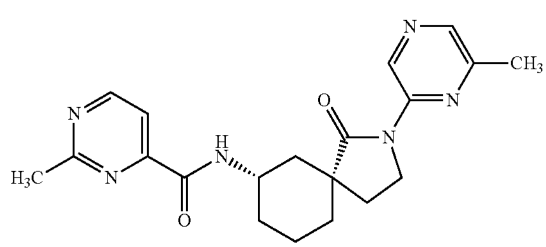 | cis-2-Methyl-pyrimidine-4-carboxylic acid [2-(6-methyl-pyrazin-2-yl)-1-oxo-2-aza-spiro[4.5]dec-7-yl]-amide | Method: C<br>RT: 1.04<br>Calcd. Mass: 380<br>m/z (M + H): 381 |
| 60 | 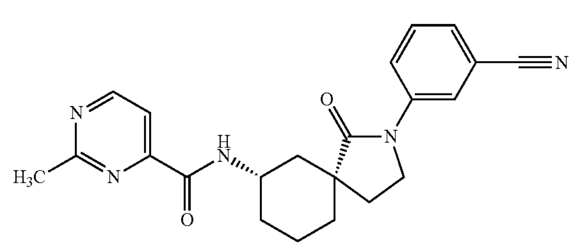 [SMILES: Cc1nccc(C(=O)N[C@H]2CCC[C@]3(CCN(c4cccc(C#N)c4)C3=O)C2)n1] | cis-2-Methyl-pyrimidine-4-carboxylic acid [2-(3-cyano-phenyl)-1-oxo-2-aza-spiro [4.5]dec-7-yl]-amide | Method: C<br>RT: 1.13<br>Calcd. Mass: 389<br>m/z (M + H): 390 |

TABLE 1-continued

Spirolactam derivatives

| Example No | STRUCTURE | CHEMICAL NAME | LC-MS |
|---|---|---|---|
| 61 | 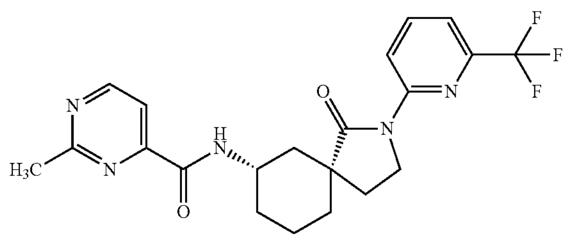 | cis-2-Methyl-pyrimidine-4-carboxylic acid [1-oxo-2-(6-trifluoromethyl-pyridin-2-yl)-2-aza-spiro[4.5]dec-7-yl]-amide | Method: C RT: 1.43 Calcd. Mass: 433 m/z (M + H): 434 |
| 62 | 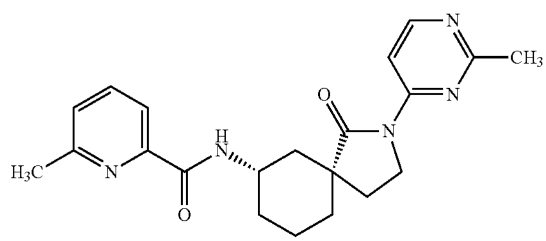 | cis-6-Methyl-pyridine-2-carboxylic acid [2-(2-methyl-pyrimidin-4-yl)-1-oxo-2-aza-spiro[4.5]dec-7-yl]-amide | Method: C RT: 1.21 Calcd. Mass: 379 m/z (M + H): 380 |
| 63 | 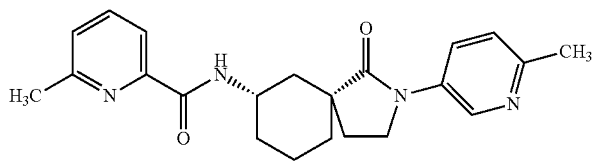 | cis-6-Methyl-pyridine-2-carboxylic acid [2-(6-methyl-pyridin-3-yl)-1-oxo-2-aza-spiro[4.5]dec-7-yl]-amide | Method: A RT: 0.90 Calcd. Mass: 378 m/z (M + H): 379 |
| 64 | 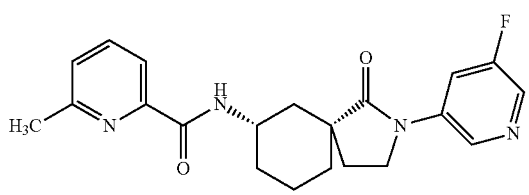 [SMILES: Cc1cccc(C(=O)N[C@H]2CCC[C@]3(CCN(c4cncc(F)c4)C3=O)C2)n1] | cis-6-Methyl-pyridine-2-carboxylic acid [2-(5-fluoro-pyridin-3-yl)-1-oxo-2-aza-spiro[4.5]dec-7-yl]-amide | Method: A RT: 1.04 Calcd. Mass: 382 m/z (M + H): 383 |
| 65 | 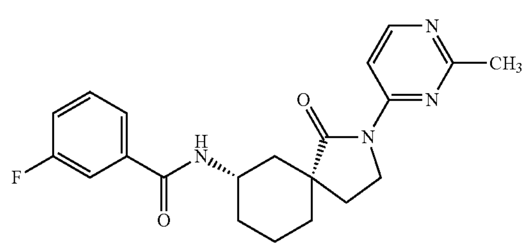 [SMILES: Cc1nccc(N2CC[C@]3(CCC[C@H](NC(=O)c4cccc(F)c4)C3)C2=O)n1] | cis-3-Fluoro-N-[2-(2-methyl-pyrimidin-4-yl)-1-oxo-2-aza-spiro[4.5]dec-7-yl]-benzamide | Method: C RT: 1.21 Calcd. Mass: 382 m/z (M + H): 383 |
| 66 | 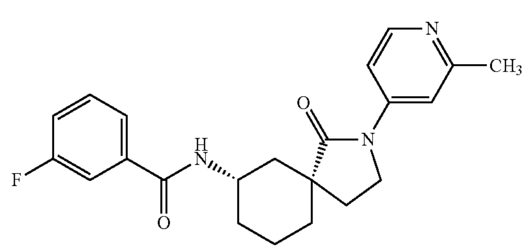 [SMILES: Cc1cc(N2CC[C@]3(CCC[C@H](NC(=O)c4cccc(F)c4)C3)C2=O)ccn1] | cis-3-Fluoro-N-[2-(2-methyl-pyridin-4-yl)-1-oxo-2-aza-spiro[4.5]dec-7-yl]-benzamide | Method: RT: 1.15 Calcd. Mass: 381 m/z (M + H): 382 |

TABLE 1-continued

Spirolactam derivatives

| Example No | STRUCTURE | CHEMICAL NAME | LC-MS |
|---|---|---|---|
| 67 | Chiral | 6-Methyl-pyridine-2-carboxylic acid [(5R,7R)-2-(3,5-difluoro-phenyl)-1-oxo-2-aza-spiro[4.5]dec-7-yl]-amide | Method: C<br>RT: 1.42<br>Calcd. Mass: 399<br>m/z (M + H): 400 |
| 68 | 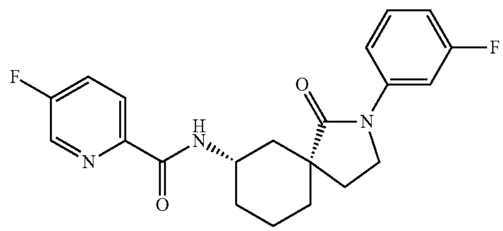 [SMILES: O=C(N[C@H]1CCC[C@]2(CCN(c3cccc(F)c3)C2=O)C1)c1ccc(F)cn1] | cis-5-Fluoro-pyridine-2-carboxylic acid [2-(3-fluoro-phenyl)-1-oxo-2-aza-spiro[4.5]dec-7-yl]-amide | Method: C<br>RT: 1.36<br>Calcd. Mass: 385<br>m/z (M + H): 386 |
| 69 | 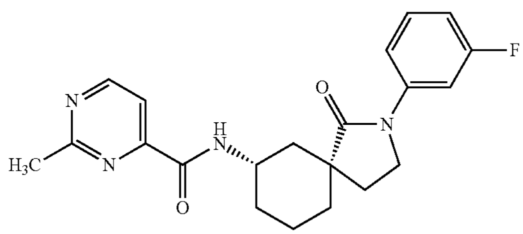 [SMILES: Cc1nccc(C(=O)N[C@H]2CCC[C@]3(CCN(c4cccc(F)c4)C3=O)C2)n1] | cis-2-Methyl-pyrimidine-4-carboxylic acid [2-(3-fluoro-phenyl)-1-oxo-2-aza-spiro[4.5]dec-7-yl]-amide | Method: C<br>RT: 1.23<br>Calcd. Mass: 382<br>m/z (M + H): 383 |
| 70 | 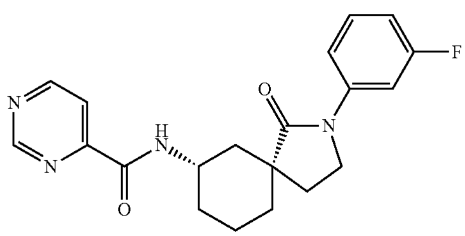 [SMILES: O=C(N[C@H]1CCC[C@]2(CCN(c3cccc(F)c3)C2=O)C1)c1ccncn1] | cis-Pyrimidine-4-carboxylic acid [2-(3-fluoro-phenyl)-1-oxo-2-aza-spiro [4.5]dec-7-yl]-amide | Method: C<br>RT: 1.16<br>Calcd. Mass: 368<br>m/z (M + H): 369 |
| 71 | 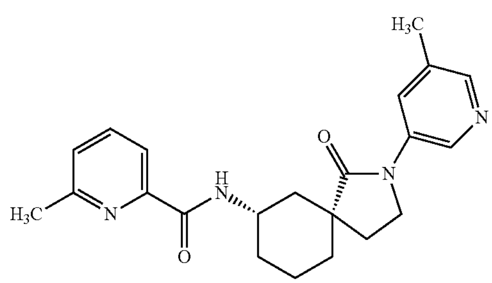 [SMILES: Cc1cncc(N2CC[C@]3(CCC[C@H](NC(=O)c4cccc(C)n4)C3)C2=O)c1] | cis-6-Methyl-pyridine-2-carboxylic acid [2-(5-methyl-pyridin-3-yl)-1-oxo-2-aza-spiro[4.5]dec-7-yl]-amide | Method: C<br>RT: 1.14<br>Calcd. Mass: 378<br>m/z (M + H): 379 |
| 72 | 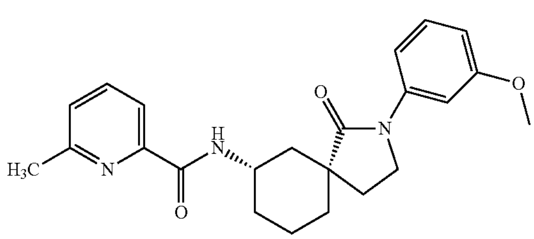 | cis-6-Methyl-pyridine-2-carboxylic acid [2-(3-methoxy-phenyl)-1-oxo-2-aza-spiro[4.5]dec-7-yl]-amide | Method: C<br>RT: 1.34<br>Calcd. Mass: 393<br>m/z (M + H): 394 |

TABLE 1-continued

Spirolactam derivatives

| Example No | STRUCTURE | CHEMICAL NAME | LC-MS |
|---|---|---|---|
| 73 | Chiral | 6-Methyl-pyridine-2-carboxylic acid [(5R,7R)-2-(5-fluoro-pyridin-2-yl)-1-oxo-2-aza-spiro[4.5]dec-7-yl]-amide | Method: A RT: 1.28 Calcd. Mass: 382 m/z (M + H): 383 |
| 74 | 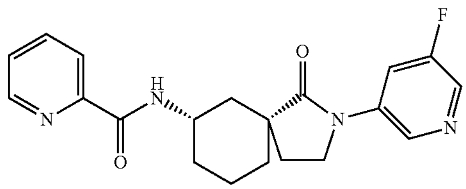 [SMILES: O=C(N[C@H]1CCC[C@]2(CCN(c3cncc(F)c3)C2=O)C1)c1ccccn1] | cis-Pyridine-2-carboxylic acid [2-(5-fluoro-pyridin-3-yl)-1-oxo-2-aza-spiro[4.5]dec-7-yl]-amide | Method: A RT: 0.94 Calcd. Mass: 368 m/z (M + H): 369 |
| 75 | 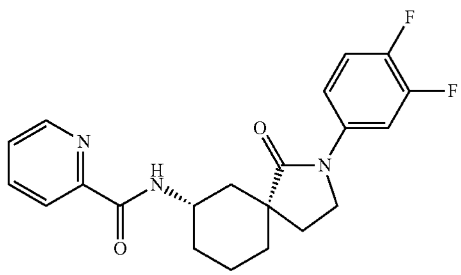 [SMILES: O=C(N[C@H]1CCC[C@]2(CCN(c3ccc(F)c(F)c3)C2=O)C1)c1ccccn1] | cis-Pyridine-2-carboxylic acid [2-(3,4-difluoro-phenyl)-1-oxo-2-aza-spiro[4.5]dec-7-yl]-amide | Method: C RT: 1.33 Calcd. Mass: 385 m/z (M + H): 386 |
| 76 | 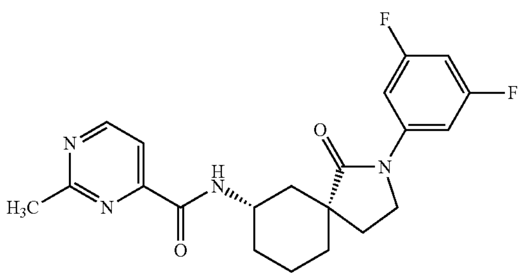 | cis-2-Methyl-pyrimidine-4-carboxylic acid [2-(3,5-difluoro-phenyl)-1-oxo-2-aza-spiro[4.5]dec-7-yl]amide | Method: C RT: 1.31 Calcd. Mass: 400 m/z (M + H): 401 |
| 77 | 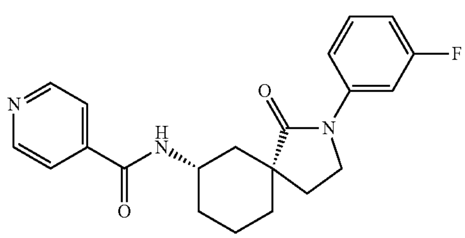 [SMILES: O=C(N[C@H]1CCC[C@]2(CCN(c3cccc(F)c3)C2=O)C1)c1ccncc1] | cis-N-[2-(3-Fluoro-phenyl)-1-oxo-2-aza-spiro[4.5]dec-7-yl]-isonicotinamide | Method: C RT: 1.13 Calcd. Mass: 367 m/z (M + H): 368 |
| 78 | 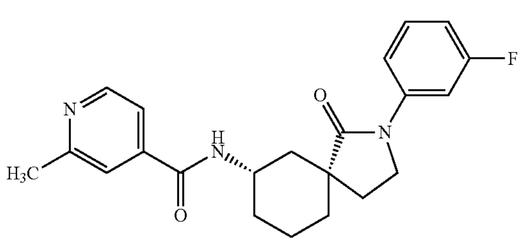 [SMILES: Cc1cc(C(=O)N[C@H]2CCC[C@]3(CCN(c4cccc(F)c4)C3=O)C2)ccn1] | cis-N-[2-(3-Fluoro-phenyl)-1-oxo-2-aza-spiro[4.5]dec-7-yl]-2-methyl isonicotinamide | Method: C RT: 1.19 Calcd. Mass: 381 m/z (M + H): 382 |

TABLE 1-continued

Spirolactam derivatives

| Example No | STRUCTURE | CHEMICAL NAME | LC-MS |
|---|---|---|---|
| 79 | 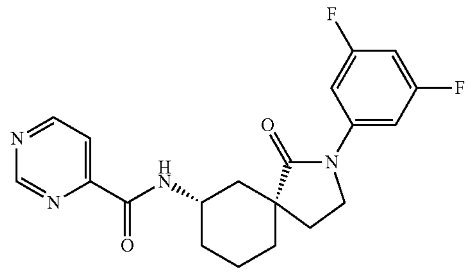 [SMILES: O=C(N[C@H]1CCC[C@]2(CCN(c3cc(F)cc(F)c3)C2=O)C1)c1ccncn1] | cis-Pyrimidine-4-carboxylic acid [2-(3,5-difluoro-phenyl)-1-oxo-2-azaspiro[4.5]dec-7-yl]-amide | Method: C RT: 1.24 Calcd. Mass: 386 m/z (M + H): 387 |
| 80 | 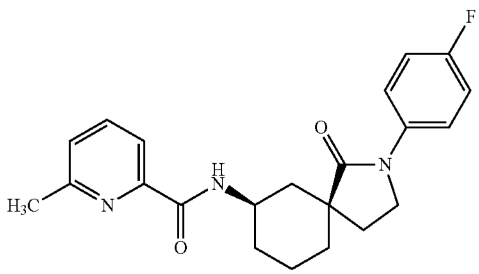 | 6-Methyl-pyridine-2-carboxylic acid [(5R,7R)-2-(4-fluoro-phenyl)-1-oxo-2-aza-spiro[4.5]dec-7-yl]-amide | Method: C RT: 1.34 Calcd. Mass: 381 m/z (M + H): 382 |
| 81 | 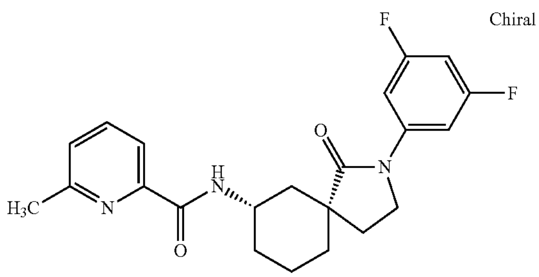 [SMILES: Cc1cccc(C(=O)N[C@H]2CCC[C@]3(CCN(c4cc(F)cc(F)c4)C3=O)C2)n1] | 6-Methyl-pyridine-2-carboxylic acid [(5S,7S)-2-(3,5-difluoro-phenyl)-1-oxo-2-aza-spiro[4.5]dec-7-yl]-amide | Method: C RT: 1.46 Calcd. Mass: 399 m/z (M + H): 400 |
| 82 | 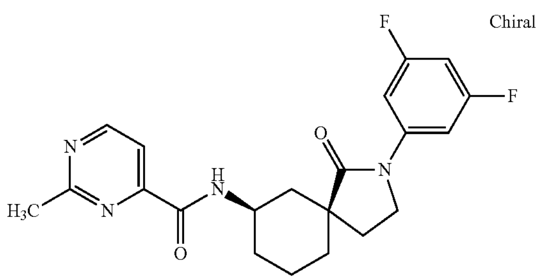 [SMILES: Cc1nccc(C(=O)N[C@@H]2CCC[C@@]3(CCN(c4cc(F)cc(F)c4)C3=O)C2)n1] | 2-Methyl-pyrimidine-4-carboxylic acid [(5R,7R)-2-(3,5-difluoro-phenyl)-1-oxo-2-aza-spiro[4.5]dec-7-yl]-amide | Method: C RT: 1.30 Calcd. Mass: 400 m/z (M + H): 401 |
| 83 | 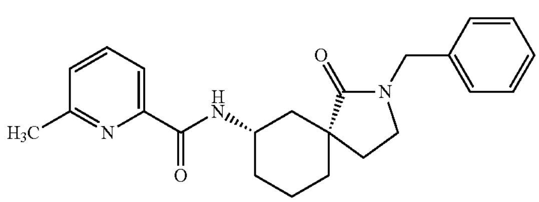 [SMILES: Cc1cccc(C(=O)N[C@H]2CCC[C@]3(CCN(Cc4ccccc4)C3=O)C2)n1] | cis-6-Methyl-pyridine-2-carboxylic acid (2-benzyl-1-oxo-2-aza-spiro[4.5]dec-7-yl)-amide | Method: C RT: 1.29 Calcd. Mass: 377 m/z (M + H): 378 |
| 84 | 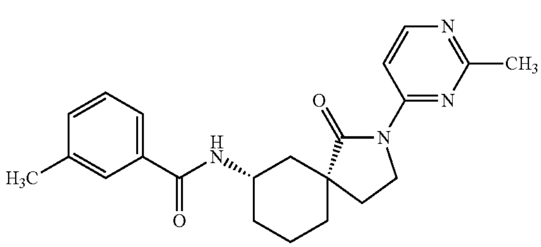 | cis-3-Methyl-N-[2-(2-methyl-pyrimidin-4-yl)-1-oxo-2-aza-spiro[4.5]dec-7-yl]-benzamide | Method: C RT: 1.24 Calcd. Mass: 378 m/z (M + H): 379 |

TABLE 1-continued

Spirolactam derivatives

| Example No | STRUCTURE | CHEMICAL NAME | LC-MS |
|---|---|---|---|
| 85 | 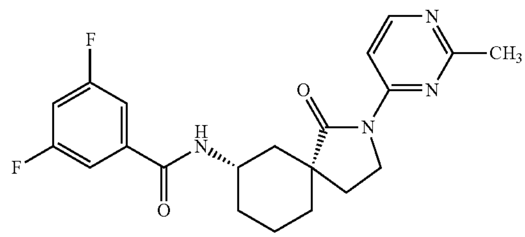 [SMILES: Cc1nccc(N2CC[C@]3(CCC[C@H](NC(=O)c4cc(F)cc(F)c4)C3)C2=O)n1] | cis-3,5-Difluoro-N-[2-(2-methyl-pyrimidin-4-yl)-1-oxo-2-aza-spiro[4.5]dec-7-yl]-benzamide | Method: C RT: 1.29 Calcd. Mass: 400 m/z (M + H): 401 |
| 86 | 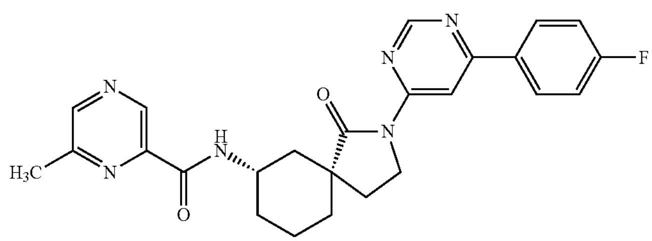 [SMILES: Cc1cncc(C(=O)N[C@H]2CCC[C@]3(CCN(c4cc(-c5ccc(F)cc5)ncn4)C3=O)C2)n1] | cis-6-Methyl-pyrazine-2-carboxylic acid {2-[6-(4-fluoro-phenyl)-pyrimidin-4-yl]-1-oxo-2-aza-spiro[4.5]dec-7-yl}-amide | Method: A RT: 1.31 Calcd. Mass: 460 m/z (M + H): 461 |
| 87 | 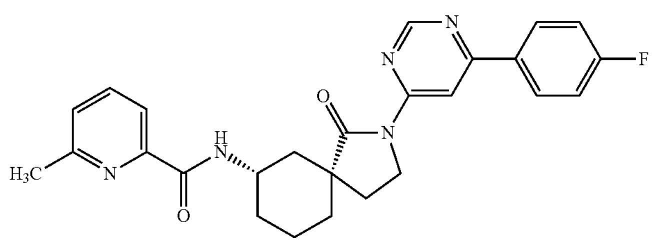 | cis-6-Methyl-pyridine-2-carboxylic acid {2-[6-(4-fluoro-phenyl)-pyrimidin-4-yl]-1-oxo-2-aza-spiro[4.5]dec-7-yl}-amide | Method: A RT: 1.54 Calcd. Mass: 459 m/z (M + H): 460 |
| 88 | 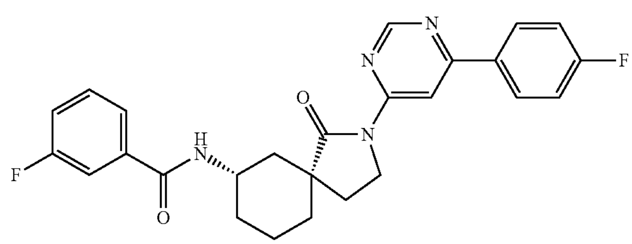 [SMILES: O=C(N[C@H]1CCC[C@]2(CCN(c3cc(-c4ccc(F)cc4)ncn3)C2=O)C1)c1cccc(F)c1] | cis-3-Fluoro-N-{2-[6-(4-fluoro-phenyl)-pyrimidin-4-yl]-1-oxo-2-aza-spiro[4.5]dec-7-yl}-benzamide | Method: A RT: 1.52 Calcd. Mass: 462 m/z (M + H): 463 |
| 89 | 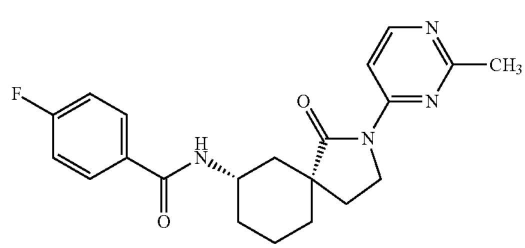 [SMILES: Cc1nccc(N2CC[C@]3(CCC[C@H](NC(=O)c4ccc(F)cc4)C3)C2=O)n1] | cis-4-Fluoro-N-[2-(2-methyl-pyrimidin-4-yl)-1-oxo-2-aza-spiro[4.5]dec-7-yl]-benzamide | Method: C RT: 1.20 Calcd. Mass: 382 m/z (M + H): 383 |
| 90 | 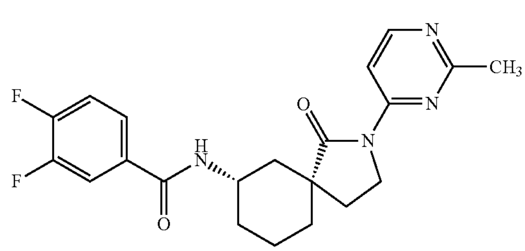 [SMILES: Cc1nccc(N2CC[C@]3(CCC[C@H](NC(=O)c4ccc(F)c(F)c4)C3)C2=O)n1] | cis-3,4-Difluoro-N-[2-(2-methyl-pyrimidin-4-yl)-1-oxo-2-aza-spiro[4.5]dec-7-yl]-benzamide | Method: C RT: 1.25 Calcd. Mass: 400 m/z (M + H): 401 |

TABLE 1-continued

Spirolactam derivatives

| Example No | STRUCTURE | CHEMICAL NAME | LC-MS |
|---|---|---|---|
| 91 | 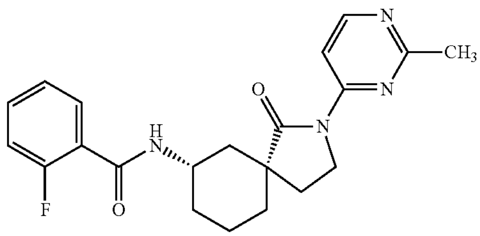 [SMILES: Cc1nccc(N2CC[C@]3(CCC[C@H](NC(=O)c4ccccc4F)C3)C2=O)n1] | cis-2-Fluoro-N-[2-(2-methyl-pyrimidin-4-yl)-1-oxo-2-aza-spiro[4.5]dec-7-yl]-benzamide | Method: C<br>RT: 1.18<br>Calcd. Mass: 382<br>m/z (M + H): 383 |
| 92 | 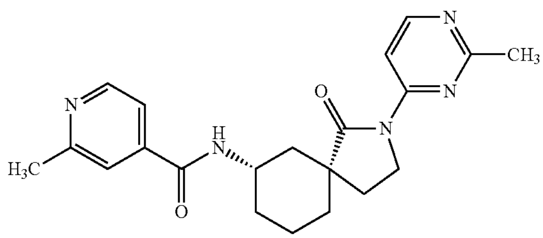 | cis-2-Methyl-N-[2-(2-methyl-pyrimidin-4-yl)-1-oxo-2-aza-spiro[4.5]dec-7-yl]-isonicotinamide | Method: C<br>RT: 0.99<br>Calcd. Mass: 379<br>m/z (M + H): 380 |
| 93 | 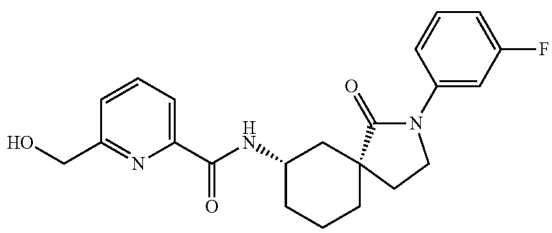 [SMILES: O=C(N[C@H]1CCC[C@]2(CCN(c3cccc(F)c3)C2=O)C1)c1cccc(CO)n1] | cis-6-Hydroxymethyl-pyridine-2-carboxylic acid [2-(3-fluoro-phenyl)-1-oxo-2-aza-spiro[4.5]dec-7-yl]-amide | Method: C<br>RT: 1.14<br>Calcd. Mass: 397<br>m/z (M + H): 398 |
| 94 | 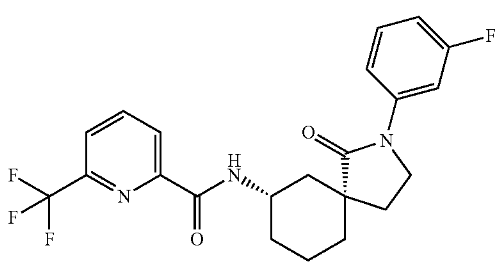 [SMILES: O=C(N[C@H]1CCC[C@]2(CCN(c3cccc(F)c3)C2=O)C1)c1cccc(C(F)(F)F)n1] | cis-6-Trifluoromethyl-pyridine-2-carboxylic acid [2-(3-fluoro-phenyl)-1-oxo-2-aza-spiro[4.5]dec-7-yl]-amide | Method : C<br>RT: 1.51<br>Calcd. Mass: 435<br>m/z (M + H): 436 |
| 95 | Chiral | N-[(5R,7R)-2-(3-Fluoro-phenyl)-1-oxo-2-aza-spiro[4.5]dec-7-yl]-2-methyl-isonicotinamide | Method: C<br>RT: 1.19<br>Calcd. Mass: 381<br>m/z (M + H): 382 |
| 96 | 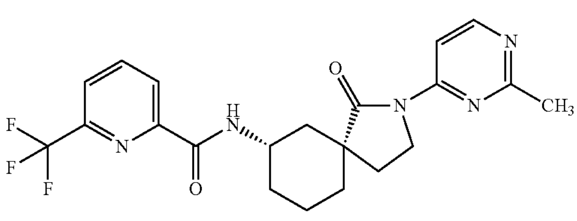 [SMILES: Cc1nccc(N2CC[C@]3(CCC[C@H](NC(=O)c4cccc(C(F)(F)F)n4)C3)C2=O)n1] | cis-6-Trifluoromethyl-pyridine-2-carboxylic acid [2-(2-methyl-pyrimidin-4-yl)-1-oxo-2-aza-spiro [4.5]dec-7-yl]-amide | Method: C<br>RT: 1.35<br>Calcd. Mass: 433<br>m/z (M + H): 434 |

TABLE 1-continued

Spirolactam derivatives

| Example No | STRUCTURE | CHEMICAL NAME | LC-MS |
|---|---|---|---|
| 97 | 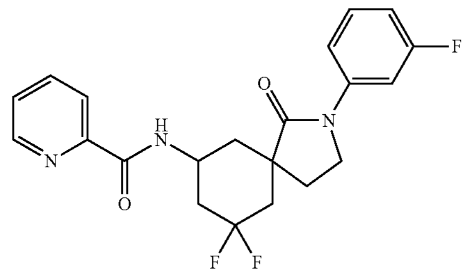 [SMILES: O=C(NC1CC(F)(F)CC2(CCN(c3cccc(F)c3)C2=O)C1)c1ccccn1] | Pyridine-2-carboxylic acid [9,9-difluoro-2-(3-fluoro-phenyl)-1-oxo-2-aza-spiro[4.5]dec-7-yl]-amide | Method: A<br>RT: 1.27<br>Calcd. Mass: 403<br>m/z (M + H): 404 |
| 98 | Chiral | Pyridine-2-carboxylic acid [(5R,7S)-9,9-difluoro-2-(3-fluoro-phenyl)-1-oxo-2-aza-spiro[4.5]dec-7-yl]-amide (the third peak from chiral HPLC, arbitrarily assignment) | Method: C<br>RT: 1.34<br>Calcd. Mass: 403<br>m/z (M + H): 404 |
| 99 | Chiral | Pyridine-2-carboxylic acid [(5S,7R)-9,9-difluoro-2-(3-fluoro-phenyl)-1-oxo-2-aza-spiro[4.5]dec-7-yl]-amide (the first peak from chiral HPLC, arbitrarily assignment) | Method: C<br>RT: 1.35<br>Calcd. Mass: 403<br>m/z (M + H): 404 |
| 100 | 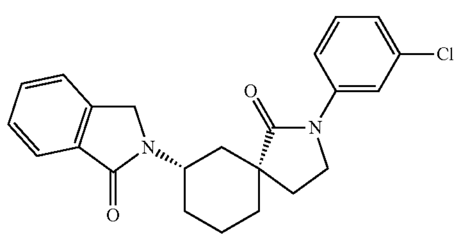 [SMILES: O=C1c2ccccc2CN1[C@H]1CCC[C@]2(CCN(c3cccc(Cl)c3)C2=O)C1] | cis-2-[2-(3-Chloro-phenyl)-1-oxo-2-aza-spiro[4.5]dec-7-yl]-2,3-dihydro-isoindol-1-one (relatively polar spot on TLC, arbitrarily assignment) | Method: C<br>RT: 1.41<br>Calcd. Mass: 394<br>m/z (M + H): 395 |
| 101 | Chiral | Pyridine-2-carboxylic acid [(5R,7R)-9,9-difluoro-2-(3-fluoro-phenyl)-1-oxo-2-aza-spiro[4.5]dec-7-yl]-amide | Method: C<br>RT: 1.37<br>Calcd. Mass: 403<br>m/z (M + H): 404 |

TABLE 1-continued

Spirolactam derivatives

| Example No | STRUCTURE | CHEMICAL NAME | LC-MS |
|---|---|---|---|
| 102 | 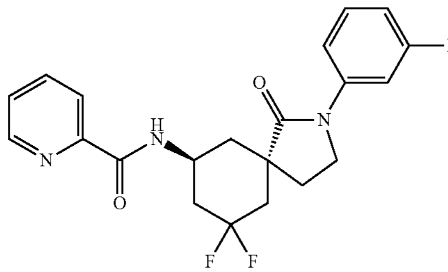 | Pyridine-2-carboxylic acid [(5S,7S)-9,9-difluoro-2-(3-fluoro-phenyl)-1-oxo-2-aza-spiro[4.5]dec-7-yl]-amide | Method: C RT: 1.33 Calcd. Mass: 403 m/z (M + H): 404 |
| 103 | 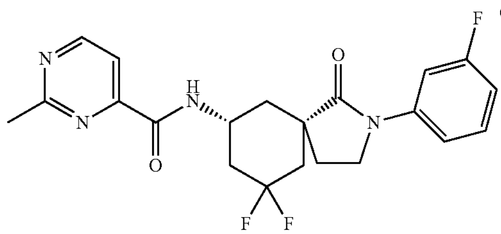 | 2-Methyl-pyrimidine-4-carboxylic acid [(5S,7R)-9,9-difluoro-2-(3-fluoro-phenyl)-1-oxo-2-aza-spiro[4.5]dec-7-yl]-amide | Method: C RT: 1.28 Calcd. Mass: 418 m/z (M + H): 419 |
| 104 | 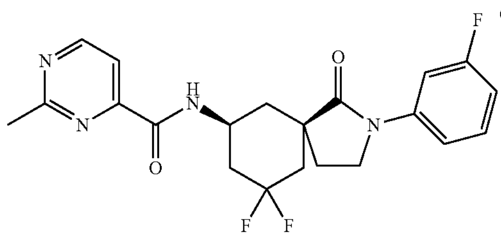 | 2-Methyl-pyrimidine-4-carboxylic acid [(5R,7S)-9,9-difluoro-2-(3-fluoro-phenyl)-1-oxo-2-aza-spiro[4.5]dec-7-yl]-amide | Method: C RT: 1.28 Calcd. Mass: 418 m/z (M + H): 419 |
| 105 | 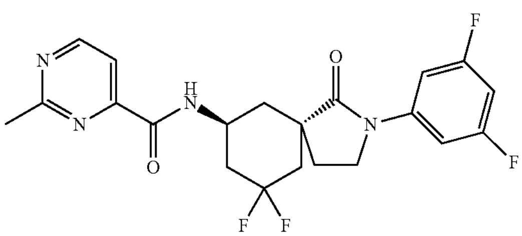 [SMILES: Cc1nccc(C(=O)N[C@@H]2CC(F)(F)C[C@]3(CCN(c4cc(F)cc(F)c4)C3=O)C2)n1] | trans-2-Methyl-pyrimidine-4-carboxylic acid [2-(3,5-difluoro-phenyl)-9,9-difluoro-1-oxo-2-aza-spiro[4.5]dec-7-yl]-amide | Method: C RT: 1.35 Calcd. Mass: 436 m/z (M + H): 437 |
| 106 | 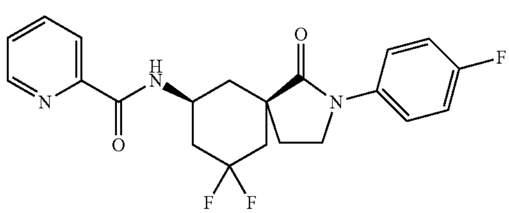 | cis-Pyridine-2-carboxylic acid [9,9-difluoro-2-(4-fluoro-phenyl)-1-oxo-2-aza-spiro[4.5]dec-7-yl]-amide | Method: C RT: 1.3 Calcd. Mass: 403 m/z (M + H): 404 |
| 107 | 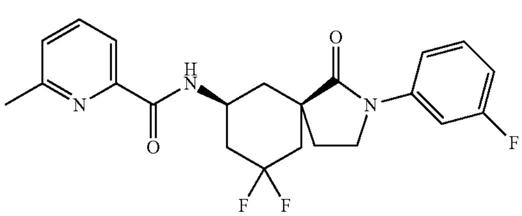 | cis-6-Methyl-pyridine-2-carboxylic acid [9,9-difluoro-2-(3-fluoro-phenyl)-1-oxo-2-aza-spiro[4.5]dec-7-yl]-amide | Method: C RT: 1.45 Calcd. Mass: 437 m/z (M + H): 438 |

TABLE 1-continued

Spirolactam derivatives

| Example No | STRUCTURE | CHEMICAL NAME | LC-MS |
|---|---|---|---|
| 108 | 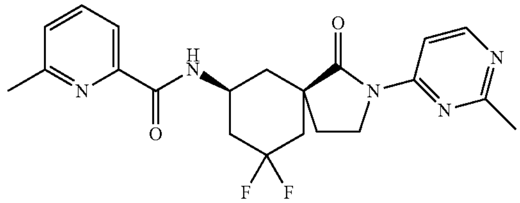 | cis-6-Methyl-pyridine-2-carboxylic acid [9,9-difluoro-2-(2-methyl-pyrimidin-4-yl)-1-oxo-2-aza-spiro[4.5]dec-7-yl]-amide | Method: C<br>RT: 1.28<br>Calcd. Mass: 415<br>m/z (M + H): 416 |
| 109 | 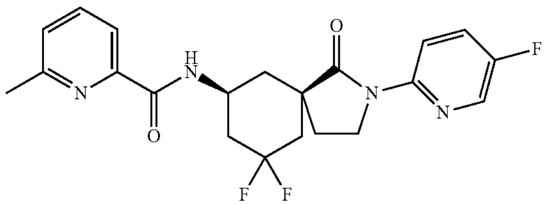 [SMILES: Cc1cccc(C(=O)N[C@@H]2CC(F)(F)C[C@@]3(CCN(c4ccc(F)cn4)C3=O)C2)n1] | cis-6-Methyl-pyridine-2-carboxylic acid [9,9-difluoro-2-(5-fluoro-pyridin-2-yl)-1-oxo-2-aza-spiro[4.5]dec-7-yl]-amide | Method: C<br>RT: 1.4<br>Calcd. Mass: 418<br>m/z (M + H): 419 |
| 110 | 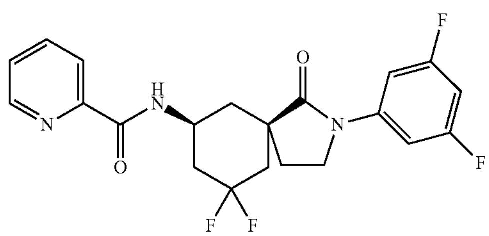 [SMILES: O=C(N[C@@H]1CC(F)(F)C[C@@]2(CCN(c3cc(F)cc(F)c3)C2=O)C1)c1ccccn1] | cis-Pyridine-2-carboxylic acid [2-(3,5-difluoro-phenyl)-9,9-difluoro-1-oxo-2-aza-spiro[4.5]dec-7-yl]-amide | Method: C<br>RT: 1.43<br>Calcd. Mass: 421<br>m/z (M + H): 422 |
| 111 | 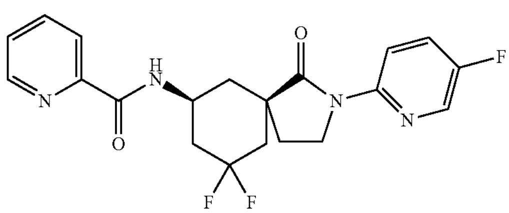 [SMILES: O=C(N[C@@H]1CC(F)(F)C[C@@]2(CCN(c3ccc(F)cn3)C2=O)C1)c1ccccn1] | cis-Pyridine-2-carboxylic acid [9,9-difluoro-2-(5-fluoro-pyridin-2-yl)-1-oxo-2-aza-spiro[4.5]dec-7-yl]-amide | Method: C<br>RT: 1.3<br>Calcd. Mass: 404<br>m/z (M + H): 405 |
| 112 | 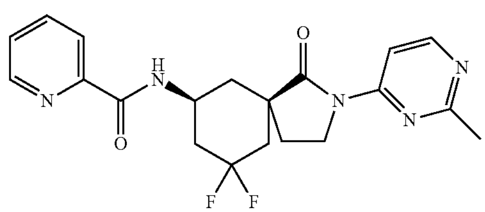 [SMILES: Cc1nccc(N2CC[C@]3(C[C@H](NC(=O)c4ccccn4)CC(F)(F)C3)C2=O)n1] | cis-Pyridine-2-carboxylic acid [9,9-difluoro-2-(2-methyl-pyrimidin-4-yl)-1-oxo-2-aza-spiro[4.5]dec-7-yl]-amide | Method: C<br>RT: 1.18<br>Calcd. Mass: 401<br>m/z (M + H): 402 |
| 113 | 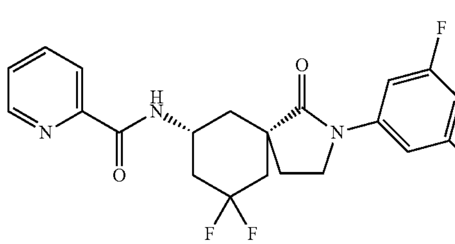 | Pyridine-2-carboxylic acid [(5S,7R)-2-(3,5-difluoro-phenyl)-9,9-difluoro-1-oxo-2-aza-spiro[4.5]dec-7-yl]-amide | Method: A<br>RT: 1.48<br>Calcd. Mass: 421<br>m/z (M + H): 422 |

TABLE 1-continued

Spirolactam derivatives

| Example No | STRUCTURE | CHEMICAL NAME | LC-MS |
|---|---|---|---|
| 114 | 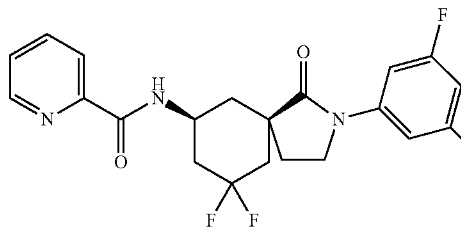 | Pyridine-2-carboxylic acid [(5R,7S)-2-(3,5-difluoro-phenyl)-9,9-difluoro-1-oxo-2-aza-spiro[4.5]dec-7-yl]-amide | Method: A<br>RT: 1.47<br>Calcd. Mass: 421<br>m/z (M + H): 422 |
| 115 | 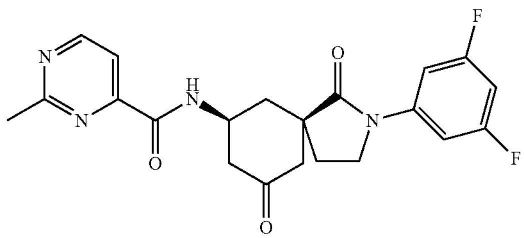 [SMILES: Cc1nccc(C(=O)N[C@@H]2CC(=O)C[C@@]3(CCN(c4cc(F)cc(F)c4)C3=O)C2)n1] | cis-2-Methyl-pyrimidine-4-carboxylic acid [2-(3,5-difluoro-phenyl)-1,9-dioxo-2-aza-spiro[4.5]dec-7-yl]-amide | Method: A<br>RT: 1.11<br>Calcd. Mass: 414<br>m/z (M + H): 415 |
| 116 | 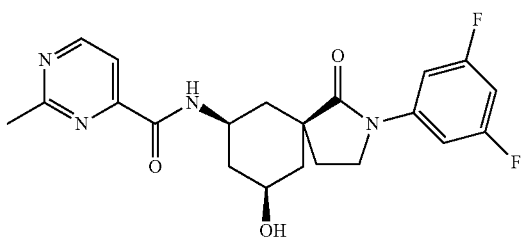 [SMILES: Cc1nccc(C(=O)N[C@@H]2C[C@H](O)C[C@@]3(CCN(c4cc(F)cc(F)c4)C3=O)C2)n1] | cis-2-Methyl-pyrimidine-4-carboxylic acid [2-(3,5-difluoro-phenyl)-9-hydroxy-1-oxo-2-aza-spiro[4.5]dec-7-yl]-amide | Method: A<br>RT: 0.96<br>Calcd. Mass: 416<br>m/z (M + H): 417 |
| 117 | 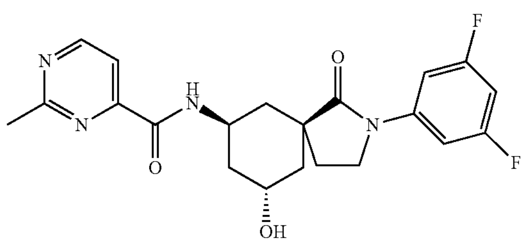 [SMILES: Cc1nccc(C(=O)N[C@@H]2C[C@@H](O)C[C@@]3(CCN(c4cc(F)cc(F)c4)C3=O)C2)n1] | trans-2-Methyl-pyrimidine-4-carboxylic acid [2-(3,5-difluoro-phenyl)-9-hydroxy-1-oxo-2-aza-spiro[4.5]dec-7-yl]-amide | Method: A<br>RT: 1.04<br>Calcd. Mass: 416<br>m/z (M + H): 417 |
| 118 | 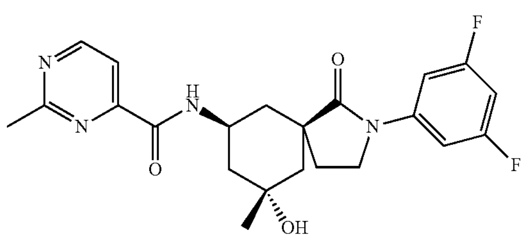 [SMILES: Cc1nccc(C(=O)N[C@@H]2C[C@@](C)(O)C[C@@]3(CCN(c4cc(F)cc(F)c4)C3=O)C2)n1] | 2-Methyl-pyrimidine-4-carboxylic acid difluoro-phenyl)-9-[(5R,7S,9S)-2-(3,5-hydroxy-9-methyl-1-oxo-2-aza-spiro[4.5]dec-7-yl]-amide | Method: A<br>RT: 1.15<br>Calcd. Mass: 430<br>m/z (M + H): 431 |
| 119 | 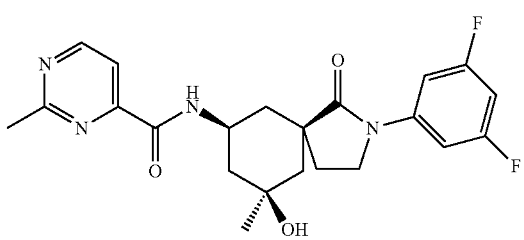 [SMILES: Cc1nccc(C(=O)N[C@@H]2C[C@](C)(O)C[C@@]3(CCN(c4cc(F)cc(F)c4)C3=O)C2)n1] | 2-Methyl-pyrimidine-4-carboxylic acid [(5R,7S,9R)-2-(3,5-difluoro-phenyl)-9-hydroxy-9-methyl-1-oxo-2-aza-spiro[4.5]dec-7-yl]-amide | Method: A<br>RT: 1.02<br>Calcd. Mass: 430<br>m/z (M + H): 431 |

TABLE 1-continued

Spirolactam derivatives

| Example No | STRUCTURE | CHEMICAL NAME | LC-MS |
|---|---|---|---|
| 120 | Chiral | N-[(5S,7R)-9,9-Difluoro-2-(2-methyl-pyrimidin-4-yl)-1-oxo-2-aza-spiro[4.5]dec-7-yl]-3-fluoro-benzamide | Method: C<br>RT: 1.38<br>Calcd. Mass: 418<br>m/z (M + H): 419 |
| 121 | Chiral | N-[(5R,7S)-9,9-Difluoro-2-(2-methyl-pyrimidin-4-yl)-1-oxo-2-aza-spiro[4.5]dec-7-yl]-3-fluoro-benzamide | Method: C<br>RT: 1.38<br>Calcd. Mass: 418<br>m/z (M + H): 419 |
| 122 | 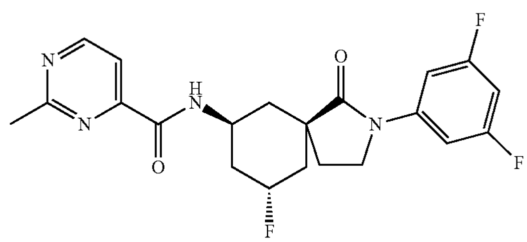 | trans-2-Methyl-pyrimidine-4-carboxylic acid [2-(3,5-difluoro-phenyl)-9-fluoro-1-oxo-2-aza-spiro[4.5]dec-7-yl]-amide | Method: C<br>RT: 1.38<br>Calcd. Mass: 418<br>m/z (M + H): 419 |
| 123 | 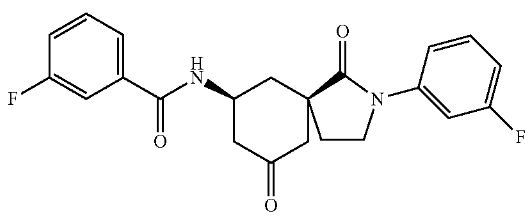 [SMILES: O=C1C[C@@H](NC(=O)c2cccc(F)c2)C[C@]2(CCN(c3cccc(F)c3)C2=O)C1] | cis-3-Fluoro-N-[2-(3-fluoro-phenyl)-1,9-dioxo-2-aza-spiro[4.5]dec-7-yl]-benzamide | Method: C<br>RT: 1.33<br>Calcd. Mass: 398<br>m/z (M + H): 399 |
| 124 | 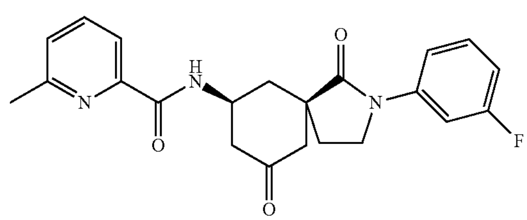 [SMILES: Cc1cccc(C(=O)N[C@@H]2CC(=O)C[C@@]3(CCN(c4cccc(F)c4)C3=O)C2)n1] | cis-6-Methyl-pyridine-2-carboxylic acid [2-(3-fluoro-phenyl)-1,9-dioxo-2-aza-spiro[4.5]dec-7-yl]-amide | Method: C<br>RT: 1.43<br>Calcd. Mass: 395<br>m/z (M + H): 396 |
| 125 | 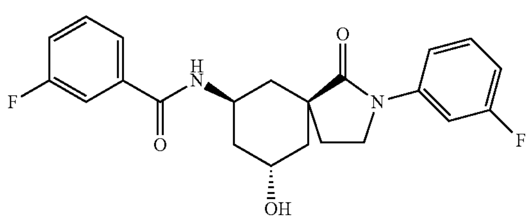 [SMILES: O=C(N[C@@H]1C[C@@H](O)C[C@@]2(CCN(c3cccc(F)c3)C2=O)C1)c1cccc(F)c1] | trans-3-Fluoro-N-[2-(3-fluoro-phenyl)-9-hydroxy-1-oxo-2-aza-spiro[4.5]dec-7-yl]-benzamide | Method: A<br>RT: 1.18<br>Calcd. Mass: 400<br>m/z (M + H): 401 |

TABLE 1-continued

Spirolactam derivatives

| Example No | STRUCTURE | CHEMICAL NAME | LC-MS |
|---|---|---|---|
| 126 | 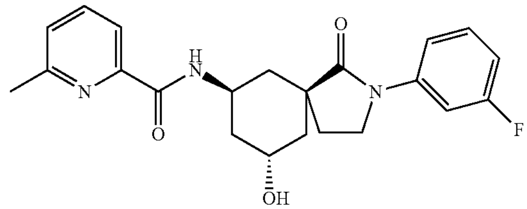 [SMILES: Cc1cccc(C(=O)N[C@@H]2C[C@@H](O)C[C@@]3(CCN(c4cccc(F)c4)C3=O)C2)n1] | trans-6-Methyl-pyridine-2-carboxylic acid [2-(3-fluoro-phenyl)-9-hydroxy-1-oxo-2-aza-spiro[4.5]dec-7-yl]-amide | Method: C<br>RT: 1.27<br>Calcd. Mass: 397<br>m/z (M + H): 398 |
| 127 | Chiral | 6-Methyl-pyridine-2-carboxylic acid [(5S,7R)-9,9-difluoro-2-(5-fluoro-pyridin-2-yl)-1-oxo-2-aza-spiro[4.5]dec-7-yl]-amide | Method: A<br>RT: 1.43<br>Calcd. Mass: 418<br>m/z (M + H): 419 |
| 128 | 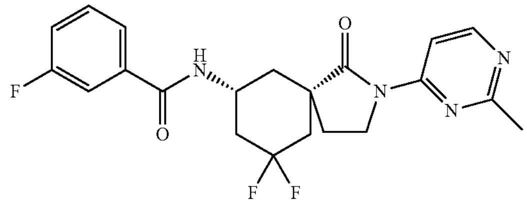 [SMILES: Cc1nccc(N2CC[C@@]3(C[C@@H](NC(=O)c4cccc(F)c4)CC(F)(F)C3)C2=O)n1] | cis-N-[9,9-Difluoro-2-(2-methyl-pyrimidin-4-yl)-1-oxo-2-aza-spiro[4.5]dec-7-yl]-3-fluoro-benzamide | Method: C<br>RT: 1.39<br>Calcd. Mass: 418<br>m/z (M + H): 419 |
| 129 | 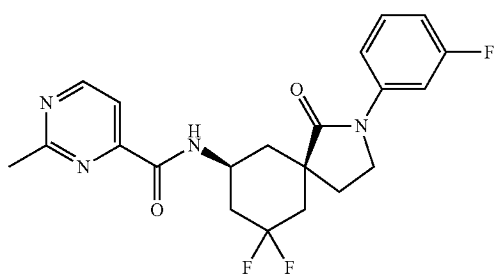 [SMILES: Cc1nccc(C(=O)N[C@@H]2CC(F)(F)C[C@@]3(CCN(c4cccc(F)c4)C3=O)C2)n1] | cis-2-Methyl-pyrimidine-4-carboxylic acid [9,9-difluoro-2-(3-fluoro-phenyl)-1-oxo-2-azaspiro[4.5]dec-7-yl]-amide | Method: A<br>RT: 1.21<br>Calcd. Mass: 418<br>m/z (M + H): 419 |
| 130 | 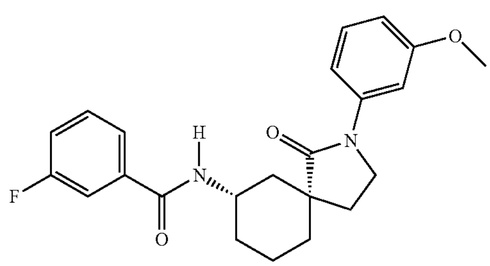 [SMILES: COc1cccc(N2CC[C@]3(CCC[C@H](NC(=O)c4cccc(F)c4)C3)C2=O)c1] | cis-3-Fluoro-N-[-2-(3-methoxy-phenyl)-1-oxo-2-aza-spiro[4.5]dec-7-yl]-benzamide | Method: A<br>RT: 1.29<br>Calcd. Mass: 396<br>m/z (M + H): 397 |
| 131 | 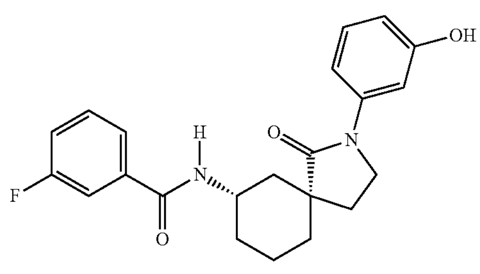 [SMILES: O=C(N[C@H]1CCC[C@]2(CCN(c3cccc(O)c3)C2=O)C1)c1cccc(F)c1] | Cis-3-Fluoro-N-[2-(3-hydroxy-phenyl)-1-oxo-2-aza-spiro[4.5]dec-7-yl]-benzamide | Method: A<br>RT: 1.02<br>Calcd. Mass: 382<br>m/z (M + H): 383 |

TABLE 1-continued

Spirolactam derivatives

| Example No | STRUCTURE | CHEMICAL NAME | LC-MS |
|---|---|---|---|
| 132 | 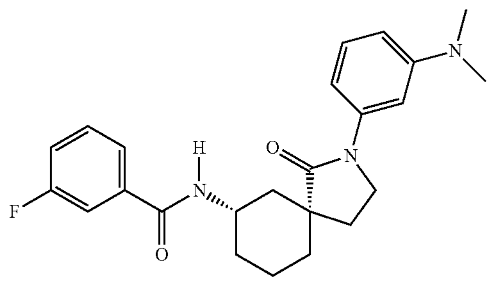 | Cis-N-[(5S,7S)-2-(3-Dimethylamino-phenyl)-1-oxo-2-aza-spiro[4.5]dec-7-yl]-3-fluoro-benzamide | Method: A<br>RT: 1.37<br>Calcd. Mass: 400<br>m/z (M + H): 401 |
| 133 | 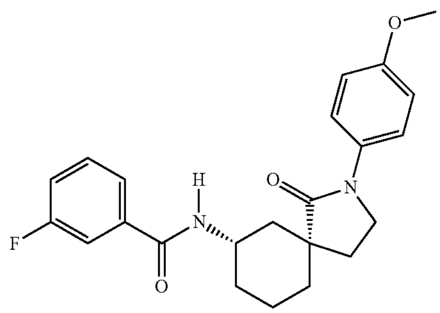 [SMILES: COc1ccc(N2CC[C@]3(CCC[C@H](NC(=O)c4cccc(F)c4)C3)C2=O)cc1] | cis-3-Fluoro-N-[(-2-(4-methoxy-phenyl)-1-oxo-2-aza-spiro[4.5]dec-7-yl]-benzamide. | Method: A<br>RT: 1.24<br>Calcd. Mass: 396<br>m/z (M + H): 397 |
| 134 | 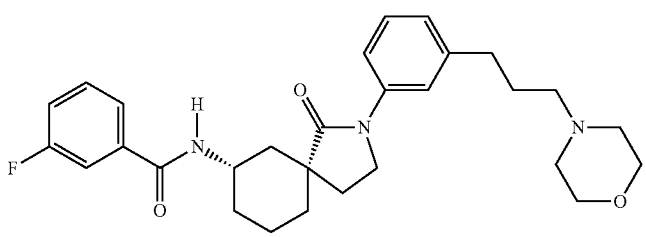 [SMILES: O=C(N[C@H]1CCC[C@]2(CCN(c3cccc(CCCN4CCOCC4)c3)C2=O)C1)c1cccc(F)c1] | cis-3-Fluoro-N-{2-[3-(3-morpholin-4-yl-propyl)-phenyl]-1-oxo-2-aza-spiro[4.5]dec-7-yl benzamide | Method: A<br>RT: 1.09<br>Calcd. Mass: 493<br>m/z (M + H): 494 |
| 135 | 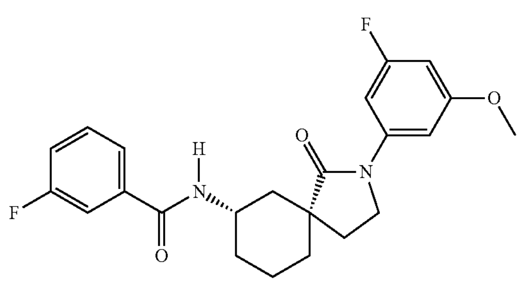 [SMILES: COc1cc(F)cc(N2CC[C@]3(CCC[C@H](NC(=O)c4cccc(F)c4)C3)C2=O)c1] | cis-3-Fluoro-N-[2-(3-fluoro-5-methoxy-phenyl)-1-oxo-2-aza-spiro[4.5]dec-7-yl]-benzamide | Method: A<br>RT: 1.36<br>Calcd. Mass: 414<br>m/z (M + H): 415 |
| 136 | 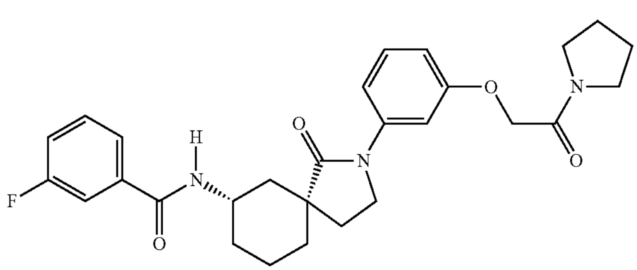 [SMILES: O=C(N[C@H]1CCC[C@]2(CCN(c3cccc(OCC(=O)N4CCCC4)c3)C2=O)C1)c1cccc(F)c1] | cis-3-Fluoro-N-{1-oxo-2-[3-(2-oxo-2-pyrrolidin-1-yl-ethoxy)-phenyl]-2-aza-spiro[4.5]dec-7-yl}-benzamide | Method: A<br>RT: 1.25<br>Calcd. Mass: 493<br>m/z (M + H): 494 |

TABLE 1-continued

Spirolactam derivatives

| Example No | STRUCTURE | CHEMICAL NAME | LC-MS |
|---|---|---|---|
| 137 | 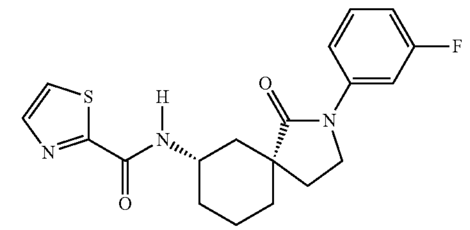 [SMILES: O=C(N[C@H]1CCC[C@]2(CCN(c3cccc(F)c3)C2=O)C1)c1nccs1] | cis-Thiazole-2-carboxylic acid [2-(3-fluoro-phenyl)-1-oxo-2-aza-spiro[4.5]dec-7-yl]-amide | Method: A<br>RT: 1.33<br>Calcd. Mass: 373<br>m/z (M + H): 374 |
| 138 | 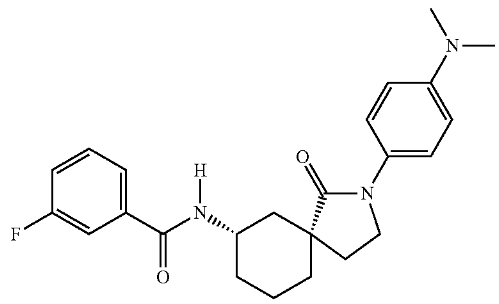 [SMILES: CN(C)c1ccc(N2CC[C@]3(CCC[C@H](NC(=O)c4cccc(F)c4)C3)C2=O)cc1] | cis-N-[2-(4-Dimethylamino-phenyl)-1-oxo-2-aza-spiro[4.5]dec-7-yl]-3-fluoro-benzamide | Method: A<br>RT: 1.42<br>Calcd. Mass: 409<br>m/z (M + H): 410 |
| 139 | 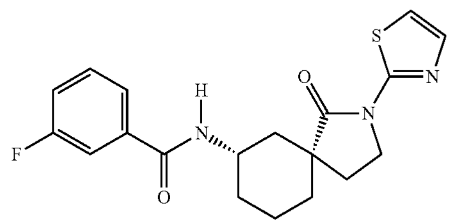 [SMILES: O=C(N[C@H]1CCC[C@]2(CCN(c3nccs3)C2=O)C1)c1cccc(F)c1] | cis-3-Fluoro-N-(1-oxo-2-thiazol-2-yl-2-aza-spiro[4.5]dec-7-yl)-benzamide | Method: A<br>RT: 1.21<br>Calcd. Mass: 373<br>m/z (M + H): 374 |
| 140 | 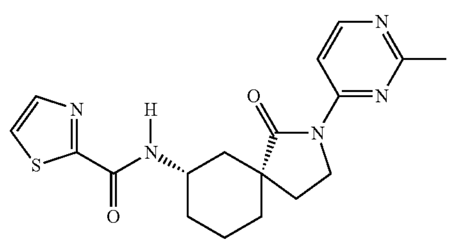 [SMILES: Cc1nccc(N2CC[C@]3(CCC[C@H](NC(=O)c4nccs4)C3)C2=O)n1] | cis-Thiazole-2-carboxylic acid [(2-(2-methyl-pyrimidin-4-yl)-1-oxo-2-aza-spiro[4.5]dec-7-yl]-amide | Method: A<br>RT: 1.05<br>Calcd. Mass: 371<br>m/z (M + H): 372 |
| 141 | 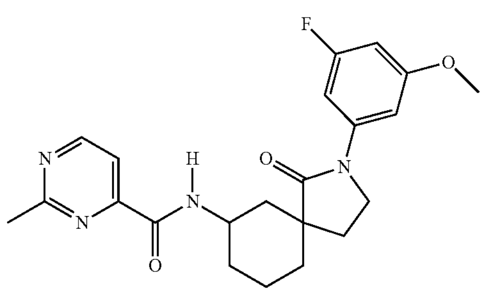 | cis-2-Methyl-pyrimidine-4-carboxylic acid [2-(3-fluoro-5-methoxy-phenyl)-1-oxo-2-aza-spiro[4.5]dec-7-yl]-amide | Method: A<br>RT: 1.30<br>Calcd. Mass: 412<br>m/z (M + H): 413 |

TABLE 1-continued

Spirolactam derivatives

| Example No | STRUCTURE | CHEMICAL NAME | LC-MS |
|---|---|---|---|
| 142 | 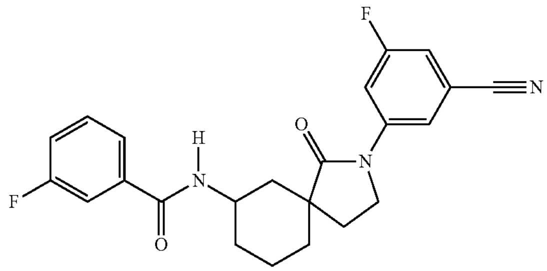 [SMILES: N#Cc1cc(F)cc(N2CCC3(CCCC(NC(=O)c4cccc(F)c4)C3)C2=O)c1] | cis-N-[2-(3-Cyano-5-fluoro-phenyl)-1-oxo-2-aza-spiro[4.5]dec-7-yl]-3-fluoro-benzamide | Method: A<br>RT: 1.44<br>Calcd. Mass: 409<br>m/z (M + H): 410 |
| 143 | 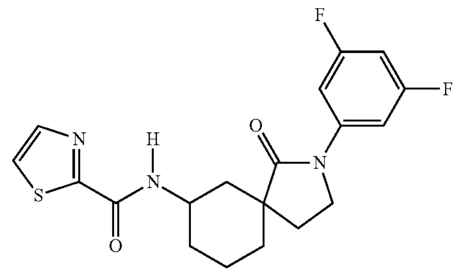 [SMILES: O=C(NC1CCCC2(CCN(c3cc(F)cc(F)c3)C2=O)C1)c1nccs1] | cis-Thiazole-2-carboxylic acid [2-(3,5-difluoro-phenyl)-1-oxo-2-aza-spiro[4.5]dec-7-yl]-amide | Method: A<br>RT: 1.43<br>Calcd. Mass: 391<br>m/z (M + H): 392 |
| 144 | 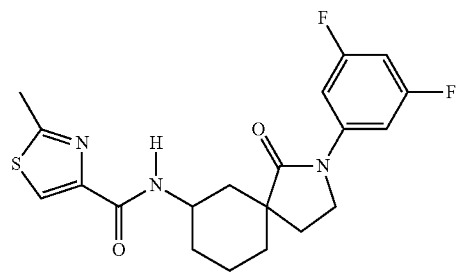 [SMILES: Cc1nc(C(=O)NC2CCCC3(CCN(c4cc(F)cc(F)c4)C3=O)C2)cs1] | cis-2-Methyl-thiazole-4-carboxylic acid [2-(3,5-difluoro-phenyl)-1-oxo-2-aza-spiro[4.5]dec-7-yl]-amide | Method: A<br>RT: 1.43<br>Calcd. Mass: 405<br>m/z (M + H): 406 |
| 145 | 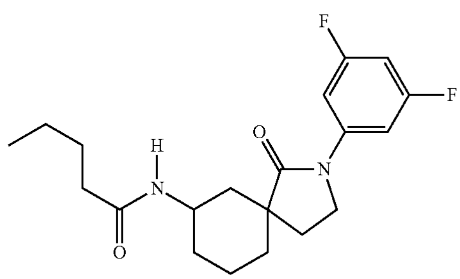 [SMILES: CCCCC(=O)NC1CCCC2(CCN(c3cc(F)cc(F)c3)C2=O)C1] | cis-Pentanoic acid [2-(3,5-difluoro-phenyl)-1-oxo-2-aza-spiro[4.5]dec-7-yl]-amide | Method: A<br>RT: 1.43<br>Calcd. Mass: 364<br>m/z (M + H): 365 |
| 146 | 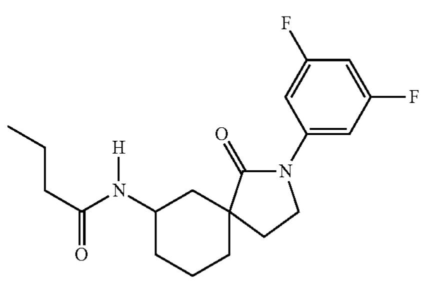 [SMILES: CCCC(=O)NC1CCCC2(CCN(c3cc(F)cc(F)c3)C2=O)C1] | cis-N-[2-(3,5-Difluoro-phenyl)-1-oxo-2-aza-spiro[4.5]dec-7-yl]-butyramide | Method: A<br>RT: 1.30<br>Calcd. Mass: 350<br>m/z (M + H): 351 |

TABLE 1-continued

Spirolactam derivatives

| Example No | STRUCTURE | CHEMICAL NAME | LC-MS |
|---|---|---|---|
| 147 | Chiral | 3-Fluoro-N-[(5R,7R)-2-(2-methyl-pyrimidin-4-yl)-1-oxo-2-aza-spiro[4.5]dec-7-yl]benzamide | Method: C RT: 1.21 Calcd. Mass: 382 m/z (M + H): 383 |
| 148 | Chiral | 3-Chloro-N-[(5R,7R)-2-(2-methyl-pyrimidin-4-yl)-1-oxo-2-aza-spiro[4.5]dec-7-yl]benzamide | Method: C RT: 1.32 Calcd. Mass: 398 m/z (M + H): 399 |
| 149 | 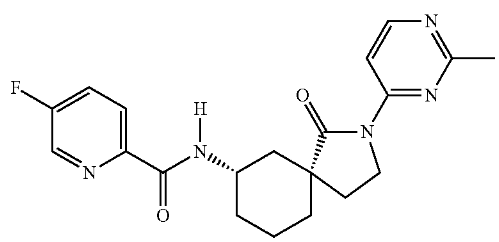 [SMILES: Cc1nccc(N2CC[C@]3(CCC[C@H](NC(=O)c4ccc(F)cn4)C3)C2=O)n1] | cis 5-Fluoro-pyridine-2-carboxylic acid [(2-(2-methyl-pyrimidin-4-yl)-1-oxo-2-aza-spiro[4.5]dec-7-yl]-amide | Method: C RT: 1.28 Calcd. Mass: 383 m/z (M + H): 384 |
| 150 | 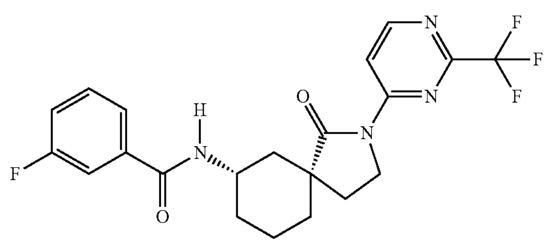 [SMILES: O=C(N[C@H]1CCC[C@]2(CCN(c3ccnc(C(F)(F)F)n3)C2=O)C1)c1cccc(F)c1] | cis-3-Fluoro-N-[1-oxo-2-(2-trifluoromethyl-pyrimidin-4-yl)-2-aza-spiro[4.5]dec-7-yl]-benzamide | Method: C RT: 1.48 Calcd. Mass: 436 m/z (M + H): 437 |
| 151 | 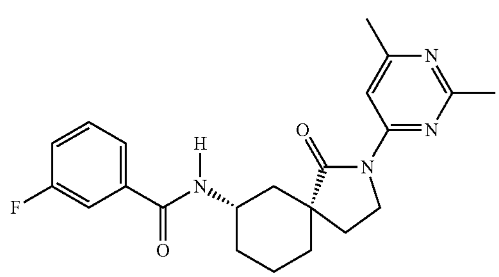 [SMILES: Cc1cc(N2CC[C@]3(CCC[C@H](NC(=O)c4cccc(F)c4)C3)C2=O)nc(C)n1] | cis-N-[2-(2,6-Dimethyl-pyrimidin-4-yl)-1-oxo-2-aza-spiro[4.5]dec-7-yl]3-fluoro-benzamide | Method: C RT: 1.34 Calcd. Mass: 396 m/z (M + H): 397 |
| 152 | Chiral | 3-Methyl-N-[(5R,7R)-2-(2-methyl-pyrimidin-4-yl)-1-oxo-2-aza-spiro[4.5]dec-7-yl]benzamide | Method: C RT: 1.24 Calcd. Mass: 378 m/z (M + H): 379 |

TABLE 1-continued

Spirolactam derivatives

| Example No | STRUCTURE | CHEMICAL NAME | LC-MS |
|---|---|---|---|
| 153 | 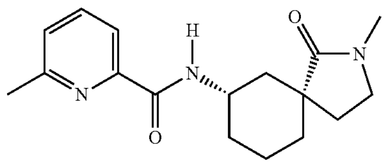 | cis-3-Fluoro-N-(2-methyl-1-oxo-2-aza-spiro[4.5]dec-7-yl)benzamide | Method: C<br>RT: 1.03<br>Calcd. Mass: 301<br>m/z (M + H): 302 |
| 154 | 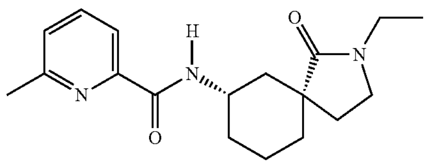 [SMILES: CCN1CC[C@]2(CCC[C@H](NC(=O)c3cccc(C)n3)C2)C1=O] | cis-3-Fluoro-N-(2-ethyl-1-oxo-2-aza-spiro[4.5]dec-7-yl)-benzamide | Method: C<br>RT: 1.11<br>Calcd. Mass: 315<br>m/z (M + H): 316 |
| 155 | 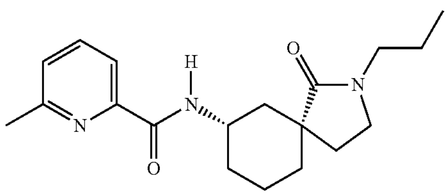 [SMILES: CCCN1CC[C@]2(CCC[C@H](NC(=O)c3cccc(C)n3)C2)C1=O] | cis-3-Fluoro-N-(2-propyl-1-oxo-2-aza-spiro[4.5]dec-7-yl)-benzamide | Method: C<br>RT: 1.20<br>Calcd. Mass: 329<br>m/z (M + H): 330 |
| 156 | Chiral | 6-Methyl-pyridine-2-carboxylic acid[(5R,7R)-1-oxo-2-(2-trifluoromethyl-pyrimidin-4-yl)-2-aza-spiro[4.5]dec-7-yl]-amide | Method: C<br>RT: 1.54<br>Calcd. Mass: 432<br>m/z (M + H): 433 |
| 157 | 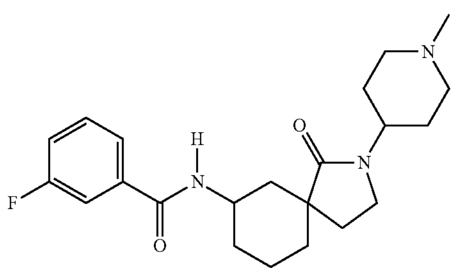 [SMILES: CN1CCC(N2CCC3(CCCC(NC(=O)c4cccc(F)c4)C3)C2=O)CC1] | 3-Fluoro-N-[2-(1-methyl-piperidin-4-yl)-1-oxo-2-aza-spiro[4.5]dec-7-yl]-benzamide | Method: C<br>RT: 0.84, 0.87<br>Calcd. Mass:<br>m/z (M + H): 388 |
| 158 | 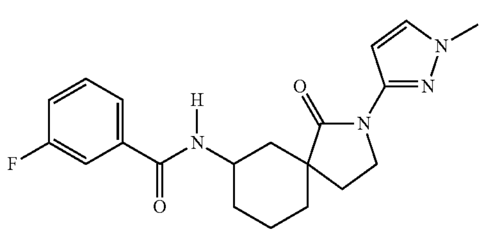 [SMILES: Cn1ccc(N2CCC3(CCCC(NC(=O)c4cccc(F)c4)C3)C2=O)n1] | 3-Fluoro-N-[2-(1-methyl-1H-pyrazol-3-yl)-1-oxo-2-aza-spiro[4.5]dec-7-yl]-benzamide | Method: C<br>RT: 1.14<br>Calcd. Mass: 370<br>m/z (M + H): 371 |

TABLE 1-continued

Spirolactam derivatives

| Example No | STRUCTURE | | CHEMICAL NAME | LC-MS |
|---|---|---|---|---|
| 159 | 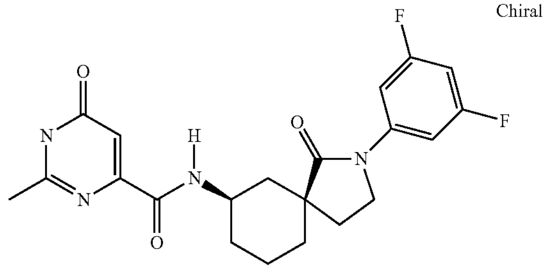 [SMILES: Cc1nc(C(=O)N[C@@H]2CCC[C@@]3(CCN(c4cc(F)cc(F)c4)C3=O)C2)cc(=O)[nH]1] | Chiral | 2-Methyl-6-oxo-1,6-dihydro-pyrimidine-4-carboxylic acid [(5R,7R)-2-(3,5-difluoro-phenyl)-1-oxo-2-aza-spiro[4.5]dec-7-yl]amide | Method: C<br>RT: 1.15<br>Calcd. Mass: 416<br>m/z (M + H): 417 |

Examples 160-162 may be made via the processes outlined in Scheme 23 herein from compound 23, which can be made from reduction of commercially available 5-hydroxy-isophthalic acid (compound 22) via the process of step a outlined in Scheme 6, supra.

Examples 163-177 may be made via the processes outlined in Scheme 19 herein from compound 41 ($R^2$=3-fluorophenyl or 3,5-difluorophenyl or 4-fluorophenyl), which may be made via the processes outlined in Scheme 8 herein from commercially available 4-oxo-cyclohexane-1,3-dicarboxylic acid dimethyl ester (compound 32).

Examples 178-201 may be made via the processes outlined in Scheme 20 herein from compound 49 ($R^2$+3-fluorophenyl or 3,5-difluorophenyl or 4-fluorophenyl), which can be made via the processes outlined in Scheme 9 herein from compound 8, which can be readily made by esterification of commercially available cyclohexane-1,3-dicarboxylic acid (compound 7) via the process of step a outlined in Scheme 4, supra.

TABLE 2

Hypothetic compounds

| Example No | STRUCTURE | CHEMICAL NAME |
|---|---|---|
| 160 | 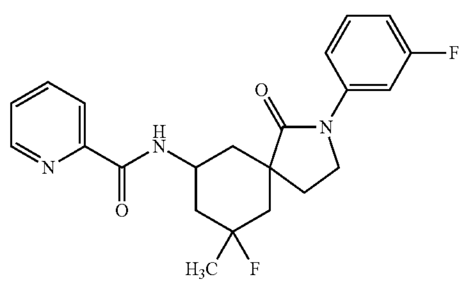 [SMILES: CC1(F)CC(NC(=O)c2ccccn2)CC2(CCN(c3cccc(F)c3)C2=O)C1] | Pyridine-2-carboxylic acid [9-fluoro-2-(3-fluoro-phenyl)-9-methyl-1-oxo-2-aza-spiro[4.5]dec-7-yl]amide |
| 161 | 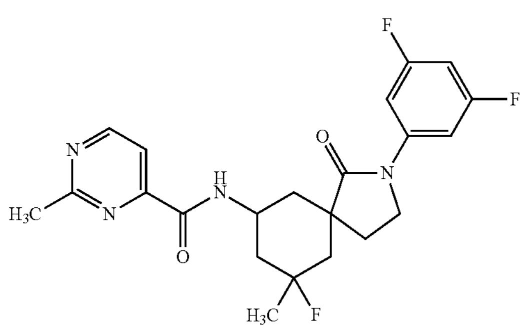 [SMILES: Cc1nccc(C(=O)NC2CC(C)(F)CC3(CCN(c4cc(F)cc(F)c4)C3=O)C2)n1] | 2-Methyl-pyrimidine-4-carboxylic acid [2-(3,5-difluoro-phenyl)-9-fluoro-9-methyl-1-oxo-2-aza-spiro [4.5]dec-7-yl]-amide |

TABLE 2-continued

Hypothetic compounds

| Example No | STRUCTURE | CHEMICAL NAME |
|---|---|---|
| 162 | 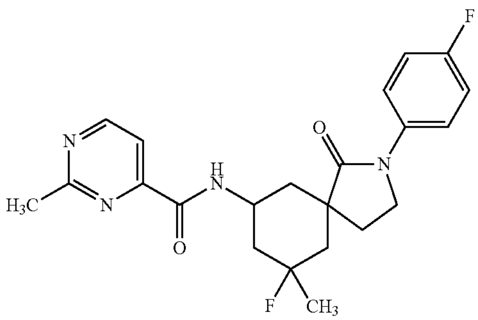 [SMILES: Cc1nccc(C(=O)NC2CC(C)(F)CC3(CCN(c4ccc(F)cc4)C3=O)C2)n1] | 2-Methyl-pyrimidine-4-carboxylic acid [9-fluoro-2-(4-fluoro-phenyl)-9-methyl-1-oxo-2-aza-spiro[4.5]dec-7-yl] amide |
| 163 | 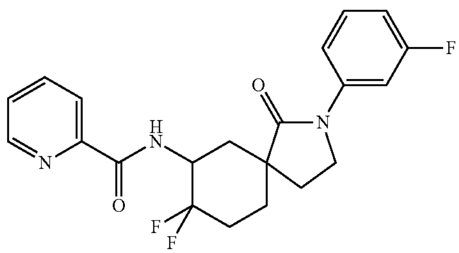 [SMILES: O=C(NC1CC2(CCN(c3cccc(F)c3)C2=O)CCC1(F)F)c1ccccn1] | Pyridine-2-carboxylic acid [8,8-difluoro-2-(3-fluoro-phenyl)-1-oxo-2-aza-spiro[4.5]dec-7-yl]-amide |
| 164 | 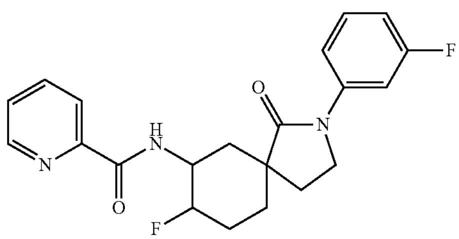 [SMILES: O=C(NC1CC2(CCC1F)CCN(c1cccc(F)c1)C2=O)c1ccccn1] | Pyridine-2-carboxylic acid [8-fluoro-2-(3-fluoro-phenyl)-1-oxo-2-aza-spiro[4.5]dec-7-yl]-amide |
| 165 | 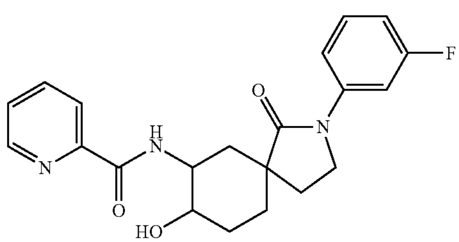 [SMILES: O=C(NC1CC2(CCC1O)CCN(c1cccc(F)c1)C2=O)c1ccccn1] | Pyridine-2-carboxylic acid [2-(3-fluoro-phenyl)-8-hydroxy-1-oxo-2-aza-spiro[4.5]dec-7-yl]-amide |
| 166 | 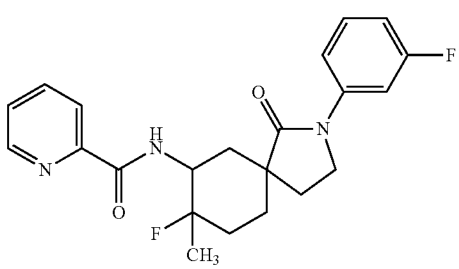 [SMILES: CC1(F)CCC2(CCN(c3cccc(F)c3)C2=O)CC1NC(=O)c1ccccn1] | Pyridine-2-carboxylic acid [8-fluoro-2-(3-fluoro-phenyl)-8-methyl-1-oxo-2-aza-spiro[4.5]dec-7-yl]-amide |

TABLE 2-continued

Hypothetic compounds

| Example No | STRUCTURE | CHEMICAL NAME |
|---|---|---|
| 167 | 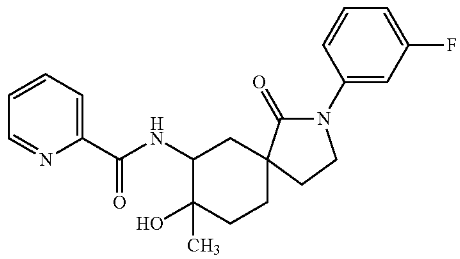 [SMILES: CC1(O)CCC2(CCN(c3cccc(F)c3)C2=O)CC1NC(=O)c1ccccn1] | Pyridine-2-carboxylic acid [2-(3-fluoro-phenyl)-8-hydroxy-8-methyl-1-oxo-2-aza-spiro[4.5]dec-7-yl]-amide |
| 168 | 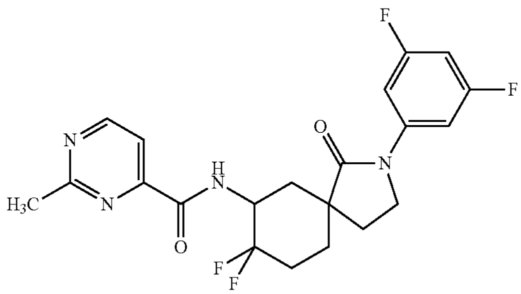 [SMILES: Cc1nccc(C(=O)NC2CC3(CCN(c4cc(F)cc(F)c4)C3=O)CCC2(F)F)n1] | 2-Methyl-pyrimidine-4-carboxylic acid [2-(3,5-difluoro-phenyl)-8,8-difluoro-1-oxo-2-aza-spiro[4.5]dec-7-yl]-amide |
| 169 | 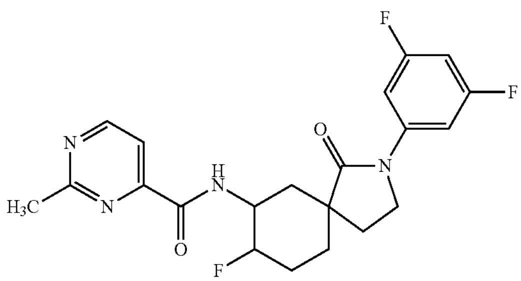 [SMILES: Cc1nccc(C(=O)NC2CC3(CCC2F)CCN(c2cc(F)cc(F)c2)C3=O)n1] | 2-Methyl-pyrimidine-4-carboxylic acid [2-(3,5-difluoro-phenyl)-8-fluoro-1-oxo-2-aza-spiro[4.5]dec-7-yl]-amide |
| 170 | 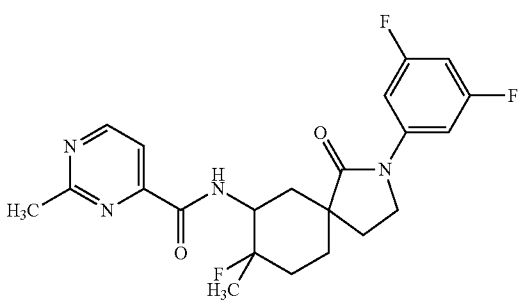 [SMILES: Cc1nccc(C(=O)NC2CC3(CCN(c4cc(F)cc(F)c4)C3=O)CCC2(C)F)n1] | 2-Methyl-pyrimidine-4-carboxylic acid [2-(3,5-difluoro-phenyl)-8-fluoro-8-methyl-1-oxo-2-aza-spiro[4.5]dec-7-yl]-amide |
| 171 | 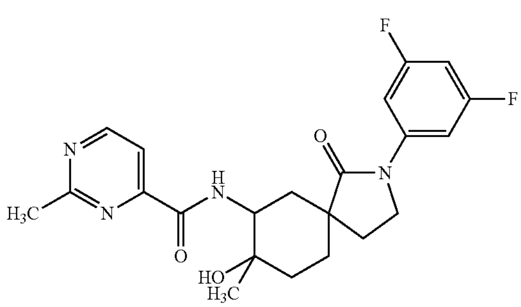 [SMILES: Cc1nccc(C(=O)NC2CC3(CCN(c4cc(F)cc(F)c4)C3=O)CCC2(C)O)n1] | 2-Methyl-pyrimidine-4-carboxylic acid [2-(3,5-difluoro-phenyl)-8-hydroxy-8-methyl-1-oxo-2-aza-spiro[4.5]dec-7-yl]-amide |

TABLE 2-continued

Hypothetic compounds

| Example No | STRUCTURE | CHEMICAL NAME |
|---|---|---|
| 172 | 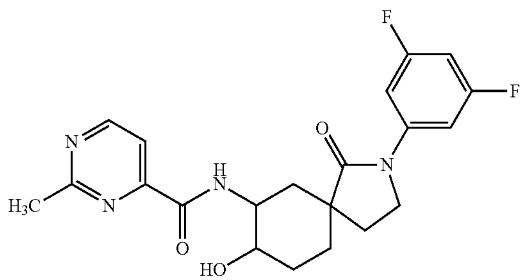 [SMILES: Cc1nccc(C(=O)NC2CC3(CCC2O)CCN(c2cc(F)cc(F)c2)C3=O)n1] | 2-Methyl-pyrimidine-4-carboxylic acid [2-(3,5-difluoro-phenyl)-8-hydroxy-1-oxo-2-aza-spiro[4.5]dec-7-yl]amide |
| 173 | 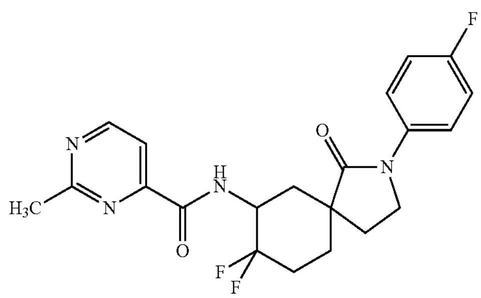 [SMILES: Cc1nccc(C(=O)NC2CC3(CCN(c4ccc(F)cc4)C3=O)CCC2(F)F)n1] | 2-Methyl-pyrimidine-4-carboxylic acid [8,8-difluoro-2-(4-fluoro-phenyl)-1-oxo-2-aza-spiro[4.5]dec-7-yl]-amide |
| 174 | 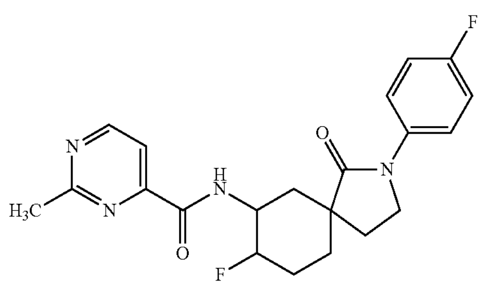 [SMILES: Cc1nccc(C(=O)NC2CC3(CCC2F)CCN(c2ccc(F)cc2)C3=O)n1] | 2-Methyl-pyrimidine-4-carboxylic acid [8-fluoro-2-(4-fluoro-phenyl)-1-oxo-2-aza-spiro[4.5]dec-7-yl]-amide |
| 175 | 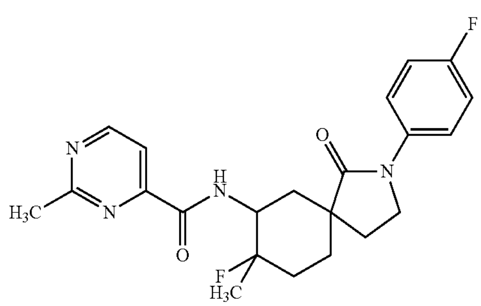 [SMILES: Cc1nccc(C(=O)NC2CC3(CCN(c4ccc(F)cc4)C3=O)CCC2(C)F)n1] | 2-Methyl-pyrimidine-4-carboxylic acid [8-fluoro-2-(4-fluoro-phenyl)-8-methyl-1-oxo-2-aza-spiro[4.5]dec-7-yl]-amide |
| 176 | 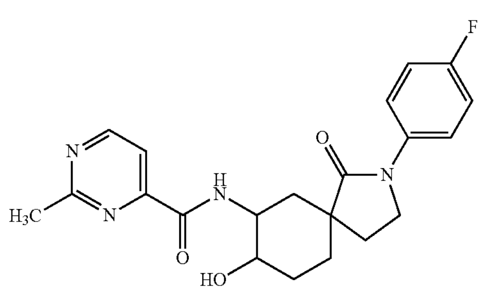 [SMILES: Cc1nccc(C(=O)NC2CC3(CCC2O)CCN(c2ccc(F)cc2)C3=O)n1] | 2-Methyl-pyrimidine-4-carboxylic acid [2-(4-fluoro-phenyl)-8-hydroxy-1-oxo-2-aza-spiro[4.5]dec-7-yl]-amide |

TABLE 2-continued

Hypothetic compounds

| Example No | STRUCTURE | CHEMICAL NAME |
|---|---|---|
| 177 | 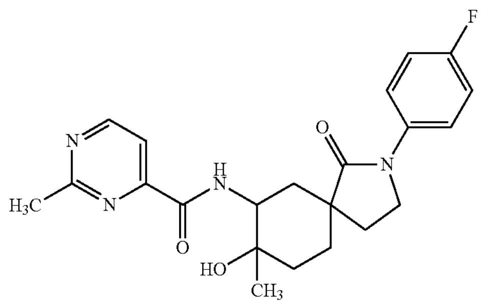 [SMILES: Cc1nccc(C(=O)NC2CC3(CCN(c4ccc(F)cc4)C3=O)CCC2(C)O)n1] | 2-Methyl-pyrimidine-4-carboxylic acid [2-(4-fluoro-phenyl)-8-hydroxy-8-methyl-1-oxo-2-aza-spiro[4.5]dec-7-yl]-amide |
| 178 | 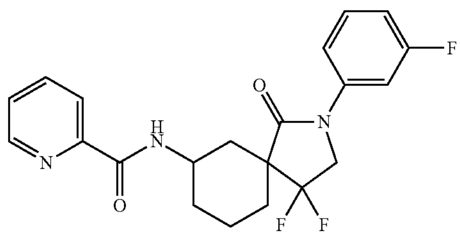 [SMILES: O=C(NC1CCCC2(C1)C(=O)N(c1cccc(F)c1)CC2(F)F)c1ccccn1] | Pyridine-2-carboxylic acid [4,4-difluoro-2-(3-fluoro-phenyl)-1-oxo-2-aza-spiro[4.5]dec-7-yl]-amide |
| 179 | 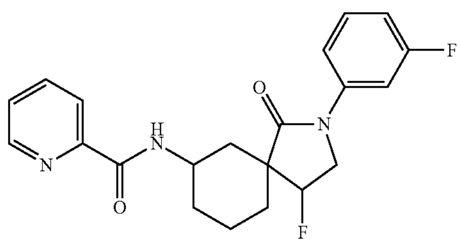 [SMILES: O=C(NC1CCCC2(C1)C(=O)N(c1cccc(F)c1)CC2F)c1ccccn1] | Pyridine-2-carboxylic acid [4-fluoro-2-(3-fluoro-phenyl)-1-oxo-2-aza-spiro[4.5]dec-7-yl]-amide |
| 180 | 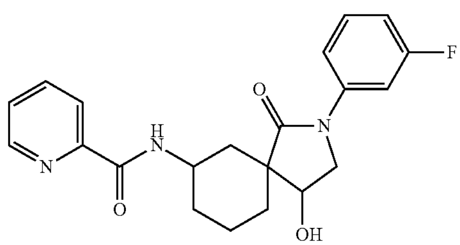 [SMILES: O=C(NC1CCCC2(C1)C(=O)N(c1cccc(F)c1)CC2O)c1ccccn1] | Pyridine-2-carboxylic acid [2-(3-fluoro-phenyl)-4-hydroxy-1-oxo-2-aza-spiro[4.5]dec-7-yl]-amide |
| 181 | 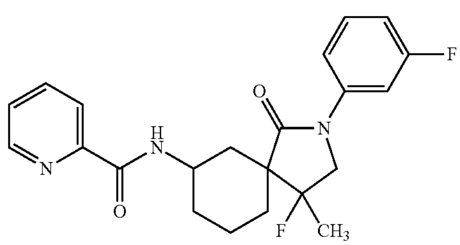 [SMILES: CC1(F)CN(c2cccc(F)c2)C(=O)C12CCCC(NC(=O)c1ccccn1)C2] | Pyridine-2-carboxylic acid [4-fluoro-2-(3-fluoro-phenyl)-4-methyl-1-oxo-2-aza-spiro[4.5]dec-7-yl]amide |
| 182 | 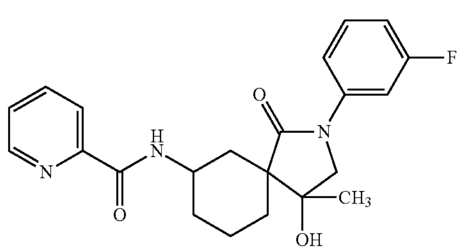 [SMILES: CC1(O)CN(c2cccc(F)c2)C(=O)C12CCCC(NC(=O)c1ccccn1)C2] | Pyridine-2-carboxylic acid [2-(3-fluoro-phenyl)-4-hydroxy-4-methyl-1-oxo-2-aza-spiro[4.5]dec-7-yl]-amide |

TABLE 2-continued

Hypothetic compounds

| Example No | STRUCTURE | CHEMICAL NAME |
|---|---|---|
| 183 | 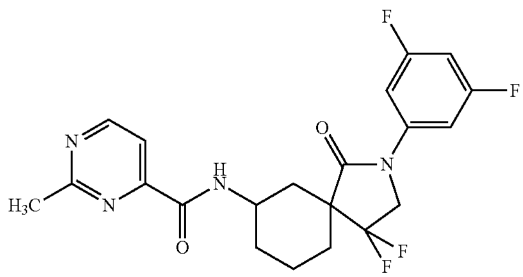 [SMILES: Cc1nccc(C(=O)NC2CCCC3(C2)C(=O)N(c2cc(F)cc(F)c2)CC3(F)F)n1] | 2-Methyl-pyrimidine-4-carboxylic acid [2-(3,5-difluoro-phenyl)-4,4-difluoro-1-oxo-2-aza-spiro[4.5]dec-7-yl]-amide |
| 184 | 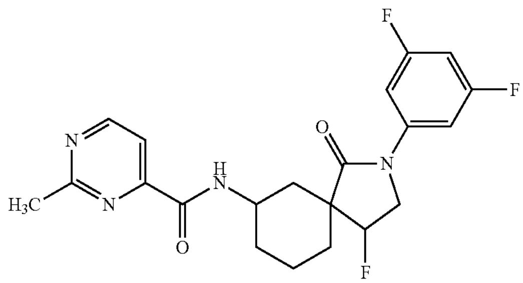 [SMILES: Cc1nccc(C(=O)NC2CCCC3(C2)C(=O)N(c2cc(F)cc(F)c2)CC3F)n1] | 2-Methyl-pyrimidine-4-carboxylic acid [2-(3,5-difluoro-phenyl)-4-fluoro-1-oxo-2-aza-spiro[4.5]dec-7-yl]-amide |
| 185 | 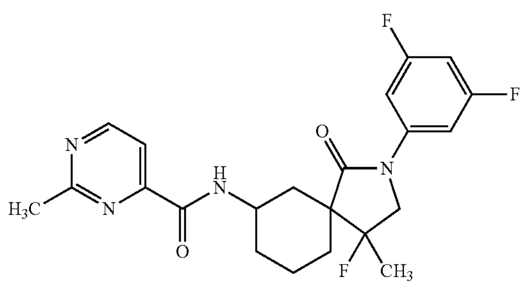 [SMILES: Cc1nccc(C(=O)NC2CCCC3(C2)C(=O)N(c2cc(F)cc(F)c2)CC3(C)F)n1] | 2-Methyl-pyrimidine-4-carboxylic acid [2-(3,5-difluoro-phenyl)-4-fluoro-4-methyl-1-oxo-2-aza-spiro [4.5]dec-7-yl]-amide |
| 186 | 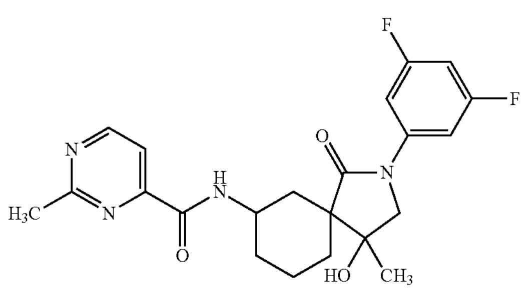 [SMILES: Cc1nccc(C(=O)NC2CCCC3(C2)C(=O)N(c2cc(F)cc(F)c2)CC3(C)O)n1] | 2-Methyl-pyrimidine-4-carboxylic acid [2-(3,5-difluoro-phenyl)-4-hydroxy-4-methyl-1-oxo-2-aza-spiro[4.5]dec-7-yl]-amide |
| 187 | 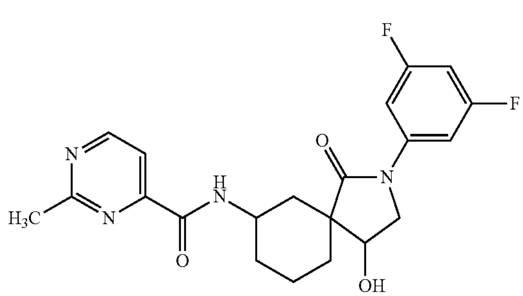 [SMILES: Cc1nccc(C(=O)NC2CCCC3(C2)C(=O)N(c2cc(F)cc(F)c2)CC3O)n1] | 2-Methyl-pyrimidine-4-carboxylic acid [2-(3,5-difluoro-phenyl)-4-hydroxy-1-oxo-2-aza-spiro[4.5]dec-7-yl]-amide |

TABLE 2-continued

Hypothetic compounds

| Example No | STRUCTURE | CHEMICAL NAME |
|---|---|---|
| 188 | 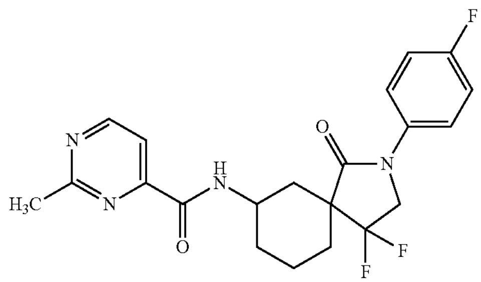 [SMILES: Cc1nccc(C(=O)NC2CCCC3(C2)C(=O)N(c2ccc(F)cc2)CC3(F)F)n1] | 2-Methyl-pyrimidine-4-carboxylic acid [4,4-difluoro-2-(4-fluoro-phenyl)-1-oxo-2-aza-spiro[4.5]dec-7-yl]-amide |
| 189 | 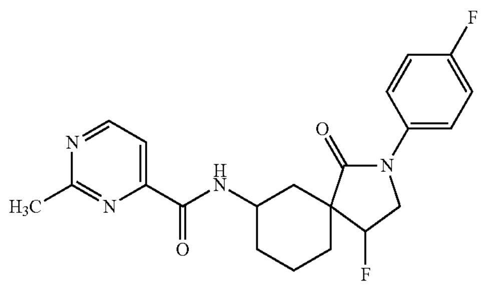 [SMILES: Cc1nccc(C(=O)NC2CCCC3(C2)C(=O)N(c2ccc(F)cc2)CC3F)n1] | 2-Methyl-pyrimidine-4-carboxylic acid [4-fluoro-2-(4-fluoro-phenyl)-1-oxo-2-aza-spiro[4.5]dec-7-yl]amide |
| 190 | 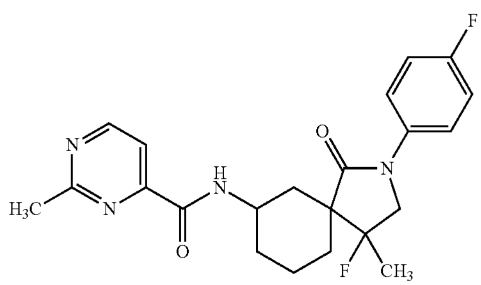 [SMILES: Cc1nccc(C(=O)NC2CCCC3(C2)C(=O)N(c2ccc(F)cc2)CC3(C)F)n1] | 2-Methyl-pyrimidine-4-carboxylic acid [4-fluoro-2-(4-fluoro-phenyl)-4-methyl-1-oxo-2-aza-spiro[4.5]dec-7-yl]-amide |
| 200 | 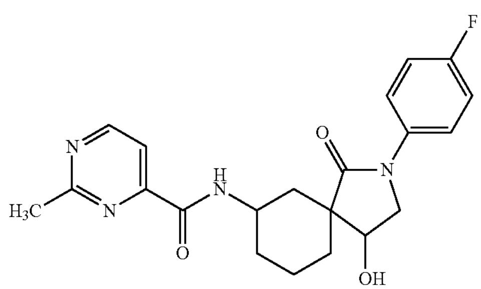 [SMILES: Cc1nccc(C(=O)NC2CCCC3(C2)C(=O)N(c2ccc(F)cc2)CC3O)n1] | 2-Methyl-pyrimidine-4-carboxylic acid [2-(4-fluoro-phenyl)-4-hydroxy-1-oxo-2-aza-spiro[4.5]dec-7-yl]amide |
| 201 | 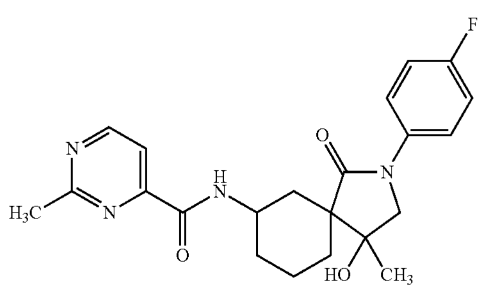 [SMILES: Cc1nccc(C(=O)NC2CCCC3(C2)C(=O)N(c2ccc(F)cc2)CC3(C)O)n1] | 2-Methyl-pyrimidine-4-carboxylic acid [2-(4-fluoro-phenyl)-4-hydroxy-4-methyl-1-oxo-2-aza-spiro[4.5]dec-7-yl]-amide |

4. Pharmacological Evaluation of Compounds of the Invention

Compounds of the present invention have been tested in vitro and in vivo, and can be tested in vitro and in vivo, in the assays as described below.

In Vitro Assays

Radioligand Binding Assays

Binding assays were performed as described in [J. A. O'Brien et al. *Mol. Pharmacol.*, 2003, 64, 731-740] with slight modifications. Briefly, after thawing, the membrane homogenates were resuspended in 50 mM Tris-HCl, 0.9% NaCl binding buffer at pH 7.4 to a final assay concentration of 40 μg protein/well for [$^3$H] 2-methyl-6-phenylethynyl-pyridine ([$^3$H] MPEP) (American Radiolabeled Chemicals, Inc., St. Louis, Mo.) filtration binding. Incubations included 5 nM [$^3$H] MPEP, membranes and either buffer or varying concentrations of compound. Samples were incubated for 60 min at room temperature with shaking. Non-specific binding was defined with 10 μM MPEP. After incubation, samples were filtered over a GF/C filter (presoaked in 0.25% polyethyleneimine (PEI)) and then washed 4 times using a Tomtec® Harvester 96® Mach III cell harvester (Tomtec, Hamden, Conn.) with 0.5 mL ice-cold 50 mM Tris-HCl (pH 7.4).

$IC_{50}$ values were derived from the inhibition curve and $K_i$ values were calculated according to the Cheng and Prusoff equation of $K_i=IC_{50}/(1+[L]/K_d)$ described in [Y. Cheng and W. H. Prusoff *Biochem. Pharmacol.* 1973, 22, 3099-3108] where [L] is the concentration of radioligand and $K_d$ is its dissociation constant at the receptor, derived from the saturation isotherm. The $K_i$ value for Examples 2, 4, 5, 23, and 25 were 250 nM, 74, 95, 190, 130, respectively.

Calcium Mobilization Assay to Test for Negative or Positive Allosteric Activity

The cDNA for rat metabotropic glutamate receptor 5 (rmGluR5) and the cDNA for human metabotropic glutamate receptor 5 (hmGluR5) were generous gifts from S. Nakanishi (Kyoto University, Kyoto, Japan). The rmGluR5 or hmGluR5 was stably expressed in a HEK 293 cell line and grown in Dulbecco's Modified Eagle Medium (DMEM) (Invitrogen, Carlsbad, Calif.) with supplements (10% bovine calf serum, 4 mM glutamine, 100 units/mL penicillin, 100 μg/mL streptomycin and 0.75 mM G1418) at 37° C., 5% $CO_2$. Twenty-four hours prior to assay, cells were seeded into 384-well black wall microtiter plates coated with poly-D-lysine. Just prior to assay, media was aspirated and cells dye-loaded (25 μL/well) with 3 μM Fluo-4/0.01% pluronic acid in assay buffer (Hank's Balanced Saline Solution (HBSS)): 150 mM NaCl, 5 mM KCl, 1 mM $CaCl_2$, 1 mM $MgCl_2$, plus 20 mM N-2-Hydroxyethylpiperazine-N'-2-ethanesulfonic acid (HEPES), pH 7.4, 0.1% bovine serum albumin (BSA) and 2.5 mM probenicid) for 1 hour in 5% $CO_2$ at 37° C. After excess dye was discarded, cells were washed in assay buffer and layered with a final volume equal to 30 μL/well. Basal fluorescence is monitored in a fluorometric imaging plate reader (FLIPR) (Molecular Devices, Sunnyvale, Calif.) with an excitation wavelength of 488 nm and an emission range of 500 to 560 nm. Laser excitation energy was adjusted so that basal fluorescence readings were approximately 10,000 relative fluorescent units. Cells were stimulated with an $EC_{20}$ or an $EC_{80}$ concentration of glutamate in the presence of a compound to be tested, both diluted in assay buffer, and relative fluorescent units were measured at defined intervals (exposure=0.6 sec) over a 3 min period at room temperature. Basal readings derived from negative controls were subtracted from all samples. Maximum change in fluorescence was calculated for each well. Concentration-response curves derived from the maximum change in fluorescence were analyzed by non-linear regression (Hill equation). A negative modulator can be identified from these concentration-response curves if a compound produces a concentration dependent inhibition of the $EC_{80}$ glutamate response. Exemplified compounds Examples 1-57 were tested in the above assay for negative allosteric modulation using rmGluR5: FLIPR maximum inhibition ranged 81% to 99% while FLIPR $IC_{50}$ ranged from 2.2 nM to 5100 nM. Examples also were tested in the above assay using hmGluR5: for Examples 58-96, FLIPR maximum inhibition ranged from 73% to 95%, while FLIPR $IC_{50}$ ranged from 3.3 nM to 500 nM; and for Examples 97-99, FLIPR maximum inhibition ranged from 88% to 93%, while FLIPR $IC_{50}$ ranged from 4.3 nM to 440 nM. For examples 100-160, FLIPR maximum inhibition ranged from 47% to 93%, while FLIPR $IC_{50}$ ranged from 4.3 nM to 440 nM.

A positive modulator (PAM) can be identified from these concentration-response curves if a compound produces a concentration dependent increase in the $EC_{20}$ glutamate response.

A silent allosteric modulator (SAM) can be identified based on results from both the radioligand assay and the calcium mobilization assay. If a compound actively binds to an allosteric site of the receptor based on the radioligand assay, but has no measurable intrinsic efficacy in the calcium mobilization assay, the compound is a SAM.

In Vivo Assays

Example 5 exhibited statistically significant in vivo anxiolytic effect at 30 mpk (sc) in a mouse marble burying (mMB) assay similar to that described in [K. Njung'e, K. and S. L. Handley, *Pharmacology, Biochemistry and Behavior*, 1991, 38, 63-67]. See FIG. 1.

More specifically for the mMB testing, adult, male CD1 mice (Charles River Laboratories (Kingston, N.Y.)), weighing 25 to 30 g, were used. All animals were group-housed in a standard colony room with a 12:12 light/dark cycle (lights on at 6:00 am) for at least one week prior to testing. Food and water were provided ad libitum. Animals were weighed, tail marked, and randomly assigned to treatment groups before testing.

For each test, sixty minutes after the injection of vehicle or test compound, or 30 min after injection of the positive control, buspirone, mice were individually placed into test cages containing 1.5 in of Aspen bedding (PWI brand) and two rows of 10 marbles (20 marbles per test cage total). Filter tops were used to cover each test cage. Thirty minutes later, mice were removed from test cages and returned to their home cages. The number of fully visible marbles (less than 2/3 covered with bedding) were counted and subtracted from 20 to arrive at the number of marbles buried. Twelve mice were tested per group.

Testing included multiple tests with each test performed to evaluate buspirone hydrochloride (BUS; Sigma Aldrich) (positive control) and/or a compound of formula (I). Each compound was dissolved immediately prior to testing in 20% beta-cyclodextrin (compound of formula (I)) or distilled water (BUS) and administered at one or more doses (such as 3, 10, and/or 30 mg/kg) via subcutaneous (SC) or intraperitoneal (IP) injection at the indicated pretreatment times (i.e., 30, 60, or 120 min pretreatment). Doses were measured in mg drug (salt form) per kg body weight. Data was analyzed using one-way ANOVA with post-hoc Dunnett's test.

Anxiolytic effect in vivo can also be tested via a modified Geller-Seifter conflict test described in [N. A. Moore et al. *Behavioural Pharmacology.* 1994, 5, 196-202]. For example, more specifically, rodent operant chambers (ENV-007CT, Med Associates Inc. (Georgia, Vt.)) and sound-attenuating chambers (ENV-018MD, Med Associates Inc.) are used and each chamber is equipped with a house light, cue lights, grid floor to deliver foot shocks via a programmable shocker, (ENV-414, Med Associates, Inc.) and food hopper. Two levers are located on either side of the food hopper. Rats are trained to only respond on the left lever. Food reinforcement is used (e.g., Dustless Precision Pellets, 45 mg, BioServ, (Frenchtown, N.J.)). MED-PCIV software (Med Associates) is used to run experimental sessions and collect data.

Prior to beginning the Conflict procedure, animals are initially trained to lever press on fixed ratio schedules (FR 1, 2, 5, and 10). Once animals obtain 25 rewards on a FR 10 schedule for 2 consecutive days, animals begin training on a three component Conflict schedule. The three components are as follows: (1) an unpunished, variable interval 30 s (VI30) schedule of food reinforcement to reinforce lever pressing on a variable time schedule that averages 30 s; this period had a duration of 9 minutes and is signaled by illumination of the rear house light only; (2) immediately following is a 3 minute time out period (TO) that is signaled by total darkness; responding is recorded but is neither rewarded nor punished; (3) a punished, fixed ratio 10 (FR10) schedule of reinforcement that simultaneously presents food and foot shock (0.3 mA, 500 ms) on every tenth lever press during a 3 minute period; this component is signaled by illumination of the rear house light and cue lights above each lever. These three components are repeated twice in the same order during the daily 30 minute session.

Testing begins when stable rates of responding are observed for 5 days (no significant trends up or down). Animals are tested using a Latin-squares design, on, e.g., Wednesdays and Fridays. Animals serve as their own controls and received all treatments. To maintain baseline performance, animals are also trained the remaining three weekdays.

Testing is performed using 12 adult, male Sprague-Dawley rats, weighing 426-567 g (Charles River Laboratories (Kingston, N.Y.)). Animals are pair-housed in colony rooms maintained at controlled temperature (68-72° F.) and a 12-h light/dark cycle (lights on 06:00). Animals are given free access to water, while food is limited to 15 g of Bacon Lover's Treats (BioServ) after training/testing Monday through Thursday. Friday through Sunday, animals have free access to Lab Diet 5012 Rat Diet (PMI Nutrition International, LLC, Brentwood, Mo.) until cages are changed and food removed on Sunday.

Testing includes multiple tests where each test is performed to evaluate either a reference compound or a compound of formula (I). Reference anxiolytics can include chlordiazepoxide, diazepam and buspirone, which are dissolved in saline or water and administered via sc, ip, and/or p.o. Test compounds are dissolved in 20% beta-cyclodextrin, and the pH is adjusted to 7 with $NaHCO_3$. For each test, the compound to be evaluated is tested at one or more doses (such as 10, 20, 30 and/or 50 mg/kg) via p.o. administration 60 minutes before the test using an injection volume of 2 mL/kg in comparison with a vehicle control group. Doses are measured in mg drug (salt form) per kg body weight. Data is analyzed using Repeated Measures ANOVA with post-hoc Dunnett's test.

The "Vogel Conflict Test" as described by Vogel et al. [*Psychopharmacologia*, 1971, 21, 1-7] was used to detect anxiolytic activity of a compound of formula (I) because anxiolytics increase punished drinking. In the test, rats were deprived of water for approximately 48 hours and were then placed individually into a transparent Plexiglas® enclosure (15×32×34 cm) with a floor consisting of stainless steel bars (0.4 cm) spaced 1 cm apart. The back wall of the enclosure was made of opaque Plexiglas® thereby concealing the observer from the experimental animal. In the center of the opposite wall, 5 cm above the floor, a metal water spout protruded into the cage and was connected to one pole of a shock generator (Apelex: Type 011346). The other pole of the shock generator was connected to the metal grid floor.

The rat was left to explore until it found the water spout. Then, every time it drank, it received a slight electric shock (1.7 mA, 1 s) 2 seconds after it started lapping. The number of punished drinks was counted during a 3 minute test. The test was performed blind with 10 rats per group. Testing included multiple tests using reference compounds and a compound of formula (I) that were prepared and administered as described below in the LES test. Male Rj: Wistar (Hans) rats as described therein were used after acclimatization conditions were achieved. Data was analyzed by comparing treated groups with appropriate controls using unpaired Student's t tests.

Example 82 showed significant activity in the Vogel Conflict Test at 10 mpk (p.o.); and Example 25 showed significant activity at 30 mpk (p.o.). See FIGS. 2 and 3, respectively. Example 147 showed significant activity in the Vogel Conflict Test at 3, 10 and 30 mpk (p.o.); see FIG. 4.

Compounds of formula (I) can be evaluated in vivo for antidepressive effects. An assessment of depression-like actions is measured using a forced swim test similar to that described in [J. F. Cryan, et al. *Neuroscience and Biobehavioral Reviews* 2005, 29, 547-569.] Animals used for testing are adult, male NIH Swiss Webster mice (Harlan Laboratories (Frederick, Md.)), weighing 22 to 24 g, which are acclimatized and housed as previously described with the mice used in the mMB tests.

For the mouse Forced Swim Test (mFST), mice are individually placed into clear Pyrex® cylinders (11 cm diameter, 16.5 cm height) containing 11 cm deep tap water (23-25° C.) sixty min after the injection of vehicle or test compound, or 30 min after injection of the positive control, imipramine hydrochloride (IMI; Sigma Aldrich, St. Louis, Mo.). Imipramine is prepared with isotonic saline and test compound is prepared as described previously with mMB tests. Doses used can be as described previously with mMB tests. The percentage of time spent floating, swimming, and struggling ("climbing") is measured during a 6 min session. Swim sessions are video monitored and can be analyzed in real-time using the Biobserve Automated FST apparatus and software (Biobserve GmbH, Bonn, Germany). Group size can range from twelve to thirteen mice. Doses are measured in mg drug (salt form) per kg body weight. Data is analyzed using one-way ANOVA with post-hoc Dunnett's test.

An in vivo effect of a compound of the present invention may also be evaluated by using the following, non-limiting, examples of in vivo behavioral animal models. The following behavioral models are not intended as the only models useful for determining the efficacy of a compound of the present invention to treat the corresponding disorder or disease.

Compounds of the invention also can be evaluated in vivo for anxiolytic effects using a light-enhanced startle (LES) reflex method as that described in [Walker and Davis. *Biol. Psychiatry,* 1997, 42, 461-471]. The startle response is a coordinated contraction of skeletal muscle groups in response to a high intensity unexpected stimulus. Most sensory modalities can be used, but sound is most frequently employed because it is easily controlled. Thus, when a short burst of sufficient intensity occurs (e.g., 115 dB) an involuntary startle response occurs. High light levels increase the startle response in nocturnal species such as the rat and this effect does not require any pre-conditioning. Anxiolytics—an agent that relieves anxiety—decrease light-enhanced startle.

For the LES test, an apparatus consisting of a commercially available soundproofed startle chamber (e.g., SR-LAB™ Startle Response System, San Diego Instruments, San Diego, Calif.) can be used. All experimental events and data recording can be controlled by computer program (e.g., SR-LAB™ control unit). Rats are placed within the startle chamber in a small Perspex® cylinder, slightly larger than the rat, which is attached to a base plate containing a strain gauge. Vertical movement of the rat such as occurs during a startle response results in deformation of the base plate, which generates a current in the strain gauge that is proportional to the size of the movement, i.e., the size of the startle response. A loudspeaker is placed directly above the rat to provide background sound and stimuli. A light source (2500-3500 Lux) is located in each startle chamber.

The LES test consists of two 20-minute sessions (first with lights off and then with lights on) of which the first 5 minutes are for habituation, during which background noise of 70 dB intensity is provided within the chamber. At the end of each habituation period, 10 stimulations of 110 dB are presented to habituate the animals. Thereafter, three trial types are presented in pseudo random order, 8 times each. Trials are separated by 15-25 seconds. The trial types are 100, 105 or 110 dB startle during which a 40 ms burst of white noise at 100, 105 or 110 dB is presented, resulting in a startle response. A period of 5 minutes without light or noise separates the two sessions. An appropriate rat species that can be use includes male Rj: Wister (Hans) rats (180-280 g weight at start of the testing with a maximum weight range per test of 50 g) (Elevage Janvier, Le Genest-Saint-Isle, France). The rats should be allowed to acclimatize to laboratory conditions at least 5 days before testing with free access to food and water. Acclimatization conditions should be comparable to those described in the scientific literature and/or known to those skilled in the art.

The output from the startle platform is recorded for 40 ms starting from the onset of the startle stimulus. Three variables are recorded for each trial: the average response over the whole recording period, the peak response and the time to peak response. The startle intensity is calculated for each rat by averaging the 8 trials of each type under dark or light conditions and calculating the percentage increase in startle amplitude (average and peak values) caused by light (LES). The time to peak response is a measure of reaction time.

The test is performed un-blinded using, e.g., 12 rats per group. Testing includes multiple tests where each test is performed to evaluate a reference compound (e.g., chlordiazepoxide), comparative compound (e.g., pregabalin) and/or a compound of the present invention. For example, in test 1, a known anxiolytic, such as chlordiazepoxide and pregabalin, is used, followed by test 2 using the mGluR5 antagonist 2-methyl-6-(phenylethynyl)-pyridine (MPEP), and then test 3 is performed using a compound of the present invention. Alternatively, each test can be performed concurrently, or in some combination of sequentially and concurrently. For each test, the compound to be evaluated is tested at one or more doses (such as 1, 3, 10, 30 and/or 100 mg/kg) via p.o. administration 60 minutes before the test in comparison with a vehicle control group. Prior to testing, test compounds can be tested for solubility by cold stirring of the highest intended dose for 10 min in distilled water. If soluble, distilled water can serve as the vehicle. If insoluble, the test compounds can be suspended in 0.2% hydroxypropylmethylcellulose (HPMC) in distilled water. Doses can be prepared as weight to volume (W/V) stock solutions and then serially diluted (VAT) for compounds in solution or separately weighted (W/V) for compounds in suspension.

For each test, data is analyzed by comparing treated groups with the vehicle control using unpaired Student's t tests. LES in each group will be analyzed by comparing within each treated group the intensity of startle reaction under dark and light conditions using paired Student's t tests.

Antidepressive effect can be evaluated using the Flinders Sensitive Line (FSL) rat in the FST and social interaction test as described in [D. H. Overstreet and G. Griebel *Pharmacol Biochem Behav.*, 2005, 82, 1: 223-227]. More specifically, compounds of the invention are tested at multiple doses (e.g., 10 mg/kg, 30 mg/kg, etc.) by preparing in 20% HP-beta-cyclodextrin and against vehicle control. In addition to an FSL vehicle control group, Flinders Resistant Line rats' vehicle control group is tested. Test compounds are administered daily by IP injection (2 mg/kg injection volume) for 14 days. Animals are tested in the social interaction and forced swim tests on Day 15, 22-24 hours after the injection on Day 14, as described in Overstreet and Griebel 2005. Six to eight animals per group are tested.

Anxiolytic and antidepressive effect can also be evaluated using a paradigm for decreased HPA axis feedback (David et al., 2007, SFN meeting in San Diego). This model based on the chronic delivery of corticosterone in the drinking water, causes anxiety- and depression-like behaviors in mice. The model consists of a sustained administration of a high dose (35 µg/mL), but not a low dose (7 µg/mL), of corticosterone for four or seven weeks. Such a treatment induced anxiety- and depression-like behaviour in C57B16/NTac mouse strain as indicated by a decreased time spent and number of entries into center of the arena during the minutes open field test (OF), whereas total ambulation was unaltered. Also, the latency to feed was increased in corticosterone-treated mice submitted to the novelty suppressed feeding (NSF) paradigm. As the corticosterone treatment did not alter food-intake in the home cage (familiar environment), changes in feeding latency were not due to changes in appetite or an underlying metabolic abnormality. Importantly, the adrenocorticotropic hormone (ACTH) and corticosterone (CORT) response to an acute stressor (6 min forced swim test (FST)), measured as plasma-concentrations, was blunted in C57BL/6NTac mice. Theses results were confirmed in CD1 strain mice. Three weeks treatment with the antidepressant imipramine (40 mg/kg/day ip) and fluoxetine (18 mg/kg/day ip) reversed the anxiety- and depression-like effects caused by a seven weeks corticosterone treatment in the OF, NSF and FST.

In such test, 240 adult male mice of C57B1/6Ntac strain (Taconic Farms (Denmark)), 8-10 weeks old, which are allowed to acclimate to the facility for at least 1 week prior to testing (e.g., 5 per cage under a 12 h (06:00-18:00) light-dark cycle at 22° C.) with food and water freely available.

A compound of the invention (30 or 60 mg/kg, per day in chow), fluoxetine (18 mg/kg per day in drinking water) or vehicle (0.45% 13-cyclodextrine, βCD in drinking water) are administered to mice treated via drinking water with either vehicle or corticosterone (35 µg/mL). After 7 weeks of treatment as indicated below, mice are tested in the following behavioral tests: OF, NSF, FST and sucrose splash grooming test. Treatment is started with either 13CD or corticosterone (35 µg/mL) given via the drinking water for 3 weeks (n=200 mice per group). Thereafter, administration with βCD or corticosterone will continue, and mice are divided into 8 groups of 30 mice as indicated below for 4 additional weeks.

| Week 1-8 | Week 3-7 |
|---|---|
| vehicle (βCD) | vehicle |
| vehicle (βCD) | fluoxetine, 18 mg/kg |
| vehicle (βCD) | test compound, 30 mg/kg |
| vehicle (βCD) | test compound, 60 mg/kg |
| 35 μg/mL/day corticosterone | vehicle |
| 35 μg/mL/day corticosterone | fluoxetine, 18 mg/kg |
| 35 μg/mL/day corticosterone | test compound, 30 mg/kg |
| 35 μg/mL/day corticosterone | test compound, 60 mg/kg |

Mice are tested in the behavioral paradigms in this order: OF, NSF, sucrose splash test and then the mouse FST (15 animals/group).

The Open-Field Test

Motor activity is quantified in Plexiglas® open field boxes 43×43 cm$^2$ (MED associates, Georgia, Vt.) over a 10 min session. Two sets of 16 pulse-modulated infrared photo beams are placed on opposite walls 2.5 cm apart to record x-y ambulatory movements. A 40-W white bulb placed in the middle of the room provided around 200-1× illumination at floor level. Activity chambers are computer interfaced for data sampling at 100 ms resolution. The computer defined grid lines that divided each open field into center and surrounds regions, with each of four lines being 11 cm from each wall. Dependant measures are total time spent in the center, the numbers of entries into the center and distance traveled in the center divided by total distance traveled. Overall motor activity is quantified as the total distance traveled (cm).

The Novelty-Suppressed Feeding

The novelty suppressed feeding (NSF) is a conflict test that elicits competing motivations: the drive to eat and the fear of venturing into the center of brightly lit arena. Latency to begin eating is used as an index of anxiety-like behavior because classical anxiolytic drugs decrease it. The NSF is carried out during a 5-min period as previously described (Santarelli et al., 2003). Briefly, the testing apparatus consisted of a plastic box 50×50×20 cm. The floor is covered with approximately 2 cm of wooden bedding. Twenty-four hours prior to behavioral testing, all food is removed from the home cage. At the time of testing, a single pellet of food (regular chow) is placed on a white paper platform positioned in the center of the box. An animal is placed in a corner of the maze and a stopwatch is immediately started. The measure of interest (chewing) is scored when the mouse is sitting on its haunches and biting with the use of forepaws. Immediately after this test, mice are transferred to their home cage and the amount of food consumed in 5 min is measured (home cage food consumption). Mice are tested during the light period. Because antidepressants are known to have various effects on appetite, the feeding drive is assessed by returning animals in their home cage (familiar environment) immediately after the test. Then, the amount of food consumed over a 5 min-period is measured.

Splash Test

The grooming latency is assessed at the end of the corticosterone regimen (end of seventh week) in the presence or absence of 3-weeks of fluoxetine treatment. This test consists in squirting 200 μl of a 10% sucrose solution on the mouse's snout. The grooming frequency is then recorded The Mouse Forced Swim Test A modified forced swim test procedure as described in [Dulawa et al. Neuropsychopharmcol., 2004, 29, 1321-1330; Holick et al. Neuropsychopharmcol., 2008, 33, 2: 406-417] is used. Mice are placed individually into glass cylinders (height: 25 cm, diameter: 10 cm) containing 18 cm water that is maintained at 23-25° C. and videotaping will be for 6 min via a tripod-mounted camera positioned directly on the side of the cylinder. An increase of swimming and climbing has been linked to an activation of serotoninergic and noradrenergic system in rats [see, e.g., Cryan and Lucki Pharmcol. & Exp. Therap., 2000, 295, 3: 1120-1126] and in mice [see, e.g., Dulawa et al. (2004); Holick et al., (2008)], respectively. Therefore, the predominant behavior (swimming, immobility or climbing) is scored here during the last 4 min of the 6 min testing period.

Anxiolytic-like properties also can be evaluated using these additional tests: (1) social interaction described in [S. E. File and P. Seth European Journal of Pharmacology, 2003. 463, 35-53], and (2) elevated plus-maze described in [S. M. Korte and S. F. De Boer European Journal of Pharmacology, 2003, 463, 163-175].

Parkinson's disease (PD) can be assessed by measuring the neurotoxicity of MPTP in rats as described in [E. H. Lee et al. Chin. J. Physiol., 1992, 35, 4: 317-36]. Also experimentally induced striatal DA depletion in animals is a valid model of Parkinsonism, as described in [W. Schultz Prog. Neurobiol., 1982, 18, 2-3: 121-66]. The capacity of certain substances to damage catecholaminergic neurons has been used extensively to produce DA deficiency in animals, as described in [L. E. Annett et al. Exp. Neurol., 1994, 125, 2: 228-46]. PD can also be assessed by measuring the neurotoxicity induced by 6-hydroxydopamine (6-OHDA) as described in [N. Breysse et al. J. Neurosci., 2002, 22, 13: 5669-5678; D. Rylander et al. J. Pharmacol. Exp. Ther., 2009, 330, 1: 227-235; and L. Chen et al., "Chronic, systemic treatment with a metabotropic glutamate receptor 5 antagonist in 6-hydroxydopamine partially lesioned rats reverses abnormal firing of dopaminergic neurons," Brain Res., 2009, 1286, 192-200].

Fragile X Syndrome can be assessed using the fmr1$^{tm1Cgr}$ mouse model as described in [Q. J. Yan et al. Neuropharmacol., 2005, 49, 1053-1066] as well as the Fmr1 knockout mice with a selective reduction in mGluR5 expression as described in [G. Dölen et al. Neuron, 2007, 56, 955-962].

Preclinically, animals also can be evaluated for blockade/attenuation of symptoms associated with schizophrenia. Positive symptoms in animal models of schizophrenia can be evaluated by measuring changes in the overall level of activity of dopamine (DA) activity with concomitant parallel changes in locomotor activity as described in [R. Depoortere et al. Neuropsychopharmacology, 2003, 28, 11: 1889-902], D-amphetamine (AMPH) and phencyclidine (PCP) via induction of model psychosis or locomotor hyperactivity as described in [W. J. Freed et al. Neuropharmacology, 1984, 23, 2A: 175-81; F. Sams-Dodd Neuropsychopharmacology, 1998 19, 1: 18-25]. For example, Depoortere et al., 2003, have described tests for evaluating locomotor activity, catalepsy, climbing and stereotypy, which relate to positive symptomology and side effect profile, by characterizing compounds with typical and atypical antipsychotic efficacy. Attenuation in apomorphine-induced climbing, stereotypy and catalepsy (AIC) can be evaluated as described in [Y. K. Fung et al. Pharmacol. Biochem. Behav., 1986, 24, 1: 139-41 and Y. K. Fung et al. Steroids, 1987, 49, 4-5: 287-94]. Additionally, negative symptoms of schizophrenia can be evaluated by measuring social interaction under the influence of NMDA antagonists such as PCP, as described in F. Sams-Dodd, 1998, supra.

Cognitive symptoms of memory, including those from Alzheimer's disease, can be evaluated by such models as the Fear Conditioning Paradigm described in [T. J. Gould et al. Behav. Pharmacol., 2002, 13, 4: 287-94, and A. O. Hamm et al. Brain, 2003, 126, Pt 2: 267-75] and the Radial Arm Test described in [J. P. Aggleton et al. Behav. Brain Res., 1996, 19, 2: 133-46], while spatial reference memory and learning can be evaluated in the Morris watermaze test as described in [Morris. *Learn. Motiv.,* 1981, 12, 239-260; B. Bontempi et al. *Eur. J. Neurosci.* 1996, 8, 11: 2348-60]. More specifically, in the Morris watermaze test, a circular water tank (150 cm diameter and 45 cm height) is filled with about 30 cm water and maintained at 26-28° C. with an escape platform (15 cm diameter) 18 cm from the perimeter and always in the same position 1.5 cm beneath the surface of the water. The water is made opaque by addition of a non-toxic coloring agent (e.g., milk powder) rendering the platform invisible. Animals are given a single training session over a single day. The training session consists of 4 consecutive trials in the watermaze, each separated by 60 seconds. For each trial, the animal is placed in the watermaze at one of two starting points equidistant from the escape platform and allowed to find the escape platform. The animal is left on the escape platform for 60 seconds before starting a new trial. If the animal does not find the platform within 120 seconds, the animal is removed from the water and placed on the platform for 60 seconds. During the 4 trials, the animals start the watermaze twice from each starting point in a randomly determined order per animal. Appropriate animals for testing with acclimatization conditions are, for example, the male Rj: Wistar (Hans) rats as previously described for the LES test.

The trials are video-recorded and the behavior of animals is analyzed using a video-tracking system (SMART, Panlab, S. L., Cornelià (Barcelona), Spain). The principal measure taken in each trial is the distance traveled to find the platform. Secondary measures taken are the swim speed and escape latency. The test is performed blind using, for example, 12 rats per test group. Testing includes multiple tests using reference compounds and compounds of the present invention that are prepared and administered as previously described LES test. For each test, data is analyzed by comparing treated groups with vehicle controls using one-way ANOVA followed by Dunnett's t tests. To increase comparability with the aforementioned Vogel conflict test, in all tests, rats are subjected to water-deprivation for approximately 24 h before the test (Day 1); however, testing is performed in non-water-deprived rats (Day 2).

Additionally, with respect to cognition, memory and hippocampal hypo-functioning can be assessed by measuring the restoration of synaptic plasticity in ovariectomized (OVX) female rats as described in [M. Day and M. Good *Neurobiol. Learn. Mem.,* 2005, 83, 1: 13-21]. Further, changes in attention function because of schizophrenia can be examined by the Five (5) Choice Serial Reaction Time Test (5CSRT) described in [J. L. Muir et al. *Psychopharmacology (Berl),* 1995, 118, 1: 82-92 and Robbins et al. *Ann. N.Y. Acad. Sci.,* 1998, 846, 222-37].

Human patients can be evaluated for cognitive diseases or disorders by any of the tests within the skill of those in the art.

Analgesic activity can be evaluated by neuropathic pain model (the "Chung model") as described in [Kim and Chung, *Pain,* 1992, 50, 355-363]. Tight ligature of spinal nerves in rats is associated with hyperalgesia, allodynia and spontaneous pain, and therefore constitutes a model for peripheral neuropathic pain in humans. Antihyperalgesics reduce these chronic signs of pain hypersensitivity. Thus, in the Chung model, rats are anesthetized (sodium pentobarbital 50 mg/kg i.p.) and an incision at the L4-S2 level is performed to expose the left L5 nerve after cleaning the flank with chlorhexidine spray. A cotton thread (standard, non-surgery quality), disinfected with pure alcohol, is placed around the L5 nerve and a simple ligature is tied tightly around the L5 nerve. The wound is then sutured and sprayed with CothiVet® (hydrocotyle tincture spray) (Neogen® Corp., Lexington, Ky.). The rats receive a s.c. injection of Clamoxyl (0.67 mL/kg) and are allowed to recover. At least 2 weeks after the surgery, when the chronic pain state is fully installed, rats are submitted consecutively to tactile and thermal stimulation of both hindpaws.

For tactile stimulation, the animal is placed under an inverted acrylic plastic box (18×11.5×13 cm) on a grid floor. The tip of an electronic Von Frey probe (Model 1610, BIO-SEB, Vitrolles Cedex, France) is then applied with increasing force first to the non-lesioned and then the lesioned hindpaw and the force required to induce paw-withdrawal is automatically recorded. This procedure is carried out 3 times and the mean force per paw is calculated.

For heat stimulation, the apparatus (No. 7371, Ugo Basile, Comerio Va., Italy) consists of individual acrylic plastic boxes (17×11×13 cm) placed upon an elevated glass floor. A rat is placed in the box and left free to habituate for 10 minutes. A mobile infrared radiant source (96±10 mW/cm$^2$) is then focused first under the non-lesioned and then the lesioned hindpaw and the paw-withdrawal latency is automatically recorded. In order to prevent tissue damage, the heat source is automatically turned off after 45 seconds.

Prior to receiving compound treatment all animals are submitted to tactile stimulation of the hindpaws and assigned to treatment groups matched on the basis of the pain response of the lesioned hindpaw. The test is performed blind using, for example, 10 water-deprived rats per group. Appropriate animals for testing are, for example, the male Rj: Wistar (Hans) rats as previously described for the LES test. Testing includes multiple tests using reference compounds and compounds of the present invention. In addition to the pregabalin and MPEP as previously described for the LES test, duloxetine can be used as a reference compound since it is an antihyperalgesic with respect to neuropathic pain associated with diabetes and fibromyalgia. Compounds are prepared and administered as previously described LES test. Testing can be performed using the same batch of operated rats repeatedly, with a minimum wash-out of 1 week between treatments. Also, to increase comparability with the aforementioned Vogel conflict test, in all tests, rats are subjected to water-deprivation for approximately 48 hours before each test. For each Chung model test, data will be analyzed by comparing treated groups with appropriate controls using unpaired Student's t tests.

Additionally, analgesic/anti-inflammatory activity can be evaluated in vivo using the Formalin Paw Test in the mouse such as that described by [Wheeler-Aceto et al, *Psychopharmacology,* 1991, 104, 35-44). For the test, mice are given an intraplantar injection of 5% formalin (25 µl) into the posterior left paw. This treatment induces paw licking in control animals. The time spent licking is counted for 5 minutes, beginning immediately after injection of formalin (early phase) and for 15 minutes starting 15 minutes after injection of formalin (late phase).

The test is performed blind using, e.g., 10 mice per group. Appropriate animals for testing are, for example, male Rj: NMRI mice (Elevage Janvier), weighing 20-30 g (max. range per experiment=5 g) at the beginning of testing. Animals are acclimatized as described for the animals used in the LES test. Testing includes multiple tests using reference compounds (e.g., morphine), comparative compounds (e.g., gabapentin and duloxetine), and compounds of the present invention. Compounds of the invention can be evaluated at multiple doses as previously described in the LES test, and administered s.c. 60 minutes before formalin in comparison with a vehicle control group, while morphine (64 mg/kg p.o.), gabapentin (300 mg/kg p.o.) and duloxetine (10 mg/kg p.o.) are administered p.o. 60 minutes before formalin. Data is analyzed by comparing treated groups with vehicle control groups using unpaired Mann-Whitney U tests.

Multiple sclerosis can be evaluated by the experimental autoimmune encephalomyelitis (EAE) model described in [H. Y. Liu et al. *J. Neurosci. Res.*, 2002, 70, 2: 238-48].

Those skilled in the art will recognize that various changes and/or modifications may be made to aspects or embodiments of this invention and that such changes and/or modifications may be made without departing from the spirit of this invention. Therefore, it is intended that the appended claims cover all such equivalent variations as will fall within the spirit and scope of this invention.

Each reference cited in the present application, including literature references, books, patents and patent applications, is incorporated herein by reference in its entirety.

What is claimed is:
1. A compound of formula (I):

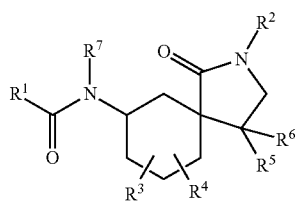

(I)

wherein:
R$^1$ and R$^2$ are each independently aryl, heteroaryl, alkyl, cycloalkyl, ketocycloalkyl, or heterocyclyl, which is optionally mono-, di-, or tri-substituted independently with alkyl, cycloalkyl, alkoxy, hydroxy, halogen, cyano, trifluoroalkyl, amino, acyl, aryl, heteroaryl, heterocyclyl, —C(O)NHR$^{30}$, —C(O)N(R$^{30}$)R$^{31}$, —NHC(O)$^{30}$, —N(R$^{30}$)C(O)R$^{31}$, —NHR$^{30}$, —N(R$^{30}$)R$^{31}$, or —OR$^{30}$; wherein:
R$^{30}$ and R$^{31}$ are each independently C$_1$-C$_6$alkyl or C$_1$-C$_6$cycloalkyl that is optionally substituted with acyl, halogen, —CN, —NH$_2$, —NH(C$_1$-C$_3$alkyl), —N(C$_1$-C$_3$alkyl)$_2$, C$_1$-C$_3$alkylheterocyclyl, C$_1$-C$_3$alkylcarbamate, —C(O)NH(C$_1$-C$_3$alkyl), —C(O)N(C$_1$-C$_3$alkyl)$_2$, —NHC(O)—C$_1$-C$_3$alkyl, —N(C$_1$-C$_3$alkyl)-C(O)—C$_1$-C$_3$alkyl, OH, or —O—C$_1$-C$_6$alkyl; and
each aryl, heteroaryl, heterocyclyl substituent is optionally substituted with C$_{1-3}$alkyl, C$_{3-5}$cycloalkyl, C$_{1-3}$alkoxy, hydroxy, halogen, cyano, trifluoroalkyl, or amino;
R$^3$, R$^4$, R$^5$ and R$^6$ are each independently H, C$_{1-3}$alkyl, C$_{3-5}$cycloalkyl, halogen, or hydroxy;
R$^7$ is H; or
R$^1$ and R$^7$ taken together with the —C(O)N— to which they are attached form a mono- or bicyclic 4- to 12-membered heterocycloalkyl or heteroaryl, which optionally contains 1-3 additional heteroatoms; or
a pharmaceutically acceptable salt thereof.

2. The compound of claim 1, wherein R$^1$ and R$^2$ are both aryl.

3. The compound of claim 1, wherein R$^1$ and R$^2$ are both heteroaryl.

4. The compound of claim 1, wherein R$^1$ is aryl and R$^2$ is heteroaryl.

5. The compound of claim 1, wherein R$^1$ is heteroaryl and R$^2$ is aryl.

6. The compound of claim 1, wherein either R$^1$ or R$^2$ is heteroaryl.

7. The compound of claim 1, wherein either R$^1$ or R$^2$ is aryl.

8. The compound of claim 1, wherein at least one aryl is phenyl.

9. The compound of claim 1, wherein R$^1$ is aryl or heteroaryl and R$^2$ is cycloalkyl, ketocycloalkyl or heterocyclyl.

10. The compound of claim 1, wherein the mono-, di-, or tri-substituents are independently selected from the group consisting of methyl, methoxy, dimethylamino-ethoxy, amino, methylamino, dimethylamino, cyano, chloro, cyano, dimethylamino, dimethylamino-ethoxy, methyl, methylamino, methoxy, fluoro, —C(O)NHCH$_3$, phenyl, furanyl, pyrrolidinyl, thiophenyl and trifluoromethyl.

11. The compound of claim 10, wherein the phenyl, 1 is optionally substituted with fluorine.

12. The compound of claim 1, wherein the compound is:
trans-Pyridine-2-carboxylic acid [2-(3-chloro-phenyl)-1-oxo-2-aza-spiro[4.5]dec-7-yl]-amide;
cis-Pyridine-2-carboxylic acid [2-(3-chloro-phenyl)-1-oxo-2-aza-spiro[4.5]dec-7-yl]-amide;
trans-6-Methyl-pyridine-2-carboxylic acid [2-(3-chloro-phenyl)-1-oxo-2-aza-spiro[4.5]dec-7-yl]-amide;
cis-6-Methyl-pyridine-2-carboxylic acid [2-(3-chloro-phenyl)-1-oxo-2-aza-spiro[4.5]dec-7-yl]-amide;
Pyridine-2-carboxylic acid [(5R,7R)-2-(3-chloro-phenyl)-1-oxo-2-aza-spiro[4.5]dec-7-yl]-amide;
Pyridine-2-carboxylic acid [(5S,7S)-2-(3-chloro-phenyl)-1-oxo-2-aza-spiro[4.5]dec-7-yl]-amide;
cis-Pyridine-2-carboxylic acid [2-(6-methyl-pyridin-2-yl)-1-oxo-2-aza-spiro[4.5]dec-7-yl]-amide;
3-Chloro-N-[2-(6-methyl-pyridin-2-yl)-1-oxo-2-aza-spiro[4.5]dec-7-yl]-benzamide;
cis-Pyridine-2-carboxylic acid [2-(3-cyano-phenyl)-1-oxo-2-aza-spiro[4.5]dec-7-yl]-amide;
cis-6-Methyl-pyridine-2-carboxylic acid [2-(3-cyano-phenyl)-1-oxo-2-aza-spiro[4.5]dec-7-yl]-amide;
cis-6-Methyl-pyrazine-2-carboxylic acid [2-(3-cyano-phenyl)-1-oxo-2-aza-spiro[4.5]dec-7-yl]-amide;
cis-6-Methyl-pyrazine-2-carboxylic acid [2-(3-chloro-phenyl)-1-oxo-2-aza-spiro[4.5]dec-7-yl]-amide;
cis-Pyrazine-2-carboxylic acid [2-(3-chloro-phenyl)-1-oxo-2-aza-spiro[4.5]dec-7-yl]-amide;
cis-1-Methyl-1H-pyrazole-3-carboxylic acid [2-(3-chloro-phenyl)-1-oxo-2-aza-spiro[4.5]dec-7-yl]-amide;
cis-N-[2-(3-Cyano-phenyl)-1-oxo-2-aza-spiro[4.5]dec-7-yl]-3-fluoro-benzamide;
cis-N-[2-(3-Cyano-phenyl)-1-oxo-2-aza-spiro[4.5]dec-7-yl]-3-chloro-benzamide;
cis-6-Methyl-pyridine-2-carboxylic acid [2-(3-fluoro-phenyl)-1-oxo-2-aza-spiro[4.5]dec-7-yl]-amide;
trans-6-Methyl-pyridine-2-carboxylic acid [2-(3-fluoro-phenyl)-1-oxo-2-aza-spiro[4.5]dec-7-yl]-amide;
cis-Pyridine-2-carboxylic acid [2-(3-fluoro-phenyl)-1-oxo-2-aza-spiro[4.5]dec-7-yl]-amide;
trans-Pyridine-2-carboxylic acid [2-(3-fluoro-phenyl)-1-oxo-2-aza-spiro[4.5]dec-7-yl]-amide;
cis-6-Methyl-pyrazine-2-carboxylic acid [2-(3-fluoro-phenyl)-1-oxo-2-aza-spiro[4.5]dec-7-yl]-amide;
trans-6-Methyl-pyrazine-2-carboxylic acid [2-(3-fluoro-phenyl)-1-oxo-2-aza-spiro[4.5]dec-7-yl]-amide;
cis-6-Methyl-pyridine-2-carboxylic acid [2-(6-methyl-pyridin-2-yl)-1-oxo-2-aza-spiro[4.5]dec-7-yl]-amide;
trans-3-Fluoro-N-[2-(6-methyl-pyridin-2-yl)-1-oxo-2-aza-spiro[4.5]dec-7-yl]-benzamide;

Pyridine-2-carboxylic acid [(5R,7R)-2-(3-fluoro-phenyl)-1-oxo-2-aza-spiro[4.5]dec-7-yl]-amide;
3-Fluoro-N-(1-oxo-2-pyridin-2-yl-2-aza-spiro[4.5]dec-7-yl)-benzamide;
cis-3-Fluoro-N-[2-(6-methyl-pyridin-2-yl)-1-oxo-2-aza-spiro[4.5]dec-7-yl]-benzamide;
3-Fluoro-N-[(5R,7R)-2-(6-methyl-pyridin-2-yl)-1-oxo-2-aza-spiro[4.5]dec-7-yl]-benzamide;
cis-Pyridine-2-carboxylic acid [2-(4-methyl-pyrimidin-2-yl)-1-oxo-2-aza-spiro[4.5]dec-7-yl]-amide;
cis-Pyridine-2-carboxylic acid [2-(4-fluoro-pyridin-2-yl)-1-oxo-2-aza-spiro[4.5]dec-7-yl]-amide;
cis-6-Methyl-pyridine-2-carboxylic acid [2-(5-fluoro-pyridin-2-yl)-1-oxo-2-aza-spiro[4.5]dec-7-yl]-amide;
cis-6-Methyl-pyridine-2-carboxylic acid [2-(4-fluoro-pyridin-2-yl)-1-oxo-2-aza-spiro[4.5]dec-7-yl]-amide;
cis-Pyridine-2-carboxylic acid [2-(5-fluoro-pyridin-2-yl)-1-oxo-2-aza-spiro[4.5]dec-7-yl]-amide;
cis-6-Methyl-pyridine-2-carboxylic acid [2-(4-methyl-pyrimidin-2-yl)-1-oxo-2-aza-spiro[4.5]dec-7-yl]-amide;
cis-3-Fluoro-N-[2-(5-fluoro-pyridin-2-yl)-1-oxo-2-aza-spiro[4.5]dec-7-yl]-benzamide;
cis-3-Fluoro-N-[2-(4-fluoro-pyridin-2-yl)-1-oxo-2-aza-spiro[4.5]dec-7-yl]-benzamide;
cis-3-Fluoro-N-[2-(4-methyl-pyrimidin-2-yl)-1-oxo-2-aza-spiro[4.5]dec-7-yl]-benzamide;
cis-3-Fluoro-N-[2-(6-methyl-pyrazin-2-yl)-1-oxo-2-aza-spiro[4.5]dec-7-yl]-benzamide;
cis-Pyridine-2-carboxylic acid [2-(6-methyl-pyrazin-2-yl)-1-oxo-2-aza-spiro[4.5]dec-7-yl]-amide;
cis-6-Methyl-pyridine-2-carboxylic acid [2-(6-methyl-pyrazin-2-yl)-1-oxo-2-aza-spiro[4.5]dec-7-yl]-amide;
cis-6-Methyl-pyridine-2-carboxylic acid [1-oxo-2-(6-trifluoromethyl-pyridin-2-yl)-2-aza-spiro[4.5]dec-7-yl]-amide;
cis-6-Methyl-pyridine-2-carboxylic acid [2-(3,5-difluoro-phenyl)-1-oxo-2-aza-spiro[4.5]dec-7-yl]-amide;
cis-6-Methyl-pyridine-2-carboxylic acid [2-(6-cyano-pyridin-2-yl)-1-oxo-2-aza-spiro[4.5]dec-7-yl]-amide;
cis-6-Methyl-pyridine-2-carboxylic acid [2-(4-fluoro-phenyl)-1-oxo-2-aza-spiro[4.5]dec-7-yl]-amide;
6-Methyl-pyridine-2-carboxylic acid (1-oxo-2-pyridin-2-yl-2-aza-spiro[4.5]dec-7-yl)-amide;
cis-6-Methyl-pyridine-2-carboxylic acid (1-oxo-2-phenyl-2-aza-spiro[4.5]dec-7-yl)-amide;
cis-6-Methyl-pyridine-2-carboxylic acid (1-oxo-2-m-tolyl-2-aza-spiro[4.5]dec-7-yl)-amide;
cis-6-Methyl-pyridine-2-carboxylic acid [2-(4-methyl-pyridin-2-yl)-1-oxo-2-aza-spiro[4.5]dec-7-yl]-amide;
cis-6-Methyl-pyridine-2-carboxylic acid [2-(5-methyl-pyridin-2-yl)-1-oxo-2-aza-spiro[4.5]dec-7-yl]-amide;
cis-6-Methyl-pyridine-2-carboxylic acid [2-(3-methyl-pyridin-2-yl)-1-oxo-2-aza-spiro[4.5]dec-7-yl]-amide;
cis-6-Methyl-pyridine-2-carboxylic acid [2-(2-fluoro-phenyl)-1-oxo-2-aza-spiro[4.5]dec-7-yl]-amide;
cis-6-Methyl-pyridine-2-carboxylic acid [2-(2-methyl-pyridin-4-yl)-1-oxo-2-aza-spiro[4.5]dec-7-yl]-amide;
cis-N-[2-(6-Cyano-pyridin-2-yl)-1-oxo-2-aza-spiro[4.5]dec-7-yl]-3-fluoro-benzamide;
cis-Pyridine-2-carboxylic acid [2-(3,5-difluoro-phenyl)-1-oxo-2-aza-spiro[4.5]dec-7-yl]-amide;
cis-6-Methyl-pyrazine-2-carboxylic acid [2-(3,5-difluoro-phenyl)-1-oxo-2-aza-spiro[4.5]dec-7-yl]-amide;
cis-Pyrazine-2-carboxylic acid [2-(3,5-difluoro-phenyl)-1-oxo-2-aza-spiro[4.5]dec-7-yl]-amide;
cis-2-Methyl-pyrimidine-4-carboxylic acid [2-(5-fluoro-pyridin-2-yl)-1-oxo-2-aza-spiro[4.5]dec-7-yl]-amide;
cis-3-Chloro-N-2-(2-methyl-pyrimidin-4-yl)-1-oxo-2-aza-spiro[4.5]dec-7-yl]-benzamide;
cis-2-Methyl-pyrimidine-4-carboxylic acid [2-(6-methyl-pyrazin-2-yl)-1-oxo-2-aza-spiro[4.5]dec-7-yl]-amide;
cis-2-Methyl-pyrimidine-4-carboxylic acid [2-(3-cyano-phenyl)-1-oxo-2-aza-spiro[4.5]dec-7-yl]-amide;
cis-2-Methyl-pyrimidine-4-carboxylic acid [1-oxo-2-(6-trifluoromethyl-pyridin-2-yl)-2-aza-spiro[4.5]dec-7-yl]-amide;
cis-6-Methyl-pyridine-2-carboxylic acid [2-(2-methyl-pyrimidin-4-yl)-1-oxo-2-aza-spiro[4.5]dec-7-yl]-amide;
cis-6-Methyl-pyridine-2-carboxylic acid [2-(6-methyl-pyridin-3-yl)-1-oxo-2-aza-spiro[4.5]dec-7-yl]-amide;
cis-6-Methyl-pyridine-2-carboxylic acid [2-(5-fluoro-pyridin-3-yl)-1-oxo-2-aza-spiro[4.5]dec-7-yl]-amide;
cis-3-Fluoro-N-[2-(2-methyl-pyrimidin-4-yl)-1-oxo-2-aza-spiro[4.5]dec-7-yl]-benzamide;
cis-3-Fluoro-N-[2-(2-methyl-pyridin-4-yl)-1-oxo-2-aza-spiro[4.5]dec-7-yl]-benzamide;
6-Methyl-pyridine-2-carboxylic acid [(5R,7R)-2-(3,5-difluoro-phenyl)-1-oxo-2-aza-spiro[4.5]dec-7-yl]-amide;
cis-5-Fluoro-pyridine-2-carboxylic acid [2-(3-fluoro-phenyl)-1-oxo-2-aza-spiro[4.5]dec-7-yl]-amide;
cis-2-Methyl-pyrimidine-4-carboxylic acid [2-(3-fluoro-phenyl)-1-oxo-2-aza-spiro[4.5]dec-7-yl]-amide;
cis-Pyrimidine-4-carboxylic acid [2-(3-fluoro-phenyl)-1-oxo-2-aza-spiro[4.5]dec-7-yl]-amide;
cis-6-Methyl-pyridine-2-carboxylic acid [2-(5-methyl-pyridin-3-yl)-1-oxo-2-aza-spiro[4.5]dec-7-yl]-amide;
cis-6-Methyl-pyridine-2-carboxylic acid [2-(3-methoxy-phenyl)-1-oxo-2-aza-spiro[4.5]dec-7-yl]-amide;
6-Methyl-pyridine-2-carboxylic acid [(5R,7R)-2-(5-fluoro-pyridin-2-yl)-1-oxo-2-aza-spiro[4.5]dec-7-yl]-amide;
cis-Pyridine-2-carboxylic acid [2-(5-fluoro-pyridin-3-yl)-1-oxo-2-aza-spiro[4.5]dec-7-yl]-amide;
cis-Pyridine-2-carboxylic acid [2-(3,4-difluoro-phenyl)-1-oxo-2-aza-spiro[4.5]dec-7-yl]-amide;
cis-2-Methyl-pyrimidine-4-carboxylic acid [2-(3,5-difluoro-phenyl)-1-oxo-2-aza-spiro[4.5]dec-7-yl]-amide;
cis-N-[2-(3-Fluoro-phenyl)-1-oxo-2-aza-spiro[4.5]dec-7-yl]-isonicotinamide;
cis-N-[2-(3-Fluoro-phenyl)-1-oxo-2-aza-spiro[4.5]dec-7-yl]-2-methyl isonicotinamide;
cis-Pyrimidine-4-carboxylic acid [2-(3,5-difluoro-phenyl)-1-oxo-2-azaspiro[4.5]dec-7-yl]-amide;
6-Methyl-pyridine-2-carboxylic acid [(5R,7R)-2-(4-fluoro-phenyl)-1-oxo-2-aza-spiro[4.5]dec-7-yl]-amide;
6-Methyl-pyridine-2-carboxylic acid [(5S,7S)-2-(3,5-difluoro-phenyl)-1-oxo-2-aza-spiro[4.5]dec-7-yl]-amide;
2-Methyl-pyrimidine-4-carboxylic acid [(5R,7R)-2-(3,5-difluoro-phenyl)-1-oxo-2-aza-spiro[4.5]dec-7-yl]-amide;
cis-6-Methyl-pyridine-2-carboxylic acid (2-benzyl-1-oxo-2-aza-spiro[4.5]dec-7-yl)-amide;
cis-3-Methyl-N-[2-(2-methyl-pyrimidin-4-yl)-1-oxo-2-aza-spiro[4.5]dec-7-yl]-benzamide;
cis-3,5-Difluoro-N-[2-(2-methyl-pyrimidin-4-yl)-1-oxo-2-aza-spiro[4.5]dec-7-yl]-benzamide;
cis-6-Methyl-pyrazine-2-carboxylic acid {2-[6-(4-fluoro-phenyl)-pyrimidin-4-yl]-1-oxo-2-aza-spiro[4.5]dec-7-yl}-amide;
cis-6-Methyl-pyridine-2-carboxylic acid {2-[6-(4-fluoro-phenyl)-pyrimidin-4-yl]-1-oxo-2-aza-spiro[4.5]dec-7-yl}-amide;
cis-3-Fluoro-N-{2-[6-(4-fluoro-phenyl)-pyrimidin-4-yl]-1-oxo-2-aza-spiro[4.5]dec-7-yl}-benzamide;

cis-4-Fluoro-N-[2-(2-methyl-pyrimidin-4-yl)-1-oxo-2-aza-spiro[4.5]dec-7-yl]-benzamide;
cis-3,4-Difluoro-N-[2-(2-methyl-pyrimidin-4-yl)-1-oxo-2-aza-spiro[4.5]dec-7-yl]-benzamide;
cis-2-Fluoro-N-[2-(2-methyl-pyrimidin-4-yl)-1-oxo-2-aza-spiro[4.5]dec-7-yl]-benzamide;
cis-2-Methyl-N-[2-(2-methyl-pyrimidin-4-yl)-1-oxo-2-aza-spiro[4.5]dec-7-yl]-isonicotinamide;
cis-6-Hydroxymethyl-pyridine-2-carboxylic acid [2-(3-fluoro-phenyl)-1-oxo-2-aza-spiro[4.5]dec-7-yl]-amide;
cis-6-Trifluoromethyl-pyridine-2-carboxylic acid [2-(3-fluoro-phenyl)-1-oxo-2-aza-spiro[4.5]dec-7-yl]-amide;
N-[(5R,7R)-2-(3-Fluoro-phenyl)-1-oxo-2-aza-spiro[4.5]dec-7-yl]-2-methyl-isonicotinamide;
cis-6-Trifluoromethyl-pyridine-2-carboxylic acid [2-(2-methyl-pyrimidin-4-yl)-1-oxo-2-aza-spiro[4.5]dec-7-yl]-amide;
Pyridine-2-carboxylic acid [9,9-difluoro-2-(3-fluoro-phenyl)-1-oxo-2-aza-spiro[4.5]dec-7-yl]-amide;
Pyridine-2-carboxylic acid [(5R,7S)-9,9-difluoro-2-(3-fluoro-phenyl)-1-oxo-2-aza-spiro[4.5]dec-7-yl]-amide;
Pyridine-2-carboxylic acid [(5S,7R)-9,9-difluoro-2-(3-fluoro-phenyl)-1-oxo-2-aza-spiro[4.5]dec-7-yl]-amide; or
cis-2-[2-(3-Chloro-phenyl)-1-oxo-2-aza-spiro[4.5]dec-7-yl]-2,3-dihydro-isoindol-1-one;
Pyridine-2-carboxylic acid [(5S,7S)-9,9-difluoro-2-(3-fluoro-phenyl)-1-oxo-2-aza-spiro[4.5]dec-7-yl]-amide;
Pyridine-2-carboxylic acid [(5R,7R)-9,9-difluoro-2-(3-fluoro-phenyl)-1-oxo-2-aza-spiro[4.5]dec-7-yl]-amide;
2-Methyl-pyrimidine-4-carboxylic acid [(5S,7R)-9,9-difluoro-2-(3-fluoro-phenyl)-1-oxo-2-aza-spiro[4.5]dec-7-yl]-amide;
2-Methyl-pyrimidine-4-carboxylic acid [(5R,7S)-9,9-difluoro-2-(3-fluoro-phenyl)-1-oxo-2-aza-spiro[4.5]dec-7-yl]-amide;
trans-2-Methyl-pyrimidine-4-carboxylic acid [2-(3,5-difluoro-phenyl)-9,9-difluoro-1-oxo-2-aza-spiro[4.5]dec-7-yl]-amide;
cis-Pyridine-2-carboxylic acid [9,9-difluoro-2-(4-fluoro-phenyl)-1-oxo-2-aza-spiro[4.5]dec-7-yl]-amide;
cis-6-Methyl-pyridine-2-carboxylic acid [9,9-difluoro-2-(3-fluoro-phenyl)-1-oxo-2-aza-spiro[4.5]dec-7-yl]-amide;
cis-6-Methyl-pyridine-2-carboxylic acid [9,9-difluoro-2-(2-methyl-pyrimidin-4-yl)-1-oxo-2-aza-spiro[4.5]dec-7-yl]-amide;
cis-6-Methyl-pyridine-2-carboxylic acid [9,9-difluoro-2-(5-fluoro-pyridin-2-yl)-1-oxo-2-aza-spiro[4.5]dec-7-yl]-amide;
cis-Pyridine-2-carboxylic acid [2-(3,5-difluoro-phenyl)-9,9-difluoro-1-oxo-2-aza-spiro[4.5]dec-7-yl]-amide;
cis-Pyridine-2-carboxylic acid [9,9-difluoro-2-(5-fluoro-pyridin-2-yl)-1-oxo-2-aza-spiro[4.5]dec-7-yl]-amide;
cis-Pyridine-2-carboxylic acid [9,9-difluoro-2-(2-methyl-pyrimidin-4-yl)-1-oxo-2-aza-spiro[4.5]dec-7-yl]-amide;
Pyridine-2-carboxylic acid [(5S,7R)-2-(3,5-difluoro-phenyl)-9,9-difluoro-1-oxo-2-aza-spiro[4.5]dec-7-yl]-amide;
Pyridine-2-carboxylic acid [(5R,7S)-2-(3,5-difluoro-phenyl)-9,9-difluoro-1-oxo-2-aza-spiro[4.5]dec-7-yl]-amide;
cis-2-Methyl-pyrimidine-4-carboxylic acid [2-(3,5-difluoro-phenyl)-1,9-dioxo-2-aza-spiro[4.5]dec-7-yl]-amide;
cis-2-Methyl-pyrimidine-4-carboxylic acid [2-(3,5-difluoro-phenyl)-9-hydroxy-1-oxo-2-aza-spiro[4.5]dec-7-yl]-amide;
trans-2-Methyl-pyrimidine-4-carboxylic acid [2-(3,5-difluoro-phenyl)-9-hydroxy-1-oxo-2-aza-spiro[4.5]dec-7-yl]-amide;
2-Methyl-pyrimidine-4-carboxylic acid [(5R,7S,9S)-2-(3,5-difluoro-phenyl)-9-hydroxy-9-methyl-1-oxo-2-aza-spiro[4.5]dec-7-yl]-amide;
2-Methyl-pyrimidine-4-carboxylic acid [(5R,7S,9R)-2-(3,5-difluoro-phenyl)-9-hydroxy-9-methyl-1-oxo-2-aza-spiro[4.5]dec-7-yl]-amide;
N-[(5S,7R)-9,9-Difluoro-2-(2-methyl-pyrimidin-4-yl)-1-oxo-2-aza-spiro[4.5]dec-7-yl]-3-fluoro-benzamide;
N-[(5R,7S)-9,9-Difluoro-2-(2-methyl-pyrimidin-4-yl)-1-oxo-2-aza-spiro[4.5]dec-7-yl]-3-fluoro-benzamide;
trans-2-Methyl-pyrimidine-4-carboxylic acid [2-(3,5-difluoro-phenyl)-9-fluoro-1-oxo-2-aza-spiro[4.5]dec-7-yl]-amide;
cis-3-Fluoro-N-[2-(3-fluoro-phenyl)-1,9-dioxo-2-aza-spiro[4.5]dec-7-yl]-benzamide;
cis-6-Methyl-pyridine-2-carboxylic acid [2-(3-fluoro-phenyl)-1,9-dioxo-2-aza-spiro[4.5]dec-7-yl]-amide;
trans-3-Fluoro-N-[2-(3-fluoro-phenyl)-9-hydroxy-1-oxo-2-aza-spiro[4.5]dec-7-yl]-benzamide;
trans-6-Methyl-pyridine-2-carboxylic acid [2-(3-fluoro-phenyl)-9-hydroxy-1-oxo-2-aza-spiro[4.5]dec-7-yl]-amide;
6-Methyl-pyridine-2-carboxylic acid [(5S,7R)-9,9-difluoro-2-(5-fluoro-pyridin-2-yl)-1-oxo-2-aza-spiro[4.5]dec-7-yl]-amide;
cis-N-[9,9-Difluoro-2-(2-methyl-pyrimidin-4-yl)-1-oxo-2-aza-spiro[4.5]dec-7-yl]-3-fluoro-benzamide;
cis-2-Methyl-pyrimidine-4-carboxylic acid [9,9-difluoro-2-(3-fluoro-phenyl)-1-oxo-2-azaspiro[4.5]dec-7-yl]-amide;
cis 3-Fluoro-N—[-2-(3-methoxy-phenyl)-1-oxo-2-aza-spiro[4.5]dec-7-yl]-benzamide;
cis 3-Fluoro-N-[2-(3-hydroxy-phenyl)-1-oxo-2-aza-spiro[4.5]dec-7-yl]-benzamide;
cis-N-[(5S,7S)-2-(3-Dimethylamino-phenyl)-1-oxo-2-aza-spiro[4.5]dec-7-yl]-3-fluoro-benzamide;
cis-3-Fluoro-N-[(2-(4-methoxy-phenyl)-1-oxo-2-aza-spiro[4.5]dec-7-yl]-benzamide;
cis-3-Fluoro-N-{2-[3-(3-morpholin-4-yl-propyl)-phenyl]-1-oxo-2-aza-spiro[4.5]dec-7-yl}-benzamide;
cis-3-Fluoro-N-[2-(3-fluoro-5-methoxy-phenyl)-1-oxo-2-aza-spiro[4.5]dec-7-yl]-benzamide;
cis-3-Fluoro-N-{1-oxo-2-[3-(2-oxo-2-pyrrolidin-1-yl-ethoxy)-phenyl]-2-aza-spiro[4.5]dec-7-yl}-benzamide;
cis-Thiazole-2-carboxylic acid [2-(3-fluoro-phenyl)-1-oxo-2-aza-spiro[4.5]dec-7-yl]-amide;
cis-N-[2-(4-Dimethylamino-phenyl)-1-oxo-2-aza-spiro[4.5]dec-7-yl]-3-fluoro-benzamide;
cis-3-Fluoro-N-(1-oxo-2-thiazol-2-yl-2-aza-spiro[4.5]dec-7-yl)-benzamide;
cis-Thiazole-2-carboxylic acid [(2-(2-methyl-pyrimidin-4-yl)-1-oxo-2-aza-spiro[4.5]dec-7-yl]-amide;
cis-2-Methyl-pyrimidine-4-carboxylic acid [2-(3-fluoro-5-methoxy-phenyl)-1-oxo-2-aza-spiro[4.5]dec-7-yl]-amide;
cis-N-[2-(3-Cyano-5-fluoro-phenyl)-1-oxo-2-aza-spiro[4.5]dec-7-yl]-3-fluoro-benzamide;
cis-Thiazole-2-carboxylic acid [2-(3,5-difluoro-phenyl)-1-oxo-2-aza-spiro[4.5]dec-7-yl]-amide;
cis-2-Methyl-thiazole-4-carboxylic acid [2-(3,5-difluoro-phenyl)-1-oxo-2-aza-spiro[4.5]dec-7-yl]-amide;

cis-Pentanoic acid [2-(3,5-difluoro-phenyl)-1-oxo-2-aza-spiro[4.5]dec-7-yl]-amide;
cis-N-[2-(3,5-Difluoro-phenyl)-1-oxo-2-aza-spiro[4.5]dec-7-yl]-butyramide;
3-Fluoro-N-[(5R,7R)-2-(2-methyl-pyrimidin-4-yl)-1-oxo-2-aza-spiro[4.5]dec-7-yl]-benzamide;
3-Chloro-N-[(5R,7R)-2-(2-methyl-pyrimidin-4-yl)-1-oxo-2-aza-spiro[4.5]dec-7-yl]-benzamide;
cis-5-Fluoro-pyridine-2-carboxylic acid [(2-(2-methyl-pyrimidin-4-yl)-1-oxo-2-aza-spiro[4.5]dec-7-yl]-amide;
cis-3-Fluoro-N-[1-oxo-2-(2-trifluoromethyl-pyrimidin-4-yl)-2-aza-spiro[4.5]dec-7-yl]-benzamide;
cis-N-[2-(2,6-Dimethyl-pyrimidin-4-yl)-1-oxo-2-aza-spiro[4.5]dec-7-yl]-3-fluoro-benzamide;
3-Methyl-N-[(5R,7R)-2-(2-methyl-pyrimidin-4-yl)-1-oxo-2-aza-spiro[4.5]dec-7-yl]-benzamide;
cis-3-Fluoro-N-(2-methyl-1-oxo-2-aza-spiro[4.5]dec-7-yl)-benzamide;
cis-3-Fluoro-N-(2-ethyl-1-oxo-2-aza-spiro[4.5]dec-7-yl)-benzamide;
cis-3-Fluoro-N-(2-propyl-1-oxo-2-aza-spiro[4.5]dec-7-yl)-benzamide;
6-Methyl-pyridine-2-carboxylic acid[(5R,7R)-1-oxo-2-(2-trifluoromethyl-pyrimidin-4-yl)-2-aza-spiro[4.5]dec-7-yl]-amide;
3-Fluoro-N-[2-(1-methyl-piperidin-4-yl)-1-oxo-2-aza-spiro[4.5]dec-7-yl]-benzamide;
3-Fluoro-N-[2-(1-methyl-1H-pyrazol-3-yl)-1-oxo-2-aza-spiro[4.5]dec-7-yl]-benzamide;
2-Methyl-6-oxo-1,6-dihydro-pyrimidine-4-carboxylic acid [(5R,7R)-2-(3,5-difluoro-phenyl)-1-oxo-2-aza-spiro[4.5]dec-7-yl]amide; or
a pharmaceutically acceptable salt thereof.

13. The compound of claim 1, wherein the compound is:
Pyridine-2-carboxylic acid [9-fluoro-2-(3-fluoro-phenyl)-9-methyl-1-oxo-2-aza-spiro[4.5]dec-7-yl]-amide;
2-Methyl-pyrimidine-4-carboxylic acid [2-(3,5-difluoro-phenyl)-9-fluoro-9-methyl-1-oxo-2-aza-spiro[4.5]dec-7-yl]-amide;
2-Methyl-pyrimidine-4-carboxylic acid [9-fluoro-2-(4-fluoro-phenyl)-1-oxo-2-aza-spiro[4.5]dec-7-yl]-amide;
Pyridine-2-carboxylic acid [8,8-difluoro-2-(3-fluoro-phenyl)-1-oxo-2-aza-spiro[4.5]dec-7-yl]-amide;
Pyridine-2-carboxylic acid [8-fluoro-2-(3-fluoro-phenyl)-1-oxo-2-aza-spiro[4.5]dec-7-yl]-amide;
Pyridine-2-carboxylic acid [2-(3-fluoro-phenyl)-8-hydroxy-1-oxo-2-aza-spiro[4.5]dec-7-yl]-amide;
Pyridine-2-carboxylic acid [8-fluoro-2-(3-fluoro-phenyl)-8-methyl-1-oxo-2-aza-spiro[4.5]dec-7-yl]-amide;
Pyridine-2-carboxylic acid [2-(3-fluoro-phenyl)-8-hydroxy-8-methyl-1-oxo-2-aza-spiro[4.5]dec-7-yl]-amide;
2-Methyl-pyrimidine-4-carboxylic acid [2-(3,5-difluoro-phenyl)-8,8-difluoro-1-oxo-2-aza-spiro[4.5]dec-7-yl]-amide;
2-Methyl-pyrimidine-4-carboxylic acid [2-(3,5-difluoro-phenyl)-8-fluoro-1-oxo-2-aza-spiro[4.5]dec-7-yl]-amide;
2-Methyl-pyrimidine-4-carboxylic acid [2-(3,5-difluoro-phenyl)-8-fluoro-8-methyl-1-oxo-2-aza-spiro[4.5]dec-7-yl]-amide;
2-Methyl-pyrimidine-4-carboxylic acid [2-(3,5-difluoro-phenyl)-8-hydroxy-8-methyl-1-oxo-2-aza-spiro[4.5]dec-7-yl]-amide;
2-Methyl-pyrimidine-4-carboxylic acid [2-(3,5-difluoro-phenyl)-8-hydroxy-1-oxo-2-aza-spiro[4.5]dec-7-yl]-amide;
2-Methyl-pyrimidine-4-carboxylic acid [8,8-difluoro-2-(4-fluoro-phenyl)-1-oxo-2-aza-spiro[4.5]dec-7-yl]-amide;
2-Methyl-pyrimidine-4-carboxylic acid [8-fluoro-2-(4-fluoro-phenyl)-1-oxo-2-aza-spiro[4.5]dec-7-yl]-amide;
2-Methyl-pyrimidine-4-carboxylic acid [8-fluoro-2-(4-fluoro-phenyl)-8-methyl-1-oxo-2-aza-spiro[4.5]dec-7-yl]-amide;
2-Methyl-pyrimidine-4-carboxylic acid [2-(4-fluoro-phenyl)-8-hydroxy-1-oxo-2-aza-spiro[4.5]dec-7-yl]-amide;
2-Methyl-pyrimidine-4-carboxylic acid [2-(4-fluoro-phenyl)-8-hydroxy-8-methyl-1-oxo-2-aza-spiro[4.5]dec-7-yl]-amide;
Pyridine-2-carboxylic acid [4,4-difluoro-2-(3-fluoro-phenyl)-1-oxo-2-aza-spiro[4.5]dec-7-yl]-amide;
Pyridine-2-carboxylic acid [4-fluoro-2-(3-fluoro-phenyl)-1-oxo-2-aza-spiro[4.5]dec-7-yl]-amide;
Pyridine-2-carboxylic acid [2-(3-fluoro-phenyl)-4-hydroxy-1-oxo-2-aza-spiro[4.5]dec-7-yl]-amide;
Pyridine-2-carboxylic acid [4-fluoro-2-(3-fluoro-phenyl)-4-methyl-1-oxo-2-aza-spiro[4.5]dec-7-yl]-amide;
Pyridine-2-carboxylic acid [2-(3-fluoro-phenyl)-4-hydroxy-4-methyl-1-oxo-2-aza-spiro[4.5]dec-7-yl]-amide;
2-Methyl-pyrimidine-4-carboxylic acid [2-(3,5-difluoro-phenyl)-4,4-difluoro-1-oxo-2-aza-spiro[4.5]dec-7-yl]-amide;
2-Methyl-pyrimidine-4-carboxylic acid [2-(3,5-difluoro-phenyl)-4-fluoro-1-oxo-2-aza-spiro[4.5]dec-7-yl]-amide;
2-Methyl-pyrimidine-4-carboxylic acid [2-(3,5-difluoro-phenyl)-4-fluoro-4-methyl-1-oxo-2-aza-spiro[4.5]dec-7-yl]-amide;
2-Methyl-pyrimidine-4-carboxylic acid [2-(3,5-difluoro-phenyl)-4-hydroxy-4-methyl-1-oxo-2-aza-spiro[4.5]dec-7-yl]-amide;
2-Methyl-pyrimidine-4-carboxylic acid [2-(3,5-difluoro-phenyl)-4-hydroxy-1-oxo-2-aza-spiro[4.5]dec-7-yl]-amide;
2-Methyl-pyrimidine-4-carboxylic acid [4,4-difluoro-2-(4-fluoro-phenyl)-1-oxo-2-aza-spiro[4.5]dec-7-yl]-amide;
2-Methyl-pyrimidine-4-carboxylic acid [4-fluoro-2-(4-fluoro-phenyl)-1-oxo-2-aza-spiro[4.5]dec-7-yl]-amide;
2-Methyl-pyrimidine-4-carboxylic acid [4-fluoro-2-(4-fluoro-phenyl)-4-methyl-1-oxo-2-aza-spiro[4.5]dec-7-yl]-amide;
2-Methyl-pyrimidine-4-carboxylic acid [2-(4-fluoro-phenyl)-4-hydroxy-1-oxo-2-aza-spiro[4.5]dec-7-yl]-amide;
2-Methyl-pyrimidine-4-carboxylic acid [2-(4-fluoro-phenyl)-4-hydroxy-4-methyl-1-oxo-2-aza-spiro[4.5]dec-7-yl]-amide; or
a pharmaceutically acceptable salt thereof.

14. A pharmaceutical composition comprising at least one compound of claim 1 or a pharmaceutically acceptable salt thereof, and at least one pharmaceutically acceptable carrier.

* * * * *